US012663562B2

(12) United States Patent
Demirci et al.

(10) Patent No.: US 12,663,562 B2
(45) Date of Patent: Jun. 23, 2026

(54) POLYSACCHARIDE HYDROGEL OPTICAL FIBERS AND THEIR FABRICATION AND USE

(71) Applicant: The Board of Trustees of the Leland Stanford Junior University, Stanford, CA (US)

(72) Inventors: Utkan Demirci, Stanford, CA (US); Rajib Ahmed, Mountain View, CA (US); Rui L. Reis, Redwood City, CA (US); Carlos F. Guimaraes, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 253 days.

(21) Appl. No.: 18/556,611

(22) PCT Filed: Apr. 22, 2022

(86) PCT No.: PCT/US2022/026021
§ 371 (c)(1),
(2) Date: Oct. 20, 2023

(87) PCT Pub. No.: WO2022/226357
PCT Pub. Date: Oct. 27, 2022

(65) Prior Publication Data
US 2024/0184016 A1     Jun. 6, 2024

Related U.S. Application Data

(60) Provisional application No. 63/178,988, filed on Apr. 23, 2021.

(51) Int. Cl.
*G02B 1/04*          (2006.01)
*G02B 6/02*          (2006.01)
(Continued)

(52) U.S. Cl.
CPC ............. *G02B 1/048* (2013.01); *G02B 1/046* (2013.01); *G02B 6/0229* (2013.01);
(Continued)

(58) Field of Classification Search
None
See application file for complete search history.

(56) References Cited

U.S. PATENT DOCUMENTS 5,280,548 A      1/1994  Atwater et al.
7,831,126 B2 * 11/2010  Foerster ............... G01N 21/645
385/12

(Continued)

OTHER PUBLICATIONS

Guimarães et al., (2021) "Engineering hydrogel-based biomedical photonics: design, fabrication and applications", Adv Mater., 33(23):1-46.

(Continued)

*Primary Examiner* — Jerry Rahll
(74) *Attorney, Agent, or Firm* — Jenny L. Buchbinder; Bozicevic, Field & Francis LLP

(57) ABSTRACT

Optical fibers containing wet-spun multi-layer hydrogel cladding with ionic-crosslinked polysaccharides are provided. Optical fibers can be formed with step- or gradient-index architectures, fusion splicing, and facile rare-earth ion doping. Plasmonic nanoparticles, functionalized light-sensitive quantum dots, or particles can be incorporated into the fiber core to generate a resonance light shift upon the presence and binding of molecular biotargets for biosensor applications. The integration of plasmonic hydrogel fibers with medical swabs provides for rapid detection of pathogens such as severe acute respiratory syndrome coronavirus 2 (SARS-COV-2). The inclusion of living cells allows for the non-invasive digitalization and quantification of complex biological responses such as cancer proliferative inva- (Continued)

Optical Hydrogel Fiber sion and discovery of anti-cancer drug susceptibility thresholds.

33 Claims, 110 Drawing Sheets

(51) Int. Cl.

| | |
|---|---|
| *G02B 6/028* | (2006.01) |
| *A61K 41/00* | (2020.01) |
| *B82Y 20/00* | (2011.01) |
| *G01N 21/64* | (2006.01) |

(52) U.S. Cl.

CPC ........ G02B 6/0286 (2013.01); *A61K 41/0057* (2013.01); *B82Y 20/00* (2013.01); *G01N 21/6428* (2013.01); *G01N 2021/6439* (2013.01)

(56) References Cited

U.S. PATENT DOCUMENTS

| | | | | |
|---|---|---|---|---|
| 9,012,415 | B2 * | 4/2015 | Da Silva Correia | ... A61L 27/54 |
| | | | | 522/89 |
| 10,126,467 | B2 * | 11/2018 | Omenetto | ........ B29D 11/00788 |
| 10,428,160 | B2 * | 10/2019 | Rege | ........................ C08J 3/075 |
| 10,653,802 | B2 * | 5/2020 | Xu | ........................ A61K 9/0024 |
| 12,099,165 | B1 * | 9/2024 | Jiang | ..................... G02B 1/048 |
| 2009/0202193 | A1 * | 8/2009 | Foerster | ................. G02B 1/046 |
| | | | | 385/12 |
| 2014/0350237 | A1 | 11/2014 | Da Silva Correia et al. | |
| 2016/0177002 | A1 | 6/2016 | Palchik et al. | |

OTHER PUBLICATIONS

Yetisen et al., (2017) "Glucose-Sensitive Hydrogel Optical Fibers Functionalized with Phenylboronic Acid", Adv Mater., 29:1-11.

Feng et al., (2020) "Printed Degradable Optical Waveguides for Guiding Light into Tissue", Adv. Funct. Mater., 30 (2004327): 1-14.

Eisherif et al., (2019) "Hydrogel optical fibers for continuous glucose monitoring. Biosens", Bioelectron., 137:25-32.

Zhou et al., (2018) "Ratiometric fluorescence sensor for Fe3+ ions detection based on quantum dot-doped hydrogel optical fiber", Sensors Actuators, B Chem., 264:52-58.

Choi et al., (2015) "Step-Index Optical Fiber Made of Biocompatible Hydrogels", Adv. Mater., 27:4081-4086.

Choi et al., (2013) "Light-guiding hydrogels for cell-based sensing and optogenetic synthesis in vivo", Nat. Photonics, 7:987-994.

Guo et al., (2016) "Highly Stretchable, Strain Sensing Hydrogel Optical Fibers", Adv. Mater., 28:10244-10249.

* cited by examiner

Multi-Output

Increasing Local RI, Decrease in >600nm transmission

3D
Printing
Nozzle

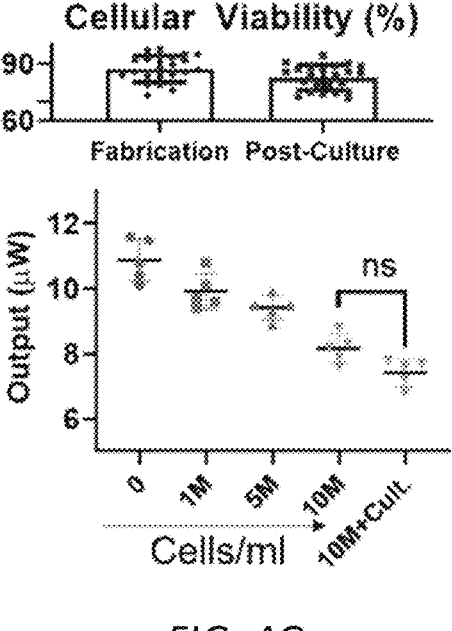
FIG. 4G
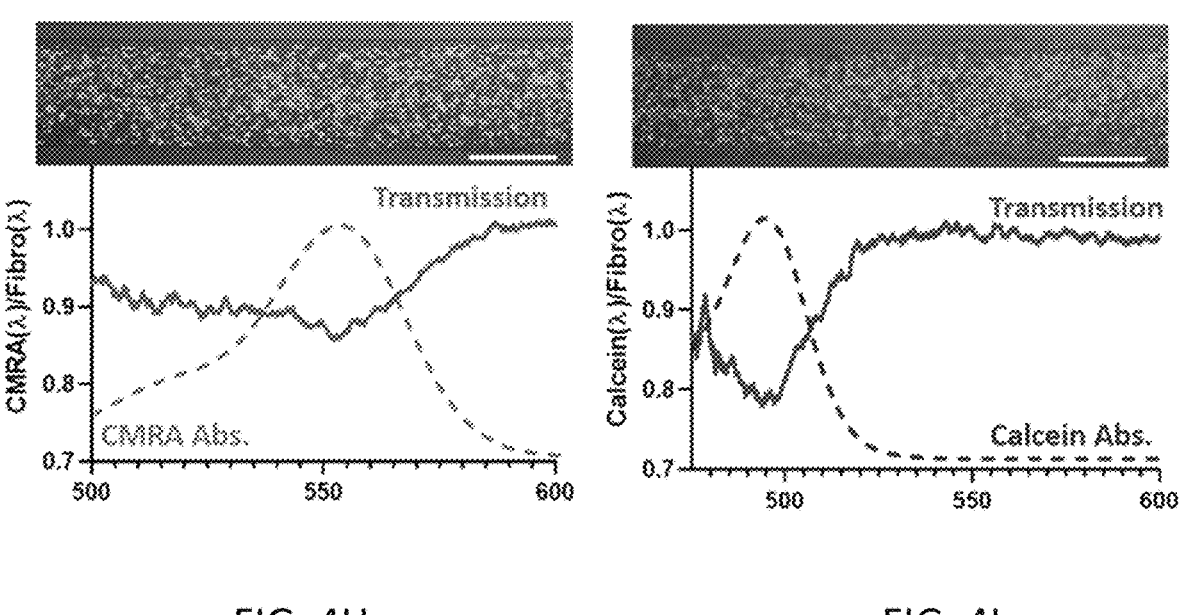
FIG. 4H                    FIG. 4I

Mature Cancer Fiberoid

As Fabricated
Single Cell-laden
Light Guiding

Cancer Tissue Develops
Invasive Proliferation
Occlusion of Optical Core

Inhibitory Drugs Prevent
Cancer Cell Growth
Increased Light Output

Power Meter

Broadband
Light Source

Doped Alginate

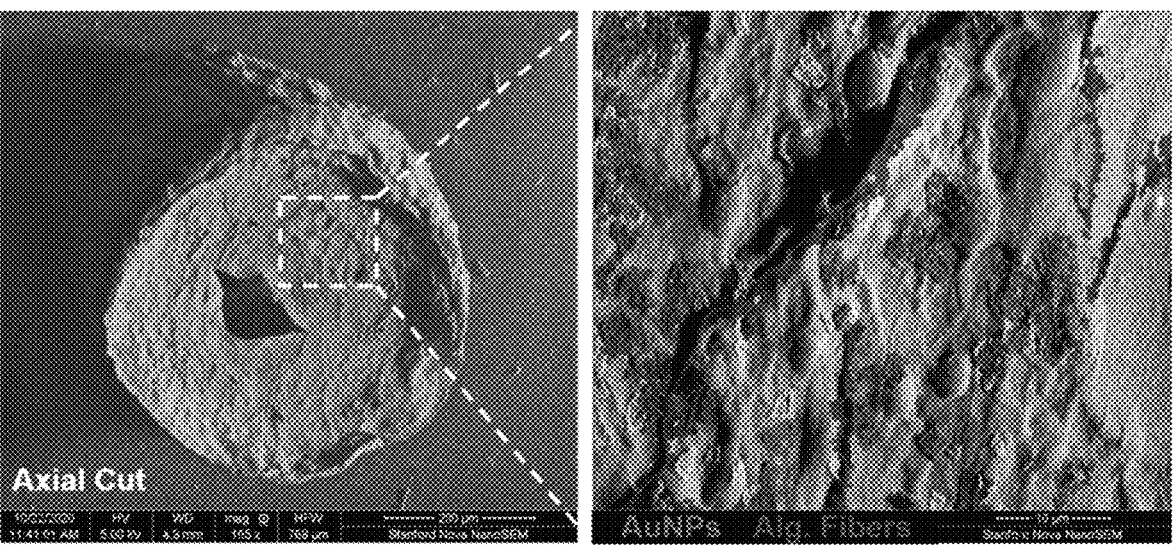
FIG. 11A                              FIG. 11B
Experiment
Resonance versus Au-Free Core
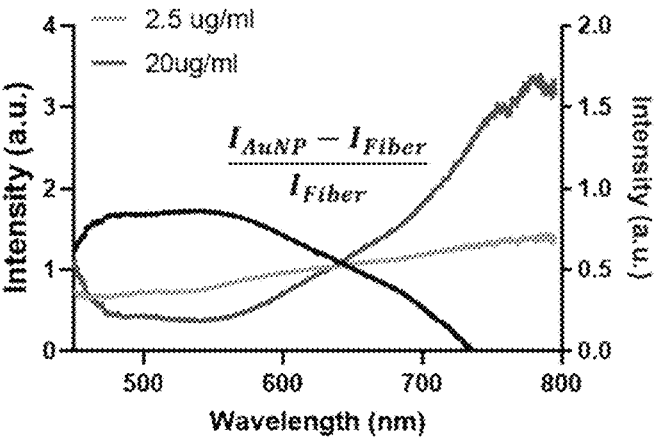
FIG. 12A

Plasmonic Fiber Core     Incubation with PBS     Wash, Add Calcium

Controlled Swelling        Unbound Analyte removal
Mesh Dilation             Fiber Stabilization
Heightened Permeation     Locked-in Recovery

Dynamic Swelling Behavior

- Alginate
- Au-Alginate
- Anti-S1-GAu-Alginate

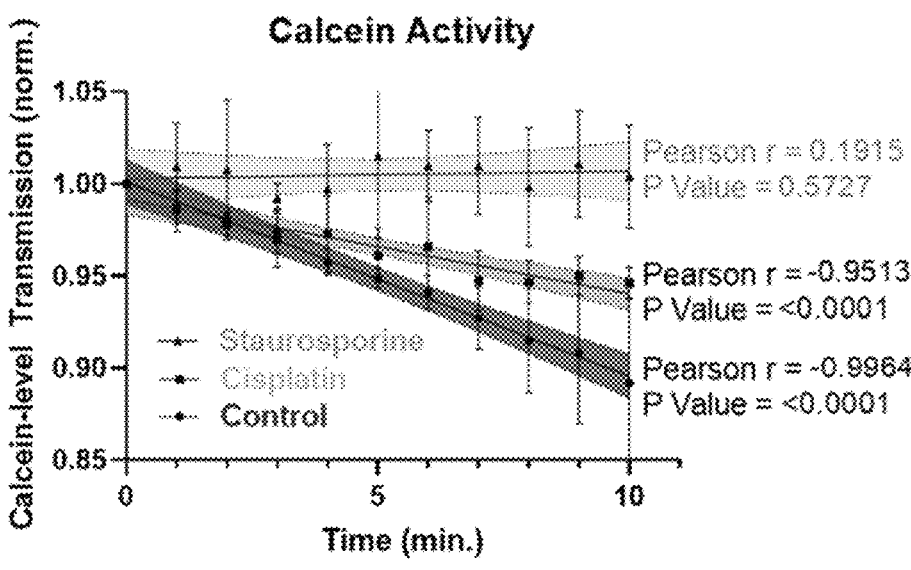
FIG. 24B
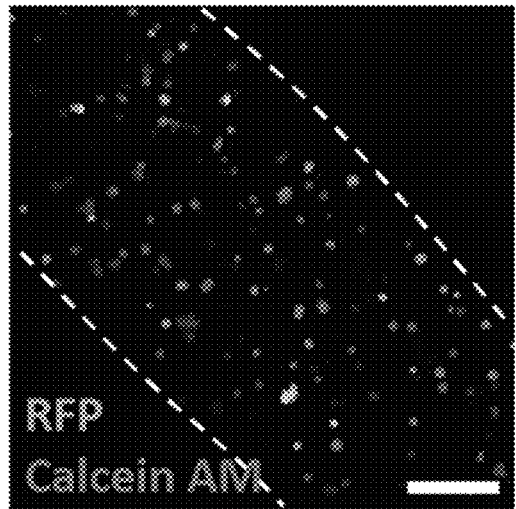
FIG. 24C

Microscopy Validation
Average Single-Cell RFP
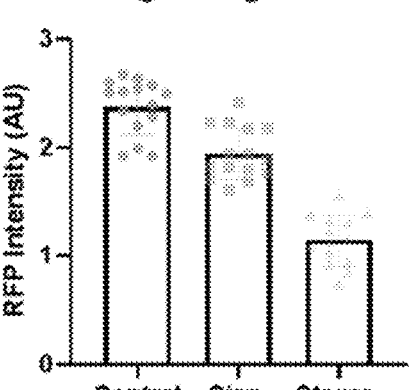
Average Single-Cell Calcein
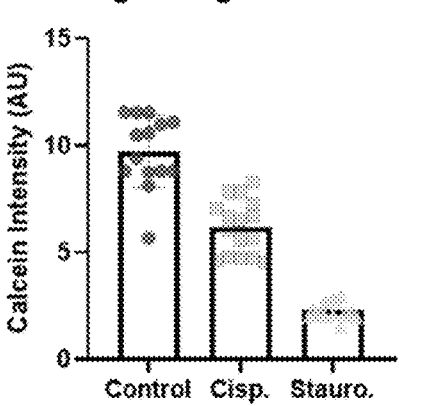
FIG. 24D
+Cisplatin
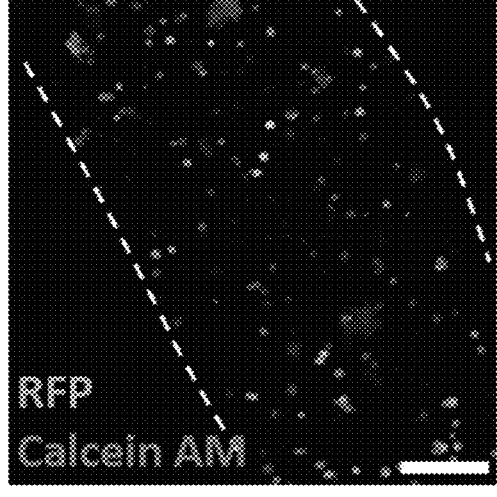
+Staurosporine
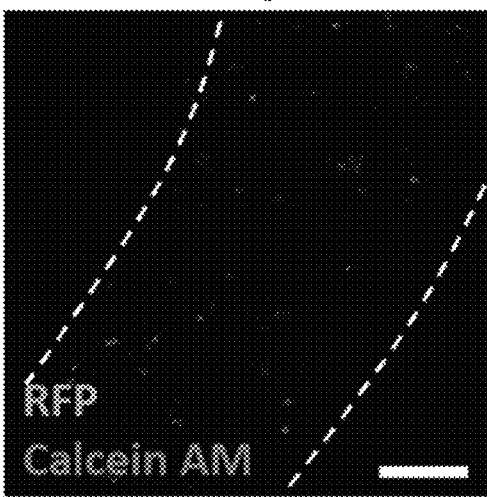
FIG. 24E                    FIG. 24F Control

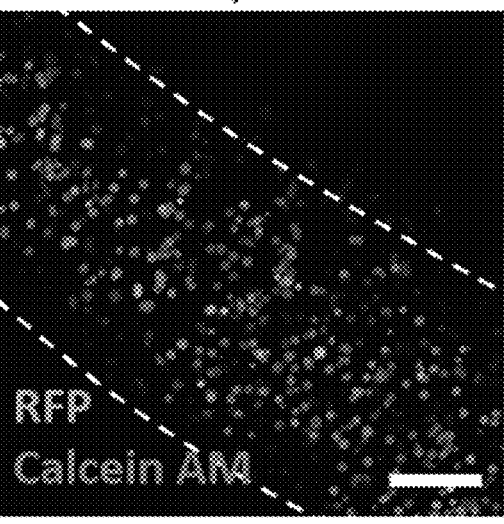
FIG. 25E
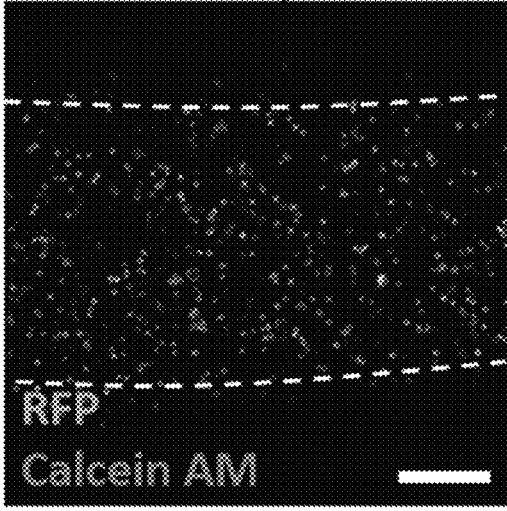
FIG. 25F

Setup

3D

1 Week Culture

Live Cells

FIG. 30A

Average Single-Cell RFP

Average Single-Cell Calcein

FIG. 31E

Application: Light-Driven Tissue Engineering: Optical Fiber as a scaffold + Guided light to enhance cellular development

Light Input ★ Vascular Core → Endothelial Cells Encapsulated in Labile environment Fiber-Optics Based Tissue Engineering Vascular stimulation at specific wavelengths
- Optical fiber as a template structure for fabrication of vasculature
- Light guiding as means for endothelial stimulation
- Pericytes and muscle layers can be integrated in the cladding hydrogels for increasing vascular support and blood vessel-like functionality

FIG. 32

POLYSACCHARIDE HYDROGEL OPTICAL FIBERS AND THEIR FABRICATION AND USE

CROSS-REFERENCE TO RELATED APPLICATION

This application claims benefit under 35 U.S.C. § 119(e) of provisional application 63/178,988, filed Apr. 23, 2021, which application is hereby incorporated by reference in its entirety.

BACKGROUND

Since the first known uses of glass for its optical aesthetics in ancient Rome decorating the windows of Hagia Sophia and other world treasures sintered with gold particles, significant progress has been made in the field of micro-/nano-optics that has culminated in uncovering microorganisms, exploring faraway stars and igniting the digital revolution with the 60s-70s advent of optical fibers (Lin *Nat. Photonics* 12, 715-717 (2018); DeCusatis *Handbook of Fiber Optic Data Communication* (2008); Palais Optical communication: Long distance fiber optic communications in *Broadcasting and Optical Communication Technology* (2017)). A classical optical fiber is a type of optical transmission medium, i.e., a hair-size cylindrical volumetric structure which can guide light waves through a 3D space due to refractive index variation (step-index, $\Delta n > 0.001$) between fiber core (inner shell) and cladding (outer shell). Light propagates in a zigzag fashion due to total internal reflection (TIR) between the core-shell interface. The study of fiber optics and the discovery of split-fusion and materials doping methods has grown to enable excellent data transmission, connection and amplification of light waves up to intercontinental ranges (Yablon *Optical Fiber Fusion Splicing. Optical Fiber Fusion Splicing* (Springer, 2005); Sulc & Jelinkova *Solid-state lasers for medical applications. Lasers for Medical Applications: Diagnostics, Therapy and Surgery* (Woodhead Publishing Limited, 2013)).

Solid-state silica based optical fibers excel in light-guiding, coupling, encoding and decoding information in micro-/nano-scales photonics. However, they are not biodegradable, and their life cycle involves high energy consumption and non-recyclable waste production (glass degradation time is estimated to be on the order of a million years). Moreover, although silica fibers are commonly used in healthcare applications such as imaging, optical detection and bio-sensing (Taffoni et al. Optical fiber-based MR-compatible sensors for medical applications: An overview. *Sensors (Switzerland)* 13, 14105-14120 (2013); Fermann & Hartl Ultrafast fibre lasers. *Nat. Photonics* 7, 868-874 (2013); Xu & Wise Recent advances in fibre lasers for nonlinear microscopy. *Nat. Photonics* 7, 875-882 (2013); Gallego & Lamela High-sensitivity ultrasound interferometric single-mode polymer optical fiber sensors for biomedical applications. *Opt. Lett.* 34, 1807 (2009)), they present limited biocompatibility when interfacing directly with biological tissues (Nizamoglu et al. All-biomaterial laser using vitamin and biopolymers. *Adv. Mater.* 25, 5943-5947 (2013)) and are dense to the point that hinders the diffusion of biological molecules (Haufová et al. Reversible buckling and diffusion properties of silica-coated hydrogel particles. *J. Colloid Interface Sci.* 357, 109-115 (2011)). Silica fibers also present light-coupling mismatch due to drastically different refractive index versus biological tissues (Guimarães et al. Engineering Hydrogel-Based Biomedical Photonics: Design, *Fabrication and Applications. Adv. Mater.* (2021)). On the other hand, hydrogels have been explored as sustainable, degradable photonic alternatives with physiological-level mechanics (Guimarães et al. The stiffness of living tissues and its implications for tissue engineering. *Nat. Rev. Mater.* 5, 351-370 (2020)) and better light-coupling with biological tissues (Guimarães et al., supra). Soft hydrogel fibers have been fabricated with synthetic, UV-crosslinking materials such as poly(ethylene glycol) (PEG) (Feng et al. Printed Degradable Optical Waveguides for Guiding Light into Tissue. *Adv. Funct. Mater.* 2004327, 1-14 (2020); Elsherif et al. Hydrogel optical fibers for continuous glucose monitoring. *Biosens. Bioelectron.* 137, 25-32 (2019); Zhou et al. Ratiometric fluorescence sensor for $Fe^{3+}$ ions detection based on quantum dot-doped hydrogel optical fiber. *Sensors Actuators, B Chem.* 264, 52-58 (2018); Yetisen et al. Glucose-Sensitive Hydrogel Optical Fibers Functionalized with Phenylboronic Acid. *Adv. Mater.* 29, (2017); Choi et al. Step-Index Optical Fiber Made of Biocompatible Hydrogels. *Adv. Mater.* 27, 4081-4086 (2015); Choi et al. Light-guiding hydrogels for cell-based sensing and optogenetic synthesis in vivo. *Nat. Photonics* 7, 987-994 (2013)) and acrylamide (Guo et al. Highly Stretchable, Strain Sensing Hydrogel Optical Fibers. *Adv. Mater.* 28, 10244-10249 (2016)). These fibers were shown capable of integrating tissues (Feng et al., supra; Choi et al. (2015), supra), stimulating cells, (Feng et al., supra; Choi et al. (2013), supra), and sensing varied phenomena (Elsherif et al., supra; Zhou et al., supra; Yetisen et al., supra; Choi et al. (2013), supra; Guo et al., supra).

Despite having favorably high refractive indexes (RI), covalently bound UV-cross-linked materials present two critical limitations. First, photocuring requires materials to be exposed to uniform light within tube-like structures, which are then extruded into fibers, limiting large-scale fabrication and throughputs. Second, these materials result in hydrogels that lack crosslinking dynamicity, thus preventing post-fabrication processes such as fusion splicing for repair or connection and assembly, processes that are essential staples of their solid-state optical fiber counterparts (Yablon et al., supra). Thus, there remains a need for improved optical fibers and methods of manufacturing them for biological applications.

SUMMARY

While solid-state optics has been the pillar of the modern digital age, the integration of soft hydrogel materials with micro/nano-optics could expand the horizons of photonics for bioengineering and biosensing applications. Optical fibers containing wet-spun multi-layer hydrogel cladding with ionic-crosslinked polysaccharides are provided. The flexible hydrogel structure and reversible crosslinking provide tunable design properties. For example, optical fibers can be formed with step- or gradient-index architectures, fusion splicing, and facile rare-earth ion doping. Plasmonic nanoparticles, functionalized light-sensitive quantum dots or particles can be incorporated into the fiber core to generate a resonance light shift upon the presence and binding of molecular biotargets for biosensor applications. The integration of plasmonic hydrogel fibers with medical swabs provides for rapid detection of pathogens such as severe acute respiratory syndrome coronavirus 2 (SARS-COV-2). In addition, cells can be encapsulated within the core of optical fibers and exposed to guided light. Living optical fibers containing cells may have many applications for quantifying complex cellular events. Protein fluorescent tagging can be combined with output power data for tracking the development of healthy and diseased tissues, drug research and functional threshold discovery, and allow optogenetic stimulation of engineered cells, e.g., for use as molecular factories.

In one aspect, an optical fiber is provided, the optical fiber comprising: a) one or more hydrogel cladding layers comprising polysaccharides crosslinked ionically by metal cations; and b) a core, wherein the core is encapsulated by the one or more hydrogel cladding layers.

In certain embodiments, the hydrogel cladding layers comprise gellan gum or alginate. In some embodiments, the hydrogel cladding layers comprise about 0.1 weight percent (wt %) to about 1.0 wt % gellan gum, including any wt % within this range such as 0.1, 0.15, 0.20, 0.25, 0.5, 0.75, or 1.0 wt %. In other embodiments, the hydrogel cladding layers comprise about 1.0 wt % to about 2.0 wt % alginate, including any weight % within this range such as 1.0, 1.2, 1.4, 1.6, 1.8, or 2.0 wt %.

In certain embodiments, the hydrogel cladding layers have a lower refractive index than the core of the optical fiber.

In certain embodiments, the optical fiber has 1 or more, 2 or more, 3 or more, 4 or more, 5 or more, 6 or more, 7 or more, 8 or more, 9 or more, or 10 or more hydrogel cladding layers. For example, the optical fiber may have 1 to 10 hydrogel cladding layers, including any number within this range such as 1, 2, 3, 4, 5, 6, 7, 8, 9, or 10 hydrogel cladding layers. In some embodiments, the optical fiber has 1 to 4 hydrogel cladding layers.

In certain embodiments, the metal cations that crosslink the hydrogel cladding layers comprise alkaline earth metal cations. In some embodiments, the alkaline earth metal cations are divalent calcium cations ($Ca^{2+}$).

In certain embodiments, the core is a hydrogel core, a liquid core, a hollow core, or a gaseous core. In some embodiments, the hydrogel core comprises alginate or gellan gum. In some embodiments, the hydrogel core comprises about 2 wt % to about 7 wt % alginate, including any wt % within this range such as 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, or 7.0 wt %. In other embodiments, the hydrogel core comprises about 1.0 wt % to about 1.5 wt % gellan gum, including any wt % within this range such as 1.0 wt %, 1.1, 1.2, 1.3, 1.4, or 1.5 wt %.

In certain embodiments, the core comprises a non-polysaccharide polymer.

In certain embodiments, the core comprises a mixture of at least two ionically crosslinked polysaccharides or at least one ionically crosslinked polysaccharide and a non-polysaccharide hydrogel polymer.

In certain embodiments, the core further comprises an extracellular matrix component, a basement membrane extract, or a biological lysate.

In certain embodiments, the hydrogel cladding layers and hydrogel core have a step-index or gradient-index architecture. In some embodiments, the optical fiber has multiple hydrogel cladding layers with alternating refractive index values. In some embodiments, the optical fiber has a gradient of refractive index values along the length of the optical fiber.

In certain embodiments, the hydrogel core comprises polysaccharides crosslinked ionically by metal cations. In some embodiments, the hydrogel core is doped with rare earth metal cations. For example, the rare earth metal cations may include, without limitation, neodymium or erbium cations. In some embodiments, the hydrogel cladding layers are crosslinked ionically by $Ca^{2+}$ and the hydrogel core is doped with $Nd^{3+}$.

In certain embodiments, the optical fiber further comprises a shielding layer. In some embodiments, the shielding layer comprises an alginate hydrogel. For example, the shielding layer may comprise a hydrogel comprising 1 wt % to 2 wt % alginate, including any wt % within this range such as 1 wt %, 1.25 wt %, 1.5 wt %, 1.75 wt %, or 2.0 wt %. In some embodiments, the shielding layer comprises a gellan gum hydrogel. For example, the shielding layer may comprise a hydrogel comprising 0.5 wt % to 1.5 wt % gellan gum, including any wt % within this range such as 0.5 wt %, 0.75 wt %, 1 wt %, 1.25 wt %, or 1.5 wt %.

In certain embodiments, the optical fiber has a multi-input architecture or a multi-output architecture. In some embodiments, the optical fiber has a multi-input architecture and a multi-output architecture.

In certain embodiments, the optical fiber further comprises a plasmonic nanoparticle, wherein the plasmonic nanoparticle is encapsulated within the core. In some embodiments, the plasmonic nanoparticle is a gold plasmonic nanoparticle.

In certain embodiments, the optical fiber further comprises a quantum dot, wherein the quantum dot is encapsulated within the core.

In certain embodiments, the optical fiber further comprises a capture agent that selectively binds to a target of interest, wherein the capture agent is attached to the outer surface of the plasmonic nanoparticle or quantum dot. For example, the target may include, without limitation, a molecule such as a protein (e.g., an antigen, an antibody, an enzyme, a transcription factor, or a receptor), a nucleic acid (e.g., messenger RNA, regulatory RNA, or viral nucleic acids), a metabolite, or an exogenous compound (e.g., drug, toxin, or pollutant); a cell, a tissue, an organoid, an organism, or a pathogen (e.g., a virus, a bacterium, a parasite, or other pathogen), a cell, a pathogen (e.g., a virus, a bacterium, a parasite, or other pathogen), a tissue, an organoid, or an organism. The capture agent may include, without limitation, an antibody, an antibody mimetic, an aptamer, a peptoid, or a ligand. In one embodiment, the plasmonic nanoparticle comprises capture agent (e.g., an antibody) that selectively binds to a spike protein of severe acute respiratory syndrome coronavirus 2 (SARS-CoV-2) attached to the outer surface of the plasmonic nanoparticle or quantum dot. In some embodiments, the plasmonic nanoparticle or quantum dot is functionalized with protein-G (e.g., to allow binding of antibodies to be used as capture agents).

In another aspect, a method of detecting a target of interest is provided, the method comprising measuring the plasmonic response of a plasmonic nanoparticle or the spectral response or change in photoluminescent lifetime of a quantum dot encapsulated within the core of an optical fiber upon binding of a target of interest to a capture agent attached to the surface of the plasmonic nanoparticle or the quantum dot.

In certain embodiments, the optical fiber further comprises an endotracheal tube coupled to the optical fiber.

In certain embodiments, the optical fiber further comprises a biotarget encapsulated within the core. In some embodiments, the biotarget is an antigen, an antibody, a protein, a nucleic acid, a cell, a pathogen (e.g., a virus, a bacterium, a parasite, or other pathogen), a tissue, an organoid, or an organism. In some embodiments, the biotarget is fluorescently labeled. In some embodiments, the biotarget expresses a fluorescent protein.

In another aspect, a photonic device comprising an optical fiber, described herein, is provided. In some embodiments, the photonic device further comprises a light source coupled to the optical fiber. In some embodiments, the light source is a laser diode, a light-emitting diode (LED), a superluminescent diode, a microfocus X-ray source, or a lamp. In some embodiments, the photonic device further comprises optics to focus light from the light source into the core of an optical fiber. In some embodiments, the photonic device further comprises a photodetector such as, but not limited to, a charge-coupled device (CCD), an active-pixel sensor (APS), or a CMOS sensor. In some embodiments, the photonic device further comprises a medical swab or endotracheal tube coupled to the optical fiber.

In another aspect, a method of guiding light to a target using an optical fiber described herein is provided, the method comprising: a) placing the optical fiber such that a first end of the optical fiber is attached to or near the target; and b) aligning a light source with a second end of the optical fiber, wherein light from the light source passes through the optical fiber to the target.

In certain embodiments, the target is an antigen, an antibody, a protein, a nucleic acid, a cell, a pathogen (e.g., a virus, a bacterium, a parasite, or other pathogen), a tissue, an organoid, or an organism. In some embodiments, the cell is an optogenetically modified cell. In certain embodiments, the light source is a broadband light source or a narrowband light source. In some embodiments, the light source is a laser diode, a light-emitting diode (LED), a superluminescent diode, a microfocus X-ray source, or a lamp. In certain embodiments, the method further comprises attaching an endotracheal tube to the optical fiber and inserting the endotracheal tube into an organism.

In another aspect, a method of guiding light to a target using an optical fiber is provided, the method comprising: a) introducing the target into the core of an optical fiber described herein; and b) aligning a light source with an end of the optical fiber, wherein light from the light source passes through the optical fiber to the target. In some embodiments, the target is a cell. In some embodiments, the cell is an optogenetically modified cell. In certain embodiments, the light source is a broadband light source or a narrowband light source. In some embodiments, the light source is a laser diode, a light-emitting diode (LED), a superluminescent diode, a microfocus X-ray source, or a lamp.

In another aspect, a method of activating a photoactivatable prodrug is provided, the method comprising: administering the photoactivatable prodrug to a subject; and exposing the photoactivatable prodrug to excitation light guided by an optical fiber, wherein activity of the prodrug is increased in response to exposure to the excitation light.

In certain embodiments, the optical fiber is used to guide light to a target site, wherein the prodrug is selectively activated at the target site.

In certain embodiments, the photoactivatable prodrug is a photoactivatable anticancer drug, and the excitation light is guided by the optical fiber to a tumor to activate the prodrug selectively at the site of a tumor.

In another aspect, a method of performing photodynamic therapy (PDT) is provided, the method comprising: administering a photosensitizing chemical substance to a subject; and exposing the photosensitizing chemical substance to excitation light guided by an optical fiber, wherein reactive oxygen species are generated by the photosensitizing chemical substance in response to exposure to the excitation light.

6

In another aspect, a kit comprising an optical fiber or reagents for producing an optical fiber, as described herein, and instructions for using the optical fiber are provided.

In another aspect, a method of monitoring proliferation of a cell is provided, the method comprising: a) culturing the cell within the core of an optical fiber described herein; b) aligning a light source with an end of the optical fiber; and c) monitoring output light power from the optical fiber, wherein the output light power decreases with increasing cell density.

In certain embodiments, the cell is a cancer cell.

In certain embodiments, the method further comprises contacting the cell with a test agent.

In another aspect, a method of monitoring expression of a fluorescently labeled protein in a cell is provided, the method comprising: a) introducing the cell into the core of an optical fiber described herein, wherein the fluorescently labeled protein is expressed in the cell; b) exposing the cell to excitation light guided by the optical fiber; and c) monitoring fluorescent light or a decrease in excitation-range light transmission intensity output from the optical fiber.

In certain embodiments, the method further comprises contacting the cell with a test agent.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A) Schematic representation of wet-spinning approach to continuously fabricate the optical fiber core (1), which can then be coated with different refractive index (n) hydrogel layers to obtain step- or gradient-index core-cladding architectures (2). FIG. 1B) Photograph of an as-fabricated optical core-clad hydrogel fiber. Scale bar: 1 cm. FIG. 1C) Schematic representation of the optical fiber input-output setup for light guiding and collection (top) and actual experimental setup (bottom). FIG. 1D) Microscopic 2D and 3D images of transversal core-clad-shield fiber sections. Core: Alginate 7%, Clad: GG 0.25+Nile red fluorescent solution, Shield: Alginate-FITC 2%. Scale bar: 200 µm. FIG. 1E) Detail of light-guiding through the core-clad fiber. Scale bar: 1 mm. FIG. 1F) Light-guiding by a core-clad-shield fiber inserted within a 3D Gelatin Matrix. Scale bar: 1 cm. FIG. 1G) High-contrast photographs of fibers coupled to a broadband light source. In each picture's center, a representation of the distinct layers and polymer concentration is visible in tones of gray. The black arrow shows the light input direction (in). Scale bar: 1 cm. FIG. 1H) Output Power measurements of light guided through different fiber configurations (core-only, gradient index, step index) with increasing length. FIG. 1I) Calculated attenuation values of light guided as a function of fiber length (distance). Statistical analysis through Turkey's Multiple Comparison, *p<0.05, *p<0.001, **p<0.0001.

FIG. 2B) Normalized intensity profile of output light power at increasing bending angles and tis regression line. The line equation is also denoted. FIG. 2C) Output power as measured upon sequential bending/unbending of core/clad fibers. FIG. 2D) Photographs of the main steps for hydrogel fiber split fusion (left) and lifting of a fused fiber (right). The white arrow indicates the point where fiber was cut and fused. FIG. 2E) Parallel behind silica fiber fusion splicing and re-crosslinked hydrogel fiber fusion. FIG. 2F) High-contrast photographs of light guided through intact, split, and fused hydrogel fibers. White arrows indicate the point of cut/fusion. Scale bar: 1 cm. FIG. 2G) Normalized output intensity of as-fabricated, cut, and fused fibers. Statistical comparison between cut/fused fibers and the original structure performed through Kruskall-Wallis multiple comparison test. FIG. 2H) High-contrast photographs of fusion splicing-assembled multi-output, multi-input, and multi-input/multi-output (MIMO) photonic architectures. FIG. 2I) Characterization of output light intensity with incremental input splicing. FIG. 2J) Evaluation of changes in output light power as a function of fiber compression, including an equation that represents the output intensity (I) as proportional to the input ($I_0$) minus the amount of light that is blocked/scattered as a function of the compressive force, S(f). FIG. 2K) Quantification of the double-output system intensities with both arms moving at the same angle to the common input branch. FIG. 2L) Multi-input photonic system arrangements and the detection of broadband and narrowband light sources in the same spectrum readout.

FIG. 3B) Output light spectrum of the hydrogel fibers with increasing AuNPs concentration. Each curve represents the average behavior of 4 individual fibers. FIG. 3C) Resonance curves obtained by normalizing the spectra of Au—NP encapsulating fibers of minimum and maximum tested AuNP concentrations against the empty fiber (no gold). In blue, the calculated absorption (1-transmission) curve for the highest concentration (20 μg/mL) is denoted. FIG. 3D) Output light spectra of Protein-G-coupled AuNP-laden fibers before and after addition of Anti-Spike antibodies and incubation with SARS-Spike antigen. Each curve represents the average behavior of 4 individual fibers. FIG. 3E) Normalized intensity (700 nm) values of the different curves upon antibody and antigen binding. Statistical comparisons performed by Mann-Whitney test, *p<0.05, **p<0.01. FIG. 3F) Schematic representation of the mechanism behind antibody and antigen-induced shifts resulting in decreased 700 nm intensity values. FIG. 3G) Rationale behind optical-fiber-coupled swabs, which can be exposed to viral structures present in bodily fluids. Upon flushing the collected material through the optical fiber, the Q-tip can be collected for routine analysis and the split fiber shaft washed and analyzed in an optical setup to look for the shift taking place in the presence of the virus. FIG. 3H) Steps behind the swab shaft adaptation and insertion of the optical fiber towards an optical-fiber-coupled medical swab. FIG. 3I) Immunofluorescence analysis of the hydrogel fibers upon incubation and reverse staining against SARS-COV-2 (Further detailed in FIG. 18). FIG. 3J) Exemplification of how a portion of the exposed fiber-coupled swab can be connected to a light source and derive an in-swab output for analysis. FIG. 3K) Output light spectra of blank (no virus) fibers as well as fibers exposed to a SARS-COV-2 solution and an Influenza solution (H3N2). All curves represent the average from measurements of 4 individual fibers. FIG. 3L) Normalized light intensity (700 nm) values of the blank (no virus) fibers as well as fibers exposed to a SARS-COV-2 solution and an Influenza solution (H3N2). Statistical analysis was performed by ordinary one-way ANOVA, *p<0.05, ns—not significant.

FIG. 4A) Schematic representation of the tri-coaxial 3D printing nozzle used to for continuous optical fiber printing under sterile conditions. FIG. 4G) Effect of cellular density (million cells/mL) in the output optical power, including after culture (+cult.). ns—not significant. FIG. 4H) Optical spectra fingerprinting of encapsulated 3T3 cells stained with orange cell tracker (CMRA), with a decrease in transmission matching the theoretical absorbance (excitation) curve of the cell tracker. CMRA(λ) represents the stained fibroblasts spectrum and Fibro (A) the unstained fibroblast spectrum. Scale bar 500 μm. FIG. 4I) Optical spectra fingerprinting analysis of encapsulated 3T3 cells stained with Calcein AM, evidencing a decrease in transmission matching the theoretical absorbance (excitation) curve of metabolized calcein AM. Calcein (A) represents the stained fibroblasts spectrum and Fibro (A) the unstained fibroblast spectrum, Scale bar 500 μm. FIG. 4N) Metabolic Calcein AM profiles of cells after culture under different conditions, together with Pearson correlation statistical analysis values for each profile.

FIG. 5B) Longitudinal microscope image of a fully over-taken fiber core, as unchecked cancer growth leads to the formation of a mature fiberoid (fiber-shaped organoid). FIG. 5C) Rationale behind the use of optical fiber output to digitalize and quantify the 3D progression of cancer within the engineered core. FIG. 5D) Representative snapshot of axial fiber cores at 3 days of incubation in control and varying drug concentrations. FIG. 5E) Optical fiber output power as function of culture time, tracking the progress of cancer growth in fibers exposed to different drug levels evidencing a threshold of efficacy above 15 μM. Statistical analysis performed through 2-way ANOVA followed by Turkey's multiple comparison test. p<0.01, *p<0.0001. FIG. 5F) RFP-level transmission in the optical fibers, reporting the expression level of model molecule RFP along time and upon different culture conditions. The RFP threshold of as-fabricated cell-laden fibers is highlighted in dashed lines. Both output power and RFP readouts are acquired instantly and simultaneously. Statistical analysis performed through multiple t-tests. *p<0.05, *p<0.001, **p<0.0001.

(FIG. 9A) Rationale behind the ion changes for fabricating neodymium-doped alginate hydrogel fibers (FIG. 9B) Photograph of a Neodymium: Alginate fiber stained with blue soluble dye. Scale bar: 1 cm. (FIG. 9C) Doping behavior evaluation setup (top) as used to obtain output ratio (bottom left, 1080 nm/808 nm) and total output power (bottom right, 1080 nm+808 nm)$^5$. Statistical comparison was performed through Kruskall-Walis multiple comparison test. *p<0.05, ns—not significant.

FIGS. 11A-11B: (FIG. 11A) SEM image of an axial cut of the hydrogel fiber and (FIG. 11B) Higher magnification of the cut surface evidencing the presence of 100 nm AuNPs throughout the fiber surface with varying proximity and random distribution. Particles and visible fibrous alginate structures were artificially colored orange and green, respectively.

FIGS. 12A-12C: (FIG. 12A) Experimental curves obtained by normalizing AuNP-fiber spectra to empty fiber spectra, representing the gold transmission or, reversely, absorbance (blue). (FIG. 12B) Spectra obtained by computational simulation of 100 nm gold plasmonic resonance transmission. (FIG. 12C) Spectra obtained by computational simulation of 100 nm gold plasmonic resonance absorption.

(FIG. 13A) Transmission curves obtained with gradual addition of glycerol solutions of increasing concentration. Curves represent the normalization between AuNP fibers and empty fibers (to derive the resonance-induced effect in transmission. (FIG. 13B) Zoomed-in detail of the simulated 100 nm gold transmission changes with similar refractive index variation. Of note, in the case of the optical fiber (FIG. 13A), the wavelength change is accompanied by a significant reduction in amplitude by the effect on the environmental refractive index and loss of guided light, which does not happen in the gold-only simulation. (FIG. 13C) Resulting output spectra of a range of some glycerol concentrations, where the normalized curves as directly obtained from the spectrometer reflect the consequence of resonance changes leading to a decrease in over-600 nm intensities. (FIG. 13D) Light intensity (700 nm) values of output spectra with gradual spiking of glycerol to higher concentrations and consequent refractive index variations.

(FIG. 15A) Optical fiber output curves with stepwise addition of SARS-CoV-2 antigen solutions with a total of 10 ng protein. (FIG. 15B) Simulated spectra of 100 nm AuNP plasmonic resonance transmission with changes in refractive index, evidencing that the most significant variations happen after 600 nm, (FIG. 15C) Simulation of the intensity variation with increasing added protein below 600 nm (570 example) and above 600 nm (790 example). (FIG. 15D) Experimental Intensity values for the same wavelengths, evidencing a similar response to that simulated for 100 nm gold AuNPs.

(FIG. 18B) Immunofluorescence figures of the virus within hydrogel fiber both at central (i) and edge (ii) core positions, as well as higher magnification details (iii, iv).

(FIG. 19A) Rationale behind the dynamic swelling behavior of fibers, where a controlled swelling takes place during PBS incubation facilitating molecule permeation, and recovery after washing in the presence of calcium. (FIG. 19B) Fiber mass variation after incubation and upon washing with calcium, evidencing the recovery of the hydrogel mesh. (FIG. 19C) Output spectra of AuNP-fibers after incubation and post-recovery, showing a similar profile validating that the gold-antibody-antigen complexes are maintained within the fiber structure and not loss during incubation.

(FIG. 20A) Photograph of PCR tubes after LAMP RNA detection, evidencing the positive change in color in the fibers containing anti-SARS-COV antibody after SARS-COV-2 incubation. Positive and negative controls are pictured at the extremes. Fibers incubated with the virus without functionalized gold nanoparticles as well as fibers with gold nanoparticles incubated with blank solution are also present as controls. (FIG. 20B) 570/650 absorbance quantification of the different solutions, showing the positive presence of SARS-CoV-2 RNA in fibers with anti-SARS AuNPs which have been incubated with the virus, validating viral capture within the hydrogel fibers.

(FIG. 21A) Tri-coaxial nozzle configuration and detailed dimensions. (FIG. 21B) Optical hydrogel fiber structures with cladding of 0.5% GG. (FIG. 21C) Optical hydrogel fiber structure with cladding layer of 0.25% GG, where the low viscosity hinders the formation of a well-arranged architecture, hence the use of a slightly higher concentration for fabrication of living optical fibers.

(FIG. 22A) Comparison between the optical fiber spectrum of cells stained with calcein versus unstained, with zoomed in region around the specific 495 nm wavelength of metabolized Calcein AM. (FIG. 22B) Comparison between the optical fiber spectrum of cells stained with orange cell tracker CMRA versus unstained, with zoomed in region around the specific 495 nm wavelength of metabolized CMRA. (FIG. 22C) Axial fiber cut of an optical core with a mixed population of calcein- and CMRA-stained cells. (FIG. 22D) Multiplex analysis of fibers with different cell populations and their 495 nm (green) and 550 nm (orange) transmission intensity values. Fibro: Fibroblasts, unstained. Calcein: Fibroblasts stained with Calcein AM. Mix: 50:50 mixed population of calcein- and CMRA-stained fibroblasts. CMRA: Fibroblasts stained with orange cell tracker only.

FIGS. 24A-24F: Additional Cell lines tested in optical fiber fingerprinting analysis: FIG. 24A: a 22RV1 RFP fingerprinting data upon incubation with cisplatin, staurosporine and control conditions. FIG. 24B: Calcein AM metabolic activity tracked in real-time for the 22RV1 cell line in different culture conditions. FIG. 24C: Fluorescent image of the cells after staining with calcein together with natively expressed RFP. FIG. 24D: Image quantification results of multiple images across replicates for RFP and calcein intensity validation of optical fiber readouts. FIGS. 24E-24F: Microscopy images of 22RV1 cells after staining with calcein post-culture in the presence of 1.5 μM cisplatin and 1 μM staurosporine, respectively.

FIGS. 25A-25F: FIG. 25A: LNCaP-RFP-Trop2-OV fingerprinting data upon incubation with cisplatin, staurosporine and control conditions. FIG. 25B: Calcein AM metabolic activity tracked in real-time for the LNCaP-RFP-Trop2-OV cell line in different culture conditions. FIG. 25C: Fluorescent image of the cells after staining with calcein together with natively expressed RFP. FIG. 25D: Image quantification results of multiple images across replicates for RFP and calcein intensity validation of optical fiber readouts. FIGS. 25E-25F: Microscopy images of LNCaP-RFP-Trop2-OV cells after staining with calcein post-culture in the presence of 1.5 UM cisplatin and 1 μM staurosporine, respectively.

(FIG. 27A) Tri-coaxial fluidic setup schematic representation where core and clad bioink materials can be spun together to fabricate step-index optical fibers in a single step.

(FIG. 27B) Photograph of the tri-coaxial needle configuration. (FIG. 27C) 2D slice of the fabricated optical fibers containing and alginate core with Gellan Gum (GG) cladding layers and (FIG. 27D) Respective 3D rendering. (FIG. 27E) Fluorescent profile of the step-index fiber demonstrating the material organization according to X-axis profile. (FIG. 27F) Characterization of the hydrogels refractive indices (RIs), with alginate allowing for higher refractive index (higher concentration) gels as fiber core and GG for lower concentration and RI, suitable for cladding layers. (FIG. 27G) High-contrast photographs of core only versus shielded step-index fibers. (FIG. 27H) Light Guiding profile of core only versus full tri-compartment fibers. (FIG. 27I) Calculated light attenuation for both configurations, showing the significant improvement of light guiding and attenuation reduction by the addition of light cladding layers.

(FIG. 28A) Microscope image of cells dispersed in the hydrogel solution. (FIG. 28B) Refractive index characterization versus cell density (bottom axis cell number per mL) evidencing no change in bulk refractive index. (FIG. 28C) Encapsulation of living 3T3 cells in the optical fiber core. (FIG. 28D) Schematic representation of the setup for light coupling and output measurement in the living optical fibers (left) and a photograph of light guiding through the fiber encapsulating 3T3 living cells in the core. (FIG. 28E) Characterization of output power as a function of cell concentration in the fiber core up to 10 million cells per mL, and comparison with post-culture measurements, showing the fibers can be placed in culture and still guide light similarly afterwards. (FIG. 28F) Live/dead image of 3T3 cells encapsulated in the fiber core immediately after fabrication and (FIG. 28G) after 1 week of cell culture. (FIG. 28H) Quantification of cell viability post-fabrication and post-culture showing similar high-viability levels for both conditions.

(FIG. 29A) Microscope image of encapsulated cells after Calcein AM incubation (green). (FIG. 29B) Output Spectra demonstrating a decrease in transmission due to Calcein absorption. (FIG. 29C) Experimental transmission versus non-incubated fibers, showing the decrease in transmission coincides with the calcein absorbance spectrum, hence reflecting the cellular response at the proper wavelength level. (FIG. 29D) Quantification of 495 nm intensities in fibers encapsulated with fibroblasts (fibro) and fibers with fibroblasts that metabolized calcein into fluorescent compound (fibro+calcein). A significant decrease in transmission intensity can be quantified. (FIG. 29E) Microscope image of encapsulated cells after Orange CMRA (cell tracker) incubation (orange). (FIG. 29F) Output Spectra demonstrating a decrease in transmission due to CMRA absorption. (FIG. 29G) Experimental transmission versus non-incubated fibers, showing the decrease in transmission coincides with the CMRA absorbance spectrum, hence reflecting the cellular response at the proper wavelength level. (FIG. 29H) Quantification of 550 nm intensities in fibers encapsulated with fibroblasts (fibro) and fibers with fibroblasts that metabolized CMRA into fluorescent compound (fibro+CMRA). A significant decrease in transmission intensity can be quantified. (FIG. 29I) Microscope image of fibers with two distinct cell populations, with a 50/50 ration between calceinAM-positive cells (green) and orange CMRA-positive cells (orange). (FIG. 29J) Confocal axial cut visualization of the distribution of the two cell populations in the fiber core. (FIG. 29K) Optical output data and quantification of the two wavelengths (Green 495 nm and Orange 550 nm) showing that multiplex analysis can be done using the distinct optical fingerprints of both cell types, being able to inform on which kind of molecules are being metabolized and causing decreases/increases in intensity on different conditions.

Figure 30A:
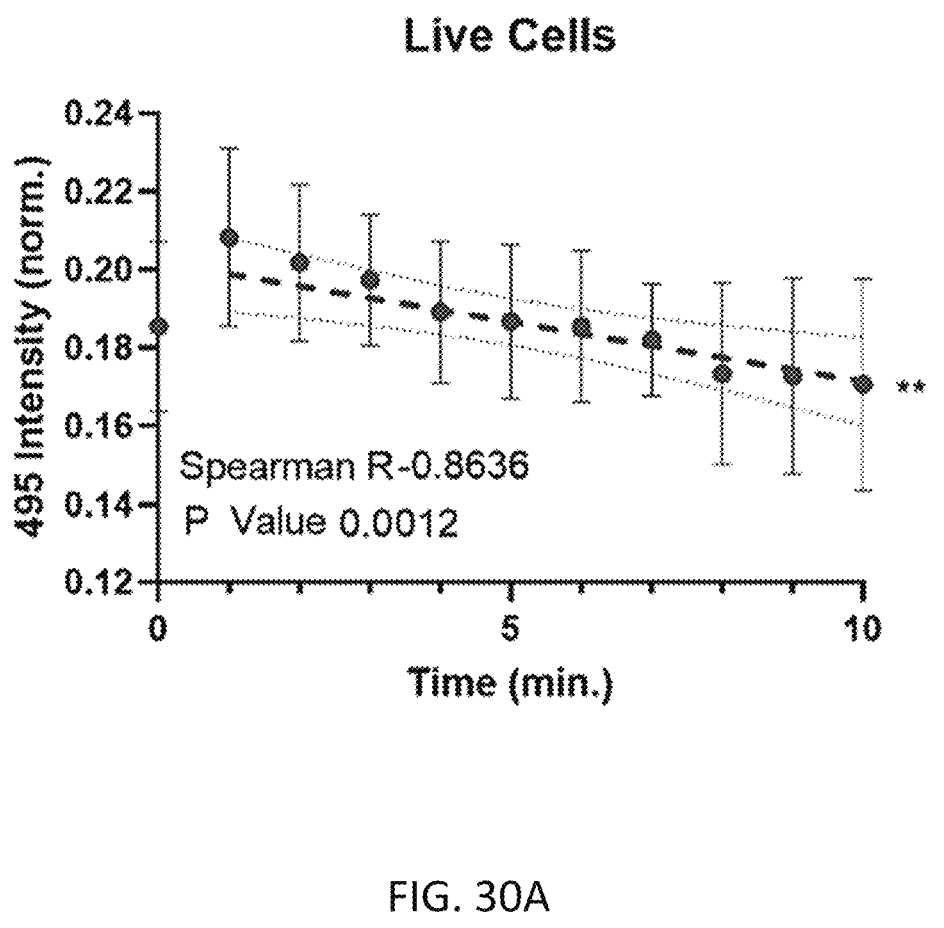

FIGS. 30A-30D: Optical Tracking of Cellular Metabolic Activity in real time: (FIG. 30A) 495 nm (Calcein AM) optical profile of Live cells post-fabrication. (FIG. 30B) 495 nm (Calcein AM) optical profile of paraformaldehyde-fixed cells post-fabrication (absence of response). (FIG. 30C) Schematic concept of the cellular behavior, with live calcein metabolization causing a detectable fluorescent response that can be measured after cell culture under selected conditions. (FIG. 30D) 495 nm optical profile of live cells after incubation, showing that their activity can still be observed and analyzed through the optical fiber output.

FIGS. 31A-31E: Using Optical Fiber Characterization for Anti-cancer drug testing: (FIG. 31A) Schematic representation and conceptual outline of the use of fluorescent-transfected cancer cells to evaluate the susceptibility to anti-cancer drugs based on two fingerprints obtainable in a single readout: native fluorescent protein expression (RFP-level, red) and additional calcein metabolism real-time profiling. (FIG. 31B) Native fluorescence analysis of RFP-level transmission of fibers encapsulating RV122 cancer cells after exposure to two distinct drugs (cisplatin and staurosporin), evidencing a significant decrease in fluorescent (increase in transmission due to lower absorption) upon incubation in staurosporine. (FIG. 31C) Calcein activity profiling of RV122 cancer cells after culture in control, staurosporine and cisplatin conditions. A decrease in the slope can be observed when cisplatin is added to the culture, showing an effect on cell metabolism but still viable responses. With staurosporine (red), it is no longer possible to observe metabolic calcein conversion hinting at drug-induced cancer cell death. (FIG. 31D) Microscopy images of cells under control, cisplatin and staurosporine conditions to validate optical fiber readouts. (FIG. 31E) Image quantification data validating optical fiber readout, and showing the more prominent effects of staurosporine in both native protein expression (RFP) and calcein metabolization in the presence of staurosporine. A moderate effect can also be seen with cisplatin, as observed in the optical fiber readout therefore validating the novel method of single-output optical analysis and direct quantification.

FIG. 32: Light Driven Tissue Engineering Application: Concept of using the living optical fibers as a scaffold where endothelial cells can be encapsulated in a biolabile environment, towards their maturation and development of tubular vascular structures. The light-guiding capabilities of the fibers are employed to stimulate the cells with red and far-red light, demonstrated to promote endothelial development. The cladding layers might not only contain light but also encapsulate different types of cells as all fiber materials and layers are cytocompatible. Therefore, the integration of pericytes and muscle layers can be done in a straightforward manner for additional vascular support and vessel-like functionality.

(FIG. 38C) Merged image showing the cladding thickness.

DETAILED DESCRIPTION OF EMBODIMENTS

Figure 1A:
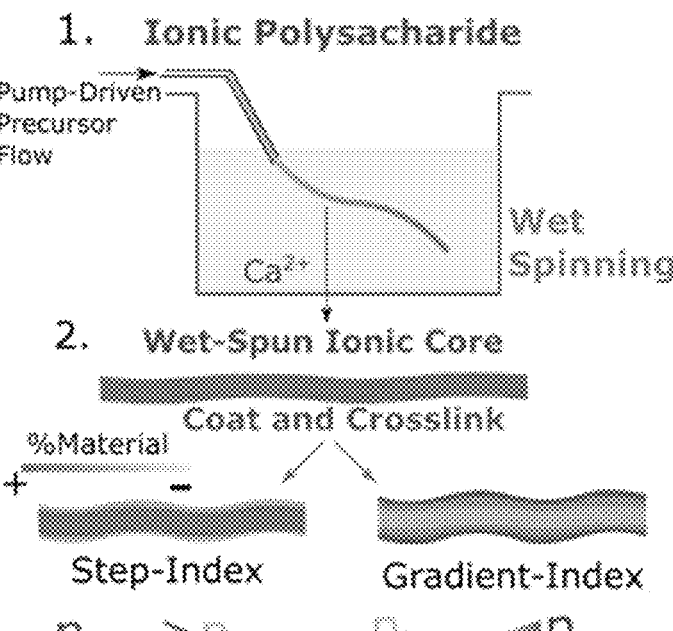
FIGS. 1A-1I: Fabrication of Purely Ionic Hydrogel Optical Fibers and their Light-Guiding Characterization.

Optical fibers containing wet-spun multi-layer hydrogel cladding with ionic-crosslinked polysaccharides are provided. Optical fibers can be formed with step- or gradient-index architectures, fusion splicing, and facile rare-earth ion doping. Plasmonic nanoparticles, functionalized light-sensitive quantum dots or particles can be incorporated into the fiber core to generate a resonance light shift upon the presence and binding of molecular biotargets for biosensor applications. The integration of plasmonic hydrogel fibers with medical swabs provides for rapid detection of pathogens such as severe acute respiratory syndrome coronavirus 2 (SARS-COV-2).

Before the present compositions comprising optical fibers and methods of fabricating and using them are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "an optical fiber" includes a plurality of such optical fibers and reference to "the nanoparticle" includes reference to one or more nanoparticles and equivalents thereof known to those skilled in the art, and so forth.

The term "hydrogel" refers to a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions that have charged side groups, or a monovalent ionic salt thereof. Biocompatible hydrogel refers to a polymer that forms a gel which is not toxic to living cells, and allows sufficient diffusion of oxygen and nutrients to the entrapped cells to maintain viability.

"Biocompatible," as used herein, refers to a property of a material that allows for prolonged contact with a cell or tissue without causing toxicity or significant damage.

"Substantially purified" generally refers to isolation of a substance (compound, polynucleotide, protein, polypeptide, peptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

The term "antibody" encompasses monoclonal antibodies as well as hybrid antibodies, altered antibodies, chimeric antibodies, and humanized antibodies. The term antibody includes: hybrid (chimeric) antibody molecules (see, for example, Winter et al. (1991) *Nature* 349:293-299; and U.S. Pat. No. 4,816,567); F(ab')₂ and F(ab) fragments; Fᵥ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (scFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); diabodies, tetrabodies, affibodies, camelid antibodies, humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

"Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, for example, Pluckthun, A. in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VA) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448.

The term "affibody molecule" refers to a molecule that consists of three alpha helices with 58 amino acids and has a molar mass of about 6 kDa. A monoclonal antibody, for comparison, is 150 kDa, and a single-domain antibody, the smallest type of antigen-binding antibody fragment, 12-15 kDa. See, for exemplary details of affibody structures and uses, Orlova, A; Magnusson, M; Eriksson, T L; Nilsson, M; Larsson, B; Hoiden-Guthenberg, I; Widstrom, C; Carlsson, J et al. (2006). "Tumor imaging using a picomolar affinity HER2 binding affibody molecule", Cancer Res. 66 (8): 4339-48. Exemplary Affibody. Molecules are commercially available from Abcam Corp. Cambridge Mass.

The term "capture agent" as used herein refers to an agent that binds to a target analyte (e.g., molecule free in solution, marker on a cell) through an interaction that is sufficient to permit the agent to bind and concentrate a target molecule or a target cell from a heterogeneous mixture. The binding interaction is typically mediated by an affinity region of the capture agent. Typical capture agents include any moiety that can specifically bind to a target analyte. Certain capture agents specifically bind a target molecule with a dissociation constant ($K_D$) of less than about $10^{-6}$ M (e.g., less than about $10^{-7}$M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other molecules. Exemplary capture agents include antibodies and fragments thereof, antibody mimetics, aptamers, peptoids, nucleic acids (e.g., oligonucleotide probes, DNA, RNA), ligands, inhibitors, agonists, antagonists, and small molecule drugs that bind to the target analyte. The capture agent may include a domain or moiety that can be covalently attached to a detectable label without substantially abolishing the binding affinity for its target analyte. By "capture" is meant that the analyte can be separated from other components of the sample by virtue of the binding of the capture agent to the analyte. Typically, the capture molecule is associated with a solid support (e.g., surface of a plasmonic nanoparticle, quantum dot, or other particle), either directly or indirectly.

As used herein, the term "capture oligonucleotide" refers to an oligonucleotide that contains a nucleic acid sequence complementary to a nucleic acid sequence present in a target nucleic acid analyte such that the capture oligonucleotide can "capture" the target nucleic acid. One or more capture oligonucleotides can be used in order to capture the target analyte. The polynucleotide regions of a capture oligonucleotide may be composed of DNA, and/or RNA, and/or synthetic nucleotide analogs.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequences. Homologous regions may vary in length, but will typically be between 4 and 500 nucleotides (e.g., from about 4 to about 40, from about 40 to about 80, from about 80 to about 120, from about 120 to about 160, from about 160 to about 200, from about 200 to about 240, from about 240 to about 280, from about 280 to about 320, from about 320 to about 360, from about 360 to about 400, from about 400 to about 440, etc.).

As used herein, the terms "complementary" or "complementarity" refers to polynucleotides that are able to form base pairs with one another. Base pairs are typically formed by hydrogen bonds between nucleotide units in an anti-parallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when a uracil is denoted in the context of the present invention, the ability to substitute a thymine is implied, unless otherwise stated. "Complementarity" may exist between two RNA strands, two DNA strands, or between an RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art.

The terms "specific binding," "specifically binds," "selectively binds," and the like, refer to non-covalent or covalent preferential binding to a molecule relative to other molecules or moieties in a solution or reaction. In some embodiments, the affinity of one molecule for another molecule to which it specifically binds is characterized by a KD (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less). "Affinity" refers to the strength of binding, increased binding affinity being correlated with a lower $K_D$. In an embodiment, affinity is determined by surface plasmon resonance (SPR). The affinity of one molecule for another molecule is determined by measuring the binding kinetics of the interaction, e.g., at 25° C.

The term "conjugated" refers to the joining by covalent or noncovalent means of two compounds or agents (e.g., capture agent specific for a target analyte conjugated to a fluorophore or other detectable label).

The term "sample" as used herein relates to a material or mixture of materials containing one or more analytes of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the analyte may be extracted from a tissue sample prior to use, methods for which are known. In particular embodiments, the sample may be a clinical sample, e.g., a sample collected from a patient.

The term "analyte" refers to a molecule (e.g., a protein, a nucleic acid, an antigen, an antibody, a metabolite, or other molecule), a cell, or a pathogen (e.g., a virus, a bacterium, a parasite, or other pathogen) that can be bound by a capture agent and detected.

The term "assaying" refers to testing a sample to detect the presence and/or abundance of an analyte.

As used herein, the terms "determining," "measuring," and "assessing," and "assaying" are used interchangeably and include both quantitative and qualitative determinations.

"Diameter" as used in reference to a shaped structure (e.g., nanoparticle, pore, cell, cell aggregate, etc.) refers to a length that is representative of the overall size of the structure. The length may in general be approximated by the diameter of a circle or sphere that circumscribes the structure.

By "nanoparticle" is meant a particle having at least one dimension (e.g., a greatest dimension) in the range of from 1 nanometer (nm) to 1000 nm, from 20 nm to 750 nm, from 50 nm to 500 nm, including from 100 nm to 300 nm. The nanoparticle may have any suitable shape, including but not limited to, spherical, spheroid, triangular, rod-shaped, bar-shaped, disk-shaped, pyramid-shaped, cube-shaped, cylinder-shaped, octahedron-shaped, dodecahedron-shaped, icosahedron-shaped, nanohelical-shaped, nanospring-shaped, nanoring-shaped, nanowire-shaped, arrow-shaped, teardrop-shaped, tetrapod-shaped, prism-shaped, star-shaped, or any other suitable geometric or non-geometric shape. In certain embodiments, the nanoparticle (e.g., a spherical or spheroid particle) has a greatest dimension of from 10 to 200 nm, e.g., from 30 to 100 nm. According to some embodiments, the greatest dimension of the nanoparticle (e.g., the diameter in the case of a spherical or spheroid nanoparticle) is greater than 10 nm but 500 nm or less, 450 nm or less, 400 nm or less, 350 nm or less, 300 nm or less, 250 nm or less, 200 nm or less, or 100 nm or less. In certain embodiments, the greatest dimension of the nanoparticle (e.g., the diameter in the case of a spherical or spheroid nanoparticle) is less than 500 nm, but 10 nm or greater, 20 nm or greater, 30 nm or greater, 40 nm or greater, 50 nm or greater, 60 nm or greater, 70 nm or greater, 80 nm or greater, 90 nm or greater, 100 nm or greater, 125 nm or greater, 150 nm or greater, 175 nm or greater, 200 nm or greater, 225 nm or greater, 250 nm or greater, 275 nm or greater, 300 nm or greater, 350 nm or greater, or 400 nm or greater.

As used herein, the terms "detectable label", "detection agent", "diagnostic agent", and "detectable moiety" are used interchangeably and refer to a molecule or substance capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of detectable labels which may be used in the practice of the invention include isotopic labels, including radioactive and non-radioactive isotopes, such as, $^3$H, $^2$H, $^{120}$I, $^{123}$I, $^{124}$I, $^{125}$I, $^{131}$I, $^{35}$S, $^{11}$C, $^{13}$C, $^{14}$C, $^{32}$P, $^{15}$N, $^{13}$N, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{9m}$Tc, $^{154}$Gd, $^{155}$Gd, $^{156}$Gd, $^{157}$Gd, $^{158}$Gd, $^{15}$O, $^{186}$Re, $^{188}$Re, $^{51}$M, $^{52m}$Mn, $^{55}$Co, $^{72}$As, $^{75}$Br, $^{76}$Br, $^{82m}$Rb, and $^{83}$Sr. In particular, detectable labels may comprise positron-emitting radionuclides suitable for PET imaging such as, but not limited to, $^{64}$Cu, $^{89}$Zr, $^{68}$Ga, $^{177}$Lu, $^{82}$Rb, $^{11}$C, $^{13}$N, $^{15}$O, and $^{18}$F; or gamma-emitting radionuclides suitable for single photon emission computed tomography (SPECT) imaging such as, but not limited to, $^{67}$Ga, $^{99m}$Tc, $^{123}$I, and $^{131}$I. Detectable labels may also include lanthanide isotopes suitable for multiplexed ion beam imaging (MIBI) such as, but not limited to, $^{139}$La, $^{143}$Nd, $^{147}$Sm, $^{154}$Sm, $^{158}$Gd, $^{162}$Dy, $^{166}$Er, $^{168}$Er, $^{176}$Yb. Detectable labels may also include non-radioactive, paramagnetic metal ions suitable for MRI imaging such as, but not limited to, $Mn^{2+}$, $Fe^{3+}$, $Fe^{2+}$, $Gd^{3+}$, $Ti^{2+}$, $Cr^{3+}$, $Co^{2+}$, $Ni^{2+}$, and $Cu^{2+}$. Detectable labels may also include fluorophores including without limitation, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, Alexa Fluor 660, Alexa Fluor 700, Alexa Fluor 750, and Alexa Fluor 784, and Alexa Fluor 790, a cyanine dye such as Cy 3, Cy3.5, Cy5, Cy5.5, Cy7, and Cy7, IRDye dyes such as IRDye 800CW, IRDye 680RD, IRDye 700, IRDye 750, and IRDye 800RS, CF dyes such as CF680, CF680R, CF750, CF770, and CF790, Tracy dyes such as Tracy 645 and Tracy 652, fluorescein, 2',4',5',7'-tetrachloro-4-7-dichlorofluorescein (TET), carboxyfluorescein (FAM), 6-carboxy-4', 5'-dichloro-2',7'-dimethoxyfluorescein (JOE), hexachlorofluorescein (HEX), rhodamine, carboxy-X-rhodamine (ROX), tetramethyl rhodamine (TAMRA), fluorescein isothiocyanate (FITC), dansyl, umbelliferone, dimethyl acridinium ester (DMAE), Texas red, and quantum dots; and enzymes such as horseradish peroxidase (HRP), alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), β-galactosidase (lacZ), xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, *Renilla* luciferase, and aequorin. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Thermo Fisher Scientific Corporation (Waltham, MA); glass coated metal nanoparticles (see e.g., SERS nanotags produced by Nanoplex Technologies, Inc. (Mountain View, CA); barcode materials (see e.g., submicron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA), near infrared (NIR) probes, and nanoshells. The terms also include contrast agents such as ultrasound contrast agents (e.g. SonoVue microbubbles comprising sulfur hexafluoride, Optison microbubbles comprising an albumin shell and octafluoropropane gas core, Levovist microbubbles comprising a lipid/galactose shell and an air core, Perflexane lipid microspheres comprising perfluorocarbon microbubbles, and Perflutren lipid microspheres comprising octafluoropropane encapsulated in an outer lipid shell), magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate).

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Polysaccharide Hydrogel Optical Fibers

Provided herein are optical fibers containing one or more layers of hydrogel cladding comprising ionically crosslinked polysaccharides encapsulating a core. In some embodiments, an optical fiber further comprises an outer shielding layer surrounding the cladding. A light source is used to deliver light into the core of the hydrogel optical fiber, which serves as a waveguide. The hydrogel optical fibers, described herein, can be used to transmit light from a light source to a target location.

An optical fiber may have a hydrogel core, a liquid core, or a gaseous or hollow core. The core may have any suitable diameter. In some cases, the core diameter of the optical fiber is 0.5 mm or more, e.g., 1 mm or more, 2 mm or more, 3 mm or more, 4 mm or more, 5 mm or more, 6 mm or more, 7 mm or more, 8 mm or more, including 10 mm or more, and is 100 mm or less, e.g., 50 mm or less, 20 mm or less, 10 mm or less, including 5 mm or less. In some embodiments, the core diameter of the optical fiber is in the range of 0.5 mm to 1,000 mm, including any diameter within this range such as 0.5 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm 90 mm, 100 mm, 200 mm, 300 mm, 400 mm, 500 mm, 600 mm, 700 mm, 800 mm, 900 mm, or 1000 mm.

In some embodiments, the hydrogel cladding layers have a lower refractive index than the core of the optical fiber. The difference in refractive index between the hydrogel cladding layers and the core should be sufficient to confine light within the core and provide light-guiding capability to the optical fiber. Without being bound by theory, the difference in refractive index between the cladding layers and the core causes light to propagate through the core of the optical fiber in a zigzag fashion due to the phenomenon of total internal reflection such that the fiber serves as a waveguide. The change in refractive index between the core and cladding may either be abrupt (e.g., step-index fiber) or gradual (i.e., gradient-index fiber). For example, an optical fiber may have a step-index profile, in which the core has one refractive index and the cladding has a lower refractive index, or a gradient-index profile, in which the refractive index varies gradually as a function of radial distance from the fiber center. In certain embodiments, the hydrogel cladding layers and hydrogel core have a step-index or gradient-index architecture. In some embodiments, the optical fiber has multiple hydrogel cladding layers with alternating refractive index values. In some embodiments, the optical fiber has a gradient of refractive index values along the length of the optical fiber. In some embodiments, the difference in refractive index between the cladding layers and the core is at least 0.01.

In certain embodiments, the optical fiber has 1 or more, 2 or more, 3 or more, 4 or more, 5 or more, 6 or more, 7 or more, 8 or more, 9 or more, or 10 or more hydrogel cladding layers. For example, the optical fiber may have 1 to 10 hydrogel cladding layers, including any number within this range such as 1, 2, 3, 4, 5, 6, 7, 8, 9, or 10 hydrogel cladding layers. In some embodiments, the optical fiber has 1 to 4 hydrogel cladding layers.

The optical fibers can be fabricated by wet-spinning polysaccharide hydrogel precursors in a crosslinking solution, followed by coating and crosslinking of the different hydrogel layers to obtain varying core-clad refractive indexes (see Example 1). Different cladding layers can be added by dip-coating the core in solutions containing polysaccharide hydrogel precursors at different concentrations, followed by crosslinking. Either step-index or gradient-index hydrogel fibers can be produced in this manner. Step-index fibers are fabricated by coating the core with a hydrogel having a lower refractive index than that of the core, whereas gradient index fibers are fabricated by adding multiple hydrogel layers of gradually increasing refractive index. Optical fibers having multiple hydrogel cladding layers with alternating refractive index values can be fabricated by alternating dip-coating in a solution containing polysaccharide hydrogel precursors at one concentration, followed by dip-coating in a solution containing polysaccharide hydrogel precursors at a different concentration.

Any suitable polysaccharide can be used to form the hydrogel cladding layers of the optical fiber as well as other parts of the optical fiber, which may optionally comprise a hydrogel, such as the core and/or shielding layer. Exemplary polysaccharides, which can be used to form a hydrogel, include, without limitation, alginate, gellan gum, hyaluronic acid, chitosan, heparin, cellulose, carboxymethyl cellulose, dextran, starch, and agarose. The refractive index increases with increasing polysaccharide concentration (wt %). Accordingly, the polysaccharide concentration (e.g., wt %) can be adjusted to obtain a desired refractive index for a hydrogel layer.

In certain embodiments, metal cations are used to ionically crosslink hydrogel portions of the optical fiber such as the hydrogel cladding layers, hydrogel core, and/or hydrogel shielding layer. For example, alkaline earth metal cations can be used to ionically crosslink hydrogel portions of the optical fiber. Exemplary alkaline earth metal cations include, without limitation, beryllium ($Be^{2+}$), magnesium ($Mg^{2+}$), calcium ($Ca^{2+}$), strontium ($Sr^{2+}$), and barium ($Ba^{2+}$). Alternatively, transition metal divalent cations can be used to ionically crosslink the hydrogel portions of the optical fiber. Exemplary transition metal divalent cations include, without limitation, $Cd^{2+}$, $Co^{2+}$, $Ni^{2+}$, $Zn^{2+}$, and $Cu^{2+}$.

In some embodiments, a hydrogel comprising alginate is used in the optical fiber. Alginate is typically obtained from brown algae (Phaeophyceae), including *Laminaria hyperborea, Laminaria digitata, Laminaria japonica, Ascophyl-*

*lum nodosum*, and *Macrocystis pyrifera*. Alternatively, bacterial alginate can be produced from *Azotobacter* or *Pseudomonas*. Alginate comprises copolymers containing blocks of (1,4)-linked ß-D-mannuronate (M) and a-L-guluronate (G) residues. The blocks are composed of consecutive G residues, consecutive M residues, and alternating M and G residues. Alginates extracted from different sources have different compositions with differences in their number of M and G residues and the length of their M-blocks and G-blocks. An alginate hydrogel can be formed by mixing an aqueous alginate solution with ionic cross-linking agents, such as divalent cations (e.g., $Ca^{2+}$), which bind to the G-blocks of the alginate chains.

In some embodiments, a hydrogel comprising gellan gum is used in the optical fiber. Gellan gum is typically obtained from bacteria such as *Pseudomonas elodea* or *Sphingomonas paucimobilis* and is composed of a repeating unit of a tetrasaccharide comprising two residues of D-glucose one residue of D-glucuronic acid, and one residue of L-rhamnose. A gellan gum hydrogel can be formed by mixing an aqueous gellan gum solution with ionic cross-linking agents, such as divalent cations (e.g., $Ca^{2+}$), which bind to two carboxylate groups belonging to glucuronic acid molecules in the gellan chains, Modified forms of gellan gum such as methacrylated gellan gum may also be used to form hydrogels in the optical fiber.

In certain embodiments, the hydrogel cladding layers comprise gellan gum or alginate. In some embodiments, the hydrogel cladding layers comprise about 0.1 weight percent (wt %) to about 1.0 wt % gellan gum, including any wt % within this range such as 0.1, 0.15, 0.20, 0.25, 0.5, 0.75, or 1.0 wt %. In other embodiments, the hydrogel cladding layers comprise about 1.0 wt % to about 2.0 wt % alginate, including any weight % within this range such as 1.0, 1.2, 1.4, 1.6, 1.8, or 2.0 wt %.

In certain embodiments, the core is a hydrogel core comprising alginate or gellan gum. In some embodiments, the hydrogel core comprises about 2 wt % to about 7 wt % alginate, including any wt % within this range such as 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, or 7.0 wt %. In other embodiments, the hydrogel core comprises about 1.0 wt % to about 1.5 wt % gellan gum, including any wt % within this range such as 1.0 wt %, 1.1, 1.2, 1.3, 1.4, or 1.5 wt %.

In an exemplary embodiment, the optical fiber comprises hydrogel cladding layers comprising gellan gum and a hydrogel core comprising alginate. In some embodiments, the hydrogel cladding layers comprise about 0.1 wt % to about 1.0 wt % gellan gum, including any wt % within this range such as 0.1 wt %, 0.15 wt %, 0.2 wt %, 0.25 wt %, 0.5 wt %, 0.75 wt %, or 1.0 wt %. In some embodiments, the hydrogel core comprises about 2 wt % to about 7 wt % alginate, including any wt % within this range such as 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, or 7.0 wt %.

An optical fiber with a hollow core can be produced by first fabricating an optical fiber with a hydrogel core followed by core hydrogel liquification. Alternatively, a core material can be used that does not crosslink upon wet spinning but remains liquid and can easily be removed or diffuse from the core. A liquid or gas core can be produced by adding a liquid or a gas, respectively, to a hollow core. In some embodiments, a hollow core is replaced by a cell culture medium or other perfusing solutions. Hollow fibers can be perfused with solutions containing cells for inner surface coating. In some embodiments, materials are added to a hollow core, which increase the range of refractive index. The core may be totally hollow (air), contain an aqueous solution, or contain other hydrogel materials not used in the cladding such as a hydrogel comprising synthetic polymers to provide a higher refractive index, e.g., for longer light guiding applications.

In some embodiments, the core comprises one or more non-polysaccharide polymers. Exemplary polymers, which may be used in the core include, but are not limited to, polyethylene glycol (PEG), acrylamide, poly(hydroxyethyl methacrylate) (PHEMA), poly(glyceryl methacrylate) (PGMA), poly(hydroxypropyl methacrylate) (PHPMA), poly(ethylene glycol) dimethacrylate (PEGDMA), polyacrylamide (PAM), polymethacrylamide (PMAM), triethylene glycol dimethacrylate (TEGDMA), 1,1,1-trimethylolpropane trimethacrylate (TMPTMA), polyvinyl alcohol (PVA), polyacrylic acid (PAA), polyvinyl pyrrolidone (PVP), poly(ε-caprolactone) (PCL), poly(butyl methacrylate) (PBMA), N-isopropyl acrylamide (NIPAAm), diethylene glycol dimethacrylate (DEGDMA), stearyl acrylate (SA), poly(2-[dimethylamino]ethyl methacrylate) (PDMAEMA), [[3(methacryloylamino)propyl]dimethy(3-sulfopropyl)ammonium hydroxide] (MPSA), oligo ethylene glycol monoacrylate (OEGA), poly(ethyleneimine) (PEI), poly (N,N-dimethylacrylamide) (PDMAM), poly(2-methoxyethyl acrylate) (PMEA), 2,2'-diethoxyacetophenone (DEOP), poly(methacrylic acid) (PMAA), ethylene glycol dimethacrylate (EGDMA), diphenyl diisocyanate (MDI), diethylene glycol (DEG), N-methyldiethanolamine (MDEA), dimethylolpropionic acid (DMPA), grapheneoxide (GO), hydroxyapatite (HA), polystyrenesulfonate (PSS), polyaniline (PANI), poly(4-vinylpyridine) (P4VP), polydopamine (PDA), poly(N-vinyl caprolactam) (PVCL), poly(2-ethyl-2-oxazine) (PEtOzi), poly(vinyl alcohol acetoacetate) (PVAA), polypyrrole (PPy), poly(ethylene glycol)methyl ether (MPEG), poly (glycidyl methacrylate) (PGMA), poly(ethylene glycol) diacrylate (PEGDA), poly(diethylaminoethyl methacrylate) (PDEAEMA), polylactic acid (PLA), poly(butylene terephthalate) (PBT), polyethylene terephthalate (PET), ethyl methacrylate (EMA), polydimethylsiloxane (PDMS), poly (N,N-diethyl acrylamide) (PDEAM), poly(methyl vinyl ether) (PMVE), and poly(N-vinylcaprolactam) (PVC).

In some embodiments, the core comprises a mixture or blend of at least two ionically crosslinked polysaccharides or an ionically crosslinked polysaccharide and one or more other types of hydrogel polymers or other components. In some embodiments, the core comprises alginate or gellan gum and one or more other components such as, but not limited to, hyaluronic acid, gelatin, collagen, fibrin, silk, dextran, chitosan, heparin, acrylamide, starch, cellulose, guar gum, xanthan gum, a non-polysaccharide polymer (e.g., polyethylene glycol), a basement membrane extract, a biological lysate, or any combination thereof. For example, the polysaccharide hydrogel core may comprise an alginate/collagen blend, an alginate/fibrin blend, or an alginate/hyaluronic acid blend. In another example, a basement membrane extract or a biological lysate may be added to the polysaccharide hydrogel in the fiber core.

Optical fibers with hydrogel cores can be produced with various geometries. By changing the flow of the core hydrogel precursor over time, it is possible to change the shape of the optical fiber core and provide different geometries to the overall structure and imbue the core with additional optical characteristics. In some embodiments, a non-continuous core medium is generated. By reducing and increasing the core flow during fabrication, it is possible to move from a continuous diameter core to regions of lower diameter or even individualized hydrogel geometries (a core made up of droplets encapsulated by cladding). A quick actuating valve can be used, for example, to turn the core flow on and off over time with different periodicity yielding core comprising material droplets of different dimensions and distributions. See, e.g., FIG. 36.

The core (e.g., ionically crosslinked hydrogel core) of an optical fiber can be doped with metal ions. In some embodiments, the core of an optical fiber is doped with metal ions that absorb incident light at specific wavelengths and convert energy to light emitted at higher wavelengths than the incident light. Accordingly, doping can be used to change the wavelength of light guided through the optical fiber. In some cases, doping is used to amplify light waves guided through the optical fiber and/or increase the distances light can travel through the core of the optical fiber without significant attenuation. Optical fibers can be doped, for example, with rare-earth metal cations. Exemplary rare-earth metals include, without limitation, scandium, yttrium, lanthanum, cerium, praseodymium, neodymium, promethium, samarium, europium, gadolinium, terbium, dysprosium, holmium, erbium, thulium, ytterbium, and lutetium. In some cases, the hydrogel core of an optical fiber is doped with trivalent cations of one or more rare-earth metals. The doping can be done during ionic crosslinking of a hydrogel (see Example 1). In some embodiments, the hydrogel core is doped with neodymium ($Nd^{3+}$) or erbium cations ($Er^{3+}$). In some embodiments, the hydrogel cladding layers are cross-linked ionically by $Ca^{2+}$ and the hydrogel core is doped with neodymium cations ($Nd^{3+}$) or erbium cations ($Er^{3+}$).

In certain embodiments, the optical fiber further comprises a shielding layer comprising a hydrogel. In some embodiments, the shielding layer comprises an alginate hydrogel. For example, the shielding layer may comprise a hydrogel comprising 1 wt % to 2 wt % alginate, including any wt % within this range such as 1 wt %, 1.25 wt %, 1.5 wt %, 1.75 wt %, or 2.0 wt %. In other embodiments, the shielding layer comprises a gellan gum hydrogel. For example, the shielding layer may comprise a hydrogel comprising 0.5 wt % to 1.5 wt % gellan gum, including any wt % within this range such as 0.5 wt %, 0.75 wt %, 1 wt %, 1.25 wt %, or 1.5 wt %.

Delivery of Light to a Target with a Hydrogel Optical Fiber

Optical fibers can be coupled with a light source to guide light towards a target. For example, one end of an optical fiber can be attached to or placed near a target; and a light source can be aligned with the other end of the optical fiber, wherein light from the light source passes through the optical fiber to the target. Alternatively, the target can be placed inside the core of the optical fiber, wherein light from a light source, aligned with an end of the optical fiber, passes through the optical fiber to the target inside the core. The target may include, without limitation, a molecule (e.g., a light responsive protein, a light activated prodrug), a pathogen (e.g., a virus, a bacterium, a parasite, or other pathogen), a cell, a tissue, an organoid, or an organism. In some embodiments, the target is optogenetically modified, as described in more detail below.

The light source can be a broadband light source or a narrowband light source. For example, light sources may include, without limitation, laser diodes, light-emitting diodes (LEDs), superluminescent diodes, microfocus X-ray sources, and lamps. Exemplary light sources include, lasers and LEDs comprising gallium arsenide (GaAs) and gallium aluminum arsenide (GaAlAs), which emit light at wavelengths in the range of 750-900 nm; lasers and LEDs comprising crystalline neodymium, which emit light at a wavelength of about 1300 nm; and quartz halogen or xenon metal halide lamps. In some embodiments, the light source, which is coupled to the optical fiber, emits light of a single color (single wavelength) or multiple colors (multiple wavelengths). In some embodiments, the light source emits visible or infrared light. In some cases, the light source is used with an emission filter. The light source may be contained in a fiber optic illuminator, which also includes optics to focus the light into the core of the optical fiber.

The hydrogel optical fibers can be used to transmit light from a light source to a target location. In some embodiments, an optical fiber is used to transmit light to a target at a distance of 5 cm or greater from a light source, 10 cm or greater from a light source, 15 cm or greater from a light source, or 20 cm or greater from a light source. In some embodiments, an optical fiber is used to transmit light to a target at a distance of 1 cm to 25 cm from a light source, including any distance within this range such as 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, or 25 cm from a light source.

Hydrogel optical fibers can be fused together to produce a multi-input fiber optic architecture and/or a multi-output fiber optic architecture. Multi-input systems can be used with multiple different light sources. Multi-output systems can be used to direct guided light to multiple different targets. Fiber optic networks can be produced having multiple branches with multiple inputs and/or outputs. Complex fiber optic networks can be produced by fusing together large numbers of optical fibers.

To fuse two hydrogel optical fibers together, a chelating agent can be used to de-crosslink the hydrogel at the tips of the optical fibers. Then, the ends of the two optical fibers are positioned in proximity to each other, and divalent cations are added to re-crosslink the hydrogel at their tips to connect the two optical fibers to each other (see Example 1). Exemplary chelating agents that can be used in de-crosslinking a hydrogel at the tip of an optical fiber include, without limitation, citrate, oxalate, malate, ethylenediamine tetraacetic acid (EDTA), ethylene glycol-bis(B-aminoethyl ether)-N,N, N',N'-tetraacetic acid (EGTA), diethylenetriaminepentaacetic acid (DTPA), N,N-bis(carboxymethyl) glycine (NTA), 1,4,7,10-tetraazacyclododecane-1,4,7,10-tetraacetic acid (DOTA), mercaptoacetylglycine (MAG3), 1,4,8,11-tetraazacyclotetradecane (CYCLAM), 1,4,7,10-tetraazacyclododecane, cyclen, 1,4,7-triazacyclononane (TACN), hydrazinonicotinamide (HYNIC), 1,2-bis(o-aminophenoxy)ethane-N,N,N',N'-tetraacetic acid (BABTA), iminodiacetic acid (IDA), nitrilotriacetic acid, 1,4,7-triazacyclononane-1,4,7-triyl)triacetic acid (NOTA), ethylenediamine-N,N'-bis(2-hydroxyphenylacetic acid) (EDDHA), ethylenediamine-N,N'-disuccinic acid (EDDS), and nicotianamine.

In some embodiments, hydrogel droplets are integrated into optical fibers. In some cases, a droplet may act as an optical lens upon interaction with light. Hydrogel droplets can be fused to an optical fiber using the fiber fusion methodology, described above.

In some embodiments, a target is detectably labeled with a light-emitting label such as a fluorescent, bioluminescent, or chemiluminescent label, wherein light generated by the light-emitting label is guided through a hydrogel optical fiber to a photodetector. The photodetector may include, without limitation, a charge-coupled device (CCD), an active-pixel sensor (APS), or a CMOS sensor. The detectably labeled target may be positioned inside the core of the optical fiber or outside in proximity to an end of the optical fiber.

In some embodiments, a target is detectably labeled with one or more fluorescent labels, wherein the target is illuminated with excitation light guided by a hydrogel optical fiber. A multi-input hydrogel optical fiber system can be used with multiple excitation light sources to excite multiple fluorophores simultaneously. In some cases, the target is inside the core of the optical fiber, wherein fluorescent light output from the optical fiber is detected. In other cases, the target is outside the optical fiber, wherein one end of the optical fiber is placed close to the target such that excitation light from the light source passes through the optical fiber to the target.

In some embodiments, the target (e.g., cell, tissue, organoid, or organism) is detectably labeled with a light-emitting label by contacting the target with detectably labeled binding agents that specifically bind to cellular markers of interest. The binding agents may bind to any type of molecule, including proteins, lipids, polysaccharides, proteoglycans, metabolites, or the like. In some embodiments, the binding agent binds to a marker of interest with high affinity. Examples of binding agents include, without limitation, antibodies, antibody fragments, antibody mimetics, and aptamers as well as small molecules, peptides, peptoids, or ligands that bind selectively to cellular markers. The conjugates used in the subject methods include at least one light-emitting label attached to the binding agent. In some embodiments, a conjugate is used that comprises a binding agent that selectively binds to a cell-specific marker. In some embodiments, multiple conjugates are used, wherein the different conjugates bind to different markers on cells of the same cell-type or different cell-types. In some embodiments, a conjugate is used that comprises a binding agent that specifically binds to a disease-associated marker or cancer marker.

In some embodiments, a target is detectably labeled with a fluorophore having a fluorescence emission in the visible, near-infrared (NIR), or infrared (IR) regions of the light spectrum, in the ranges from about 380 nm to 750 nm, 750 nm-1100 nm, and 1100 nm to 1500 nm, respectively. Exemplary NIR fluorophores include, without limitation, IRDye dyes (e.g., IRDye 800CW, IRDye 680RD, IRDye 700, IRDye 750, and IRDye 800RS), CF dyes (e.g., CF680, CF680R, CF750, CF770, and CF790), Tracy dyes (e.g., Tracy 645 and Tracy 652), Alexa dyes (e.g., Alexa Fluor® 660 dye, Alexa Fluor® 700 dye, Alexa Fluor® 750 dye, and Alexa Fluor® 790), cyanine dyes (e.g., Cy7 and Cy7.5), thienothiadiazole dyes, phthalocyanine dyes, squaraine dyes, rhodamine dyes and analogues (e.g., Si-pyronine, Si-rhodamine, Te-rhodamine, and Changsha), borondipyrromethane (BODIPY) dyes, seminaphthofluorone xanthene dyes, benzo[c]heterocycle dyes (e.g., isobenzofuran dyes), and quantum dots. For a review of NIR fluorophores and their use in fluorescence imaging, see, e.g., Escobedo et al. (2010) Curr. Opin. Chem. Biol. 14(1):64-70, Hilderbrand et al. (2010) Curr. Opin. Chem. Biol. 14(1):71-79, Yuan et al. (2013) Chem. Soc. Rev. 42(2):622-661, Vats et al. (2017) Int. J. Mol. Sci. 18(5), Zhang et al. (2017) Nat. Rev. Clin. Oncol. 14(6):347-364, Gao et al. (2010) Curr. Top. Med. Chem. 10(12):1147-1157, Zhao et al. (2018) Wiley Interdiscip. Rev. Nanomed. Nanobiotechnol. 10(3):e1483, and Haque et al. (2017) Bioorg. Med. Chem. 25(7):2017-2034; herein incorporated by reference in their entireties. Exemplary fluorophores with emissions in the visible region of the light spectrum include, without limitation, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 488, Alexa Fluor 546, Alexa Fluor 555, Alexa Fluor 594, Alexa Fluor 647, and Alexa Fluor 784, a cyanine dye such as Cy3, Cy3.5, Cy5, Cy5.5, and Cy7, fluorescein, 2', 4', 5', 7'-tetrachloro-4-7-dichlorofluorescein (TET), carboxyfluorescein (FAM), fluorescein isothiocyanate (FITC), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), and Texas Red.

In another embodiment, a method of monitoring expression of a fluorescently labeled protein in a cell is provided, the method comprising: a) introducing the cell into the core of an optical fiber described herein, wherein the fluorescently labeled protein is expressed in the cell; b) exposing the cell to excitation light guided by the optical fiber; and c) monitoring fluorescent light or a decrease in excitation-range light transmission intensity output from the optical fiber.

In certain embodiments, a fluorescent dye or a quantum dot is encapsulated within the core. The fluorescent dye or quantum dot can be illuminated with excitation light guided by the optical fiber, wherein fluorescent light is output from the optical fiber.

In another embodiment, a method of activating a photo-activatable prodrug is provided, the method comprising exposing the photoactivatable prodrug to excitation light guided by an optical fiber, wherein activity of the prodrug is increased in response to exposure to the excitation light. The optical fiber can be used to guide light to a target site, wherein the prodrug is selectively activated at the target site (i.e., to selectively treat the target site and minimize toxicity outside of the target site). In some embodiments, the prodrug is a photoactivatable anticancer drug. In some embodiments, a subject is administered a prodrug, and the excitation light is guided by an optical fiber to a tumor to activate the prodrug selectively at the site of a tumor.

In another embodiment, a method of performing photo-dynamic therapy (PDT) is provided, the method comprising: administering a photosensitizing chemical substance to a subject; and exposing the photosensitizing chemical substance to excitation light guided by an optical fiber, wherein reactive oxygen species are generated by the photosensitizing chemical substance in response to exposure to the excitation light. Exemplary photosensitizing chemical substances include, without limitation, porphyrins, chlorins and dyes such as aminolevulinic acid (ALA), silicon phthalocyanine Pc 4, m-tetrahydroxyphenylchlorin (mTHPC) and mono-L-aspartyl chlorin e6 (NPe6). A number of photosensitizing substances are commercially available, including, without limitation, Allumera, Photofrin, Visudyne, Levulan, Foscan, Metvix, Hexvix, Cysview and Laserphyrin, with others in development, e.g., Antrin, Photochlor, Photosens, Photrex, Lumacan, Cevira, Visonac, BF-200 ALA, Amphinex and Azadipyrromethenes. PDT can be used for treatment of various conditions and diseases including, but not limited to, acne, wet age-related macular degeneration, psoriasis, atherosclerosis, viral infections, and cancer.

In another aspect, a photonic device comprising an optical fiber, described herein, is provided. In some embodiments, the photonic device further comprises a light source coupled to the optical fiber. The light source may include, without limitation, laser diodes, light-emitting diodes (LEDs), super-luminescent diodes, microfocus X-ray sources, or lamps. In some embodiments, the photonic device further comprises optics to focus light from the light source into the core of an optical fiber. In some embodiments, the photonic device further comprises a photodetector such as, but not limited to, a charge-coupled device (CCD), an active-pixel sensor (APS), or a CMOS sensor. In some embodiments, the photonic device further comprises a medical swab or endotracheal tube coupled to the optical fiber.

Optogenetics

Optical fibers can be used in conjunction with optogenetics to provide optical control of activation (i.e., depolarization) or inhibition (i.e., hyperpolarization) of neurons that have been genetically modified to express light-responsive ion channels. In some embodiments, the light-responsive ion channel is a naturally occurring or synthetic opsin that uses a retinal-based cofactor (e.g., all-trans retinal for the microbial opsins) to respond to light. For example, light-responsive cation-conducting opsins (e.g., channelrhodopsin that conducts $Ca^{2+}$) can be used to activate or depolarize neurons. Light-responsive anion-conducting opsins (e.g., channelrhodopsin or halorhodopsin that conduct chloride ions) or light-responsive proton conductance regulators (e.g., bacteriorhodopsin or archaerhodopsin) can be used to inhibit or hyperpolarize neurons. The levels of retinoids present in a mammalian brain are usually sufficient for expressed opsins to function without supplementation of cofactors. For a description of optogenetics and its use in controlling neural activity, see, e.g., Aravanis et al. (2007) *J Neural Eng* 4: S143-S156, Arenkiel et al. (2007) *Neuron* 54: 205-218, Boyden et al. (2005) *Nat Neurosci* 8: 1263-1268, Chow et al. (2010) *Nature* 463: 98-10, Gradinaru et al. (2007) *J Neurosci* 27: 14231-14238, Gradinaru et al. (2008) *Brain Cell Biol* 36: 129-139, Gradinaru et al. (2010) *Cell* 141: 1-12, Li et al. (2005) *Proc Natl Acad Sci* 102: 17816-17821, Lin et al. 2009. Characterization of engineered channelrhodopsin variants with improved properties and kinetics. *Biophys J* 96: 1803-1814, Yizhar et al. (2011) Microbial opsins: A family of single-component tools for optical control of neural activity. *Cold Spring Harbor Protoc*, Zhang et al. (2007) *Nat Methods* 4: 139-141, Zhang et al. (2006) *Nat Methods* 3: 785-792, Zhang et al. (2007) *Nature* 446: 633-639, Zhang et al. (2008) *Nat Neurosci* 11: 631-633; and U.S. Pat. Nos. 10,914,803; 10,589,123; 10,583,309; 10,568,516; 10,568,307; 10,538,560; 10,478,499; 10,220,092; 10,196,431; 10,087,223; 10,052,383; 9,969,783; 9,878,176; 9,855,442; 9,757,587; 9,458,208; and 8,834,546; herein incorporated by reference in their entireties.

In some embodiments, a target neuron is genetically modified to express a light-responsive ion channel that, when stimulated by an appropriate light stimulus, hyperpolarizes or depolarizes the stimulated target neuron. The term "genetic modification" refers to a permanent or transient genetic change induced in a cell following introduction into the cell of a heterologous nucleic acid (i.e., nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include the use of viral infection, transfection, conjugation, protoplast fusion, electroporation, particle gun technology, calcium phosphate precipitation, direct microinjection, and the like.

In some cases, a target cell that expresses a light-responsive polypeptide can be activated or inhibited upon exposure to optical fiber-guided light of varying wavelengths. In some cases, a target cell that expresses a light-responsive polypeptide is a neuronal cell that expresses a light-responsive polypeptide, and exposure to optical fiber-guided light of varying wavelengths results in depolarization or polarization of the neuron.

In some instances, the light-responsive polypeptide is a light-responsive ion channel polypeptide. The light-responsive ion channel polypeptides are adapted to allow one or more ions to pass through the plasma membrane of a target cell when the polypeptide is illuminated with light of an activating wavelength. Light-responsive proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the excitable cell when activated by light of an activating wavelength. In some embodiments, the light-responsive polypeptide hyperpolarizes the excitable cell when activated by optical fiber-guided light of an activating wavelength.

In some cases, a light-responsive polypeptide mediates a hyperpolarizing current in the target cell it is expressed in when the cell is illuminated with light. Non-limiting examples of light-responsive polypeptides capable of mediating a hyperpolarizing current can be found, e.g., in U.S. Pat. Nos. 9,359,449 and 9,175,095. Non-limiting examples of hyperpolarizing light-responsive polypeptides include NpHr, eNpHr2.0, eNpHr3.0, eNpHr3.1 or GtR3. In some cases, a light-responsive polypeptide mediates a depolarizing current in the target cell it is expressed in when the cell is illuminated with light. Non-limiting examples of depolarizing light-responsive polypeptides include "C1V1", ChR1, VChR1, ChR2. Additional information regarding other light-responsive cation channels, anion pumps, and proton pumps can be found in U.S. Patent Application Publication No: 2009/0093403; and U.S. Pat. No. 9,359,449.

In some embodiments, the light-responsive polypeptide can be activated by blue light (e.g., in range of 490 nm-450 nm). In one embodiment, the light-responsive polypeptide can be activated by light having a wavelength of about 473 nm. In some embodiments, the light-responsive polypeptide can be activated by yellow light (e.g., in range of 590 nm-560 nm). In another embodiment, the light-responsive polypeptide can be activated by light having a wavelength of about 560 nm. In another embodiment, the light-responsive polypeptide can be activated by red light (e.g., in range of 700 nm-635 nm). In another embodiment, the light-responsive polypeptide can be activated by light having a wavelength of about 630 nm. In other embodiments, the light-responsive polypeptide can be activated by violet light (e.g., in range of 450 nm-400 nm). In one embodiment, light-responsive polypeptide can be activated by light having a wavelength of about 405 nm. In other embodiments, the light-responsive polypeptide can be activated by green light (e.g., in range of 560 nm-520 nm). In other embodiments, the light-responsive polypeptide can be activated by cyan light (e.g., in range of 520 nm-490 nm). In other embodiments, the light-responsive polypeptide can be activated by orange light (e.g., in range of 635 nm-590 nm). A person of skill in the art would recognize that each light-responsive polypeptide will have its own range of activating wavelengths.

In some cases, the regions of the brain with neurons containing a light-responsive polypeptide are illuminated using one or more optical fibers. The optical fibers may be configured in any suitable manner to direct light emitted from a suitable source of light (e.g., a laser or LED) to the region of the brain. An end of an optical fiber can be implanted in a target region of the brain in any suitable configuration suitable for illuminating a region of the brain with a light stimulus delivered through the optical fiber. In some cases, the optical fiber includes an attachment device at or near the distal end of the optical fiber, where the distal end of the optical fiber corresponds to the end inserted into the subject. In some cases, the attachment device is configured to connect to the optical fiber and facilitate attachment of the optical fiber to the subject, such as to the skull of the subject. Any suitable attachment device may be used. In some cases, the attachment device includes a ferrule, e.g., a metal, ceramic or plastic ferrule. The ferrule may have any suitable dimensions for holding and attaching the optical fiber.

In certain embodiments, methods of the present disclosure may be performed using any suitable electronic components to control and/or coordinate the various optical components used to illuminate the regions of the brain. The optical components (e.g., light source, optical fiber, lens, objective, mirror, and the like) may be controlled by a controller, e.g., to coordinate the light source illuminating the regions of the brain with light pulses. The controller may include a driver for the light source that controls one or more parameters associated with the light pulses, such as, but not limited to the frequency, pulse width, duty cycle, wavelength, intensity, etc. of the light pulses. The controllers may be in communication with components of the light source (e.g., collimators, shutters, filter wheels, moveable mirrors, lenses, etc.).

In some embodiments, the light-responsive polypeptides are activated by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 sec, about 1.25 sec, about 1.5 sec, or about 2 sec, inclusive, including any times in between these numbers. In some embodiments, the light-responsive polypeptides are activated by light pulses that can have a light power density of any of about 0.05 mW/mm$^2$, about 0.1 mW/mm$^2$, about 0.25 mW/mm$^2$, about 0.5 mW/mm$^2$, about 0.75 mW/mm$^2$, about 1 mW/mm$^2$, about 2 mW/mm$^2$, about 3 mW/mm$^2$, about 4 mW/mm$^2$, about 5 mW/mm$^2$, about 6 mW/mm$^2$, about 7 mW/mm$^2$, about 8 mW/mm$^2$, about 9 mW/mm$^2$, about 10 mW/mm$^2$, about 20 mW/mm$^2$, about 50 mW/mm$^2$, about 100 mW/mm$^2$, about 250 mW/mm$^2$, about 500 mW/mm$^2$, about 750 mW/mm$^2$, about 1000 mW/mm$^2$, about 1100 mW/mm$^2$, about 1200 mW/mm$^2$, about 1300 mW/mm$^2$, about 1400 mW/mm$^2$, about 1500 mW/mm$^2$, about 1600 mW/mm$^2$, about 1700 mW/mm$^2$, about 1800 mW/mm$^2$, about 1900 mW/mm$^2$, about 2000 mW/mm$^2$, about 2100 mW/mm$^2$, about 2200 mW/mm$^2$, about 2300 mW/mm$^2$, about 2400 mW/mm$^2$, about 2500 mW/mm$^2$, about 2600 mW/mm$^2$, about 2700 mW/mm$^2$, about 2800 mW/mm$^2$, about 2900 mW/mm$^2$, about 3000 mW/mm$^2$, about 3100 mW/mm$^2$, about 3100 mW/mm$^2$, about 3300 mW/mm$^2$, about 3400 mW/mm$^2$, or about 3500 mW/mm$^2$, inclusive, including any values between these numbers.

The light stimulus used to activate the light-responsive polypeptide may include light pulses characterized by, e.g., frequency, pulse width, duty cycle, wavelength, intensity, etc. In some cases, the light stimulus includes two or more different sets of light pulses, where each set of light pulses is characterized by different temporal patterns of light pulses. The temporal pattern may be characterized by any suitable parameter, including, but not limited to, frequency, period (i.e., total duration of the light stimulus), pulse width, duty cycle, etc.

The light pulses may have any suitable frequency. In some cases, the set of light pulses contains a single pulse of light that is sustained throughout the duration of the light stimulus. In some cases, the light pulses of a set have a frequency of 0.1 Hz or more, e.g., 0.5 Hz or more, 1 Hz or more, 5 Hz or more, 10 Hz or more, 20 Hz or more, 30 Hz or more, 40 H or more, including 50 Hz or more, or 60 Hz or more, or 70 Hz or more, or 80 Hz or more, or 90 Hz or more, or 100 Hz or more, and have a frequency of 100,000 Hz or less, e.g., 10,000 Hz or less, 1,000 Hz or less, 500 Hz or less, 400 Hz or less, 300 Hz or less, 200 Hz or less, including 100 Hz or less. In some embodiments, the light pulses have a frequency in the range of 0.1 to 100,000 Hz, e.g., 1 to 10,000 Hz, 1 to 1,000 Hz, including 5 to 500 Hz, or 10 to 100 Hz.

In some cases, the two sets of light pulses are characterized by having different parameter values, such as different pulse widths, e.g. short or long. The light pulses may have any suitable pulse width. In some cases, the pulse width is 0.1 ms or longer, e.g., 0.5 ms or longer, 1 ms or longer, 3 ms or longer, 5 ms or longer, 7.5 ms or longer, 10 ms or longer, including 15 ms or longer, or 20 ms or longer, or 25 ms or longer, or 30 ms or longer, or 35 ms or longer, or 40 ms or longer, or 45 ms or longer, or 50 ms or longer, and is 500 ms or shorter, e.g., 100 ms or shorter, 90 ms or shorter, 80 ms or shorter, 70 ms or shorter, 60 ms or shorter, 50 ms or shorter, 45 ms or shorter, 40 ms or shorter, 35 ms or shorter, 30 ms or shorter, 25 ms or shorter, including 20 ms or shorter. In some embodiments, the pulse width is in the range of 0.1 to 500 ms, e.g., 0.5 to 100 ms, 1 to 80 ms, including 1 to 60 ms, or 1 to 50 ms, or 1 to 30 ms.

The average power of the light pulse, measured at the tip of an optical fiber delivering the light pulse to regions of the brain, may be any suitable power. In some cases, the power is 0.1 mW or more, e.g., 0.5 mW or more, 1 mW or more, 1.5 mW or more, including 2 mW or more, or 2.5 mW or more, or 3 mW or more, or 3.5 mW or more, or 4 mW or more, or 4.5 mW or more, or 5 mW or more, and may be 1,000 mW or less, e.g., 500 mW or less, 250 mW or less, 100 mW or less, 50 mW or less, 40 mW or less, 30 mW or less, 20 mW or less, 15 mW or less, including 10 mW or less, or 5 mW or less. In some embodiments, the power is in the range of 0.1 to 1,000 mW, e.g., 0.5 to 100 mW, 0.5 to 50 mW, 1 to 20 mW, including 1 to 10 mW, or 1 to 5 mW.

The wavelength and intensity of the light pulses may vary and may depend on the activation wavelength of the light-responsive polypeptide, optical transparency of the region of the brain, the desired volume of the brain to be illuminated, etc. For example, light delivery may alternate between a stimulation interval and a non-stimulation interval, wherein the light at the wavelength that activates the light-responsive polypeptide (e.g., light-responsive ion channel) is delivered during the stimulation interval, and no light or light that is not at the wavelength that activates the light-responsive polypeptide (e.g., light-responsive ion channel) or that inhibits the light-responsive polypeptide (e.g., light-responsive ion channel) is delivered during the non-stimulation interval.

The volume of a brain region illuminated by the light pulses may be any suitable volume. In some cases, the illuminated volume is 0.001 mm$^3$ or more, e.g., 0.005 mm$^3$ or more, 0.001 mm$^3$ or more, 0.005 mm$^3$ or more, 0.01 mm$^3$ or more, 0.05 mm$^3$ or more, including 0.1 mm$^3$ or more, and is 100 mm$^3$ or less, e.g., 50 mm$^3$ or less, 20 mm$^3$ or less, 10 mm$^3$ or less, 5 mm$^3$ or less, 1 mm$^3$ or less, including 0.1 mm$^3$ or less. In certain cases, the illuminated volume is in the range of 0.001 to 100 mm$^3$, e.g., 0.005 to 20 mm$^3$, 0.01 to 10 mm$^3$, 0.01 to 5 mm$^3$, including 0.05 to 1 mm$^3$.

In some embodiments, the light-responsive polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive polypeptide. In some cases, the one or more amino acid sequence motifs which enhance light-responsive polypeptide transport to the plasma membranes of mammalian cells is fused internally within a light-responsive polypeptide. Optionally, the light-responsive polypeptide and the one or more amino acid sequence motifs may be separated by a linker. In some embodiments, the light-responsive polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In some embodiments, the signal peptide sequence in the protein can be deleted or substituted with a signal peptide sequence from a different protein.

Exemplary light-responsive polypeptides and amino acid sequence motifs that find use in the present system and method are disclosed in, e.g., U.S. Pat. Nos. 10,538,560; 10,568,307; 9,284,353; 9,359,449; and 9,365,628; herein incorporated by reference.

Light-responsive polypeptides of interest include, for example, a step function opsin (SFO) protein or a stabilized step function opsin (SSFO) protein that can have specific amino acid substitutions at key positions in the retinal binding pocket of the protein. See, for example, WO 2010/056970, the disclosure of which is hereby incorporated by reference in its entirety. The polypeptide may be a cation channel derived from Volvox carteri (VChR1), optionally comprising one or more amino acid substitutions, e.g., C123A; C123S; D151A, etc. A light-responsive cation channel protein can be a C1V1 chimeric protein derived from the VChR1 protein of Volvox carteri and the ChR1 protein from Chlamydomonas reinhardti, wherein the protein comprises the amino acid sequence of VChR1 having at least the first and second transmembrane helices replaced by the first and second transmembrane helices of ChR1, optionally having an amino acid substitution at amino acid residue E122 or E162. In other embodiments, the light-responsive cation channel protein is a C1C2 chimeric protein derived from the ChR1 and the ChR2 proteins from Chlamydomonas reinhardti, wherein the protein is responsive to light and is capable of mediating a depolarizing current in the cell when the cell is illuminated with light. In some embodiments, a depolarizing light-responsive polypeptide is a red shifted variant of a depolarizing light-responsive polypeptide derived from Chlamydomonas reinhardtii, referred to as a "ReaChR polypeptide" or "ReaChR protein" or "ReaChR." In some embodiments, a depolarizing light-responsive polypeptide is a SdChR polypeptide derived from Scherffelia dubia, wherein the SdChR polypeptide is capable of transporting cations across a cell membrane when the cell is illuminated with light. In some embodiments, a depolarizing light-responsive polypeptide is CnChR1, derived from Chlamydomonas noctigama, wherein the CnChR1 polypeptide is capable of transporting cations across a cell membrane when the cell is illuminated with light. In some embodiments, the light-responsive cation channel protein is a CsChrimson chimeric protein derived from a CsChR protein of Chloromonas subdivisa and CnChR1 protein from Chlamydomonas noctigama, wherein the N-terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. In some embodiments, a depolarizing light-responsive polypeptide can be, e.g., ShChR1, derived from Stigeoclonium helveticum, wherein the ShChR1 polypeptide is capable of transporting cations across a cell membrane when the cell is illuminated with light.

In some embodiments, a depolarizing light-responsive polypeptide is derived from Chlamydomonas reinhardtii (CHR1, and particularly CHR2) wherein the polypeptide is capable of transporting cations across a cell membrane when the cell is illuminated with light; and is capable of mediating a depolarizing current in the cell when the cell is illuminated with light. In some embodiments CaMKIIa-driven, humanized channelrhodopsin CHR2 H134R mutant fused to EYFP is used for optogenetic activation. The light used to activate the light-responsive cation channel protein derived from Chlamydomonas reinhardtii can have a wavelength between about 460 and about 495 nm or can have a wavelength of about 480 nm. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. The protein may comprise various amino acid substitutions, e.g., one or more of H134R; T159C; L132C; E123A; etc. The protein may further comprise a fluorescent protein, for example, but not limited to, a yellow fluorescent protein, a red fluorescent protein, a green fluorescent protein, or a cyan fluorescent protein.

Neurons can be selectively activated or inhibited optogenetically by engineering neurons to express one or more light-responsive polypeptides configured to hyperpolarize or depolarize the neurons. Suitable light-responsive polypeptides and methods used thereof are described further below.

A light-responsive polypeptide for use in the present disclosure may be any suitable light-responsive polypeptide for selectively activating neurons of a subtype by illuminating the neurons with an activating light stimulus. In some instances, the light-responsive polypeptide is a light-responsive ion channel polypeptide. The light-responsive ion channel polypeptides are adapted to allow one or more ions to pass through the plasma membrane of a target cell when the polypeptide is illuminated with light of an activating wavelength. Light-responsive proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the cell when activated by light of an activating wavelength. In some embodiments, the light-responsive polypeptide hyperpolarizes the cell when activated by light of an activating wavelength. Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T), iC1C2, C1C2, GtACR2, NpHR, eNpHR3.0, C1V1, VChR1, VChR2, SwiChR, Arch, ArchT, KR2, ReaChR, ChIEF, Chronos, ChRGR, CsChrimson, and the like. In some cases, the light-responsive polypeptide includes bReaCh-ES, as described in, e.g., Rajasethupathy et al., Nature. 2015 Oct. 29; 526(7575):653, which is incorporated by reference. Hyperpolarizing and depolarizing opsins have been described in various publications; see, e.g., Berndt and Deisseroth (2015) Science 349:590; Berndt et al. (2014) Science 344:420; and Guru et al. (Jul. 25, 2015) Intl. J. Neuropsychopharmacol. pp. 1-8 (PMID 26209858).

The light-responsive polypeptide may be introduced into the neurons using any suitable method. In some cases, the neurons of a subtype of interest are genetically modified to express a light-responsive polypeptide. In some cases, the neurons may be genetically modified using a viral vector, e.g., an adeno-associated viral vector, containing a nucleic acid having a nucleotide sequence that encodes the light-responsive polypeptide. The viral vector may include any suitable control elements (e.g., promoters, enhancers, recombination sites, etc.) to control expression of the light-responsive polypeptide according to neuronal subtype, timing, presence of an inducer, etc.

"Operably linked" refers to a juxtaposition wherein the components so described are in a relationship permitting them to function in their intended manner. For instance, a promoter is operably linked to a nucleotide sequence (e.g., a protein coding sequence, e.g., a sequence encoding an mRNA; a non-protein coding sequence, e.g., a sequence encoding a light-reactive protein; and the like) if the promoter affects its transcription and/or expression.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-.beta. promoter (see, e.g., Liu et al. (2620) Gene Therapy 11:52-60); a motor neuron-specific gene Hb9 promoter (see, e.g., U.S. Pat. No. 7,632,679; and Lee et al. (2620) Development 131:3295-3306); and an alpha subunit of $Ca^{2+}$-calmodulin-dependent protein kinase II (CaMKII) promoter (see, e.g., Mayford et al. (1996) Proc. Natl. Acad. Sci. USA 93:13250). Other suitable promoters include elongation factor (EF) 1 and dopamine transporter (DAT) promoters.

In some cases, neuronal subtype-specific expression of the light-responsive polypeptide may be achieved by using recombination systems, e.g., Cre-Lox recombination, Flp-FRT recombination, etc. Cell type-specific expression of genes using recombination has been described in, e.g., Fenno et al., Nat Methods, 2014 July; 11(7):763; and Gompf et al., Front Behav Neurosci. 2015 Jul. 2; 9:152, which are incorporated by reference herein.

In some embodiments, the vector is a recombinant adeno-associated virus (AAV) vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The application of AAV as a vector for gene therapy has been rapidly developed in recent years. Wild-type AAV could infect, with a comparatively high titer, dividing or non-dividing cells, or tissues of mammal, including human, and also can integrate into in human cells at specific site (on the long arm of chromosome 19) (Kotin et al, Proc. Natl. Acad. Sci. U.S.A., 1990. 87: 2211-2215; Samulski et al, EMBO J., 1991. 10: 3941-3950 the disclosures of which are hereby incorporated by reference herein in their entireties). AAV vector without the rep and cap genes loses specificity of site-specific integration, but may still mediate long-term stable expression of exogenous genes. AAV vector exists in cells in two forms, wherein one is episomic outside of the chromosome; another is integrated into the chromosome, with the former as the major form. Moreover, AAV has not hitherto been found to be associated with any human disease, nor any change of biological characteristics arising from the integration has been observed. There are sixteen serotypes of AAV reported in literature, respectively named AAV1, AAV2, AAV3, AAV4, AAV5, AAV6, AAV7, AAV8, AAV9, AAV10, AAV11, AAV12, AAV13, AAV14, AAV15, and AAV16, wherein AAV5 is originally isolated from humans (Bantel-Schaal, and H. zur Hausen. Virology, 1984. 134: 52-63), while AAV1-4 and AAV6 are all found in the study of adenovirus (Ursula Bantel-Schaal, Hajo Delius and Harald zur Hausen. J. Virol., 1999. 73: 939-947).

AAV vectors may be prepared using any convenient methods. Adeno-associated viruses of any serotype are suitable (See, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, U K (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos: 91/18088 and WO 93/09239; U.S. Pat. Nos. 4,797,368, 6,596,535, and 5, 139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the invention are encapsidated into a virus particle (e.g., AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596, 535.

It is understood that one or more vectors may be administered to neural cells. If more than one vector is used, it is understood that they may be administered at the same or at different times.

Fiber Optic Sensors

Plasmonic nanoparticles, quantum dots, or other light-sensitive particles can be incorporated into the optical fiber core to generate a resonance light shift upon the presence and binding of molecular biotargets for biosensor applications.

A plasmonic sensor can be produced by encapsulating functionalized plasmonic nanoparticles within the core of an optical fiber. Light can be guided along the length of the optical fiber to the plasmonic nanoparticles inside the core, wherein the plasmonic nanoparticles within the core interact with visible light and are used to detect surrounding environmental changes due to refractive index-sensitive plasmonic resonance shifting. Molecular interactions at the surface of a plasmonic nanoparticle produce detectable resonance-induced shifts in plasmon resonance spectra.

Plasmonic nanoparticles include metallic nanoparticles comprising noble metals such as gold, silver and platinum; nanoparticles comprising metal-oxides such as CdO, CdZnO, $MoO_2$, and $VO_2$; nanoparticles comprising transition metal nitrides such as ZIN and TIN; nanoparticles comprising noble metals encapsulated by a metal oxide shell (e.g., gold, silver or platinum encapsulated by a $TiO_2$, $SiO_2$, or NiO shell), and nanoparticles comprising plasmonic metal-metal oxide nanocomposites (e.g., metal oxide nanoparticles doped with other metal atoms that exhibit plasmon resonances).

The plasmonic nanoparticles may have at least one dimension (e.g., a greatest dimension) in the range of from 1 nanometer (nm) to 1000 nm, from 20 nm to 750 nm, from 50 nm to 500 nm, including from 100 nm to 300 nm. The plasmonic nanoparticle may have any suitable shape, including, but not limited to, spherical, spheroid, triangular, rod-shaped, bar-shaped, disk-shaped, pyramid-shaped, cube-shaped, cylinder-shaped, octahedron-shaped, dodecahedron-shaped, icosahedron-shaped, nanohelical-shaped, nanospring-shaped, nanoring-shaped, nanowire-shaped, arrow-shaped, teardrop-shaped, tetrapod-shaped, prism-shaped, star-shaped, or any other suitable geometric or non-geometric shape. In certain embodiments, the nanoparticle (e.g., a spherical or spheroid particle) has a greatest dimension of from 10 to 200 nm, e.g., from 30 to 100 nm. According to some embodiments, the greatest dimension of the nanoparticle (e.g., the diameter in the case of a spherical or spheroid nanoparticle) is greater than 10 nm but 500 nm or less, 450 nm or less, 400 nm or less, 350 nm or less, 300 nm or less, 250 nm or less, 200 nm or less, or 100 nm or less. In certain embodiments, the greatest dimension of the nanoparticle (e.g., the diameter in the case of a spherical or spheroid nanoparticle) is less than 500 nm, but 10 nm or greater, 20 nm or greater, 30 nm or greater, 40 nm or greater, 50 nm or greater, 60 nm or greater, 70 nm or greater, 80 nm or greater, 90 nm or greater, 100 nm or greater, 125 nm or greater, 150 nm or greater, 175 nm or greater, 200 nm or greater, 225 nm or greater, 250 nm or greater, 275 nm or greater, 300 nm or greater, 350 nm or greater, or 400 nm or greater.

A plasmonic sensor specific for detecting a target analyte of interest can be made by attaching capture agents (as described further below) to the surface of the plasmonic nanoparticle, wherein the resonance output spectrum of the plasmonic nanoparticle changes with refractive index variation resulting from binding of a target analyte to the capture agent on the surface of the plasmonic nanoparticle.

Alternatively, a sensor can be produced by encapsulating functionalized quantum dots within the core of an optical fiber. The luminescence of quantum dots is sensitive to the surrounding environment. Molecular interactions at the surface of a quantum dot produce detectable changes in their emission spectrum. Binding of a target analyte to a capture agent on the surface of a quantum dot may quench or enhance luminescence of a quantum dot. Accordingly, a sensor specific for detecting a target analyte of interest can be made by attaching capture agents to the surface of a quantum dot.

Quantum dots include semiconductor nanoparticles comprising silicon, germanium, lead sulfide, lead selenide, cadmium selenide, cadmium sulfide, cadmium telluride, indium arsenide, or indium phosphide, and typically range in size from 1 nm to 10 nm. Their high quantum yields, narrow fluorescence emissions, and broad absorption spectra provide advantages over fluorescent dyes. The optical properties of quantum dots are tunable and depend on their particle size (i.e., size tunable emission wavelength). Numerous quantum dots with a wide range of emission wavelengths are commercially available, for example, from Thermo Fisher Scientific Corporation (Waltham, MA), Ocean NanoTech (San Diego, CA), and Sigma-Aldrich (St. Louis, MO).

By "capture agent" is meant an agent that binds to a target analyte (e.g., molecule free in solution, marker on a cell) through an interaction that is sufficient to permit the agent to bind and concentrate a target analyte from a heterogeneous mixture. The binding interaction is typically mediated by an affinity region of the capture agent. Typical capture agents include any moiety that can specifically bind to a target analyte. Certain capture agents specifically bind a target molecule with a dissociation constant ($K_D$) of less than about $10^{-6}$ M (e.g., less than about $10^{-7}$M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other molecules. Exemplary capture agents include antibodies and fragments thereof, antibody mimetics, aptamers, peptoids, nucleic acids (e.g., oligonucleotide probes, DNA, RNA), ligands, inhibitors, agonists, antagonists, and small molecule drugs that bind to the target analyte, wherein the capture agent is attached to the outer surface of the plasmonic nanoparticle, quantum dot, or other light-sensitive particle.

A capture agent may bind to any type of molecule, including nucleic acids, proteins, lipids, polysaccharides, proteoglycans, metabolites, or the like. The target analyte may include, without limitation, a molecule such as a protein (e.g., an antigen, an antibody, an enzyme, a transcription factor, or a receptor), a nucleic acid (e.g., messenger RNA, regulatory RNA, or viral nucleic acids), a metabolite, or an exogenous compound (e.g., drug, toxin, or pollutant); a cell, a tissue, an organoid, an organism, or a pathogen (e.g., a virus, a bacterium, a parasite, or other pathogen). By suitable choice of the capture agent, a sensor (e.g., comprising a plasmonic nanoparticle, quantum dot, or other light-sensitive particle) can be designed to detect many types of interactions, including, but not limited to, protein-DNA, protein-cell (e.g., antibody specific for a cell marker on the surface of a cell), protein-pathogen (e.g., antibody specific for a cell marker on the surface of a viral particle or bacterium), RNA-DNA, DNA-DNA, protein-protein, protein-carbohydrate, small molecule-macromolecule (e.g., receptor-ligand, enzyme-inhibitor), and protein-peptide interactions.

In certain embodiments, the capture agent is an oligonucleotide comprising a nucleotide sequence that is complementary to the sequence of a target nucleic acid analyte in a sample such that the oligonucleotide can "capture" the target nucleic acid analyte. One or more capture oligonucleotides can be used in order to capture the target analyte. The polynucleotide regions of a capture oligonucleotide may be composed of DNA, and/or RNA, and/or synthetic nucleotide analogs.

In certain embodiments, the capture agent is an antibody that specifically binds to the target analyte of interest. Any type of antibody may be used, including, without limitation, monoclonal antibodies, polyclonal antibodies, as well as hybrid antibodies, altered antibodies, chimeric antibodies, and humanized antibodies. Antibodies may include hybrid (chimeric) antibody molecules (see, for example, Winter et al. (1991) Nature 349:293-299; and U.S. Pat. No. 4,816,567); F(ab')2 and F(ab) fragments; $F_v$ molecules (noncovalent heterodimers, see, for example, Inbar et al. (1972) Proc Natl Acad Sci USA 69:2659-2662; and Ehrlich et al. (1980) Biochem 19:4091-4096); single-chain $F_v$ molecules (scFv) (see, e.g., Huston et al. (1988) Proc Natl Acad Sci USA 85:5879-5883); nanobodies or single-domain antibodies (sdAb) (see, e.g., Wang et al. (2016) Int J Nanomedicine 11:3287-3303, Vincke et al. (2012) Methods Mol Biol 911: 15-26; dimeric and trimeric antibody fragment constructs; minibodies (see, e.g., Pack et al. (1992) Biochem 31:1579-1584; Cumber et al. (1992) J Immunology 149B:120-126); diabodies, tetrabodies, affibodies, camelid antibodies, humanized antibody molecules (see, e.g., Riechmann et al. (1988) Nature 332:323-327; Verhoeyan et al. (1988) Science 239:1534-1536; and U.K. Patent Publication No. GB 2,276, 169, published 21 Sep. 1994); and, any functional fragments obtained from such molecules, wherein such fragments retain specific-binding properties of the parent antibody molecule.

In other embodiments, the capture agent is an aptamer that specifically binds to the target analyte of interest. Any type of aptamer may be used, including a DNA, RNA, xenonucleic acid (XNA), or peptide aptamer that specifically binds to the target analyte. Such aptamers can be identified, for example, by screening a combinatorial library. Nucleic acid aptamers (e.g., DNA or RNA aptamers) that bind selectively to a target analyte can be produced by carrying out repeated rounds of in vitro selection or systematic evolution of ligands by exponential enrichment (SELEX). Peptide aptamers that bind to a target analyte of interest may be isolated from a combinatorial library and improved by directed mutation or repeated rounds of mutagenesis and selection. For a description of methods of producing aptamers, see, e.g., Aptamers: Tools for Nanotherapy and Molecular Imaging (R. N. Veedu ed., Pan Stanford, 2016), Nucleic Acid and Peptide Aptamers: Methods and Protocols (Methods in Molecular Biology, G. Mayer ed., Humana Press, 2009), Nucleic Acid Aptamers: Selection, Characterization, and Application (Methods in Molecular Biology, G. Mayer ed., Humana Press, 2016), Aptamers Selected by Cell-SELEX for Theranostics (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol. Biol. 118:217-231; Platella et al. (2016) Biochim. Biophys. Acta November 16 pii: S0304-4165(16)30447-0, and Lyu et al. (2016) Theranostics 6(9): 1440-1452; herein incorporated by reference in their entireties.

In other embodiments, the capture agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1): 172-185), affimers (Johnson et al. (2012) Anal. Chem. 84 (15):6553-6560), affitins (Krehenbrink et al. (2008) J. Mol. Biol. 383 (5): 1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In other embodiments, the capture agent is a small molecule ligand. Small molecule ligands encompass numerous chemical classes, e.g., small organic compounds having a molecular weight of less than about 10,000 daltons, less than about 5,000 daltons, or less than about 2,500 daltons. The small molecule will include one or more functional groups necessary for structural interaction with the target analyte, e.g., groups necessary for hydrophobic, hydrophilic, electrostatic or even covalent interactions. Where the target analyte is a protein (e.g., cellular marker, receptor, or enzyme), the ligand will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, or preferably at least two of the functional chemical groups. The small molecule may also comprise a region that may be modified and/or participate in conjugation to a detectable label, without substantially adversely affecting the small molecule's ability to bind to its target analyte.

Small molecule ligands can comprise cyclical carbon or heterocyclic structures and/or aromatic or polyaromatic structures substituted with one or more of the above functional groups. Small molecule ligands may also include organic compounds comprising alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Small molecule ligands are also found among biomolecules including peptides, carbohydrates, fatty acids, steroids, purines, pyrimidines, derivatives, structural analogs, or combinations thereof. The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e., a compound diversity combinatorial library. When obtained from such libraries, the small molecule employed will have demonstrated some desirable affinity for the protein target in a convenient binding affinity assay. Combinatorial libraries, as well as methods for the production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Small molecule ligands may also include known drugs that selectively bind to receptors on cells, including, without limitation, growth factor receptors, receptor tyrosine kinases, receptor protein serine/threonine kinases, G-protein coupled receptors, cytokine receptors, lectin receptors, folate receptors, prostate-specific membrane antigen (PSMA), carbonic anhydrase IX receptor, and biotin receptors. For example, anti-cancer drugs that bind to such cellular receptors may be used as ligands to target a detectable label to cancer cells. Exemplary drugs that may be used as ligands to target cancer cells include, without limitation, Acitinib, Afatinib, Axitinib, Erlotinib, Cabozantinib, Crizotinib, Gefitinib, Imatinib, Ibrutinib, Lapatinib, Neovastat, Nilotinib, Pazopanib, Perifosine, Ponatinib, Regorafenib, Sorafenib, Sunitinib, Trametinib, and Vandetenib.

Generally, a sample suspected of comprising an analyte of interest is introduced into the core of an optical fiber under conditions suitable to allow the analyte to flow through the optical fiber to reach the plasmonic nanoparticle, quantum dot, or other light-sensitive particle and bind to a capture agent that is attached to the surface of plasmonic nanoparticle, quantum dot, or other light-sensitive particle within the core of the optical fiber. If the analyte of interest is present in the sample, it binds to the plasmonic nanoparticle, quantum dot, or other light-sensitive particle at the site of the capture agent and a complex is formed on the surface of the plasmonic nanoparticle, quantum dot, or other light-sensitive particle within the core of the optical fiber.

The plasmonic response to binding of a target analyte to a capture agent at the surface of plasmonic nanoparticles may include changes in the local index of refraction and the resonance conditions of the surface plasmon waves. Accordingly binding of the target analyte to the capture agent on the surface of the plasmonic nanoparticle can be detected based on refractive index variation and plasmonic resonance shifts in the output spectrum of the plasmonic nanoparticle. In addition, the surface plasmonic resonance signal associated with the response to binding of the target analyte to the capture agent on the plasmonic nanoparticle within the core of an optical fiber can be used to determine the binding affinity of the target analyte for the capture agent, including calculation of the rate of association ($k_a$), the rate of dissociation ($k_d$), and the equilibrium dissociation constant ($K_D$).

The response to binding of a target analyte to a capture agent at the surface of quantum dots may include quenching or enhancement of luminescence and detectable changes in their emission spectra. Accordingly binding of the target analyte to the capture agent on the surface of a quantum dot can be detected based on the spectral response and changes in the photoluminescent lifetime of the quantum dot.

The selection of suitable conditions for the specific binding of a target analyte in a sample to the capture agent may include selection of a proper temperature, incubation time, solution pH, chemical reagent concentration, capture agent-target analyte ratio, etc. The sample may be a liquid sample and, in certain embodiments, the sample may be a clinical sample derived from cells, tissues, or bodily fluids. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

A subject fiber optic sensor (e.g., with a plasmonic nanoparticle, quantum dot, or other light-sensitive particle) may be employed in a method of diagnosing a disease or condition by using a capture agent that specifically binds to a pathogen (e.g., a virus, a bacterium, a parasite, or other pathogen), biomarker associated with the disease, or cell associated with the disease (e.g., cancerous, inflamed, or damaged cell, or cell overexpressing a cell marker linked to the disease). For example, a liquid sample can be collected from a patient suspected of having a disease or condition and introduced into the core of an optical fiber under conditions suitable to allow a pathogen, biomarker, or cell to bind to the capture agent attached to the surface of the plasmonic nanoparticles, quantum dots, or other light-sensitive particles within the core of the optical fiber.

The optical fiber may be coupled to a device to facilitate collection of a sample from a subject and introduction of the sample into the core of the optical fiber. In some embodiments, the optical fiber is coupled to a medical swab to facilitate collection of a sample, for example, from the mouth, throat, nose, or ear. In certain embodiments, an endotracheal tube is coupled to the optical fiber to facilitate collection of a sample from the trachea of a subject. Such devices may be coupled to the optical fiber, for example, to collect samples containing pathogens such as viruses, bacteria, or other pathogens from subjects suspected of having an infection.

In some embodiments, the fiber optic biosensor is used diagnose an infection by a pathogen by detecting the response to binding of a capture agent to a target nucleic acid from a pathogen in a sample. The target nucleic acid may be captured, for example, using an oligonucleotide capture agent attached to the surface of a plasmonic particle or quantum dot within the core of an optical fiber.

In some embodiments, the fiber optic biosensor is used diagnose an infection of a pathogen by detecting the response to binding of the capture agent to a target protein (surface marker) of a pathogen in a sample. The target protein may be, for example, from a virus, bacterium, or other pathogen. The target protein may be captured, for example, using an antibody capture agent attached to the surface of a plasmonic particle or quantum dot within the core of an optical fiber. In some cases, the pathogen itself may be captured by using an antibody capture agent that binds to a surface marker on the pathogen, such as a bacterial cell membrane marker or viral coat or viral envelope marker.

Various pathogens may be analyzed by the methods described herein including viruses, bacteria, fungi, and parasites. Exemplary pathogenic viruses include, without limitation, Adenoviridae such as, but not limited to, adenovirus; Herpesviridae such as, but not limited to, Herpes simplex, type 1, Herpes simplex, type 2, Varicella-zoster virus, Epstein-Barr virus, human cytomegalovirus, human herpesvirus, type 8; Papillomaviridae such as, but not limited to, human papillomavirus; Polyomaviridae such as, but not limited to, BK virus, and JC virus; Poxviridae such as, but not limited to, smallpox; Hepadnaviridae such as, but not limited to, hepatitis B virus; Parvoviridae such as, but not limited to, parvovirus B19; Astroviridae such as, but not limited to, Caliciviridae such as, but not limited to, Norwalk virus; Picornaviridae such as, but not limited to, coxsackievirus, hepatitis A virus, poliovirus, and rhinovirus; Coronaviridae such as, but not limited to, severe acute respiratory syndrome-related coronavirus, strains, including severe acute respiratory syndrome virus and severe acute respiratory syndrome coronavirus 2; Flaviviridae such as, but not limited to, hepatitis C virus, yellow fever virus, dengue virus, West Nile virus, TBE virus, and Zika virus; Matonaviridae such as, but not limited to, rubella virus; Hepeviridae such as, but not limited to, hepatitis E virus; Retroviridae such as, but not limited to, human immunodeficiency virus (HIV); Orthomyxoviridae such as, but not limited to, influenza virus; Arenaviridae such as, but not limited to, lassa virus; Bunyaviridae such as, but not limited to, Crimean-Congo hemorrhagic fever virus, Hantaan virus; Filoviridae such as, but not limited to, Ebola virus and Marburg virus; Paramyxoviridae such as, but not limited to, measles virus, mumps virus, and parainfluenza virus; Pneumoviridae such as, but not limited to, respiratory syncytial virus; Rhabdoviridae such as, but not limited to, rabies virus; hepatitis D; and Reoviridae such as, but not limited to, rotavirus, orbivirus, coltivirus, and banna virus.

In one embodiment, an optical fiber comprises a plasmonic nanoparticle comprising an antibody that selectively binds to a spike protein of severe acute respiratory syndrome coronavirus 2 (SARS-COV-2) attached to the outer surface of the plasmonic nanoparticle for use as a capture agent for detection of SARS-COV-2. In certain embodiments, a medical swab or an endotracheal tube is coupled to the optical fiber to facilitate collection of a sample from a subject suspected of having a viral infection for testing for the presence of SARS-COV-2.

Pathogenic bacteria include Gram-positive and Gram-negative bacteria, including rods, bacilli, cocci, coccobacilli, and spirochetes. Exemplary pathogenic bacteria include, without limitation, *Bacillus* such as, but not limited to, *Bacillus anthracis* and *Bacillus cereus; Bartonella* such as, but not limited to, *Bartonella henselae* and *Bartonella quintana; Bordetella* such as, but not limited to, *Bordetella pertussis; Borrelia* such as, but not limited to, *Borrelia burgdorferi, Borrelia garinii, Borrelia afzelii,* and *Borrelia recurrentis; Brucella* such as, but not limited to, *Brucella abortus, Brucella canis, Brucella melitensis,* and *Brucella suis; Chlamydia* and *Chlamydophila* such as, but not limited to *Chlamydia pneumoniae, Chlamydia trachomatis,* and *Chlamydophila psittaci; Clostridium* such as, but not limited to, *Clostridium botulinum, Clostridium difficile, Clostridium perfringens,* and *Clostridium tetani; Corynebacterium* such as, but not limited to, *Corynebacterium diphtheriae; Enterococcus* such as, but not limited to, *Enterococcus faecalis* and *Enterococcus faecium; Escherichia* such as, but not limited to *Escherichia coli, Francisella* such as, but not limited to, *Francisella tularensis; Haemophilus* such as, but not limited to, *Haemophilus influenzae; Helicobacter* such as, but not limited to, *Helicobacter pylori; Legionella* such as, but not limited to, *Legionella pneumophila; Leptospira* such as, but not limited to, *Leptospira interrogans, Leptospira santarosai, Leptospira weilii,* and *Leptospira noguchii; Listeria* such as, but not limited to *Listeria monocytogenes; Mycobacterium* such as, but not limited to, *Mycobacterium leprae, Mycobacterium tuberculosis,* and *Mycobacterium ulcerans; Mycoplasma* such as, but not limited to, *Mycoplasma pneumoniae; Neisseria* such as, but not limited to, *Neisseria gonorrhoeae* and *Neisseria meningitidis; Pseudomonas* such as, but not limited to, *Pseudomonas aeruginosa; Rickettsia* such as, but not limited to, *Rickettsia rickettsii; Salmonella* such as, but not limited to, *Salmonella typhi* and *Salmonella typhimurium; Shigella* such as, but not limited to, *Shigella sonnei; Staphylococcus* such as, but not limited to, *Staphylococcus aureus, Staphylococcus epidermidis,* and *Staphylococcus saprophyticus; Streptococcus* such as, but not limited to, *Streptococcus agalactiae, Streptococcus pneumoniae,* and *Streptococcus pyogenes; Treponema* such as, but not limited to, *Treponema pallidum; Ureaplasma* such as, but not limited to, *Ureaplasma urealyticum; Vibrio* such as, but not limited to *Vibrio cholerae;* and *Yersinia* such as, but not limited to, *Yersinia pestis, Yersinia enterocolitica,* and *Yersinia pseudotuberculosis.*

Parasitic pathogens include ectoparasites and endoparasites. Exemplary parasites include, without limitation, protozoa such as, but not limited to *Excavata* including *Giardia intestinalis, Hexamita salmonis, Histomonas meleagridis, Trichonympha, Trichomonadida, Trypanosoma cruzi, Trypanosoma brucei rhodensiense,* and *Trypanosoma brucei gambiense; Amoebozoa* including *Entamoeba histolytica, Naeglaria,* and Acanthomoeba; SAR including *Phytophthora infestans,* Archaeplastida, *Balantidium coli, Theileria*

*parva, Theileria annulata, Phipicephalus appendiculatus, Spongospora subterranea*, Mikrocytos mackini, and Prototheca moriformis; and helminths including tapeworms such as, but not limited to *Echinococcus, Hymenolepis, Taenia* (e.g., *T. multiceps, T. serialis, T. glomerata*, and *T. brauni*); roundworms/nematodes such as, but not limited to *Necator americanus, Ancylostoma duodenale, Wuchereria bancrofti, Brugia malayi, Onchocerca volvulus, Ascaris lumbricoides, Trichuris, Trichostrongylus* spp., *Dracunculus medinensis*, and *Baylisascaris*; and flukes/trematodes such as, but not limited to, amphistomes, *Clonorchis sinensis, Fasciolopsis buski, Fascioloides magna, Fasciola hepatica, Opisthorchis, Paragonimus*, and *Schistosoma*.

Exemplary pathogenic fungi include, without limitation, *Candida* such as, but not limited to, *Candida albicans; Aspergillus* such as, but not limited to, *Aspergillus fumigatus, Aspergillus flavus*, and *Aspergillus clavatus; Cryptococcus* such as, but not limited to, *Cryptococcus neoformans, Cryptococcus gattii, Cryptococcus laurentii*, and *Cryptococcus albidus; Histoplasma* such as, but not limited to, *Histoplasma capsulatum; Pneumocystis* such as, but not limited to, *Pneumocystis jirovecii*; and Stachybotrys such as, but not limited to, *Stachybotrys chartarum; Blastomyces* sp.; *Coccidiode* such as, but not limited to, *Coccidiodes immitis* and Coccidiodes posadasii; *Fusarium* sp.; *Paecilomyces* sp.; *Paracoccidioides brasiliensis; Penicillium marneffei; Pseudallescheria boydii; Scedosporium* including, but not limited to, *Scedosporium apiospermum* and *Scedosporium prolificans; Rhizopus* sp.; *Mucor* sp.; *Absidia* sp.; *Cunninghamella* sp.; *Trichoderma longibrachiatium*; and *Trichosporon* sp.

In some embodiments, the fiber optic biosensor is used to diagnose cancer using a capture agent that selectively binds to a cancer marker. The cancer-targeted capture agent may comprise, for example, an antibody, an antibody mimetic, a peptide, a peptoid, an aptamer, or a small molecule ligand that selectively binds to a tumor-specific antigen or a tumor-associated antigen on cancerous cells. Exemplary tumor-specific antigens and tumor-associated antigens include, without limitation, oncogene protein products, mutated or dysregulated tumor suppressor proteins, oncovirus proteins, oncofetal antigens, mutated or dysregulated differentiation antigens, overexpressed or aberrantly expressed cellular proteins (e.g., mutated or aberrantly expressed growth factors, mitogens, receptor tyrosine kinases, cytoplasmic tyrosine kinases, serine/threonine kinases and their regulatory subunits, G proteins, and transcription factors), and altered cell surface glycolipids and glycoproteins on cancerous cells. For example, tumor-specific antigens and tumor-associated antigens may include without limitation, dysregulated or mutated RAS, WNT, MYC, ERK, TRK, CTAG1B, MAGEA1, Bcr-Abl, p53, c-Sis, epidermal growth factor receptor (EGFR), platelet-derived growth factor receptor (PDGFR), vascular endothelial growth factor receptor (VEGFR), HER2/neu, Src-family, Syk-ZAP-70 family proteins, and BTK family of tyrosine kinases, Abl, Raf kinase, cyclin-dependent kinases, alphafetoprotein (AFP), carcinoembryonic antigen (CEA), CA-125, MUC-1, epithelial tumor antigen (ETA), tyrosinase, melanoma-associated antigen (MAGE), and other abnormal or dysregulated proteins expressed on cancerous cells. In some embodiments, the cancer-targeted capture agent binds to a tumor antigen of interest with high affinity.

In certain embodiments, the tumor marker targeted by a capture agent is the urokinase plasminogen activator receptor (uPAR) or urokinase plasminogen activator (uPA). A number of anti-uPAR antibodies are available including the 2G10 antibody, which inhibits the uPAR interaction with urokinase plasminogen activator, and anti-uPAR antibody, 3C6, which inhibits the association of uPAR with b1 integrin (see, e.g., LeBeau et al. (2013) Cancer Res. 73(7):2070-2081). Anti-PAR and anti-uPA antibodies can be used as capture agents for detection of cancerous cells expressing uPAR or uPA, respectively, including, without limitation, those of breast cancer including triple negative breast cancer, pancreas cancer, prostate cancer, and melanoma.

In certain embodiments, the tumor marker targeted by a capture agent is PD-L1. A number of anti-PD-L1 antibodies are commercially available including durvalumab, pembrolizumab, atezolizumab and avelumab. Other anti-PD-L1 antibodies include C4 and DFO-C4 (see, e.g., Truillet C et al. (2018) Bioconjug. Chem. 29(1):96-103). Such anti-PD-L1 antibodies can be used as capture agents for detection of cancerous cells expressing PD-L1, including, without limitation, those of melanoma, lung cancer, including non-small cell lung cancer (NSCLC) and small cell lung cancer (SCLC), head and neck cancer, Hodgkin lymphoma, stomach cancer, prostate cancer, bladder cancer, urothelial carcinoma, breast cancer including triple-negative breast cancer (TNBC), hepatocellular carcinoma (HCC), Merkel cell carcinoma, and renal cell carcinoma.

In certain embodiments, the tumor marker targeted by a capture agent is the epidermal growth factor receptor (EGFR). A number of anti-EGFR antibodies are available including panitumumab, cetuximab, zalutumumab, nimotuzumab, and matuzumab, which can be used as capture agents for detection of cancerous cells expressing EGFR, including, without limitation, those of head and neck cancer, colorectal cancer, lung cancer, ovarian cancer, breast cancer, endometrial cancer, cervical cancer, bladder cancer, gastric cancer, and esophageal cancer. A number of small molecule drugs are also available that target EGFR including, without limitation, Gefitinib, Erlotinib, Lapatinib, Sorafenib, and Vandetenib, which can be used as capture agents to detect cancerous cells expressing EGFR, according to the methods described herein.

In other embodiments, the tumor marker targeted by a capture agent is HER2. A number of anti-HER2 antibodies are also available including trastuzumab, pertuzumab, and margetuximab, which can be used as capture agents for detection of cancerous cells expressing HER2, including, without limitation, those of breast cancer, ovarian cancer, stomach cancer, lung cancer, uterine cancer, gastric cancer, colon cancer, head and neck cancer, and salivary duct carcinoma. A number of small molecule drugs are also available that target HER2 including, without limitation, Lapatinib and Neratinib, which can be used as capture agents to detect cancerous cells expressing HER2, according to the methods described herein.

In other embodiments, the tumor marker targeted by a capture agent is the epithelial cell adhesion molecule (EpCAM) 17-1A. A number of anti-EpCAM 17-1A antibodies are also available including edrecolomab, catumaxomab, and nofetumomab, which can be used as capture agents to detect cancerous cells expressing EpCAM 17-1A to detect cancerous cells in epithelial-derived neoplasms and various carcinomas, such as lung cancer, gastrointestinal cancer, breast cancer, ovarian cancer, pancreatic cancer, renal cancer, cervical cancer, colorectal cancer, and bladder cancer.

In other embodiments, the tumor marker targeted by a capture agent is CD20. A number of anti-CD20 antibodies are also available including rituximab, tositumomab, ocrelizumab, obinutuzumab, ocaratuzumab, ofatumumab, ibritumomab tiuxetan, ublituximab, and veltuzumab, which can be used as capture agents for detection of cancerous cells expressing CD20, including, without limitation, those of lymphoma such as, but not limited to, marginal zone lymphoma, Hodgkins lymphoma, non-Hodgkins lymphoma; leukemia such as, but not limited to, chronic lymphocytic leukemia, acute lymphoblastic leukemia, myelogenous leukemia, and chemotherapy-resistant hairy cell leukemia; and thyroid cancer.

In other embodiments, the tumor marker targeted by a capture agent is CD52. A number of anti-CD52 antibodies are also available including alemtuzumab, which can be used as capture agents to detect cancerous cells expressing CD52, including, without limitation, those of lymphoma such as, but not limited to, cutaneous T-cell lymphoma (CTCL) and T-cell lymphoma and chronic lymphocytic leukemia (CLL).

In other embodiments, the tumor marker targeted by a capture agent is CD22. A number of anti-CD22 antibodies are also available including inotuzumab, which can be used as capture agents to detect cancerous cells expressing CD22, including, without limitation, those of leukemia such as, but not limited to, lymphoblastic leukemia and hairy cell leukemia; lymphoma, and lung cancer.

In other embodiments, the tumor antigen targeted by a capture agent is CD19. A number of anti-C19 antibodies are also available including blinatumomab, MEDI-551 and MOR-208, which can be used as capture agents to detect cancerous cells expressing CD19, including, without limitation, those of B-cell neoplasms, non-Hodgkin lymphoma (NHL), chronic lymphocytic leukemia (CLL), acute lymphoblastic leukemia (ALL), and multiple myeloma (MM).

In certain embodiments, the tumor marker targeted by a capture agent is carcinoembryonic antigen (CEA). A number of anti-CEA antibodies are available including arcitumomab, which can be used as capture agents to detect cancerous cells expressing CEA, including, without limitation, those of colorectal carcinoma, gastric carcinoma, pancreatic carcinoma, lung carcinoma, breast carcinoma, and medullary thyroid carcinoma.

In certain embodiments, the tumor marker targeted by a capture agent is prostate-specific membrane antigen (PSMA). A number of anti-PSMA antibodies are available including capromab, PSMA30 nanobody, and IAB2M minibody, which can be used as capture agents for detection of cancerous cells expressing PSMA, including, without limitation, those of prostate cancer. A number of small molecule drugs are also available that target PSMA including, without limitation, zinc binding compounds linked to a glutamate isostere or glutamate, phosphonate, phosphate, and phosphoramidates and ureas, fluciclovine (Axumin), MIP-1072, MIP-1095, N—(N—((S)-1,3-dicarboxypropyl) carbamoyl)-4-(18F) fluorobenzyl-L-cysteine (18F-DCFBC), which can be used as capture agents to detect cancerous cells expressing PSMA, according to the methods described herein.

In certain embodiments, the tumor marker targeted by a capture agent is the folate receptor (FR). A number of anti-FR antibodies are available including farletuzumab and m909, which can be used as capture agents to detect cancerous cells expressing FR, including, without limitation, those of ovarian cancer, breast cancer, lung cancer, pleura cancer, cervical cancer, endometrial cancer, kidney cancer, bladder cancer and brain cancer, The small molecule, folate, can also be used as a capture agent to detect cancerous cells expressing FR, according to the methods described herein.

In certain embodiments, the tumor marker targeted by a capture agent is a matrix-metalloproteinase (MMP), including, without limitation, MMP1, MMP3, MMP7, MMP9, MMP10, MMP11, MMP12, MMP13, and MMP14. A number of anti-MMP antibodies are available including, which can be used as capture agents to detect cancerous cells expressing MMPs, including, without limitation, those of ovarian cancer, breast cancer, lung cancer, prostate cancer, stomach cancer, thyroid cancer, skin cancer, brain cancer, kidney cancer, colon cancer, bladder cancer, esophageal cancer, endometrial cancer, hepatocellular cancer, and head and neck cancer. Endogenous glycoprotein inhibitors such as tissue inhibitor of metalloproteinases (TIMPs), including TIMP-1, TIMP-2, TIMP-3, and TIMP-4 as well as a number of small molecule drugs are available that target MMPs including, without limitation, doxycycline, marimastat (BB-2516), and cipemastat, which can be used as capture agents to detect cancerous cells expressing MMPs, according to the methods described herein.

In other embodiments, the capture agent selectively binds to an immune activation marker, which may include adaptive immunity activation markers and innate immunity activation markers. Exemplary immune activation markers include, without limitation, B220, CTLA-4, PD-1, CD1c, CD3, CD5, CD8, CD11b, CD11c, CD13, CD14, CD16, CD18, CD20, CD21, CD23, CD25, CD27, CD28, CD32, CD38, CD40, CD41, CD43, CD44, CD45RA, CD45RO, CD54, CD56, L-selectin (CD62L), CD63, CD66b, CD68, CD69, CD80, CD83, CD86, CD88, CD95, CD107a, CD161, CD163, CD164, CD200R, CD203c, MHCII (HLA-DR), MMR/CD206, MGL1, MGL2, Egr2, CD107a, LAMP-2 (CD107b), CD115, Ly-6C, LAMP-I (CD1-7a), NKp46, NKp30, CRTH2/DP2, CCR7, OX40, 4-1BBL, granzymes, perforin, IL-1, IL-1B, IL-2, IL-4, IL-5, IL-6, IL-8, IL-10, IL-12, IL-13, IL-17, IL-18, IL-21, IL-22, IL-25, IL-26, IL-10, TGF-beta, IFN-gamma, TNF-alpha, TNF-beta, NKG2D, CXCR5, IRTA1, IRTA2, lymphotoxin, leukotriene B4, granulocyte-macrophage colony stimulating factor (GM-CSF), and macrophage migration inhibitory factor (MIF).

In some cases, the fiber optic sensor may be employed to detect an analyte that is present at a low concentration. For example, the fiber optic sensor may be used to detect target analytes in a bodily fluid (e.g., blood, saliva, urine, tears, cerebrospinal fluid, breast milk, etc.) such as cancer biomarkers (e.g., cancer antigens, circulating tumor cells), biomarkers for tissue-specific diseases (e.g., tissue-specific disease-associated biomarkers deposited into blood or urine), biomarkers for an immune disorder (e.g., autoantibodies, inflammatory markers), biomarkers for a neurological disorder (e.g., Alzheimer's antigens), infections (particularly detection of low titer latent viruses (e.g., HIV), fetal antigens in maternal blood, or exogenous compounds (e.g., drugs, toxins, or pollutants) in a subject's bloodstream.

Capture agents can be attached to the surface of a plasmonic nanoparticle, quantum dot, or other light-sensitive particle using any convenient method. For example, plasmonic gold nanoparticles can be readily functionalized with thiolated capture agents because of the high binding affinity of gold nanoparticles to thiol groups. In some embodiments, a plasmonic nanoparticle, quantum dot, or other light-sensitive particle further comprises a coating, wherein a capture agent is attached via a functional group of the coating. Coatings may comprise silica or polymers such as, but not limited to, polyethylene glycol (PEG), polyvinylpyrrolidone (PVP) and polyoxazolines (POX), polyglycerols, polyacrylamides, polyaminoacids, and polysaccharides. Plasmonic nanoparticles, quantum dots, or other light-sensitive particles can be functionalized with streptavidin, which can bind biotinylated capture agents. Plasmonic nanoparticles, quantum dots, or other light-sensitive particles functionalized with protein G can bind antibodies used as capture agents. An amine group in a lysine residue of a protein or an aminated oligonucleotide can be conjugated with an N-hydroxysuccinimide (NHS) ester to produce an amide bond to attach a capture agent to a nanoparticle. A reaction between a sulfhydryl group in a cysteine residue of a protein or a sulfhydryl-oligonucleotide can be conjugated with a sulfhydryl-reactive maleimide to attach a capture agent to plasmonic nanoparticles, quantum dots, or other light-sensitive particles.

Protocols for linking capture agents to various reactive groups are well known in the art. Any convenient method of conjugation may be used including, but not limited to, glutaraldehyde crosslinking, carbodiimide crosslinking, succinimide ester crosslinking, imidoester, crosslinking, maleimide crosslinking, iodoacetamide crosslinking, benzidine crosslinking, periodate crosslinking, isothiocyanate crosslinking, and the like. Such conjugation methods may optionally use a reactive sidechain group of an amino acid residue of the capture agent (e.g., a reactive side-chain group of a Lys, Cys, Ser, Thr, Tyr, His or Arg amino acid residue of the protein, i.e., a polypeptide linking group may be aminoreactive, thiol-reactive, hydroxyl-reactive, imidazolyl-reactive or guanidinyl-reactive). In some cases, a chemoselective reactive functional group may be utilized. Other conjugation reagents that can be used include, but are not limited to, e.g., homobifunctional conjugation reagents (e.g., (bis(2-[succinimidooxycarbonyloxy]ethyl) sulfone, 1,4-Di-(3'-[2'pyridyl-dithio]-propionamido) butane, disuccinimidyl suberate, disuccinimidyl tartrate, sulfodisuccinimidyl tartrate, dithiobis (succinimidyl propionate), 3,3'-dithiobis(sulfosuccinimidyl propionate), ethylene glycol bis(succinimidyl succinate), and the like), heterobifunctional conjugation reagents (e.g., m-maleimidobenzoyl-N-hydroxysuccinimide ester, m-maleimidobenzoyl-N-hydroxysulfosuccinimide ester, N-y-maleimidobutyryloxysuccinimide ester, N-y-maleimidobutyryloxysulfosuccinimide ester, N-(8-maleimidocaproic acid) hydrazide, N-(E-maleimidocaproyloxy) succinimide ester, N-(8-maleimidocaproyloxy) sulfo succinimide ester, N-(p-maleimidophenyl) isocyanate, N-succinimidyl(4-iodoacetyl)aminobenzoate, succinimidyl 4-(N-maleimidomethyl) cyclohexane-I-carboxylate, succinimidyl 4-(p-maleimidophenyl) butyrate, N-sulfosuccinimidyl(4-iodoacetyl)aminobenzoate, sulfosuccinimidyl 4-(N-maleimidomethyl) cyclohexane-I-carboxylate, sulfo succinimidyl 4-(p-maleimidophenyl) butyrate, I-ethyl-3-(3-dimethylaminopropyl) carbodiimide hydrochloride, I-ethyl-3-(3-dimethylaminopropyl) carbodiimide hydrochloride, maleimide PEG N-hydroxysuccinimide ester, and the like), photoreactive conjugation reagents (e.g., p-azidobenzoyl hydrazide, N-5-azido-2-nitrobenzyloxysuccinimide, p-azidophenyl glyoxal monohydrate, N-(4-[p-azidosalicylamido] butyl)-3'-(2'-pyridyldithio) propionamide, bis(P-[4-azidosalicylamido]-ethyl) disulfide, N-hydroxysuccinimideyl-4-azidosalicyclic acid, N-hydroxysulfosuccinimidyl-4-azidobenzoate, sulfosuccinimidyl 2-(7-azido-4-methylcoumarin-3-acetamide)ethyl-1,3-dithiopropionate, azido phenyl 2-(m-azido-o-nitrobenzamido)-ethyl-1,3'-propionate, sulfosuccinimidyl 6-(4'-azido-2'-nitrophenylamino) hexanoate, sulfosuccinimidyl (4-azidophenyl dithio)propionate, sulfosuccinimidyl-2-(p-azidosalicylamido)ethyl-1,3-dithiopropionate, and the like).

In some instances, attachment of a capture agent of interest to the surface of plasmonic nanoparticles, quantum dots, or other light-sensitive particles is mediated by one or more functional linkers. A functional linker, as used herein, refers to any suitable linker that has one or more functional groups for the attachment of one molecule to another. For example, in some instances the functional linker comprises an amino functional group, a thiol functional group, a hydroxyl functional group, an imidazolyl functional group, a guanidinyl functional group, an alkyne functional group, an azide functional group, or a strained alkyne functional group. Further exemplary functional groups and methods of crosslinking and conjugation are described in, e.g., Hermanson Bioconjugate Techniques (Academic Press, 3rd edition, 2013), herein incorporated by reference in its entirety.

Culturing Cells in Optical Fibers

A hydrogel optical fiber can be used as a bioreactor for culturing cells. An optical fiber can be perfused with one or more types of cells, which can be cultured within a fiber-confined liquid core or hydrogel core environment. Proliferation of a cell can be monitored by culturing a cell within the core of an optical fiber; aligning a light source with an end of the optical fiber; and monitoring output light power from the optical fiber, wherein the output light power decreases with increasing cell density. External driven actuation such as magnetic or acoustic forces can be employed to arrange cells within the liquid core for the biofabrication of different biological architectures.

Any types of cells can be cultured in an optical fiber, including, without limitation, normal healthy cells, cancerous cells, inflammatory cells, damaged cells, diseased cells, or genetically modified cells. In certain embodiments, a non-human organism is grown in a hydrogel optical fiber. Non-human organisms may include, for example, without limitation, bacteria, archaea, protists, fungi, or algae. In some embodiments, the organism is transgenic or genetically modified. In some embodiments, a cell or organism is grown in the optical fiber, wherein the cell or organism is genetically modified to produce a product of interest.

In some embodiments, cells are obtained from a subject for the purpose of growing cultures of cells, populations of cells, tissue, or organoids in an optical fiber. The cells may be derived from any tissue, including connective tissue, muscle tissue, nervous tissue, or epithelial tissue. Cells may be obtained by any convenient method including, without limitation, by biopsy, e.g., during endoscopy, during surgery, by needle, etc., and are preferably obtained as aseptically as possible. In some embodiments, the cells are from a mammalian species such as, but not limited to a human, equine, bovine, porcine, canine, feline, rodent (e.g., mice, rats, hamster), or primate subject. The subject may be of any age, e.g., a fetus, neonate, juvenile, or adult.

Cells used in cultures can be primary cells obtained directly from a subject. Alternatively, the cells may be derived from the culture and expansion of a cell obtained from a subject or a cell obtained from a cell line. In some embodiments, the cell is an adult cell. In other embodiments, the cell is a progenitor cell or stem cell, or a differentiated cell derived from a progenitor cell or stem cell. Immortalized cells may also be used in cultures. In some embodiments, the cell has been genetically engineered to express a recombinant protein and/or nucleic acid.

Cells used in cultures may be obtained from any part of the body of a subject, including, without limitation, from the cardiovascular system, including the heart, blood, blood vessels, and lungs; digestive system, including the salivary glands, esophagus, stomach, liver, gallbladder, pancreas, intestines, colon, rectum and anus; endocrine system, including the endocrine glands such as the hypothalamus, pituitary gland, pineal body or pineal gland, thyroid, parathyroids and adrenals (adrenal glands); excretory system, including kidneys, ureters, bladder and urethra involved in fluid balance, electrolyte balance and excretion of urine; lymphatic system, including structures involved in the transfer of lymph between tissues and the blood stream, the lymph and the nodes and vessels that transport it, the immune system, including leukocytes, tonsils, adenoids, thymus and spleen; integumentary system, including skin, hair and nails of mammals, and scales of fish, reptiles, and birds, and feathers of birds; muscular system, including skeletal, smooth and cardiac muscles; nervous system, including the brain, spinal cord, nerves, and glia; reproductive system, including the sex organs, such as ovaries, fallopian tubes, uterus, vulva, vagina, testes, vas deferens, seminal vesicles, prostate and penis; respiratory system, including the organs used for breathing, the pharynx, larynx, trachea, bronchi, lungs and diaphragm; skeletal system, including bones, cartilage, ligaments and tendons.

Cells included in cultures may be of any type such as, but not limited to, exocrine secretory epithelial cells such as a Brunner's gland cell in the duodenum, insulated goblet cell of respiratory and digestive tracts, stomach cells such as foveolar cell (mucus secretion), a chief cell (pepsinogen secretion), parietal cell (hydrochloric acid secretion), and pancreatic acinar cell; a paneth cell of the small intestine, a type II pneumocyte of lung, a club cell of the lung; barrier cells such as a type I pneumocyte (lung), gall bladder epithelial cell, centroacinar cell (pancreas), intercalated duct cell (pancreas), and intestinal brush border cell (with microvilli); hormone-secreting cells such as an enteroendocrine cell, K cell, L cell, I cell, G cell, enterochromaffin cell, enterochromaffin-like cell, N cell, S cell, D cell, Mo cell, thyroid gland cells, thyroid epithelial cell, parafollicular cell, parathyroid gland cells, parathyroid chief cell, oxyphil cell, pancreatic islets (islets of Langerhans), alpha cell (secretes glucagon), beta cell (secretes insulin and amylin), delta cell (secretes somatostatin), epsilon cell (secretes ghrelin), pp cell (gamma cell), cells derived primarily from ectoderm such as exocrine secretory epithelial cells, salivary gland mucous cell, salivary gland serous cell, von Ebner's gland cell in tongue, mammary gland cell, lacrimal gland cell, ceruminous gland cell in ear, eccrine sweat gland dark cell, eccrine sweat gland clear cell, apocrine sweat gland cell, gland of moll cell in eyelid, sebaceous gland cell, and bowman's gland cell in nose; hormone-secreting cells such as anterior/intermediate pituitary cells, corticotropes, gonadotropes, lactotropes, melanotropes, somatotropes, thyrotropes, magnocellular neurosecretory cells, parvocellular neurosecretory cells, and chromaffin cells (adrenal gland); epithelial cells such as a keratinocyte, epidermal basal cell, melanocyte, trichocyte, medullary hair shaft cell, cortical hair shaft cell, cuticular hair shaft cell, Huxley's layer hair root sheath cell, Henle's layer hair root sheath cell, outer root sheath hair cell, surface epithelial cell of cornea, tongue, mouth, nasal cavity, distal anal canal, distal urethra, and distal vagina, basal cell (stem cell) of cornea, tongue, mouth, nasal cavity, distal anal canal, distal urethra, and distal vagina, intercalated duct cell (salivary glands), striated duct cell (salivary glands), lactiferous duct cell (mammary glands), ameloblast, oral cells such as an odontoblast and cementoblast; nervous system cells such as neurons, sensory transducer cells such as auditory inner hair cells of organ of Corti, auditory outer hair cells of organ of Corti, basal cells of olfactory epithelium, cold-sensitive primary sensory neurons, heat-sensitive primary sensory neurons, merkel cells of epidermis, olfactory receptor neurons, pain-sensitive primary sensory neurons, photoreceptor cells of retina in the eye such as photoreceptor rod cells, photoreceptor blue-sensitive cone cells of eye, photoreceptor green-sensitive cone cells of eye, and photoreceptor red-sensitive cone cells of eye; proprioceptive primary sensory neurons, touch-sensitive primary sensory neurons, chemoreceptor glomus cells of carotid body cell, outer hair cells of vestibular system of ear, inner hair cells of vestibular system of ear, taste receptor cells of taste bud, autonomic neuron cells, cholinergic neurons, adrenergic neural cells, peptidergic neural cells, sense organ and peripheral neuron supporting cells, inner pillar cells of organ of Corti, outer pillar cells of organ of Corti, inner phalangeal cells of organ of Corti, outer phalangeal cells of organ of Corti, border cells of organ of Corti, Hensen's cells of organ of Corti, vestibular apparatus supporting cells, taste bud supporting cells, olfactory epithelium supporting cells, olfactory ensheathing cells, schwann cells, satellite glial cells, enteric glial cells, central nervous system neurons and glial cells, interneurons basket cells, cartwheel cells, stellate cells, golgi cells, granule cells, lugaro cells, unipolar brush cells, martinotti cells, chandelier cells, Cajal-Retzius cells, double-bouquet cells, neurogliaform cells, retina horizontal cells, amacrine cells, starburst amacrine cells, spinal interneurons, renshaw cells, principal cells, spindle neurons, fork neurons, pyramidal cells, place cells, grid cells, speed cells, head direction cells, betz cells, stellate cells, boundary cells, bushy cells, Purkinje cells, medium spiny neurons, astrocytes, oligodendrocytes, ependymal cells, tanycytes, pituicytes, lens cells, anterior lens epithelial cell, crystallin-containing lens fiber cell; metabolism and storage cells such as adipocytes; white fat cell, brown fat cell, and liver lipocyte; secretory cells such as cells of the adrenal cortex, cells of the zona glomerulosa produce mineralocorticoids, cells of the zona fasciculata produce glucocorticoids, cells of the zona reticularis produce androgens, theca interna cell of ovarian follicle secreting estrogen, corpus luteum cell of ruptured ovarian follicle secreting progesterone, granulosa lutein cells, theca lutein cells, leydig cell of testes secreting testosterone, seminal vesicle cell, prostate gland cell, bulbourethral gland cell, Bartholin's gland cell, gland of littre cell, uterus endometrium cell, juxtaglomerular cell, macula densa cell of kidney, peripolar cell of kidney, and mesangial cell of kidney; urinary system cells such as parietal epithelial cell, podocyte, proximal tubule brush border cell, loop of henle thin segment cell, kidney distal tubule cell, kidney collecting duct cell, principal cell, intercalated cell, and transitional epithelium (lining urinary bladder); reproductive system cells such as duct cell (of seminal vesicle, prostate gland, etc.), efferent ducts cell epididymal principal cell, and epididymal basal cell; circulatory system cells, endothelial cells, extracellular matrix cells, planum semilunatum epithelial cell of vestibular system of ear, organ of *Corti* interdental epithelial cell, loose connective tissue fibroblasts, corneal fibroblasts (corneal keratocytes) tendon fibroblasts, bone marrow reticular tissue fibroblasts, other non-epithelial fibroblasts, pericyte, hepatic stellate cell (ito cell), nucleus pulposus cell of intervertebral disc, hyaline cartilage chondrocyte, fibrocartilage chondrocyte, elastic cartilage chondrocyte, osteoblast/osteocyte, osteoprogenitor cell, hyalocyte of vitreous body of eye, stellate cell of perilymphatic space of ear, and pancreatic stellate cell; contractile cells such as skeletal muscle cells, red skeletal muscle cell (slow twitch), white skeletal muscle cell (fast twitch), intermediate skeletal muscle cell, nuclear bag cell of muscle spindle, nuclear chain cell of muscle spindle, myosatellite cell (stem cell), cardiac muscle cells, cardiac muscle cell, SA node cell, Purkinje fiber cell, smooth muscle cell (various types) myoepithelial cell of iris myoepithelial cell of exocrine glands; blood and immune system cells such as an erythrocyte (red blood cell) and precursor erythroblasts megakaryocyte (platelet precursor) platelets, a monocyte, connective tissue macrophage (various types), epidermal langerhans cell osteoclast (in bone), dendritic cell (in lymphoid tissues), microglial cell (in central nervous system), neutrophil granulocyte and precursors (myeloblast, promyelocyte, myelocyte, metamyelocyte), an eosinophil granulocyte and precursors basophil granulocyte and precursors, a mast cell, helper T cell, regulatory T cell, cytotoxic T cell, natural killer T cell, B cell, plasma cell, natural killer cell, and hematopoietic stem cells; germ cells such as an oogonium/oocyte, spermatid, spermatocyte, spermatogonium cell, spermatozoon, nurse cell, granulosa cell, sertoli cell, and epithelial reticular cell; and interstitial cells such as interstitial kidney cells.

In some embodiments, the cells are stem cells or stem cell-derived cells. Stem cells of interest include, without limitation, hematopoietic stem cells, embryonic stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, hematopoietic stem cells, induced pluripotent stem cells; and the like; as well as differentiated cells that can be cultured in vitro and used in a therapeutic regimen, where such cells include, but are not limited to, keratinocytes, adipocytes, cardiomyocytes, neurons, osteoblasts, pancreatic islet cells, retinal cells, and the like.

Suitable human embryonic stem (ES) cells include, but are not limited to, any of a variety of available human ES lines, e.g., BG01 (hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIII) code, followed in parentheses by the provider code.

Hematopoietic stem cells (HSCs) are mesoderm-derived cells that can be isolated from bone marrow, blood, cord blood, fetal liver and yolk sac. HSCs are characterized as CD34+ and CD3". HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

Mesenchymal stem cells (MSC), originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC.

An induced pluripotent stem (iPS) cells is a pluripotent stem cell induced from a somatic cell, e.g., a differentiated somatic cell. iPS cells are capable of self-renewal and differentiation into cell fate-committed stem cells, including neural stem cells, as well as various types of mature cells. iPS cells can be generated from somatic cells, including skin fibroblasts, using, e.g., known methods. iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and K1f4. In some embodiments, somatic cells are genetically modified with one or more expression constructs comprising nucleotide sequences encoding Oct-4, Sox2, Nanog, and LIN28. Methods of generating iPS are known in the art, and any such method can be used to generate iPS.

In some cases, the cells are lymphocytes, such as CD4+ and/or CD8+T lymphocytes, or B lymphocytes. In some embodiments, the therapeutic cells are cytotoxic T lymphocytes. In some embodiments, the lymphocytes are genetically modified lymphocytes, e.g., chimeric antigen receptor (CAR) T lymphocytes. The lymphocytes, e.g., cytotoxic T lymphocytes, may specifically recognize an antigen that is associated with a disease, e.g., cancer or tumor.

In some embodiments, the cells include insulin-secreting cells. The insulin-secreting cells may be any suitable type of insulin-secreting cell. In some cases, the insulin-secreting cells are a type of cell that secretes insulin (e.g., pancreatic ß islet cells, or ß-like cells). In some cases, the insulin-secreting cells are primary ß islet cells (e.g., mature ß islet cells isolated from a pancreas). In some cases, the insulin-secreting cells are ß cells, or ß-like cells that are derived in vitro from immature cell, precursor cells, progenitor cells, or stem cells. The insulin-secreting cells may be derived from (i.e., obtained by differentiating) stem and/or progenitor cells such as hepatocytes (e.g., transdifferentiated hepatocytes), acinar cells, pancreatic duct cells, stem cells, embryonic stem cells (ES), partially differentiated stem cells, non-pluripotent stem cells, pluripotent stem cells, induced pluripotent stem cells (iPS cells), etc. Suitable insulin-secreting cells and methods of generating the same are described in, e.g., US20030082810; US20120141436; and Raikwar et al. (PLOS One. 2015 Jan. 28; 10(1): e0116582), each of which are incorporated herein by reference.

Various culture media, methods of generating tissue explants and organoids, and methods of culturing cells, tissue, and organoids are known in the art. See, e.g., Methods in Enzymology Volume 58 on Cell Culture, edited by N. P. Kaplan, N. P. Colowick, W. B. Jakoby, and I. H. Pastan, Academic Press, 1st edition, 1979; Freshney and Capes-Davis, Freshney's Culture of Animal Cells: A Manual of Basic Technique and Specialized Applications, Wiley-Blackwell, 8th edition, 2021; 3D Cell Culture: Methods and Protocols (Methods in Molecular Biology, 695), edited by J. Haycock, Humana, 2011th edition, 2010; Organoids and Mini-Organs, edited by J. Davies and M. Lawrence, Academic Press, 1st edition, 2018; Organoids: Stem Cells, Structure, and Function (Methods in Molecular Biology, 1576), Springer, 1st edition, 2019; and Human Pluripotent Stem Cell Derived Organoid Models (Volume 159) (Methods in Cell Biology, Volume 159), Academic Press, 1$^{st}$ edition, 2020; herein incorporated by reference in their entireties.

The growth of cultures may be confirmed by any convenient method, e.g., phase contrast microscopy, stereomicroscopy, histology, immunohistochemistry, electron microscopy, fluorescence microscopy, etc. In some instances, cellular ultrastructure and multi-lineage differentiation may be assessed. Ultrastructure of a culture can be determined by performing hematoxylin-eosin staining, proliferating cell nuclear antigen (PCNA) staining, electron microscopy, and the like using methods known in the art. Multi-lineage differentiation can be determined by performing labeling with antibodies to terminal differentiation markers. Antibodies to detect differentiation markers are commercially available from a number of sources.

In some embodiments, the cells in cultures may be experimentally modified. For example, cells may be modified by exposure to viral or bacterial pathogens, e.g., to develop a reagent for experiments to assess the anti-viral or anti-bacterial effects of therapeutic agents. The cells may be modified by altering patterns of gene expression, e.g., by providing reprogramming factors to induce pluripotency or otherwise alter differentiation potential, or to determine the effects of a gain or loss of gene function.

In some embodiments, cells cultured within the core of an optical fiber are treated with a test agent to determine if the test agent inhibits or promotes cell proliferation. The cell is contacted with the test agent and a light source is aligned with an end of the optical fiber. The effect of the test agent on cell proliferation is determined by monitoring output light power from the optical fiber. In some embodiments, anticancer agents are screened for their effects on proliferation of cancer cells within the core of an optical fiber using the methods described herein. Assays may further include suitable controls (e.g., a cell grown in the absence of the test agent). Generally, a plurality of assay mixtures is run in parallel with different agent concentrations to obtain a differential response to the various concentrations. Typically, one of these concentrations serves as a negative control, i.e., at zero concentration or below the level of detection.

Introduction of Air Bubbles for Air-Light Interaction and Sonoluminescence

By replacing the inner hydrogel material by an air flow, the introduction of air droplets within the optical fiber core is possible. The air bubbles, trapped in the hydrogel core, scatter light due to the abrupt decrease in refractive index at the hydrogel-air interface. The distribution of droplets along the fiber can be controlled to reduce the intensity of traveling light as a function of distance. In some embodiments, air is stimulated through high intensity acoustic bursts, causing the air bubbles to collapse and emit light (sonoluminescence), which is guided through the optical fiber. In certain embodiments, one or more types of input stimuli are applied such as, but not limited to, acoustic, electric, magnetic, or mechanical stimuli, which modulate the optical output from the fiber.

Kits

Also provided are kits comprising a hydrogel optical fiber, or reagents for fabricating a hydrogel optical fiber, as described herein. In some embodiments, the kit comprises an optical fiber system having a multi-input fiber optic architecture and/or a multi-output fiber optic architecture. In some embodiments, the kit further comprises reagents for fusing optical fibers together (chelating agent, divalent cations, polysaccharide for producing a hydrogel). In certain embodiments, the kit further comprises a light source such as a laser diode or LED that can be coupled to a hydrogel optical fiber. In some embodiments, the optical fibers are contained in a sterile package.

In addition to the above components, the subject kits may further include (in certain embodiments) instructions for practicing the subject methods. In some embodiments, instructions for using the hydrogel optical fibers are provided in the kits. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), DVD, flash drive, SD drive, and the like, on which the information has been recorded. Yet another form of these instructions that may be present is a website address which may be used via the internet to access the information at a removed site.

It will be apparent to one of ordinary skill in the art that various changes and modifications can be made without departing from the spirit or scope of the invention.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-78 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. An optical fiber comprising:
   a) one or more hydrogel cladding layers comprising polysaccharides crosslinked ionically by metal cations; and
   b) a core, wherein the core is encapsulated by the one or more hydrogel cladding layers.
2. The optical fiber of aspect 1, wherein the hydrogel cladding layers comprise gellan gum or alginate.
3. The optical fiber of aspect 1 or 2, wherein the hydrogel cladding layers comprise about 0.1 weight % to 1.0 weight % gellan gum.
4. The optical fiber of aspect 1 or 2, wherein the hydrogel cladding layers comprise about 1.0 weight % to 2.0 weight % alginate.
5. The optical fiber of any one of aspects 1-4, wherein the hydrogel cladding layers have a lower refractive index than the core of the optical fiber.
6. The optical fiber of any one of aspects 1-5, wherein the metal cations comprise alkaline earth metal cations.
7. The optical fiber of aspect 6, wherein the alkaline earth metal cations are divalent calcium cations ($Ca^{2+}$).
8. The optical fiber of any one of aspects 1-7, wherein the core is a hydrogel core, a liquid core, a hollow core, or a gaseous core.
9. The optical fiber of aspect 8, wherein the hydrogel core comprises alginate or gellan gum.

10. The optical fiber of aspect 9, wherein the hydrogel core comprises about 2 weight % to about 7 weight % alginate.

11. The optical fiber of aspect 9, wherein the hydrogel core comprises about 1.0 weight % to about 1.5 weight % gellan gum.

12. The optical fiber of aspect 8, wherein the core comprises a non-polysaccharide polymer.

13. The optical fiber of aspect 8, wherein the hydrogel core comprises a mixture of at least two ionically crosslinked polysaccharides or at least one ionically crosslinked polysaccharide and a non-polysaccharide hydrogel polymer.

14. The optical fiber of aspect 1, wherein the core further comprises an extracellular matrix component, a basement membrane extract, or a biological lysate.

15. The optical fiber of any one of aspects 8-14, wherein the hydrogel cladding layers and the hydrogel core have a step-index or gradient-index architecture.

16. The optical fiber of any one of aspects 8-14, wherein the hydrogel cladding layers have alternating refractive index values.

17. The optical fiber of any one of aspects 8-14, wherein the optical fiber has a gradient of refractive index values along the length of the optical fiber.

18. The optical fiber of any one of aspects 8-17, wherein the optical fiber comprises 1 to 10 hydrogel cladding layers.

19. The optical fiber of any one of aspects 8-18, wherein the hydrogel core comprises polysaccharides crosslinked ionically by metal cations.

20. The optical fiber of aspect 19, wherein the hydrogel core is doped with rare earth metal cations.

21. The optical fiber of aspect 20, wherein the rare earth metal cations are neodymium or erbium cations.

22. The optical fiber of aspect 21, wherein the hydrogel cladding layers are crosslinked ionically by $Ca^{2+}$ and the hydrogel core is doped with Nd3+.

23. The optical fiber of any one of aspects 1-22, further comprising a shielding layer.

24. The optical fiber of aspect 23, wherein the shielding layer comprises alginate or gellan gum.

25. The optical fiber of aspect 24, wherein the shielding layer comprises 1 weight % to 2 weight % alginate or 0.5 weight % to 1.5 weight % gellan gum.

26. The optical fiber of any one of aspects 1-25, wherein the optical fiber has a multi-input architecture or a multi-output architecture.

27. The optical fiber of any one of aspects 1-25, wherein the optical fiber has a multi-input architecture and a multi-output architecture.

28. The optical fiber of any one of aspects 1-27, further comprising a plasmonic nanoparticle or a quantum dot, wherein the plasmonic nanoparticle or the quantum dot is encapsulated within the core.

29. The optical fiber of aspect 28, wherein the plasmonic nanoparticle comprises a noble metal, a metal-oxide, a transition metal nitride, or a plasmonic metal-metal oxide nanocomposite.

30. The optical fiber of aspect 29, wherein the noble metal is gold.

31. The optical fiber of aspect 28, wherein the quantum dot comprises silicon, germanium, lead sulfide, lead selenide, cadmium selenide, cadmium sulfide, cadmium telluride, indium arsenide, or indium phosphide.

32. The optical fiber of any one of aspects 28-31, further comprising a capture agent that selectively binds to a target of interest, wherein said capture agent is attached to the outer surface of the plasmonic nanoparticle or the quantum dot.

33. The optical fiber of aspect 32, wherein the target is an antigen, an antibody, a protein, a nucleic acid, a metabolite, a toxin, a drug, a pollutant, a cell, a virus, a bacterium, a parasite, a tissue, an organoid, or an organism.

34. The optical fiber of aspect 32 or 33, wherein the capture agent is an antibody, an antibody mimetic, an aptamer, a peptoid, or a ligand.

35. The optical fiber of aspect 34, wherein the antibody selectively binds to a spike protein of severe acute respiratory syndrome coronavirus 2 (SARS-COV-2).

36. The optical fiber of aspect 34 or 35, wherein the plasmonic nanoparticle or quantum dot is functionalized with protein-G.

37. The optical fiber of aspect 36, wherein the antibody is bound to the protein-G.

38. The optical fiber of any one of aspects 1-37, further comprising an endotracheal tube or a medical swab coupled to the optical fiber.

39. The optical fiber of any one of aspects 1-38, further comprising a cell encapsulated within the core.

40. The optical fiber of aspect 39, wherein the cell is fluorescently labeled.

41. The optical fiber of aspect 39 or 40, wherein the cell expresses a fluorescent protein.

42. The optical fiber of any one of aspects 1-41, wherein the core has a continuous diameter, a varying diameter, or is discontinuous along the length of the optical fiber.

43. A photonic device comprising the optical fiber of any one of aspects 1-42.

44. The photonic device of aspect 43, further comprising a medical swab or an endotracheal tube coupled to the optical fiber.

45. The photonic device of aspect 43 or 44, further comprising a light source coupled to the optical fiber.

46. The photonic device of aspect 45, wherein the light source is a laser diode, a light-emitting diode (LED), a superluminescent diode, a microfocus X-ray source, or a lamp.

47. The photonic device of aspect 45 or 46, further comprising optics to focus light from the light source into the core of the optical fiber.

48. The photonic device of any one of aspects 43-47, further comprising a photodetector.

49. The photonic device of aspect 48, wherein the photodetector is a charge-coupled device (CCD), an active-pixel sensor (APS), or a CMOS sensor.

50. A method of detecting a target of interest, the method comprising measuring the plasmonic response of the plasmonic nanoparticle or the spectral response or change in photoluminescent lifetime of the quantum dot encapsulated within the core of the optical fiber of any one of aspects 28-42 upon binding of the target of interest to the capture agent.

51. A method of guiding light to a target using the optical fiber of any one of aspects 1-42, the method comprising:

placing the optical fiber of any one of aspects 1-42 such that a first end of the optical fiber is attached to or near the target; and aligning a light source with a second end of the optical fiber, wherein light from the light source passes through the optical fiber to the target.

52. The method of aspect 51, wherein the target is a cell, a tissue, an organoid, an organism, or a light-activated prodrug.

53. The method of aspect 52, wherein the target is optogenetically modified.

54. The method of any one of aspects 51-53, wherein the light source is a broadband light source or a narrow-band light source.

55. The method of aspect 54, wherein the light source is a laser diode, a light-emitting diode (LED), a superluminescent diode, a microfocus X-ray source, or a lamp.

56. The method of any one of aspects 52-55, further comprising attaching an endotracheal tube to the optical fiber and inserting the endotracheal tube into the organism.

57. The method of any one of aspects 51-56, further comprising introducing a bubble into the core of the optical fiber.

58. The method of any one of aspects 51-57, further comprising applying an acoustic stimulus, an electric stimulus, a magnetic stimulus, or a mechanical stimulus to the optical fiber, wherein optical output from the optical fiber is modulated.

59. The method of aspect 58, wherein sonoluminescence is produced from applying the acoustic stimulus.

60. A kit comprising the optical fiber of any one of aspects 1-42 and instructions for using the optical fiber.

61. A method of monitoring proliferation of a cell, the method comprising:
culturing the cell within the core of the optical fiber of any one of aspects 1-42;
aligning a light source with an end of the optical fiber; and
monitoring output light power from the optical fiber, wherein the output light power decreases with increasing cell density resulting from proliferation of the cell.

62. The method of aspect 61, wherein the cell is a cancer cell.

63. The method of aspect 61 or 62, further comprising contacting the cell with a test agent.

64. A method of monitoring expression of a fluorescently labeled protein in a cell, the method comprising:
introducing the cell into the core of the optical fiber of any one of aspects 1-42, wherein the fluorescently labeled protein is expressed in the cell;
exposing the cell to excitation light guided by the optical fiber; and monitoring fluorescent light or a decrease in excitation-range light transmission intensity output from the optical fiber.

65. The method of aspect 64, further comprising contacting the cell with a test agent.

66. A method of guiding light to a target using the optical fiber of any one of aspects 1-42, the method comprising:
introducing the target into the core of the optical fiber of any one of aspects 1-42; and
aligning a light source with an end of the optical fiber, wherein light from the light source passes through the optical fiber to the target.

67. The method of aspect 66, wherein the target is a cell, a tissue, an organoid, an organism, or a light-activated prodrug.

68. The method of aspect 67, wherein the target is optogenetically modified.

69. The method of any one of aspects 66-68, wherein the light source is a broadband light source or a narrow-band light source.

70. The method of aspect 69, wherein the light source is a laser diode, a light-emitting diode (LED), a superluminescent diode, a microfocus X-ray source, or a lamp.

71. The method of any one of aspects 66-70, further comprising introducing a bubble into the core of the optical fiber.

72. The method of any one of aspects 66-71, further comprising applying an acoustic stimulus, an electric stimulus, a magnetic stimulus, or a mechanical stimulus to the optical fiber, wherein optical output from the optical fiber is modulated.

73. The method of aspect 72, wherein sonoluminescence is produced from applying the acoustic stimulus.

74. A method of activating a photoactivatable prodrug, the method comprising:
administering the photoactivatable prodrug to a subject;
exposing the photoactivatable prodrug to excitation light guided by the optical fiber of any one of aspects 1-42, wherein activity of the prodrug is increased in response to exposure to the excitation light.

75. The method of aspect 74, wherein the optical fiber is used to guide light to a target site, wherein the prodrug is selectively activated at the target site.

76. The method of aspect 74 or 75, wherein the photoactivatable prodrug is a photoactivatable anticancer drug, and the excitation light is guided by the optical fiber to a tumor to activate the prodrug selectively at the site of a tumor.

77. A method of performing photodynamic therapy (PDT), the method comprising:
administering a photosensitizing chemical substance to a subject; and
exposing the photosensitizing chemical substance to excitation light guided by the optical fiber of any one of aspects 1-42, wherein radicals or reactive oxygen species are generated by the photosensitizing chemical substance in response to exposure to the excitation light.

78. The method of aspect 77, wherein the optical fiber is used to guide light to a target site, wherein the radicals or reactive oxygen species are selectively generated at the target site.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1

Polysaccharide Hydrogel Optical Fibers and Tunable Photonic Architectures for Multi-Scale Sensing and Biomedical Detection Herein, we present multi-layered hydrogel optical fibers based solely on ionic-crosslinking, cytocompatible, natural polysaccharides, taking advantage of high-throughput wet-spinning fabrication 21.22. First, we describe how the widely used polysaccharides alginate and gellan gum 23.24 can be manipulated to guide light in step-index optical fibers. Second, we demonstrate how these soft and reversibly crosslinked structures can be used to assemble varied photonic architectures capable of reporting on force and 3D shape and simultaneously guide different wavelength light. Third, we leverage the high permeability of these materials versus silica 25.26 to create a plasmonic platform, where resonance-induced shifts in spectra can inform on molecular target's presence, proven by the detection of SARS-COV-2 antigens and viruses.

Lastly, we take advantage of the material's cytocompatibility and common crosslinking across all layers to continuously print living optical fibers. Living entities interact with light within the fibers, leading to fast, non-invasive optical readouts which digitalize complex biological phenomena such as cancer proliferation and drug susceptibility into directly quantifiable data. These structures are highly tunable and of facile fabrication, thus adaptable by other researchers for a plethora of biomedically relevant applications.

Results

Fabrication of Ionic Polysaccharide Hydrogel Optical Fibers

Figure 1B:
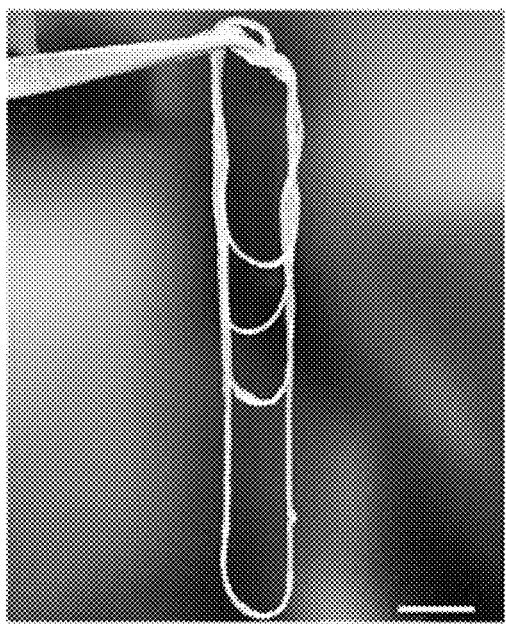
Figure 1C:
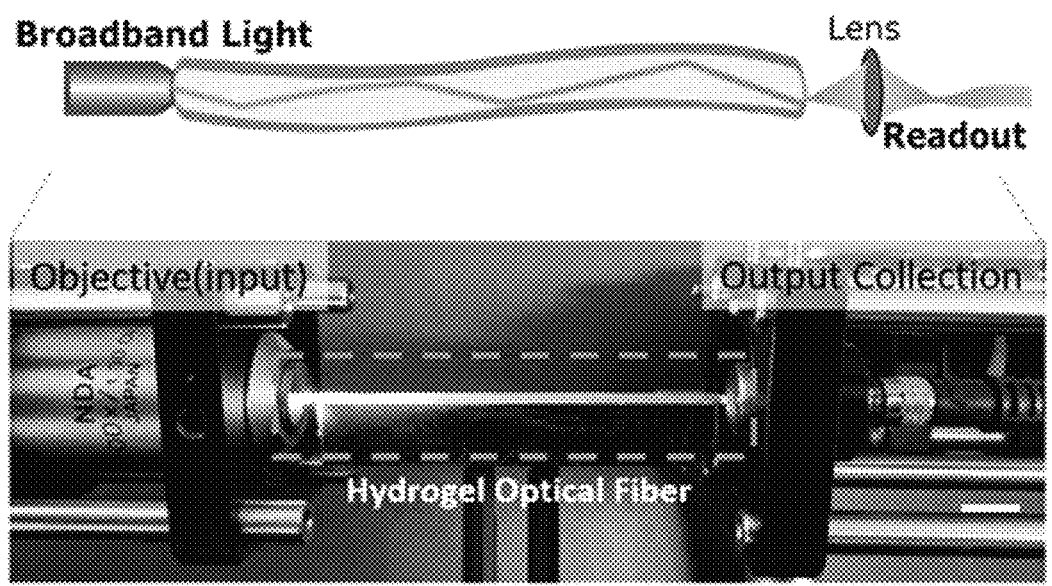

We investigated the continuous fabrication of tunable ionic sugar-based hydrogel optical fibers based on the highly dynamic crosslinking properties of natural polysaccharides (FIG. 6). Fibers were fabricated by wet-spinning the polysaccharide hydrogel precursor into a crosslinking bath, followed by coating and crosslinking of different hydrogel layers to obtain varying core-clad refractive indexes (either step-index or gradient-index hydrogel fibers) (FIGS. 1A, 1B, Tables 1 and 2). These can easily couple with a light source, guiding light towards an output collector for analysis (FIG. 1C).

Figure 1D:
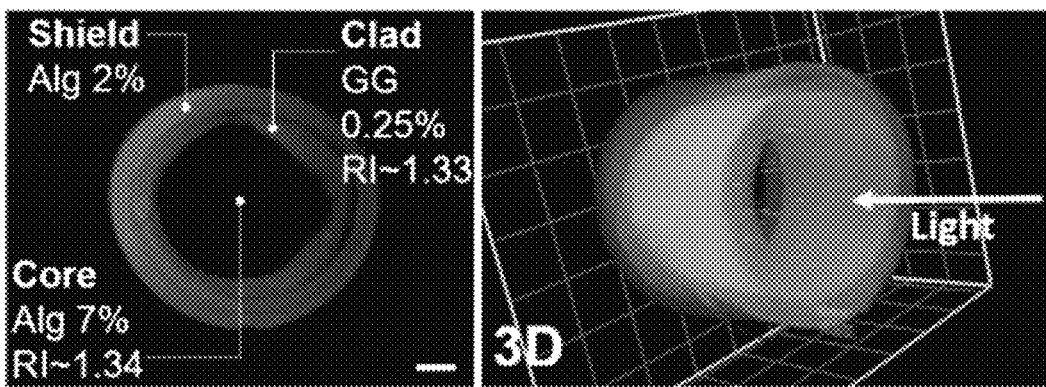
Figure 7A:
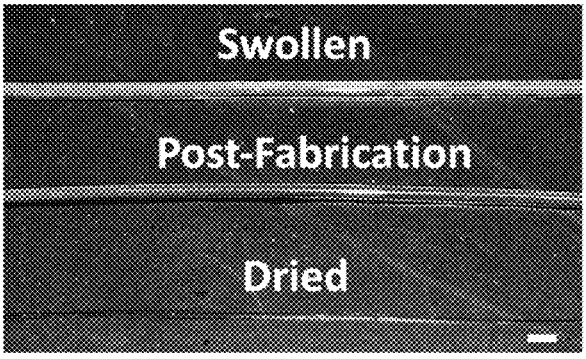
FIGS. 7A-7C: Comparison of fibers as fabricated, swollen and dried (FIG. 7A), together with the swelling (FIG. 7B) and drying (FIG. 7C) quantitative data over a period of 24 h for both core only and full core-clad-shield fibers. Scale bar: 1 mm.
Figure 7B:
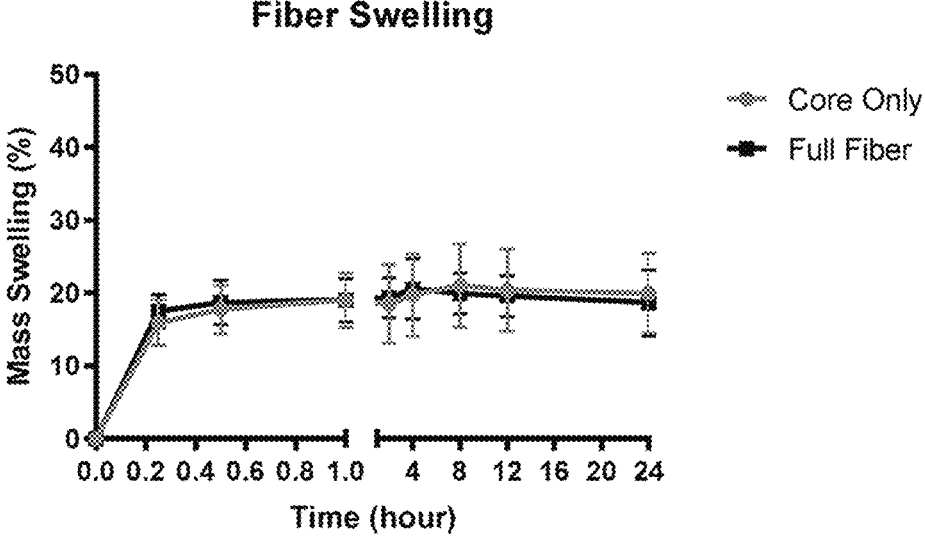
Figure 7C:
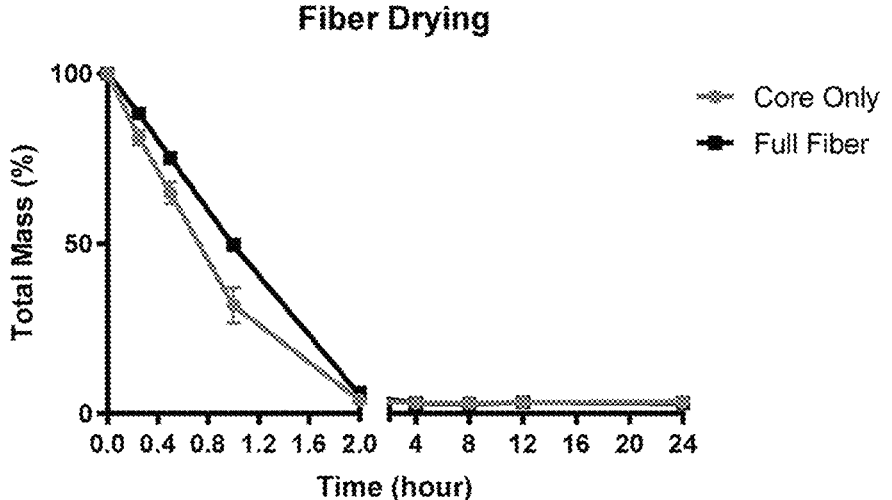

To optimize light-guiding capabilities, we studied how the refractive index (RI) of Gellan Gum (GG) and alginate changed with varying concentrations. We observed a linear relationship between polymer concentration and RI for both materials (FIG. 6), evidencing similar RI at same concentrations, despite known different molecular weights and consequent viscoelastic properties 27.28. To maximize total internal reflection, we investigated the lowest GG (0.25%) and highest alginate (7%) concentrations, at which solutions could still be manipulated and yield stable hydrogels while enabling a considerable RI difference (~0.01) (FIG. 6). To protect the low-concentration GG cladding, 2% alginate was added as a shielding layer, a common silica fiber optics approach. This distinct type of hydrogel core-clad-shield architecture was possible and resulted in well-structured fibers (FIG. 1D) with moderate swelling behavior (FIG. 7).

Figure 1E:
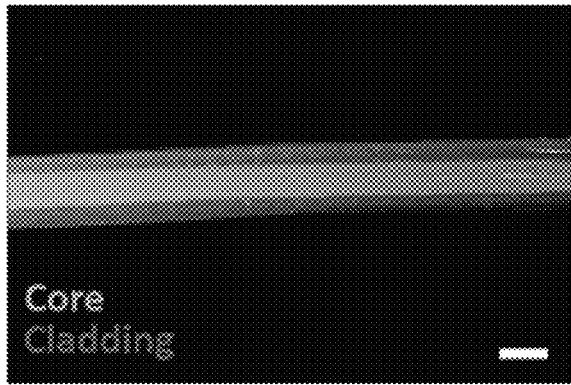
Figure 1F:
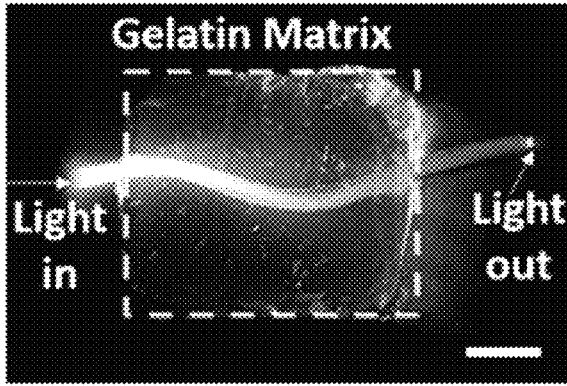
Figure 1G:
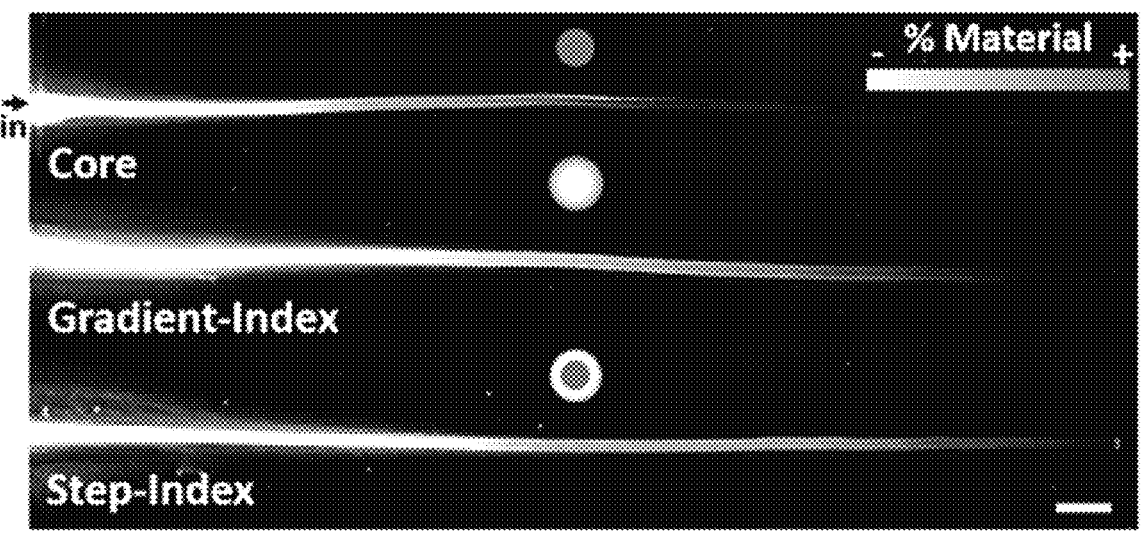
Figure 1H:
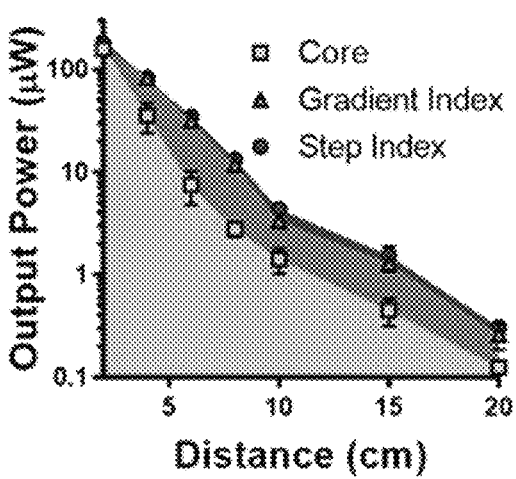
Figure 1I:
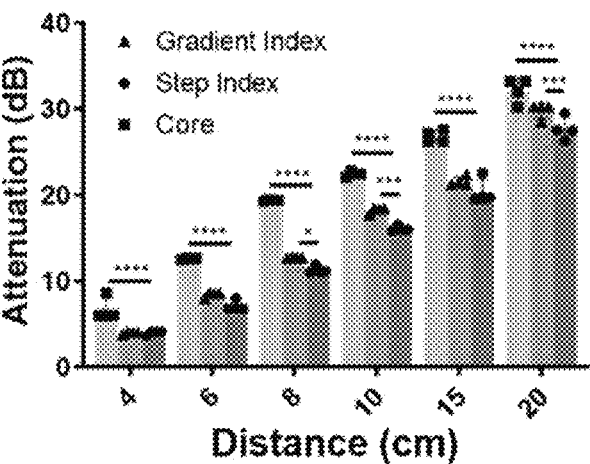
Figure 8:
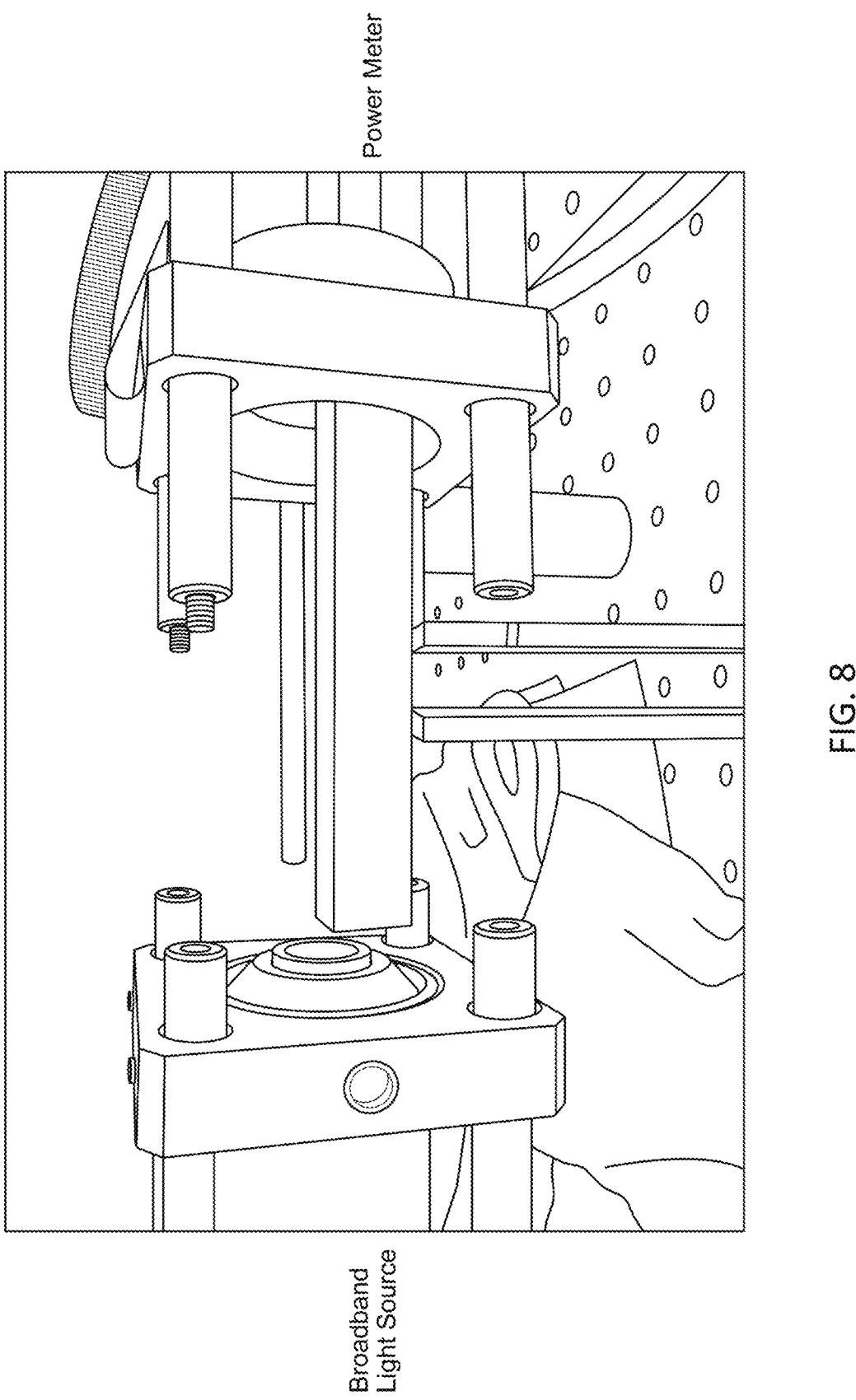
FIG. 8: Photograph of the setup used for Power Meter quantification of light output power.

We characterized the optical power of guided broadband light over distance (FIG. 8). The ability of cladding layers to contain light within the core (FIG. 1E) improved light-guiding even within higher RI environments, as with fibers inserted into a 3D denatured collagen (gelatin) matrix (FIG. 1F). Cladding layers significantly reduced light attenuation and led to efficient light guiding to lengths over 20 cm (FIGS. 1G-1I). Similar distances have been reported for synthetic hydrogel fibers 17, but in this case with lower RI differences. Step-index fibers performed significantly better than gradient-index ones (FIG. 1I, Tables 1 and 2), and as such were selected for further testing.

Exploring the Versatility of Soft, Ionic Crosslinked Hydrogel Optical Fibers

Figure 2A:
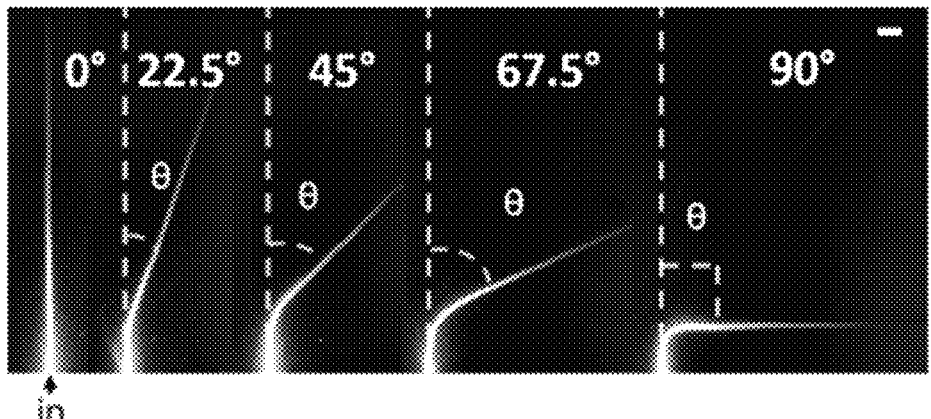
FIGS. 2A-2L: Exploring ionic soft hydrogel versatility and fusion splicing for responsiveness to macro-scale force and shape—FIG. 2A) Photographs of light guidance in fibers at increasing angles of bending. The black arrow shows light input direction (in). Scale bar: 1 cm.
Figure 2B:
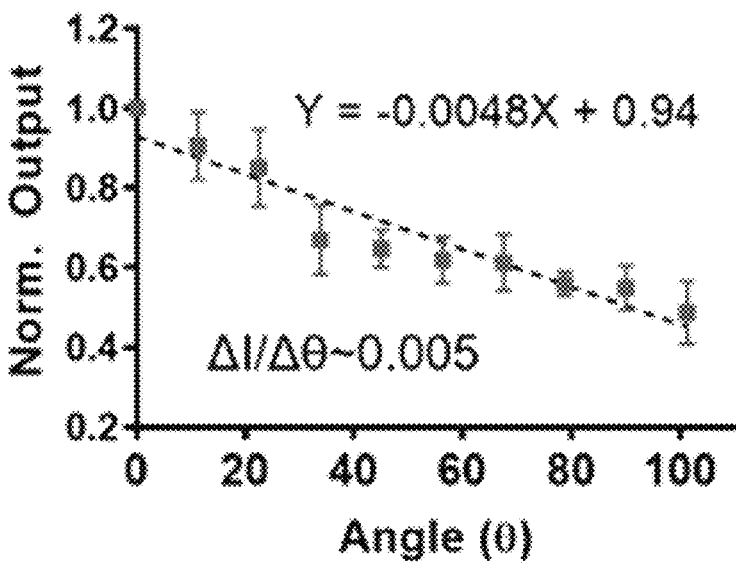
Figure 2C:
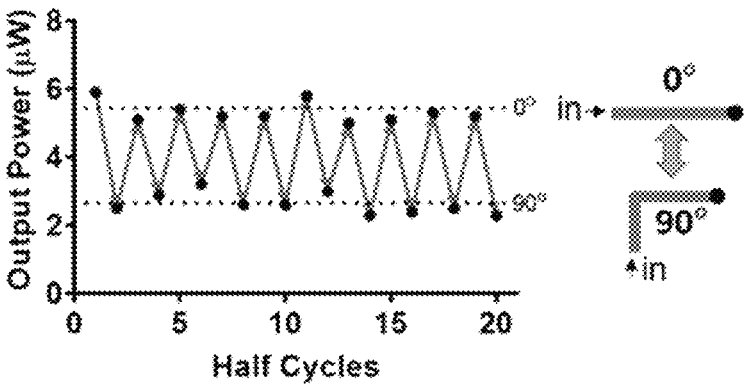

After linear light-guiding, we investigated the modulation of the optical readout under physical stimuli on these easily deformable structures. We tested the fibers' light guidance upon bending (FIG. 2A), observing linearly decreasing output power with increasing bending angles (FIG. 2B), similar to previous reports on synthetic hydrogel fibers 17. Cyclic bending demonstrated complete light-guiding recovery with output powers maintained over ten full cycles (FIG. 2C).

Figure 9A:
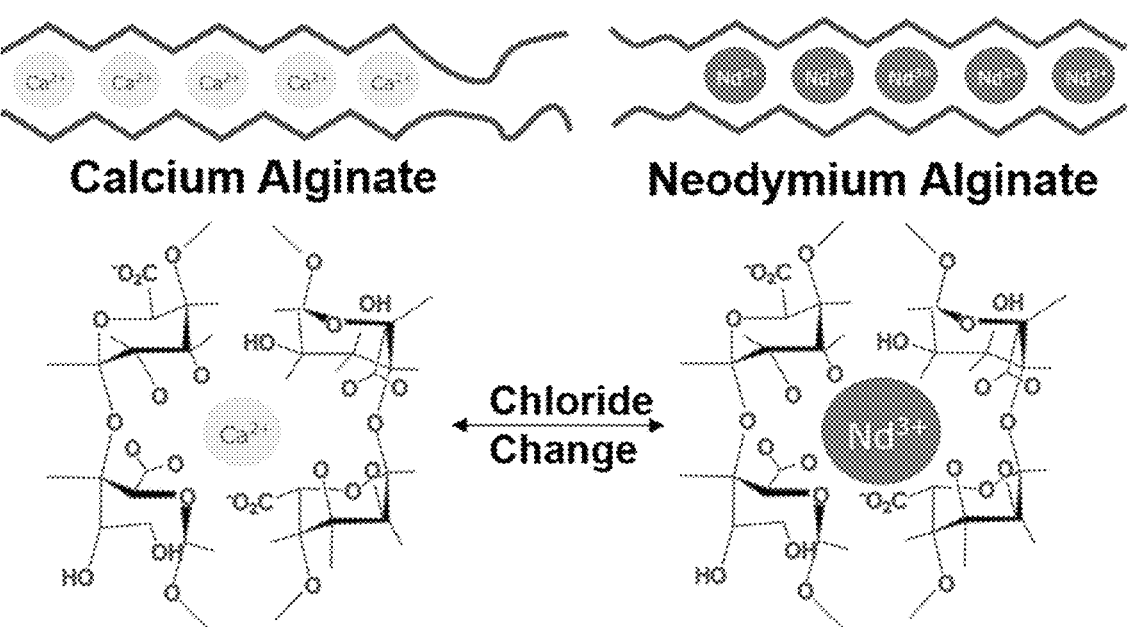
FIGS. 9A-9C.
Figure 9B:
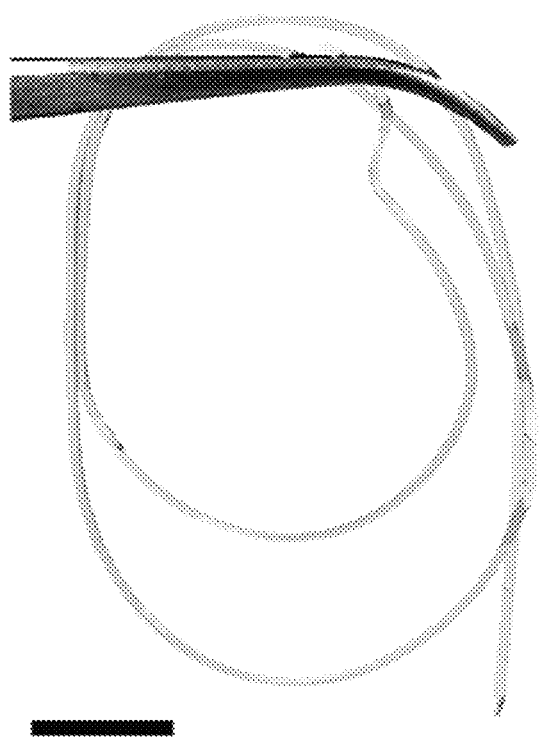
Figure 9C:
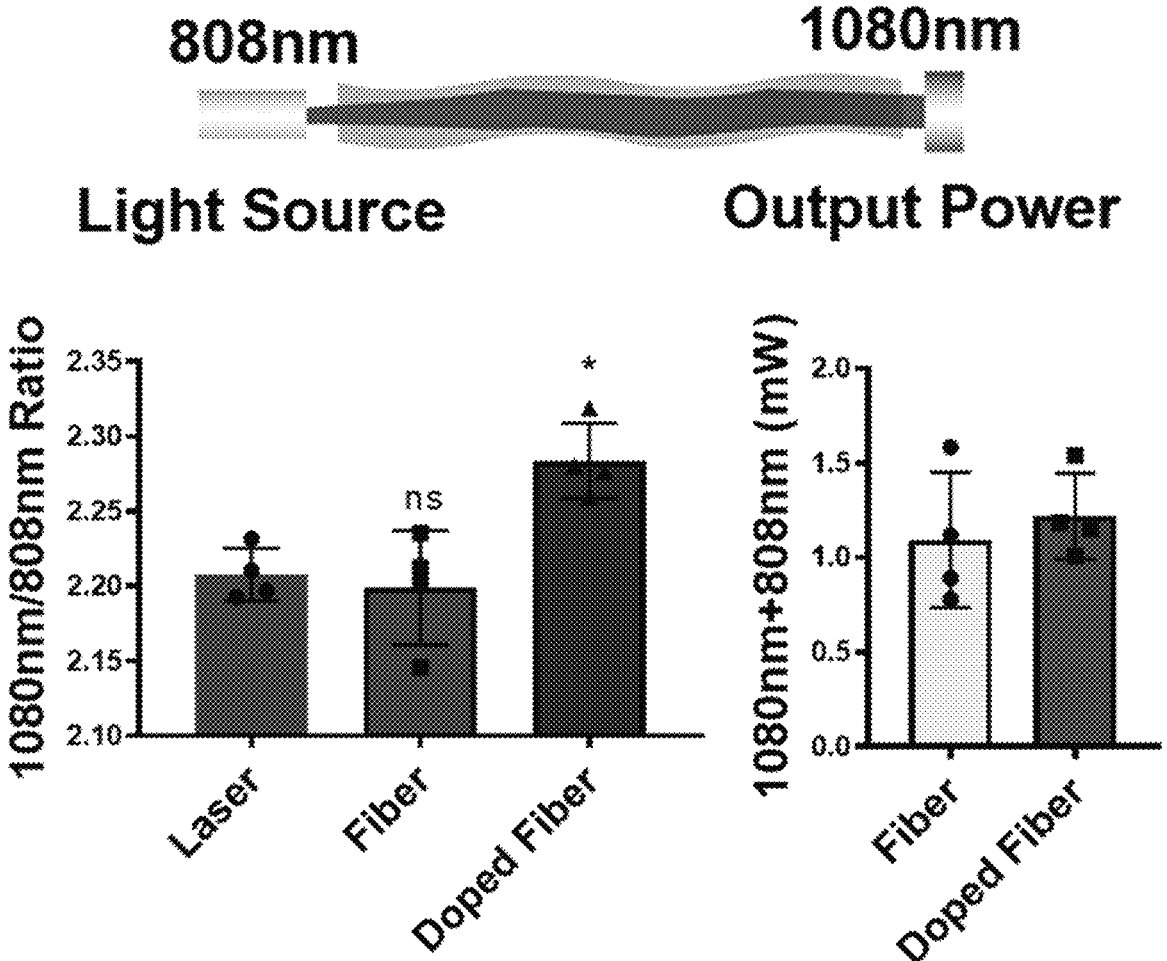

We then explored the reversibility of a fully ionic-crosslinked structure to approach essential fiber optics advances—doping and fusion splicing. We observed that the ionic crosslinking can be easily adapted to the introduction of rare-earth metals for doping fibers in a very facile manner (FIG. 9), as opposed to the more complex silica rare-earth doping 5.29.

Figure 2D:
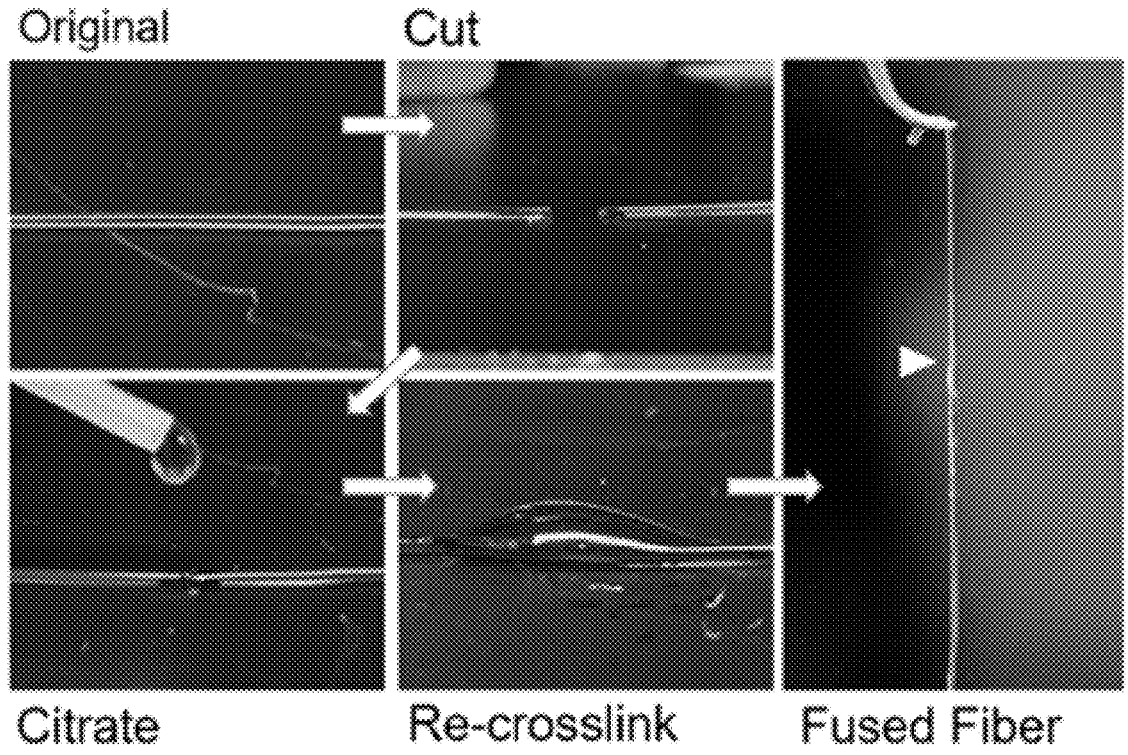
Figure 2E:
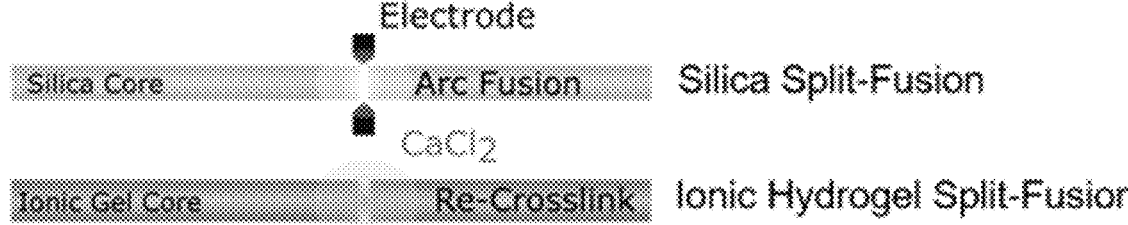
Figure 2F:
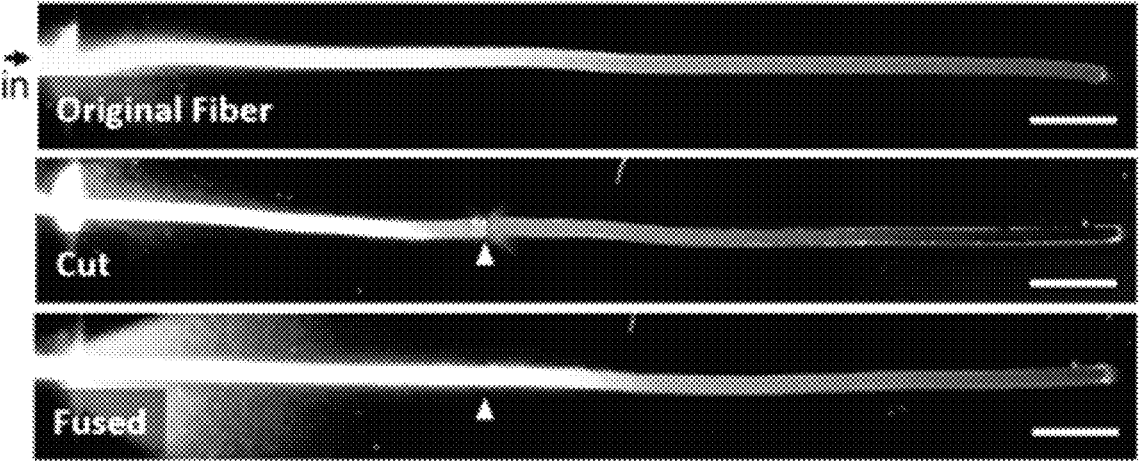
Figure 2G:
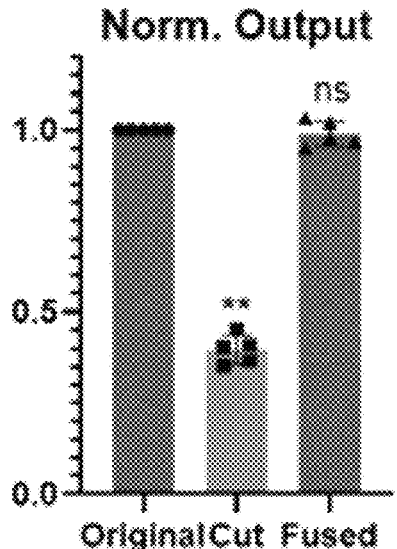
Figure 2H:
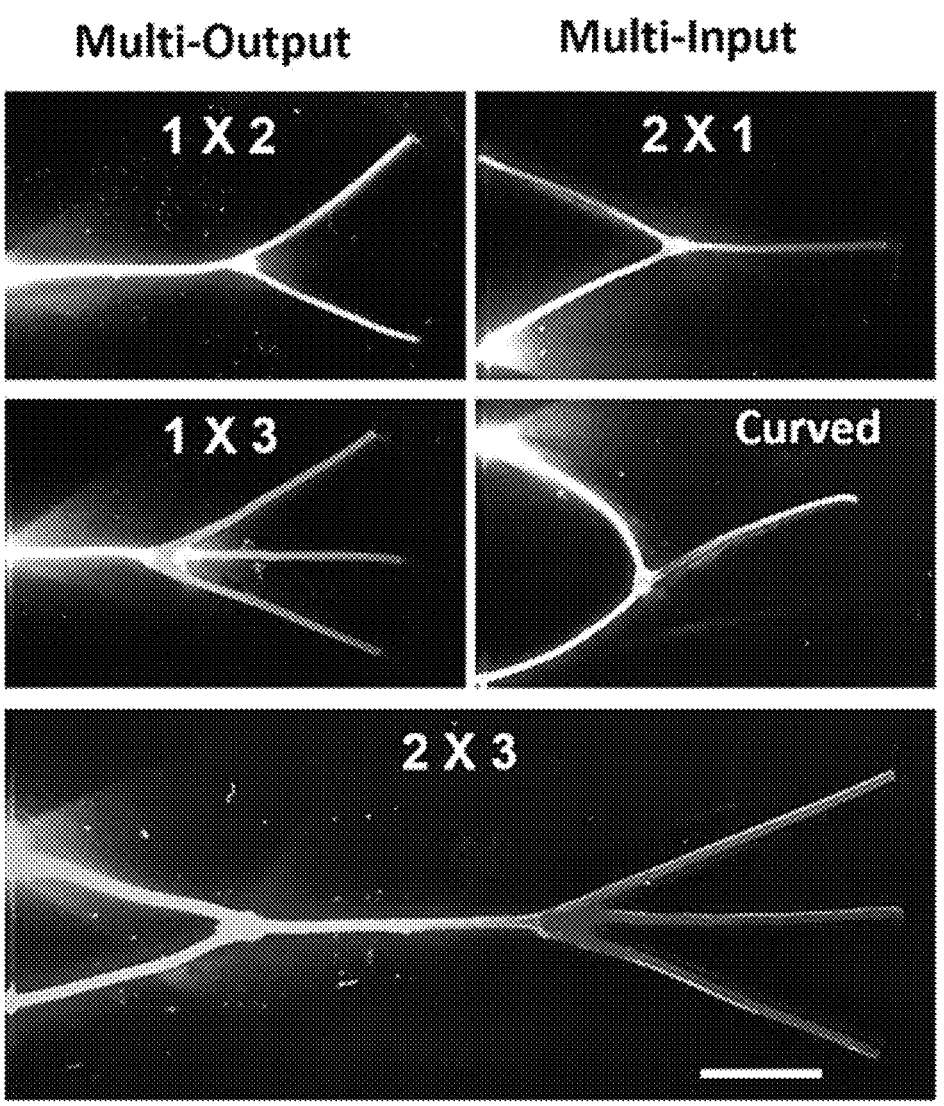

We hypothesized that ionic crosslinking's reversibility could also be explored towards fusion splicing. We developed a materials method in which fibers separated by a full incision were fused in facile steps. First, a local de-crosslinking of the fiber tips by chelating calcium ions with sodium citrate. Second, with the ends in proximity, interfacing alginate and re-crosslinking by adding calcium chloride (FIG. 2D). The fused fibers were stable (FIG. 2E) and fully recovered light-guiding capacities, validating this fusion splicing technique as a hydrogel equivalent to traditional silicon approaches (FIGS. 2F-2H).

Figures 2I, 2J:
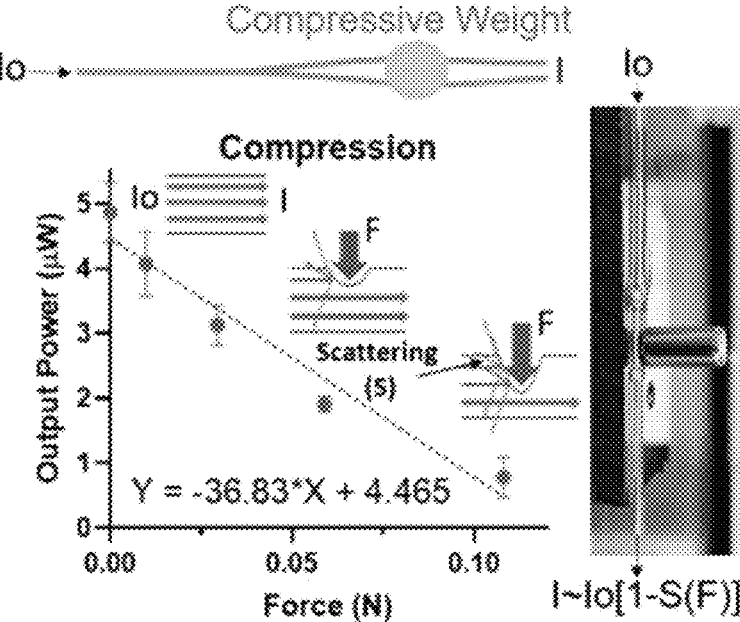

We then leveraged fusion for assembling complex multi-input divider, multi-output combiner, and multi-input/multi-output (MIMO) optical architectures (FIG. 2I). We observed that these integrated systems could split a single input into multiple outputs with low incremental loss: normalized light intensity per output channel number, n, was only partly below $1/n$ (FIG. 2J).

Figure 2K:
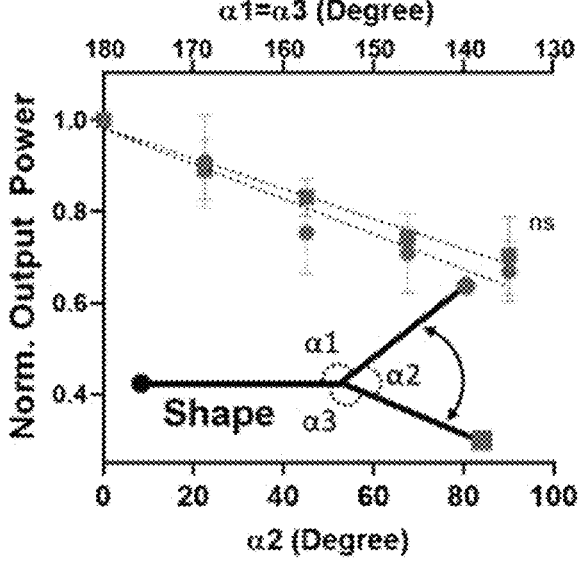

These integrated systems can act as macro-level reporters of force and shape. First, we observed that the fibers' compression led to changes in output light intensity (FIG. 2K). A homogeneous force was generated by placing weight on top of the fibers, used to quantify compressive force (F) deformation-induced light-scattering, S(F), based on an optical output, I, as approximated by equations 1 and 2.

$$I \sim I_0[1 - S(F)] \tag{1}$$

Experimentally (FIG. 2K) being:

$$I(\rho W) \sim 4.5[1 - 8.2F(N)] \tag{2}$$

Naturally, the initial or zero-compression output, $I_0$, will depend on the fiber length (FIG. 1H), and the compressive loss factor (here ~8.2 µW/N) will depend on the degree of hydrogel fiber deformation due to external forces or weights, which may vary based on the mechanical properties of different hydrogels.

Figure 2L:
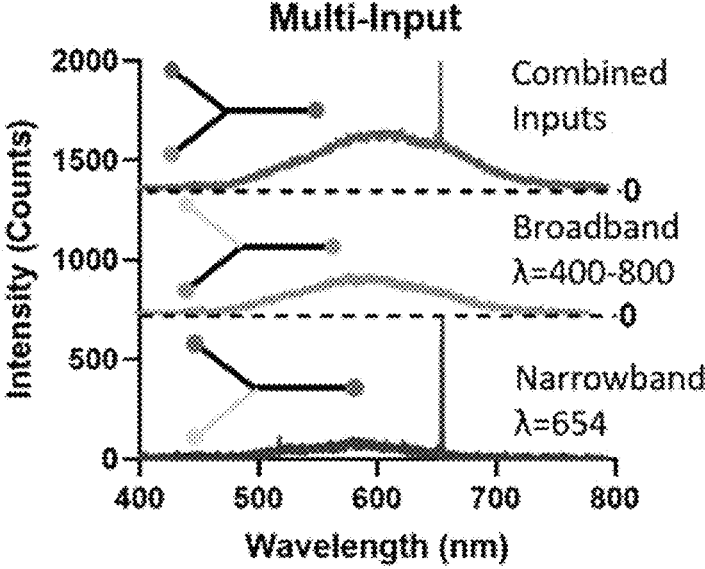
Figure 10:
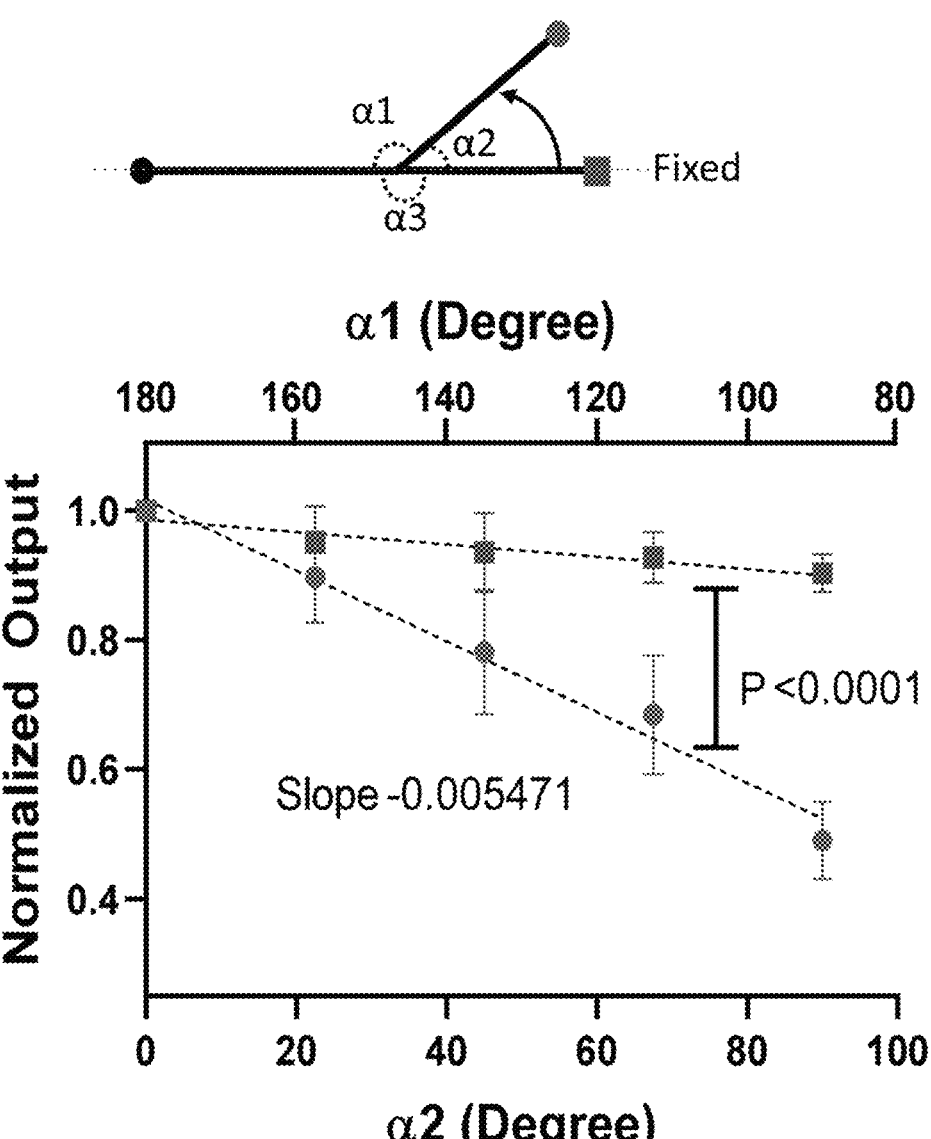
FIG. 10: Quantification of the double-output system intensities with one fixed arm and a second one gradually moving away with increasing angle in relation to the common input branch (as schematized on the top).

We then leveraged 1×2 coupler systems to inform on the relative angle of the whole structure, considering each output segment as an individual arm. We observed that output light intensity decreased proportionally (−0.0038/degree) to the angle between the output arm and the common input branch. While a fixed arm maintains constant output light intensity (FIG. 10), changes in shape leading to angular increase can be detected by looking for proportional decreases in light power (FIG. 2L).

Furthermore, 1×2 coupler can easily be reversed into multi-input architectures (FIG. 2I), which can combine light from different sources into a single output for readout. By coupling light from a broadband light source (400-800 nm) into one arm and another narrowband light source with 654 nm wavelength into the other arm, light from both sources were detected at the output, in a single spectrometer readout. (FIG. 2M).

Engineering a Nanoplasmonic Hydrogel Core Towards Molecular-Level Detection

Figure 3A:
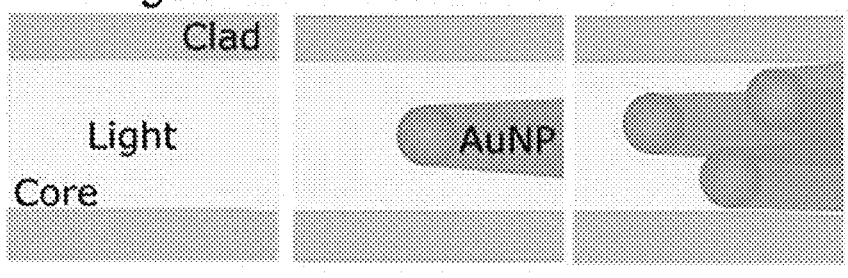
FIGS. 3A-3L: Engineering a plasmonic core modified hydrogel fiber for molecular-level SARS-COV-2 detection—FIG. 3A) Schematic of the rationale behind the integration of gold nanoparticles in the hydrogel fiber and for the integration of sensitive plasmonic resonance.
Figure 3B:
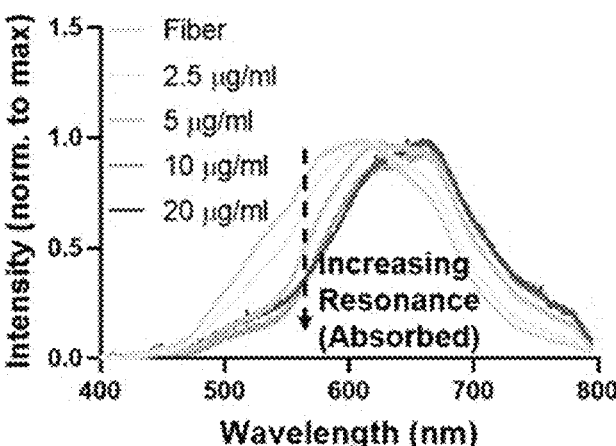

After macro-level detection, we explored nano/micro-scale light-matter interactions to detect biological targets at the molecular level. It is well described that nanostructures such as plasmonic metals respond to surrounding environmental changes due to refractive index-sensitive plasmonic resonance shifting[30,31]. We hypothesized that the integration of plasmonic nanoparticles (NPs) in the core of the hydrogel fibers, could lead to resonance-induced variations in output spectra (FIG. 3A). We verified that the encapsulation of gold NPs (AuNPs) within the hydrogel fiber core (FIG. 1I) directly affected spectral output with gradually increasing AuNPs concentrations leading to higher resonant absorption (FIG. 3B).

For a blank fiber, the output intensity spectra $I_B$ ($\lambda$) can be approximated as a function of the input light, $I_{bulb}$ ($\lambda$), multiplied by the fiber transmission function, $H_{Fiber}$ ($\lambda$) (equation 3). When AuNPs are introduced into core, the output spectra will further be affected by the gold transmission, $T_{AuNP}$ (equation 4).

$$I_B(\lambda)=I_{bulb}(\lambda)\times H_{Fiber}(\lambda) \qquad (3)$$

$$I_{AuNP}(\lambda)=I_{bulb}(\lambda)\times H_{Fiber}(\lambda)\times T_{AuNP}(\lambda) \qquad (4)$$

Figure 3C:
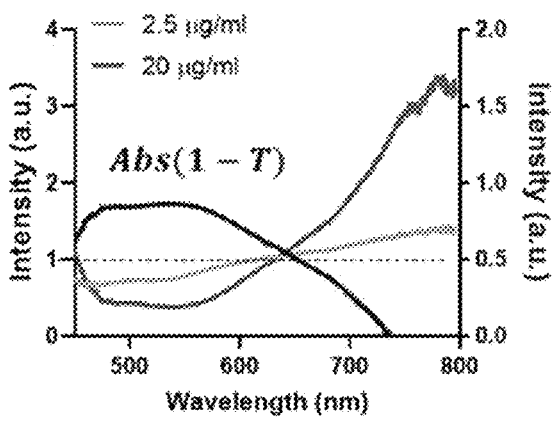
Figure 12B:
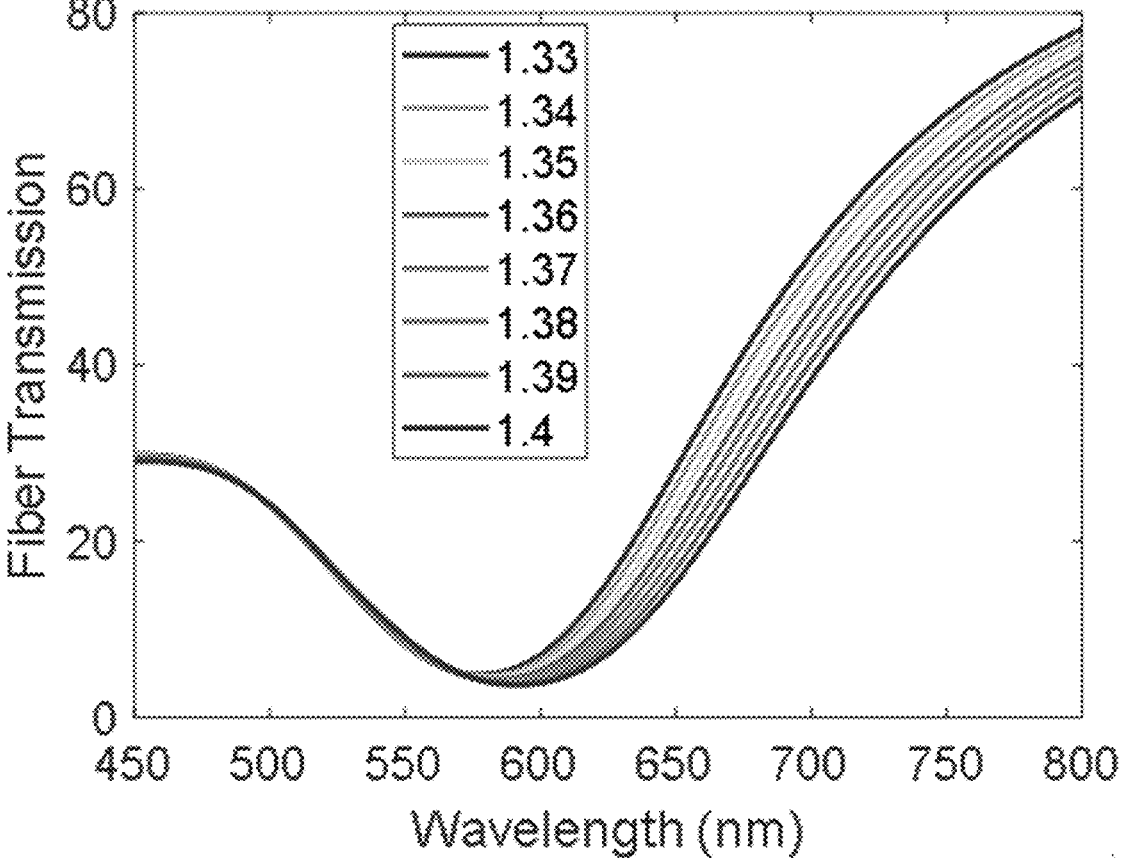
Figure 12C:
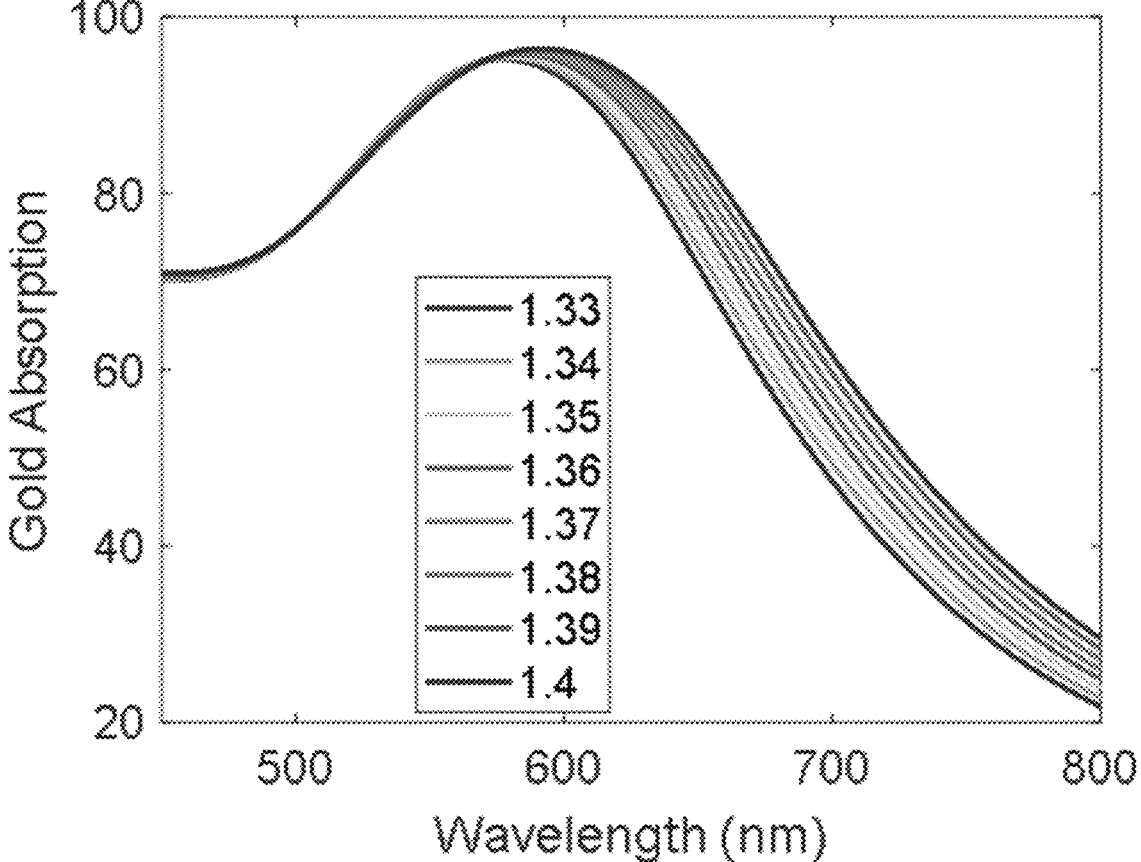
Figure 13A:
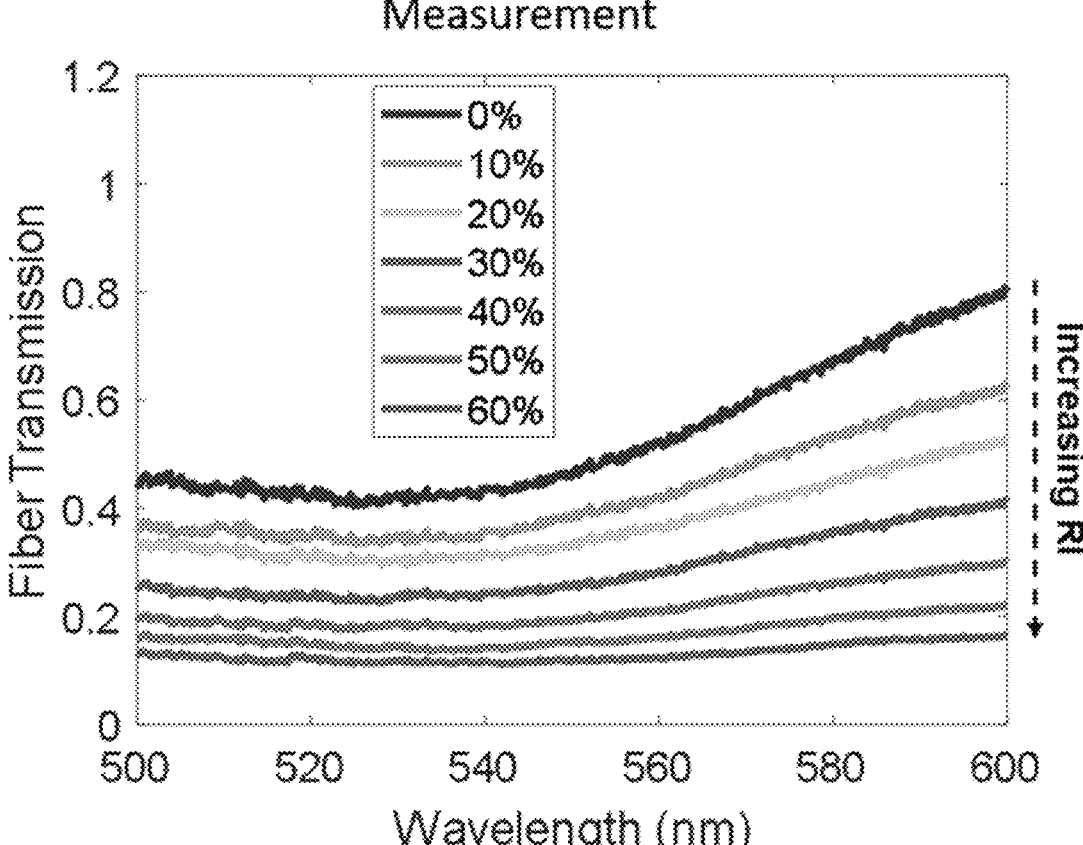
FIGS. 13A-13D.
Figure 13B:
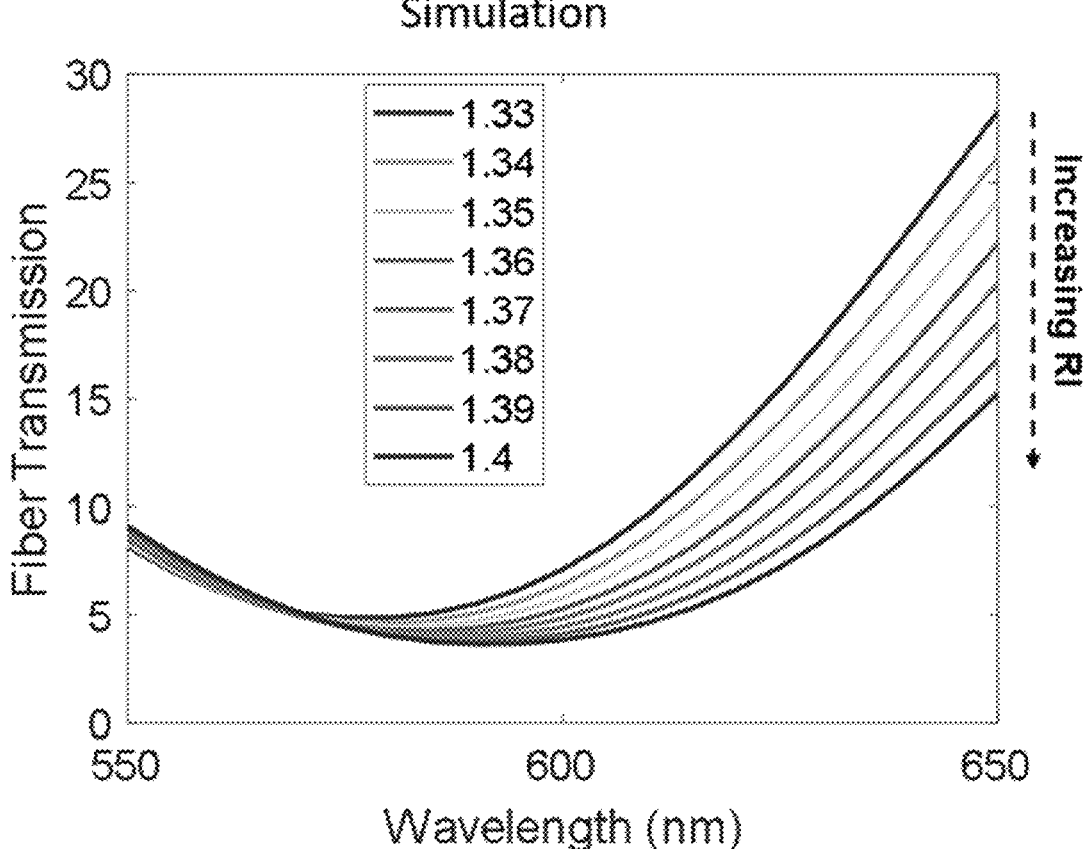
Figure 13C:
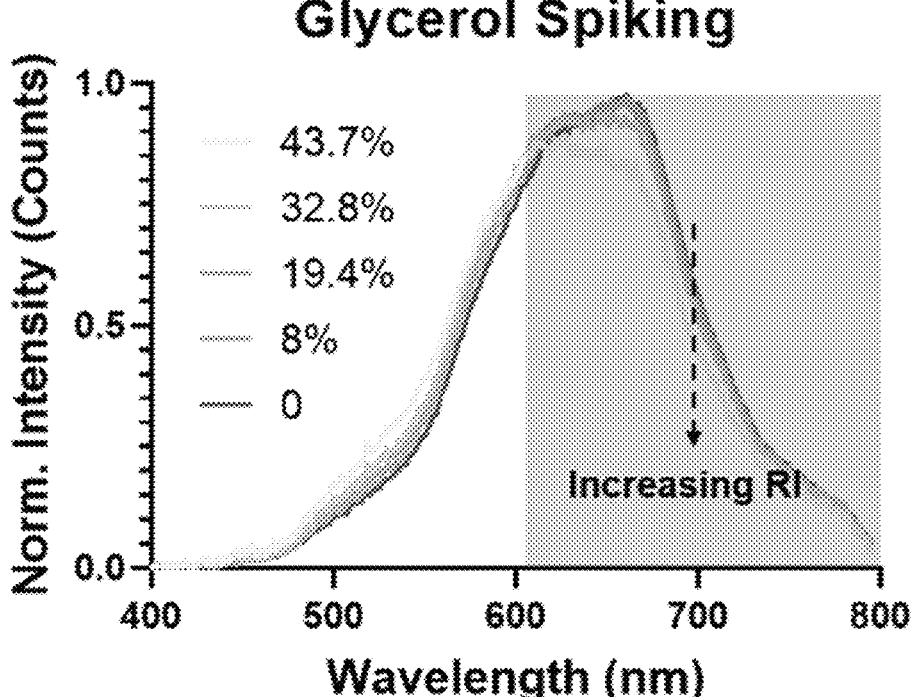
Figure 13D:
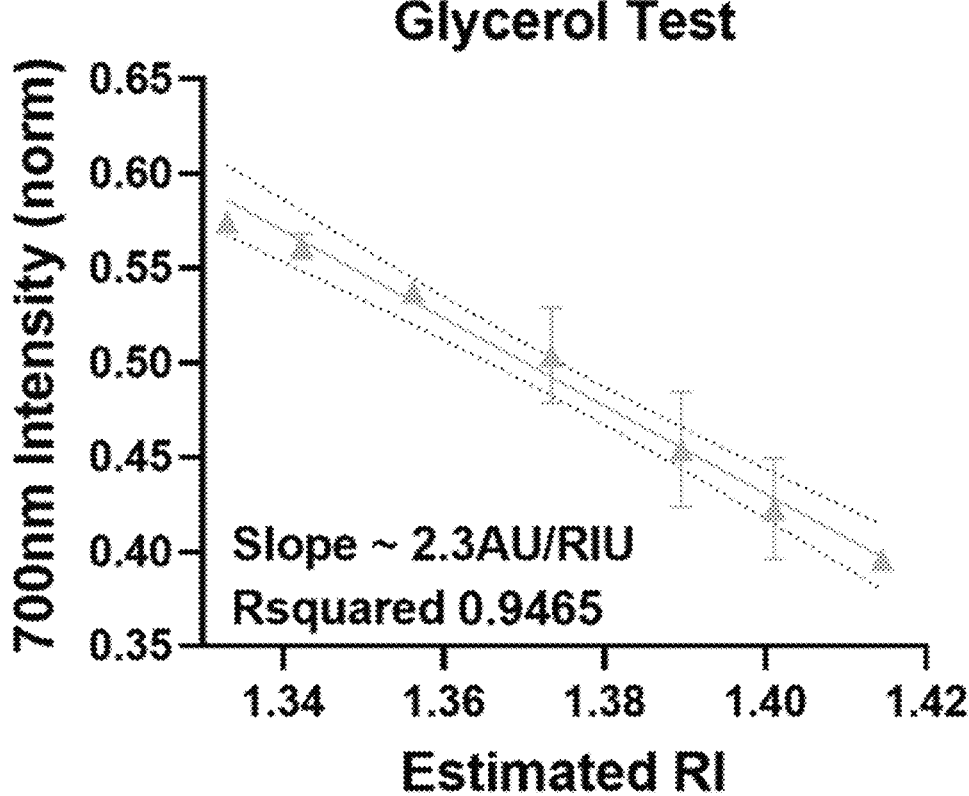

By dividing the output spectra of the AuNP-core fiber, $I_{AuNP}$, by that of the empty fiber, $I_B$ ($\lambda$), it is possible to isolate the effect of gold transmission $T_{AuNP}$, or absorption (1−transmission, as amount of back-reflection is negligible) in the final spectra (Supplementary Equations 1-5). While low gold concentrations (2.5 µg/mL) show very slight plasmonic resonance-induced variation, at 20 µg/mL, a significant resonance effect in light transmission happens (FIG. 3C), comparable to computational simulations of 100 nm AuNP spectra (FIG. 12).

Using glycerol solutions, we observed that increasing refractive index shifted plasmonic transmission causing the most prominent decreases in output intensity after the resonance peak wavelength, namely at 700 nm-level transmissions (FIG. 12), which linearly decreased with increasing RI, representing a meaningful detection parameter (FIG. 13).

Figure 3D:
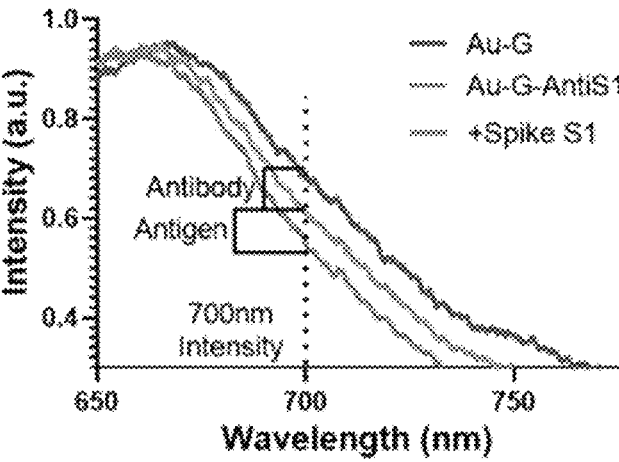
Figures 3E, 3F:
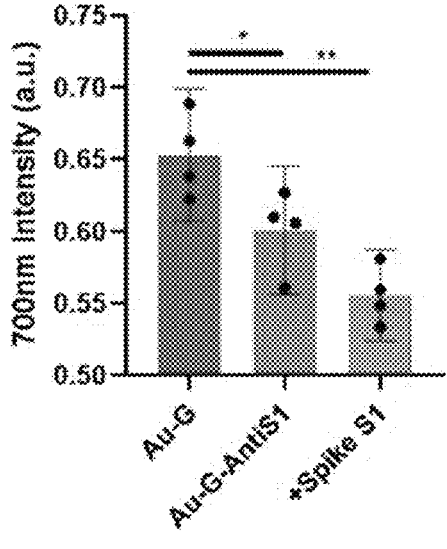
Figure 14A:
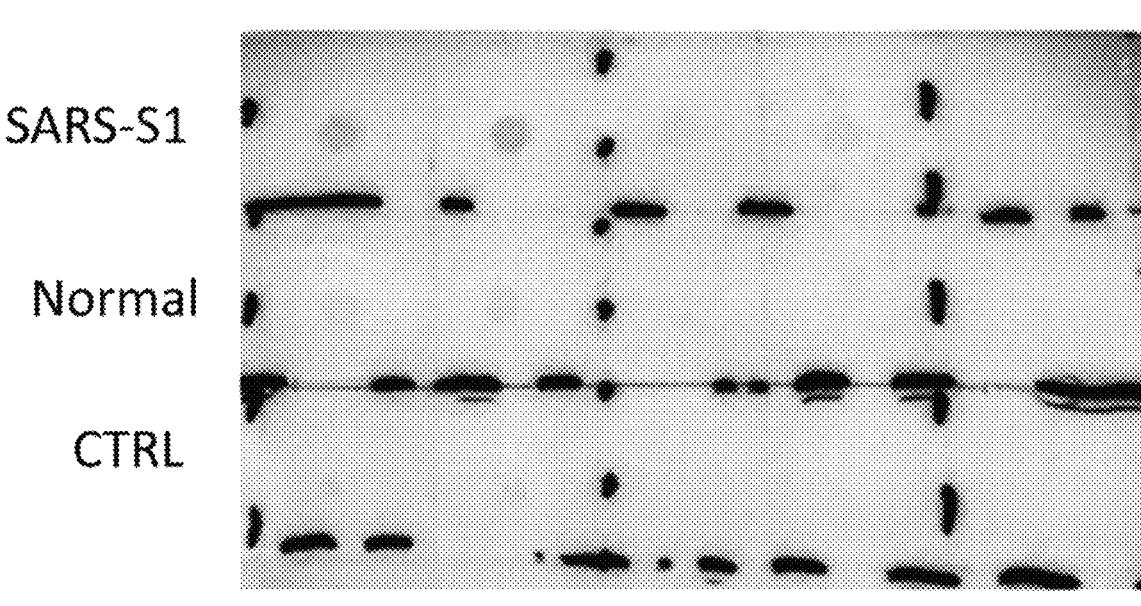
FIGS. 14A-14B: Dot-blot validation of the Antigen/Antibody affinity (FIG. 14A) and relative quantification data (FIG. 14B). SARS-S1: Supernatant with SARS-Spike antigen, Normal: Normal Supernatant, Control: Normal without first antibody incubation. An intermediate dilution of 1:40 was then used for detection in the optical fibers.
Figure 14B:
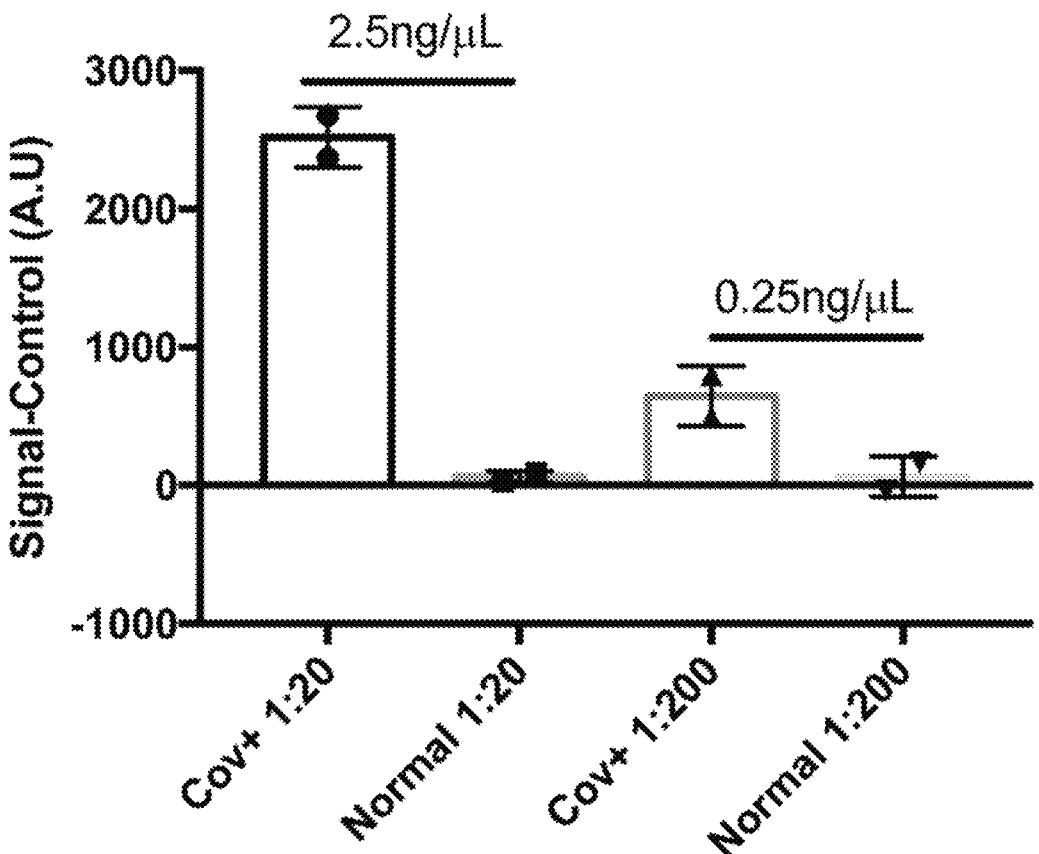
Figure 15A:
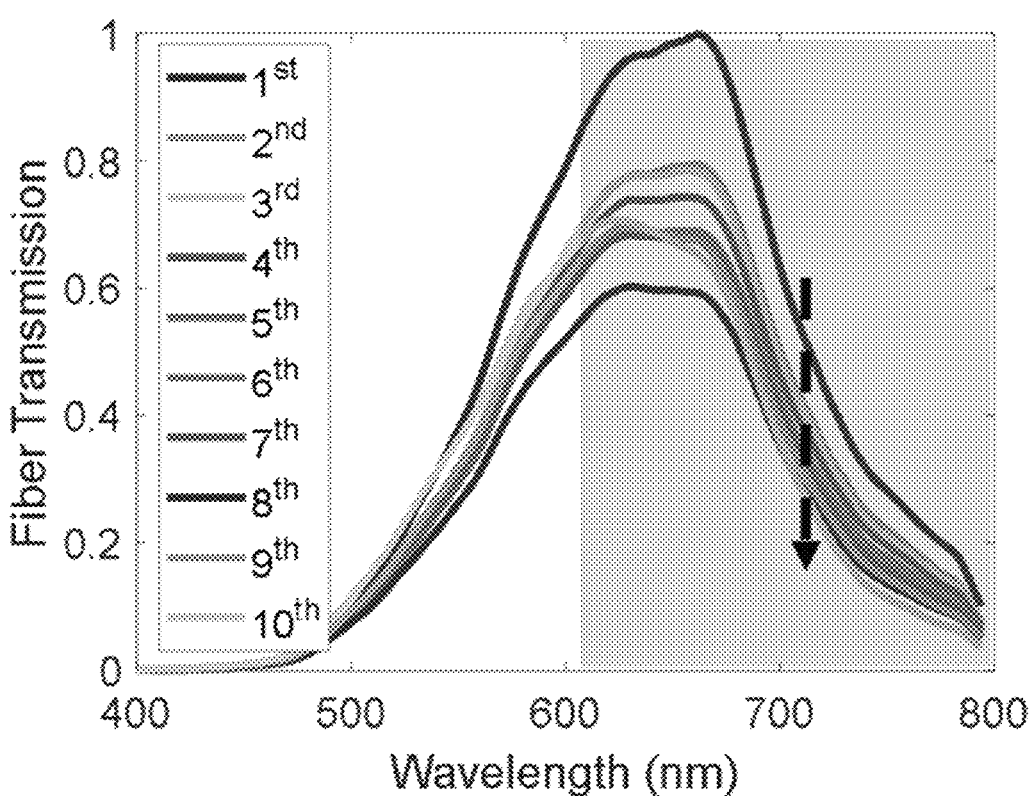
FIGS. 15A-15D.
Figure 15B:
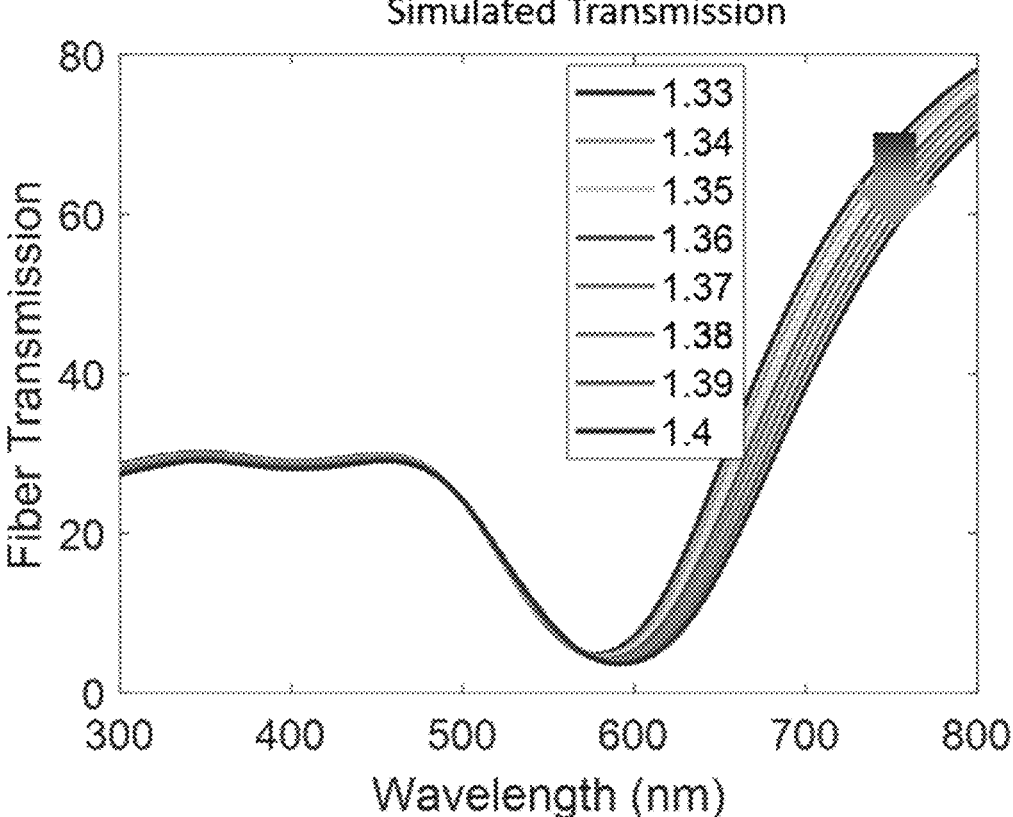
Figure 15C:
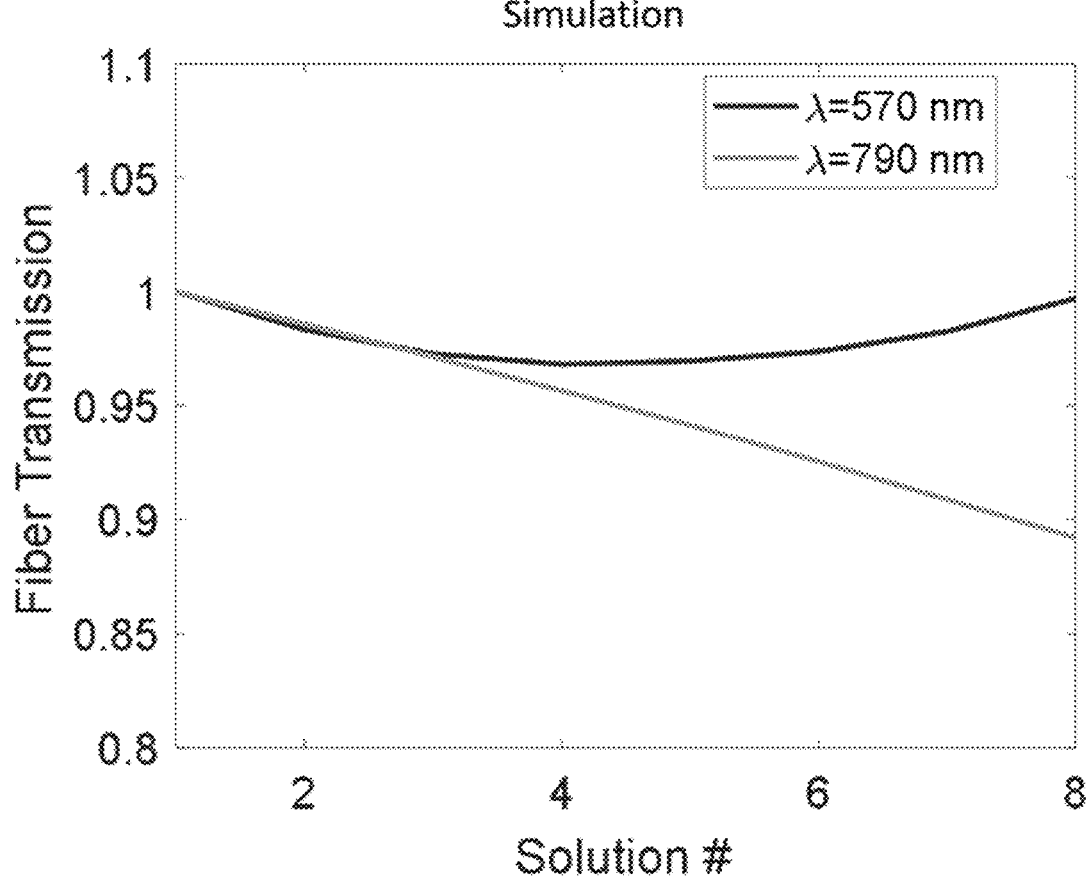
Figure 15D:
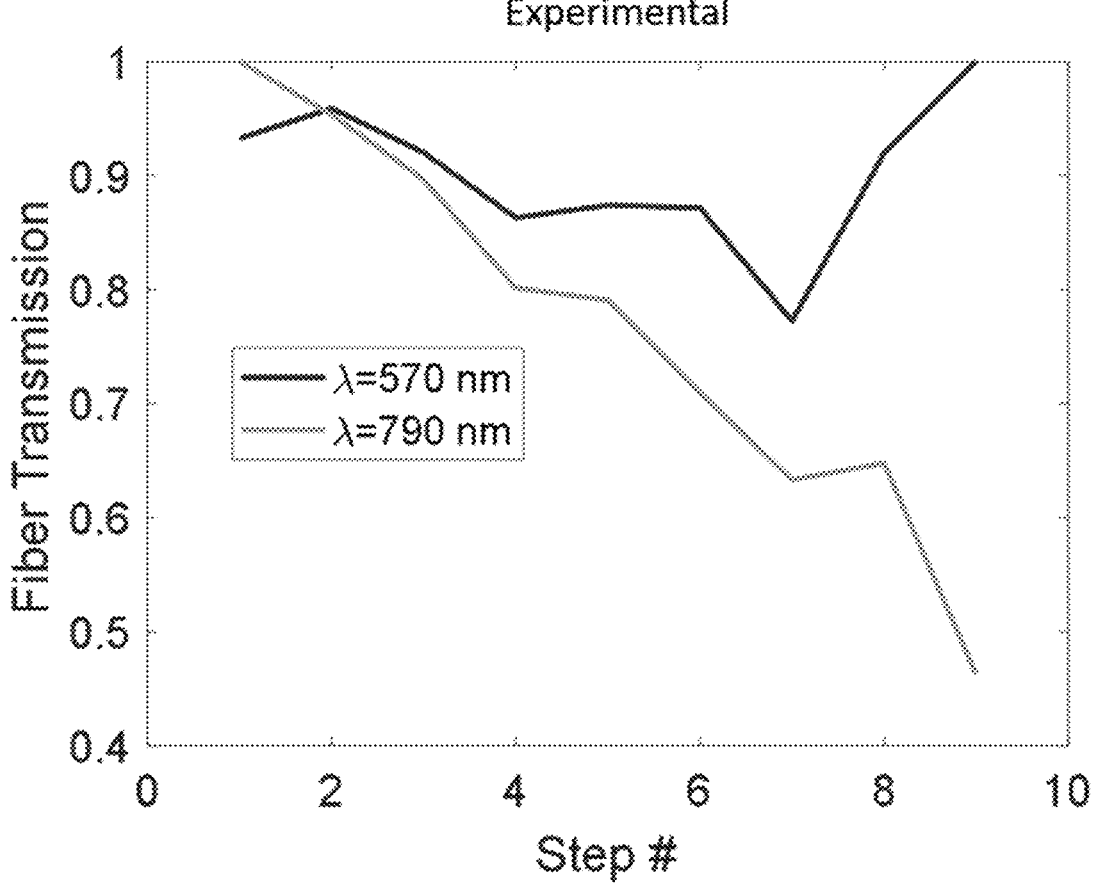
Figure 16:
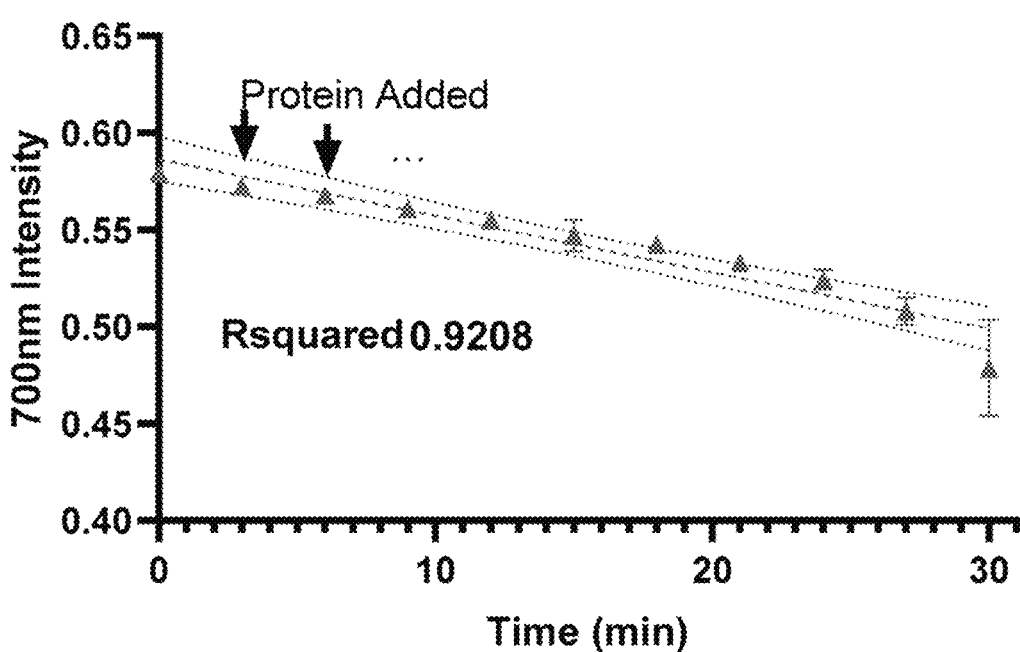
FIG. 16: 700 nm intensity variation over time (each measurement represents the addition of ~10 ng of protein solution). A linear decrease in 700 nm intensity is observed, the parameter used in the main text to detect the binding of targets.

Previously, Protein G-based[32] functionalization was used to detect antibody/antigen interactions via changes in local refractive index [33]. We thus encapsulated protein-G-coupled AuNPs within the fiber core, and compared the output light spectra with the same plus antibodies against SARS-COV-2 Spike (S1) protein [34] (FIG. 14). As observed in glycerol tests, the antibody binding to the protein-G-AuNPs caused a reduction at higher-wavelength transmission (FIGS. 3D, 3E). A further decrease was observed by incubating the functionalized-AuNP fibers with SARS-COV-2 Spike antigen, lowering the 700 nm intensity at each step, from ~0.65 to ~0.55 (normalized intensity) (FIG. 3E). A parallel experiment where protein solution was added to the fibers over time confirmed similar agreement with computational simulations (FIGS. 15, 16). This validates the optical fiber detection mechanism based on the resonance shifts caused by binding biotargets (FIG. 3F).

Figures 3G, 3H:
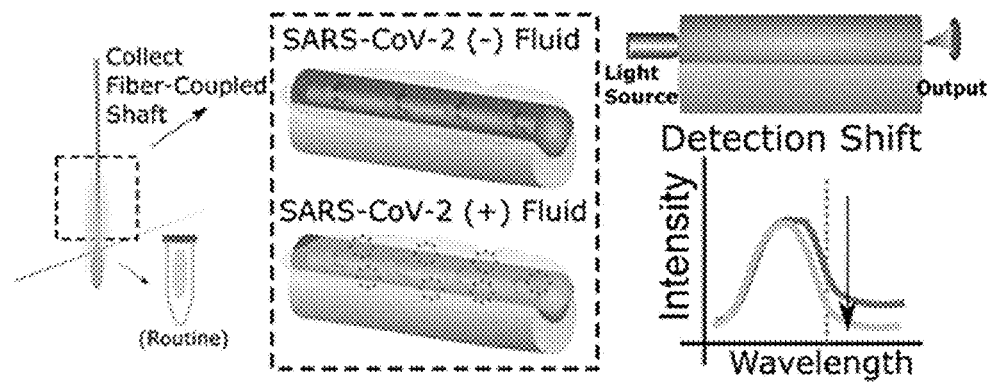
Figure 3I:
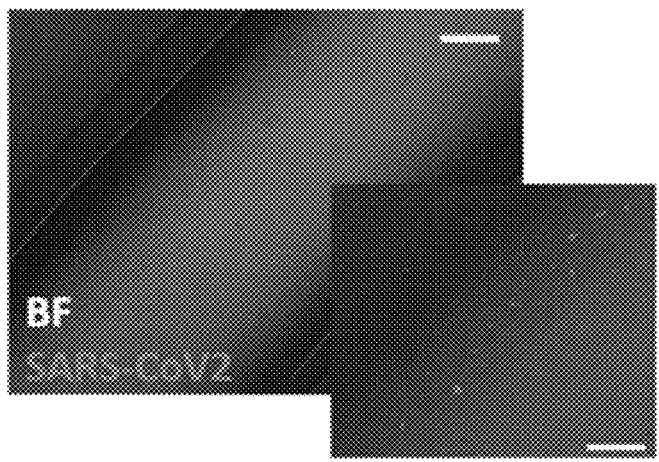
Figure 3J:
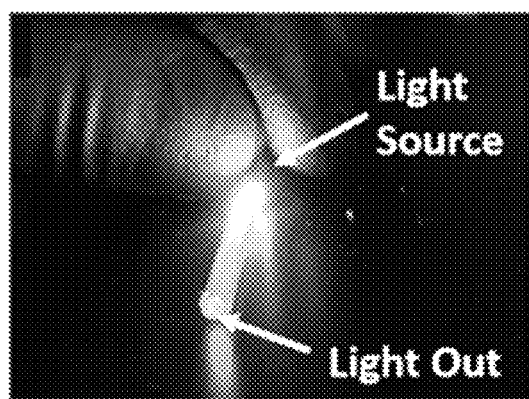
Figure 3K:
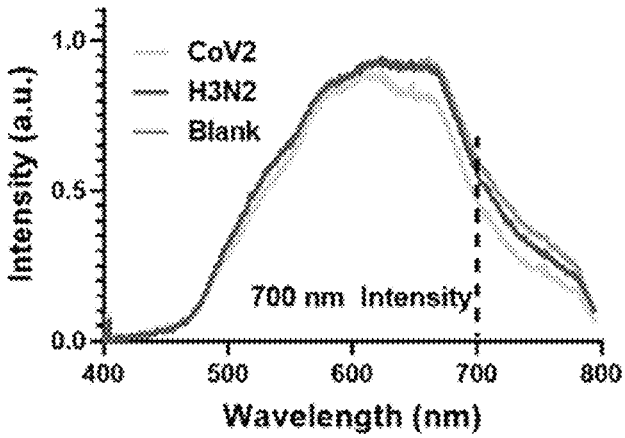
Figure 3L:
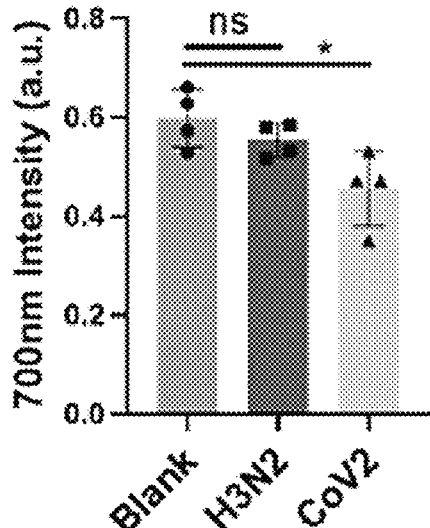
Figure 17:
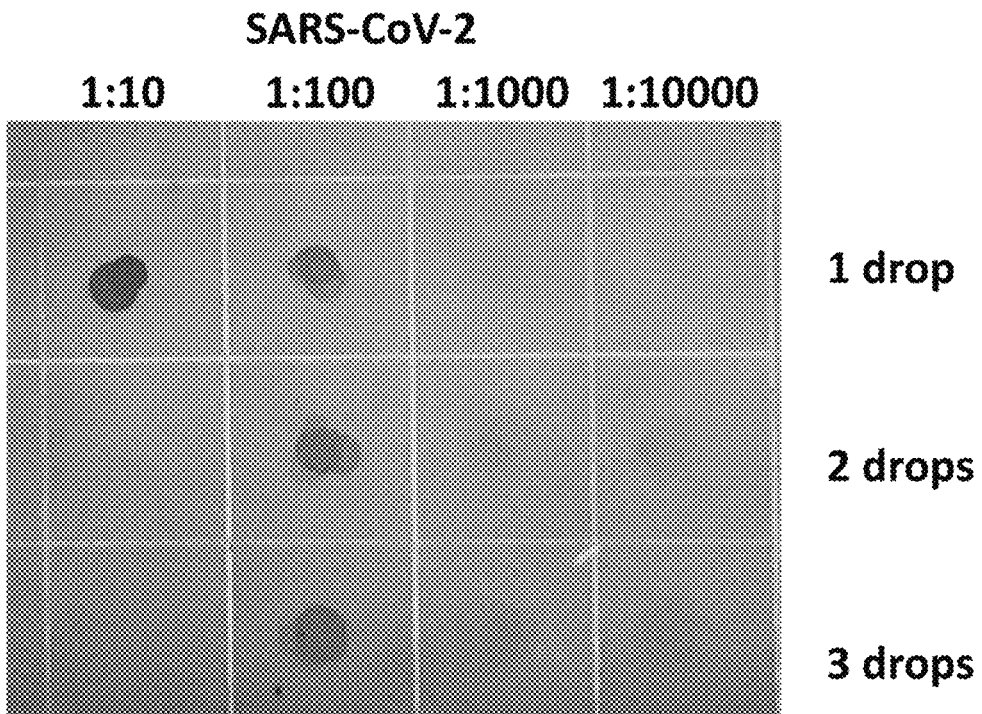
FIG. 17: Dot-blot validation of the antigen-virus interaction. Different Dilutions of the SARS-COV-2 virus were tested. 1:1000 was used as working dilution as it was the minimum detectable concentration with 1 single drop dot.
Figure 18A:
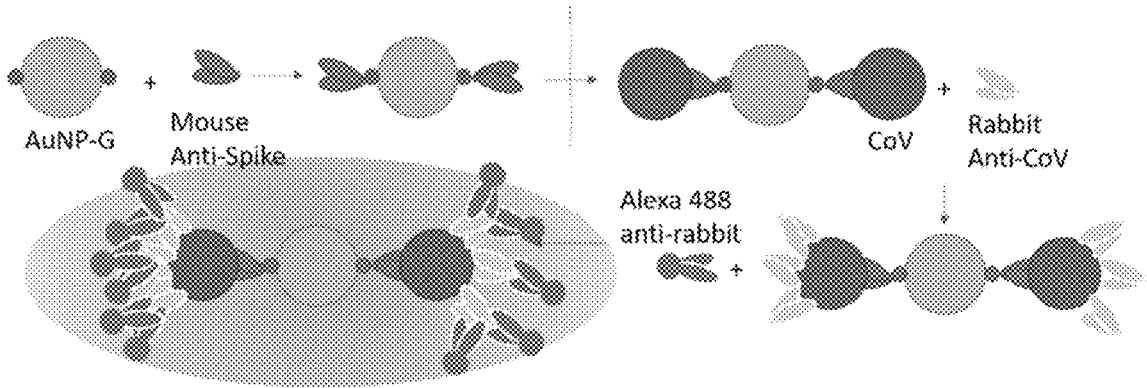
FIGS. 18A-18B: Schematic representation of the reverse-immuno protocol used to stain and amplify the signal derived from SARS-COV-2 bound to gold NPs within the fiber (FIG. 18A).
Figure 18B:
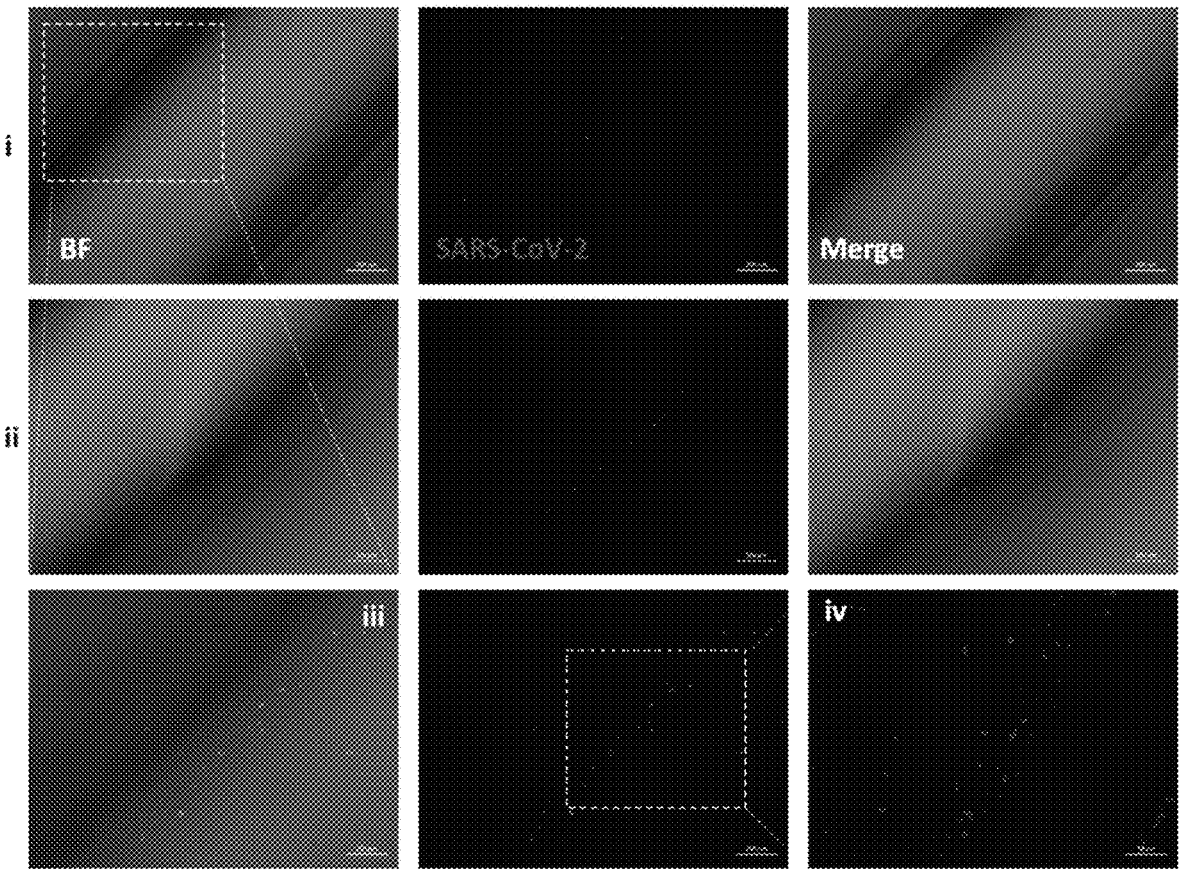
Figure 19A:
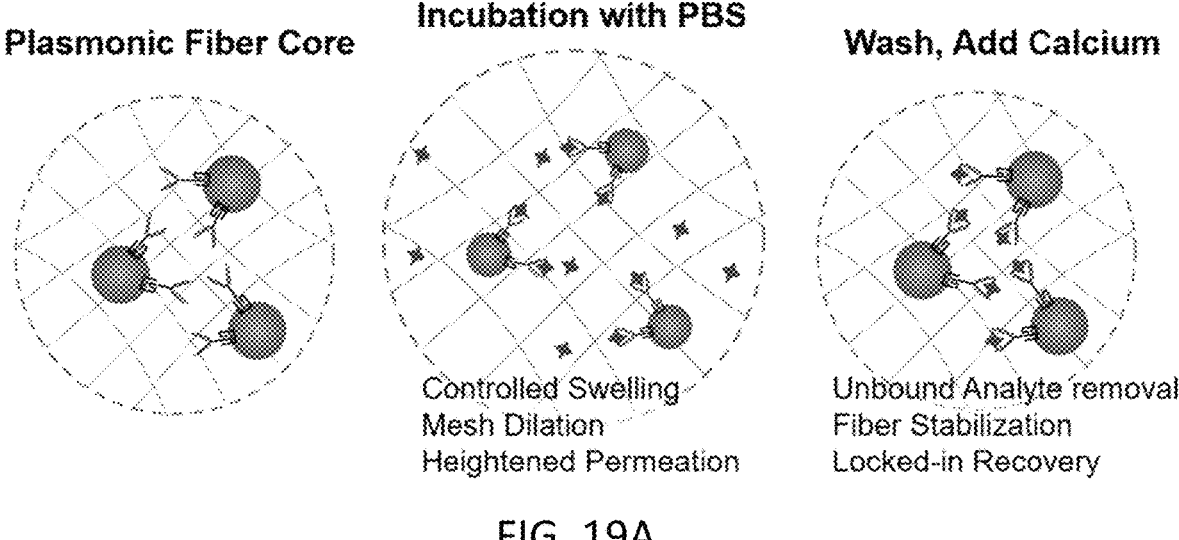
FIGS. 19A-19C.
Figure 19B:
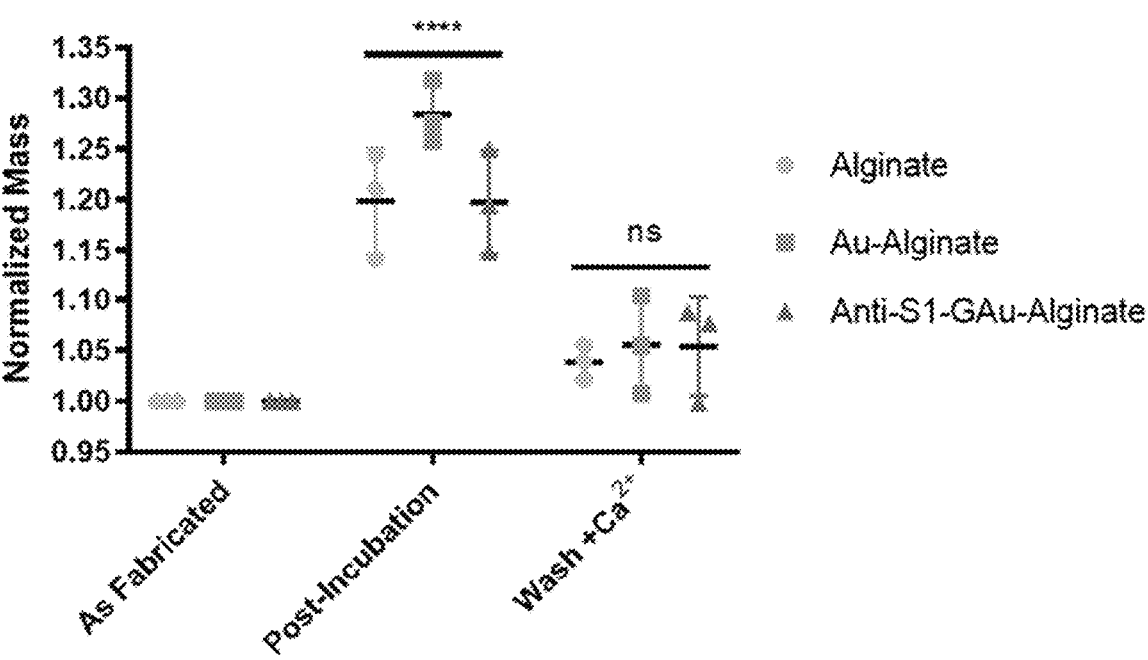
Figure 19C:
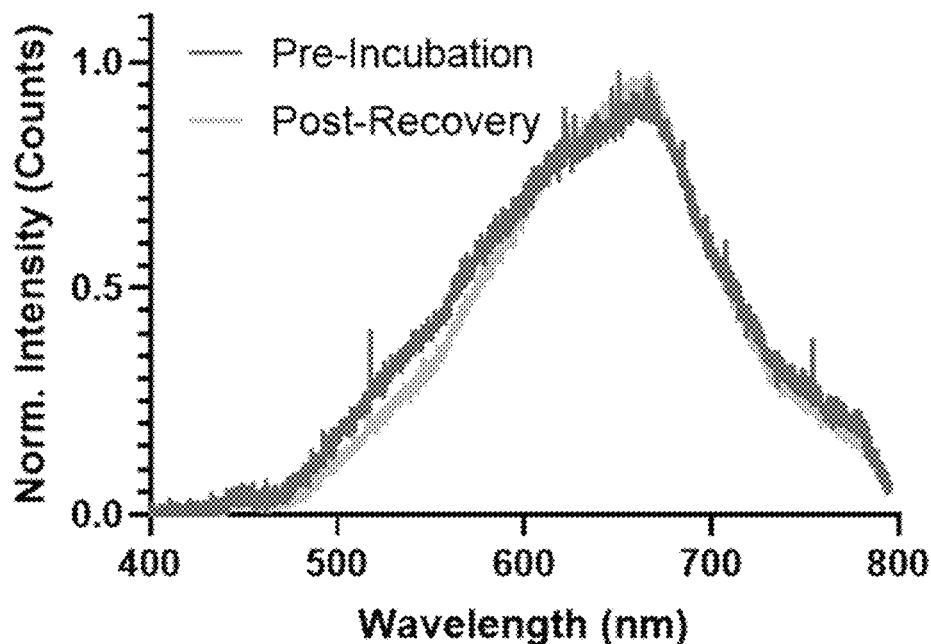
Figure 20A:
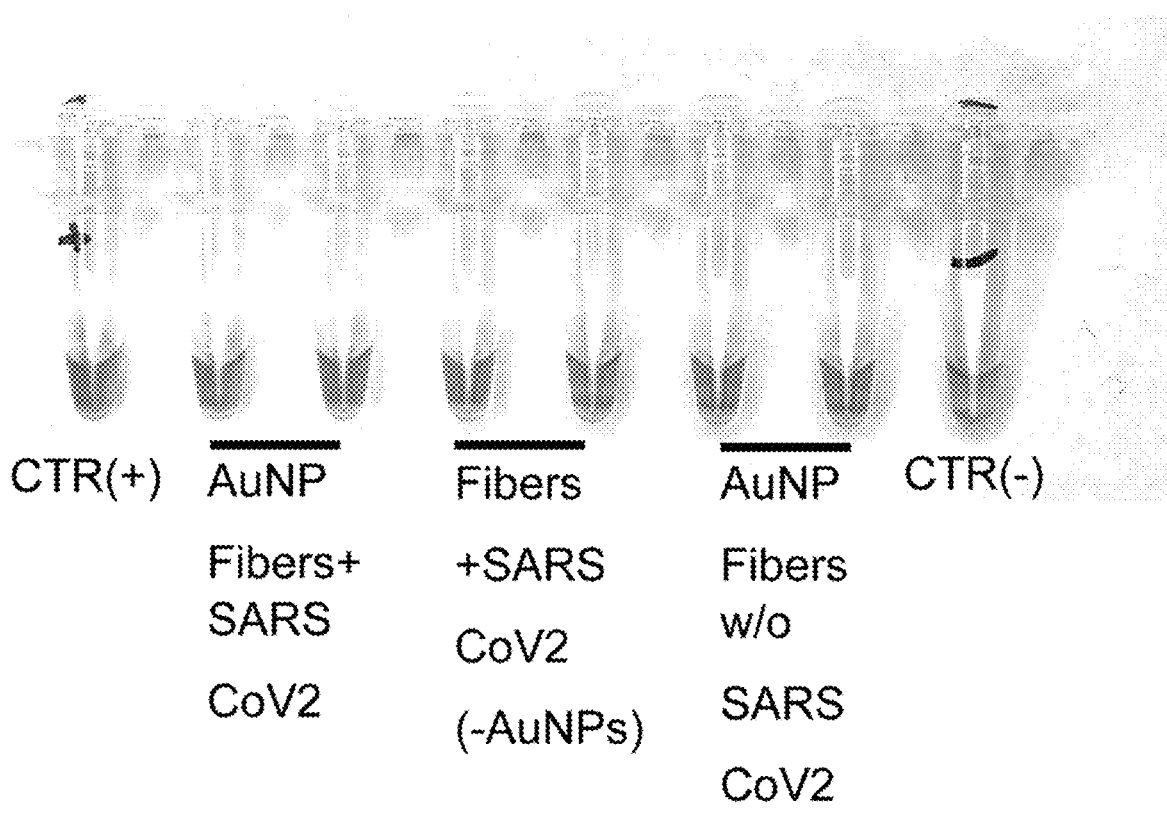
FIGS. 20A-20B.
Figure 20B:
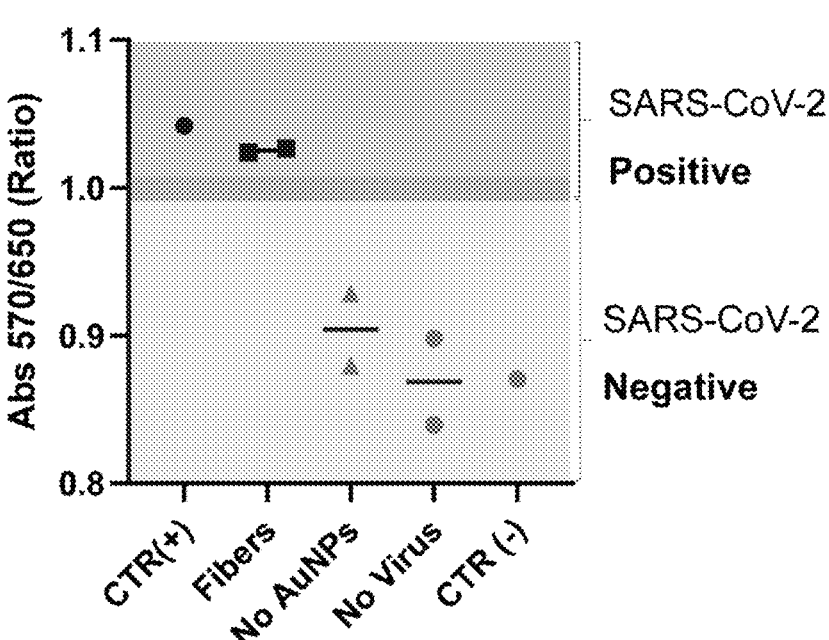

We then interrogated the detection of full viral structures using the antibody/virus affinity (FIG. 17). We interfaced optical hydrogel fibers with medical swabs employed in standard sample collection, adding a layer of positive/negative in situ screening (FIGS. 3G, 3H). SARS-COV-2 has sizes ranging from 60 to 140 nm [35], and previous studies showed that these hydrogels have mesh sizes below 200 nm [36] that enable diffusion of viral structures of around 100 nm [25,26], compatible with SARS-COV-2 structures. Viral capture was confirmed after incubating plasmonic fibers with gamma-inactivated SARS-COV-2 for 1 hour (FIGS. 4I, 18, 19). Further validation was done by RNA extraction and specific Loop-mediated Isothermal Amplification (LAMP), positively detecting the presence of SARS-COV-2 RNA in the fibers (FIG. 20).

Afterwards, we exposed swab-coupled hydrogel fibers to SARS-COV-2 positive, negative (blank), and influenza control (H3N2) solutions. Upon analysis of guided light (FIG. 4J), we observed a similar shift to that reported for antibody-antigen events: a decrease in 700 nm light intensity from ~0.6 to ~0.5 (FIGS. 4K, 4L). Even though a slight decrease was also seen with influenza, it was smaller in magnitude and not statistically significant. The slight variation likely derives from H3N2 viruses that might not thoroughly wash from the hydrogel, remaining there albeit in much smaller number—as these do not bind to the anti-SARS-COV-2 Spike antibody in the surface of AuNPs.

The Biofabrication of Living Optical Fibers

Figure 4A:
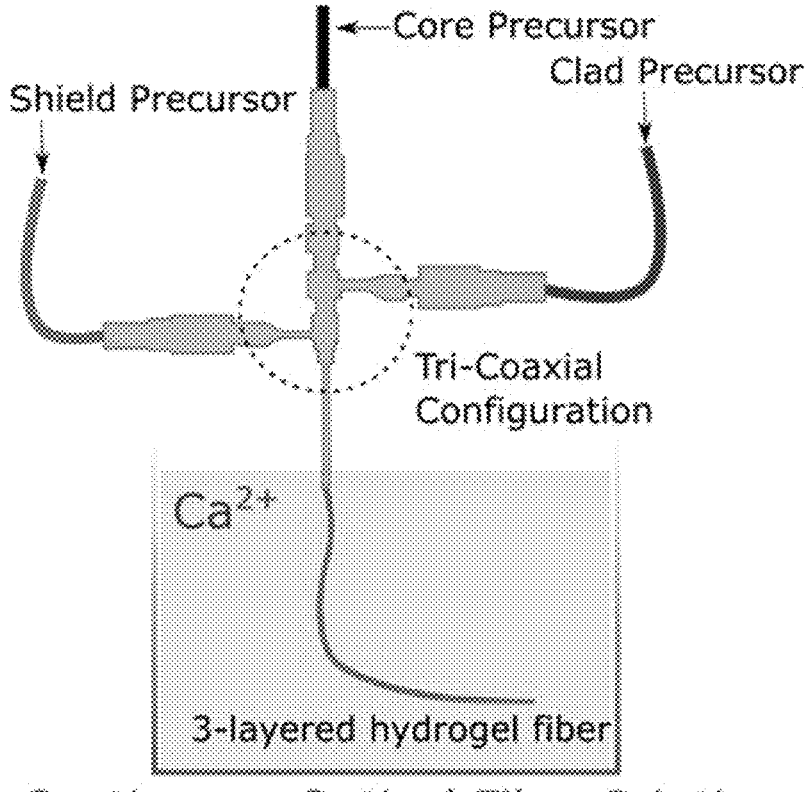
FIGS. 4A-4N: Continuous single-step printing of living hydrogel optical fibers.
Figure 4B:
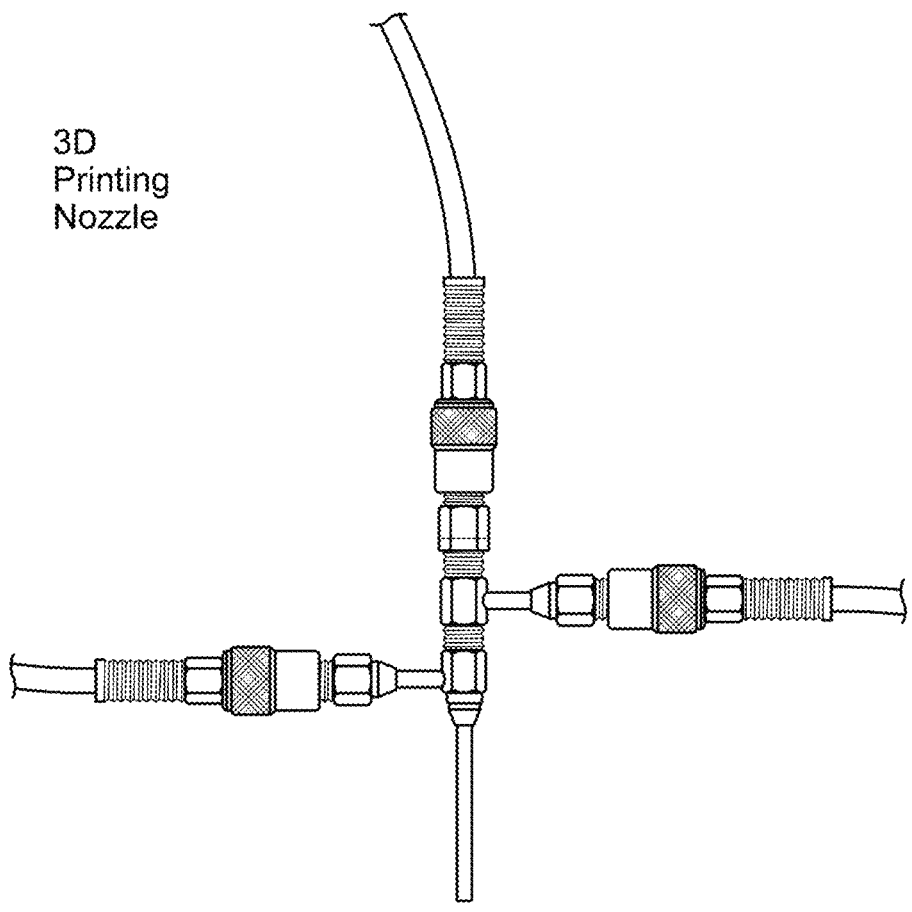
FIG. 4B) Photograph of the employed 3D printing nozzle, further detailed in FIG. 21.
Figure 4C:
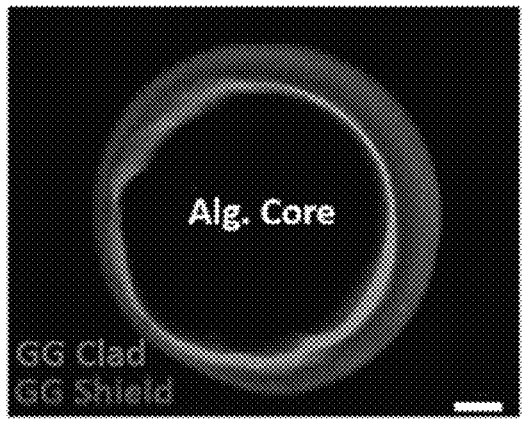
FIG. 4C) Microscope imaging of the fabricated fiber axial plane evidencing the successful core-clad-shield structure (hydrogels blended with different color particles).
Figure 4D:
FIG. 4D) Live/Dead (Calcein AM/Ethidium Homodimer) assessment of 3T3 fibroblasts' viability after encapsulation in the fiber core (top) and quantification of the percentage of viable cells post-fabrication and after 5 days of culture (bottom).
Figure 4E:
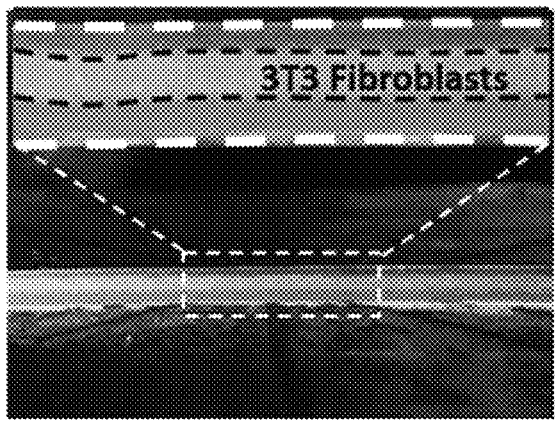
FIG. 4E) Photograph detail of a light-guiding living optical fiber with 3T3 fibroblasts encapsulated in the core.
Figure 4F:
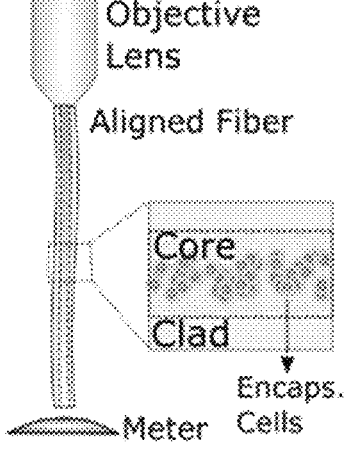
FIG. 4F) Schematic representation of living optical fiber platform for the guiding and collection of optical readouts.
Figure 4J:
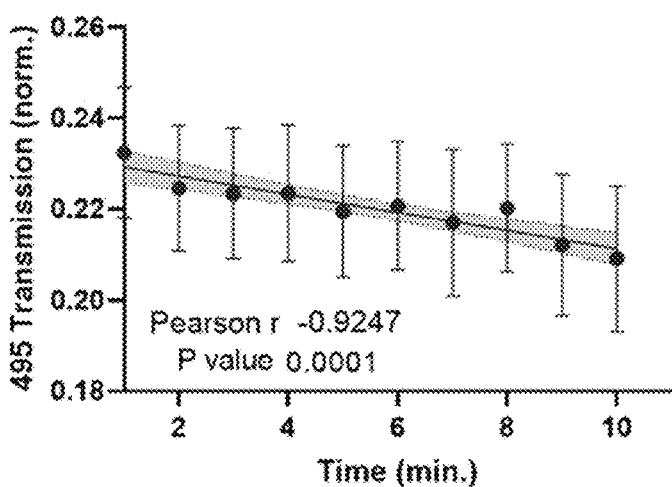
FIG. 4J) Real-time tracking of live-cell metabolic conversion of calcein AM to a fluorescent compound.
Figure 4K:
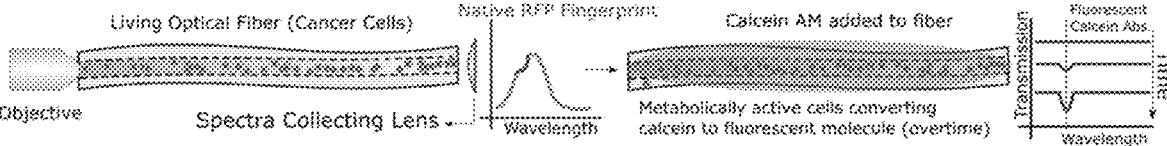
FIG. 4K) Rationale behind the use of living optical fiber spectral fingerprinting to detect two simultaneous responses: immediate effect on the expression fluorescent-tagged proteins (herein modeled by RFP), combined with the addition of calcein AM solution real-time tracking of metabolic profile.
Figure 4L:
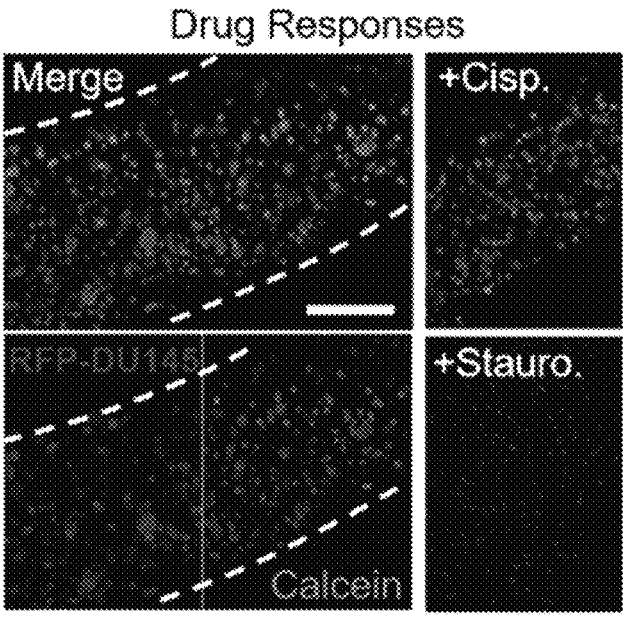
FIG. 4L) Microscopy images of proof-of-concept tests with optical fibers encapsulating prostate cancer cell line DU145 after 48 h of culture with model anti-cancer drugs (1.5 μM cisplatin, 1 μM Staurosporine and control media). Scale bar 200 μm.
Figure 21A:
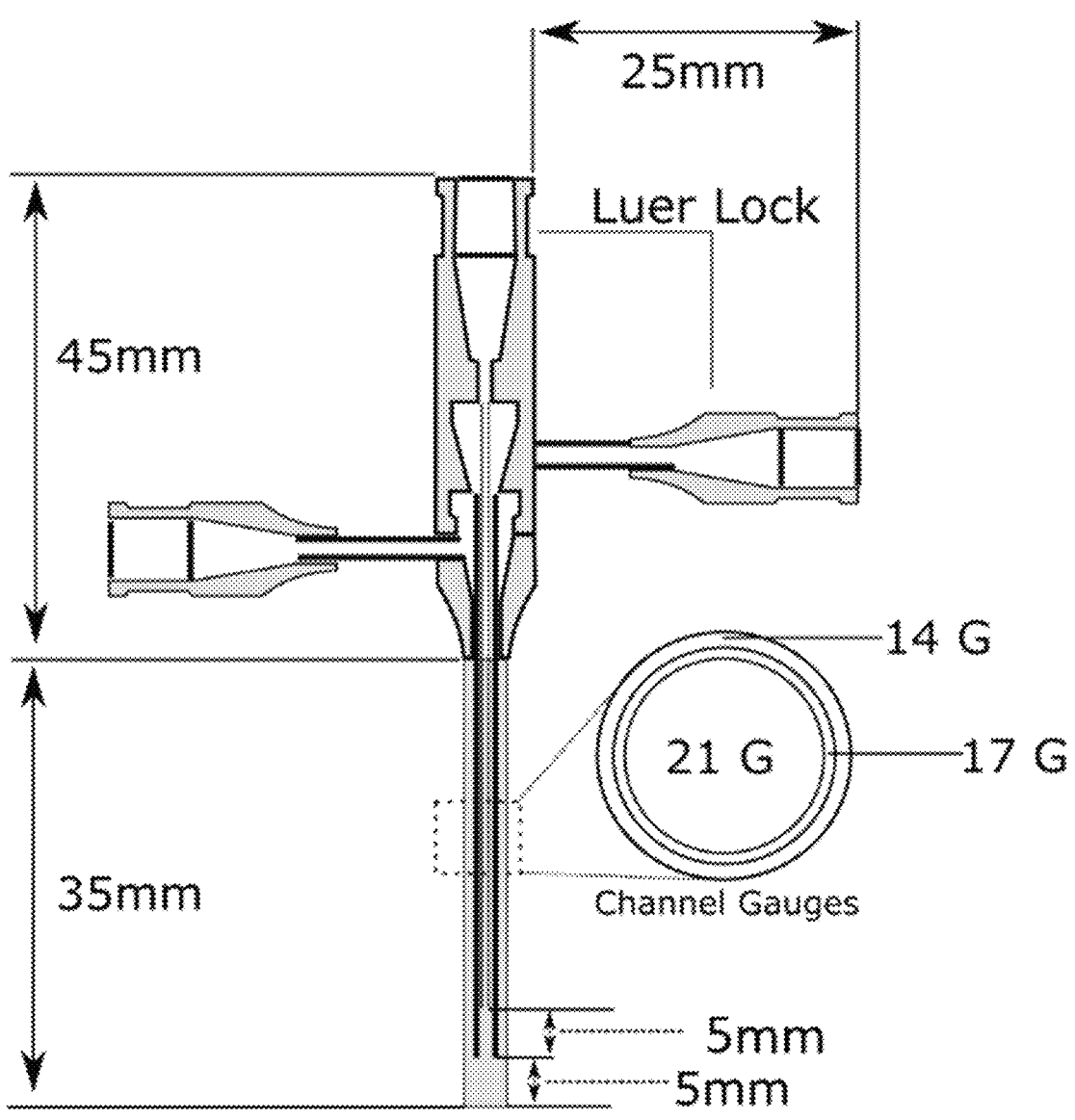
FIGS. 21A-21C.
Figures 21B, 21C:
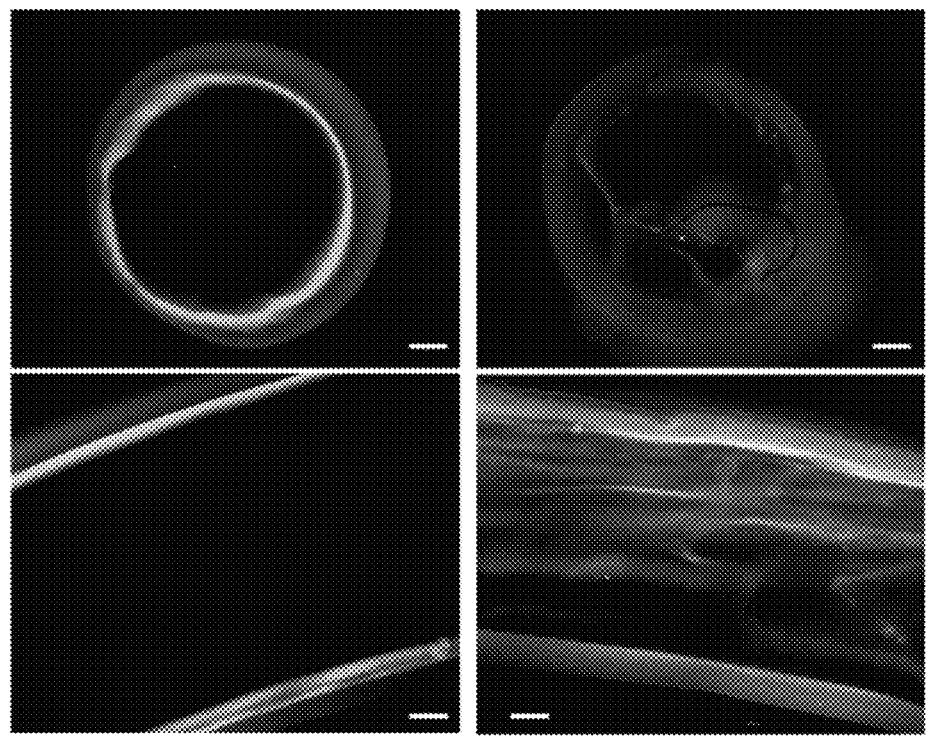
Figure 22A:
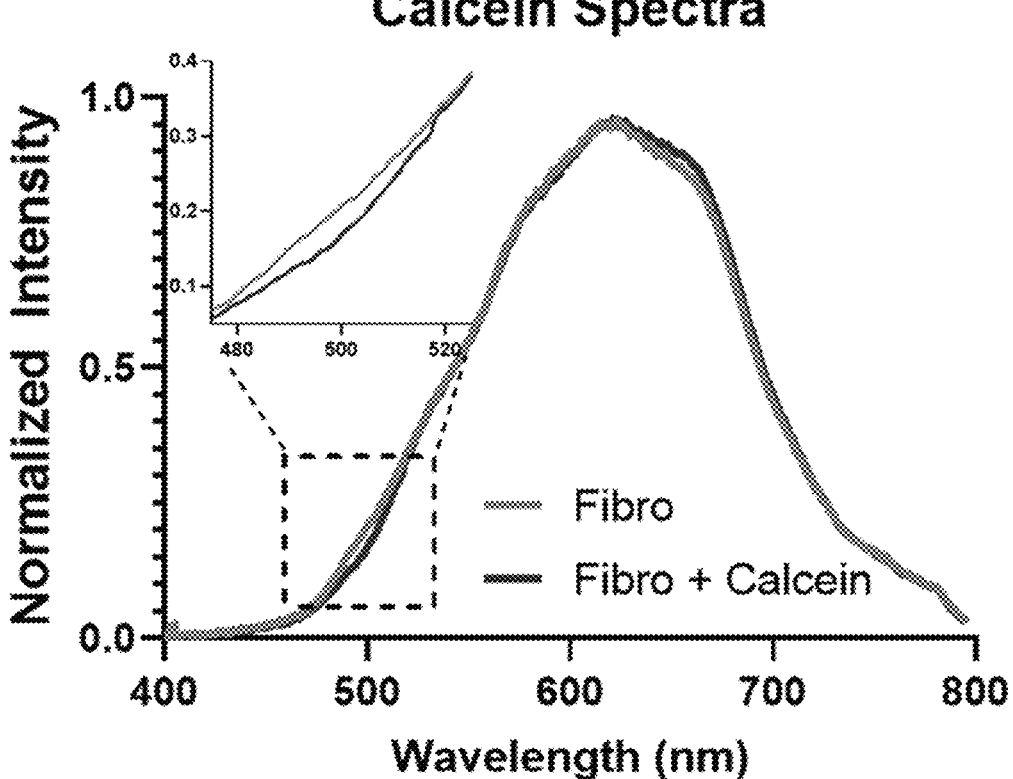
FIGS. 22A-22D.
Figure 22B:
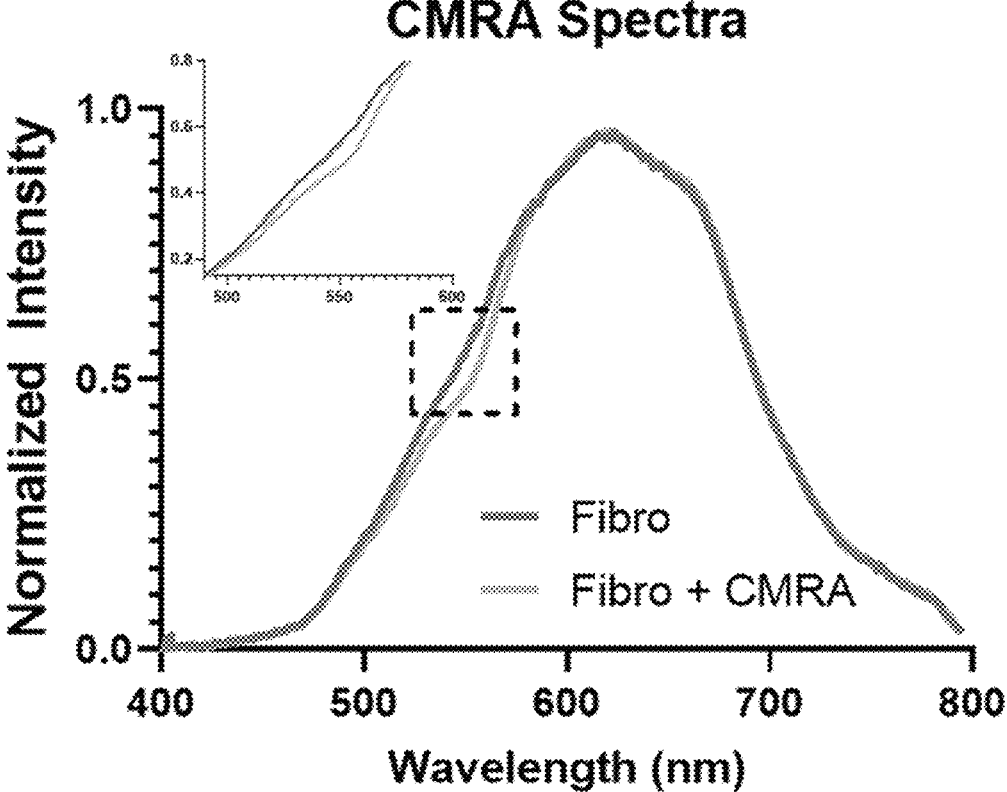
Figure 22C:
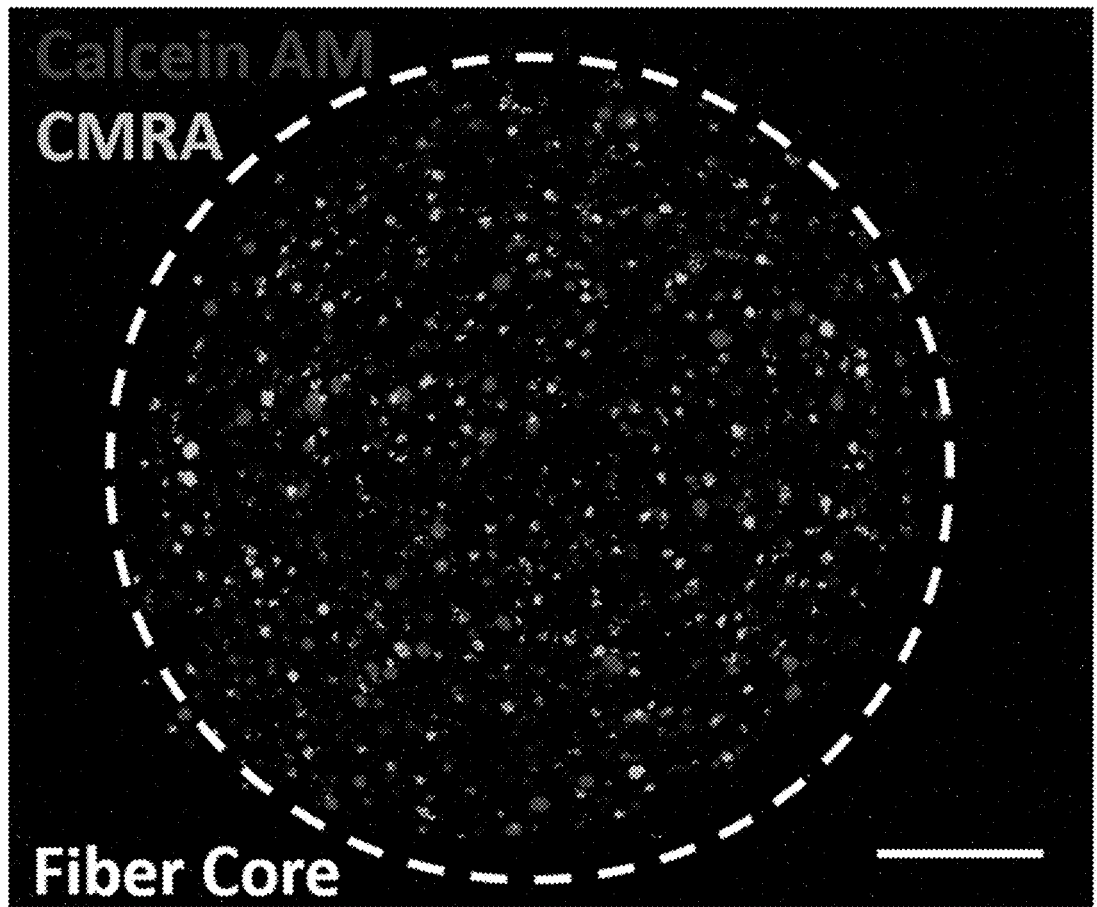
Figure 22D:
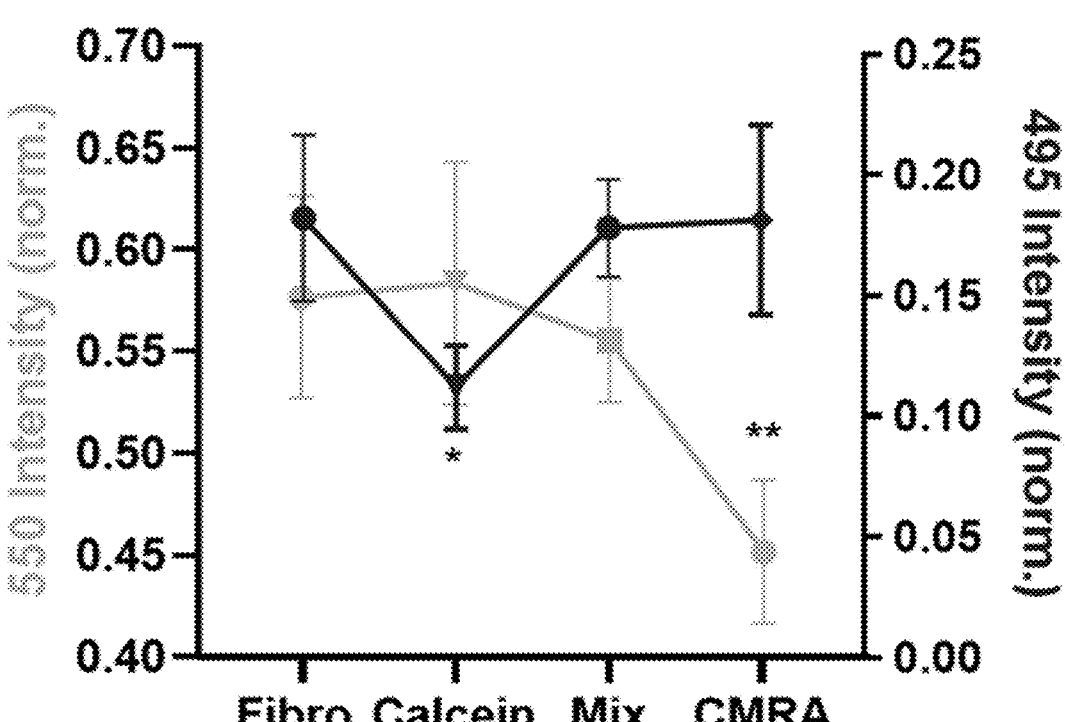
Figure 23A:
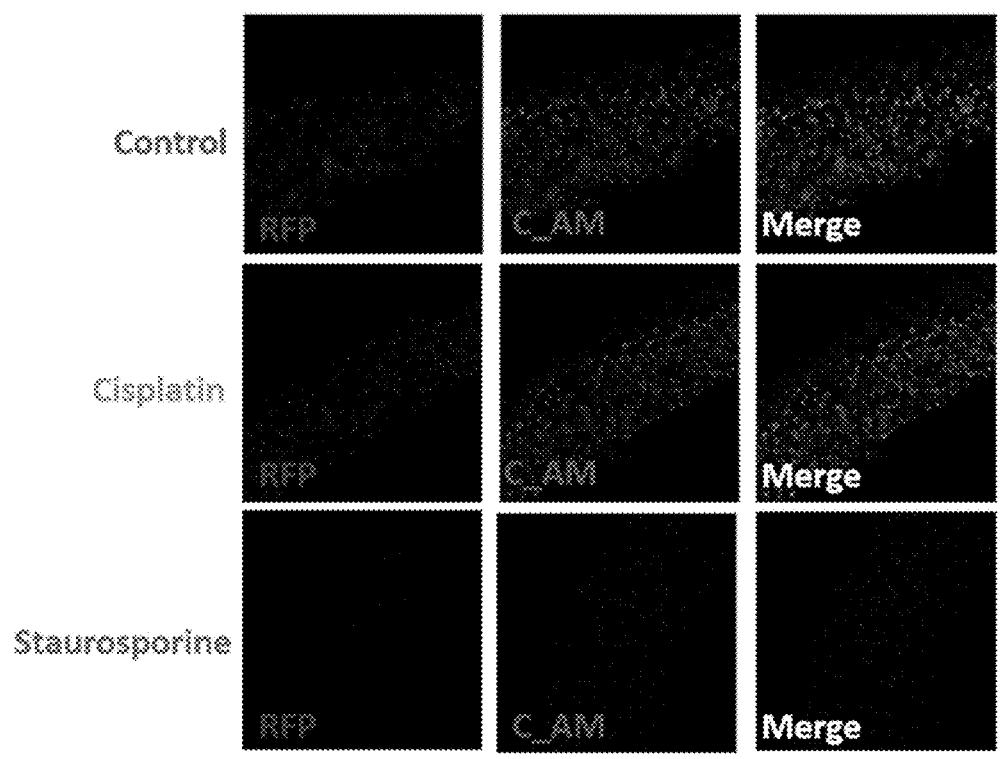
FIGS. 23A-23B: DU145 individual channel fluorescent tests (representative images shown in FIG. 23A), followed by microscopic image analysis and quantification of RFP and Calcein intensities on different culture conditions (FIG. 23B).
Figure 23B:
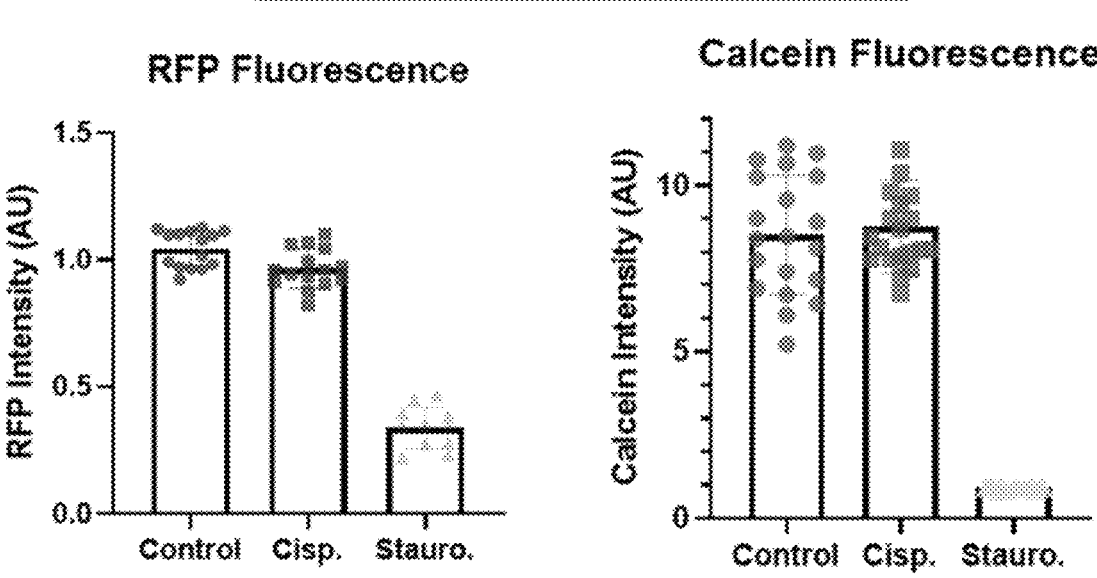
Figure 24A:
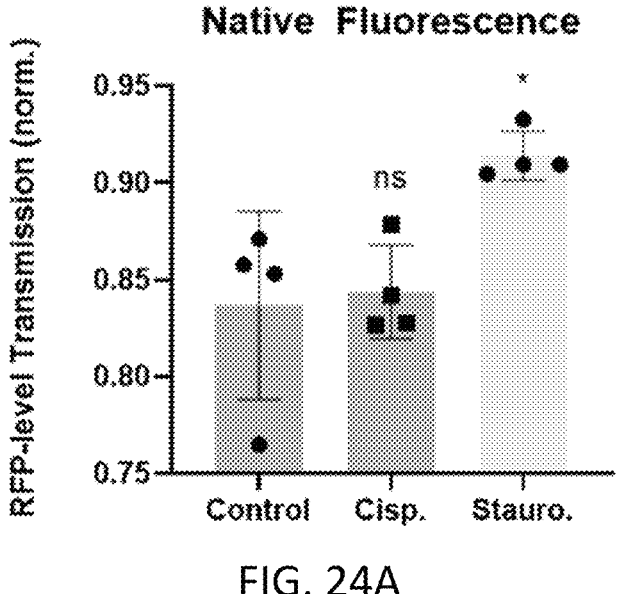
Figure 25A:
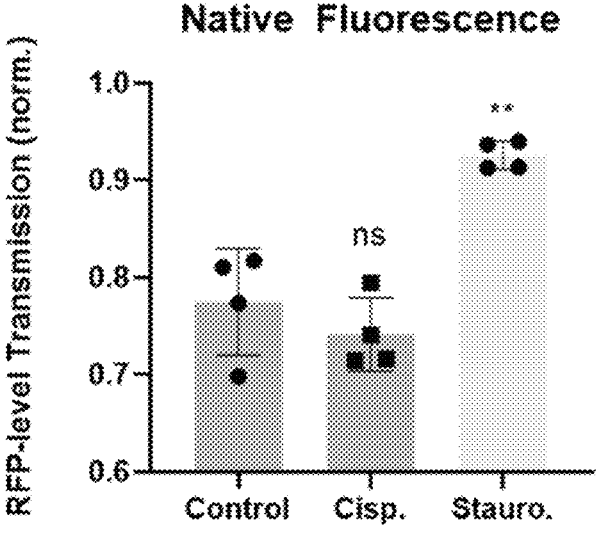
Figure 25B:
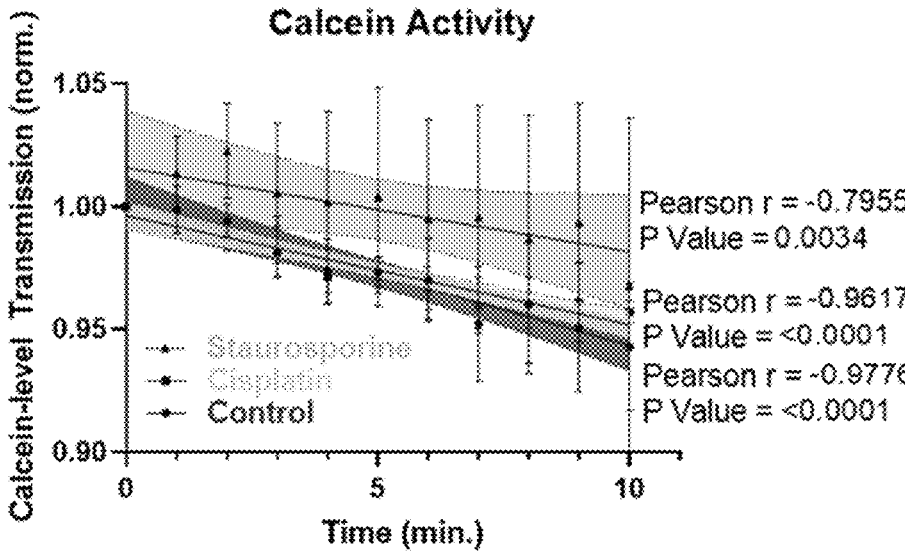
Figure 25C:
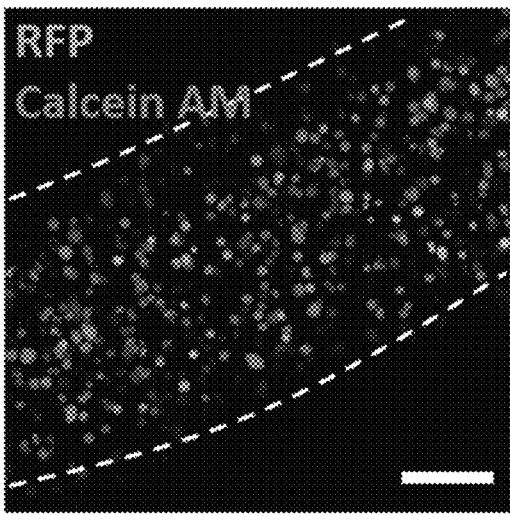
Figure 25D:
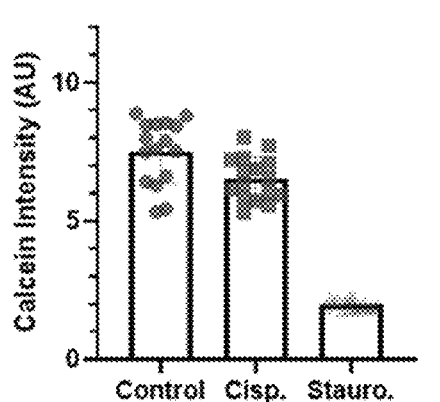
Figure 26A:
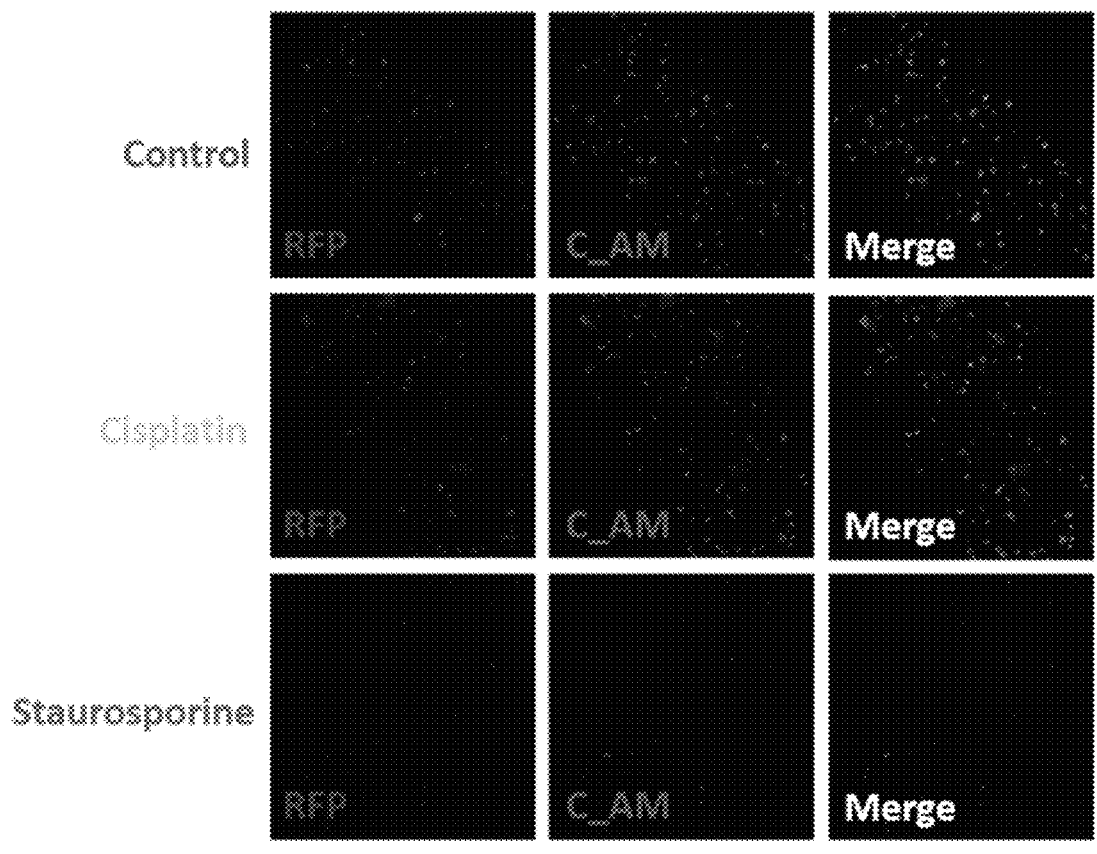
FIGS. 26A-26B: Individual channel fluorescent images of representative 22RV1 (FIG. 26A) and LNCaP-RFP-Trop2-OV FIG. 26B) optical fibers after culture in the presence of drugs and control conditions.
Figure 26B:
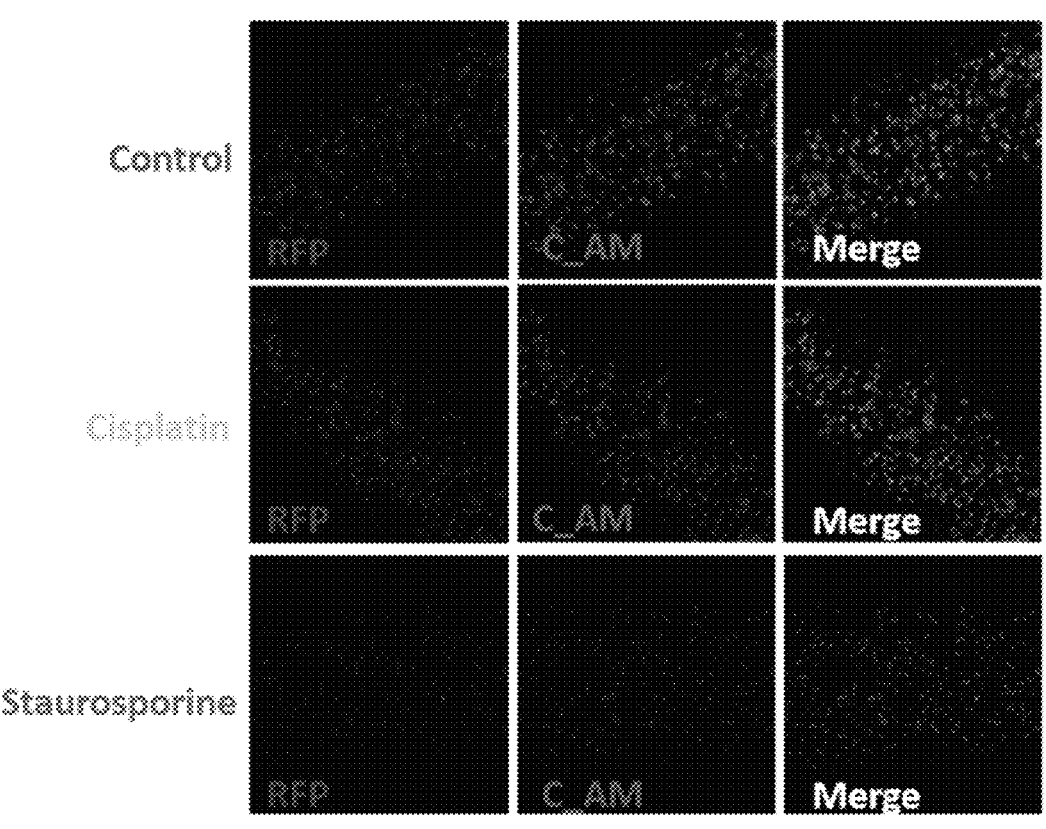
Figure 27A:
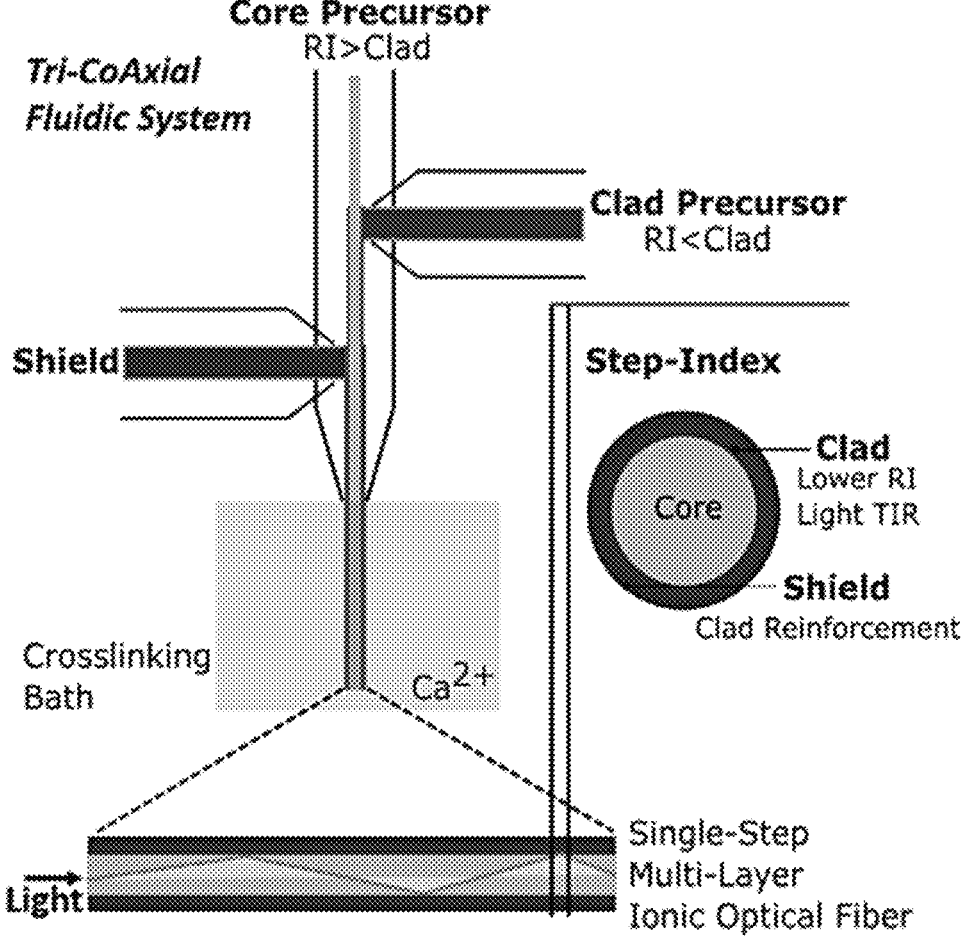
FIGS. 27A-27I: Single-Step Bioprinting Optical Fibers.
Figure 27B:
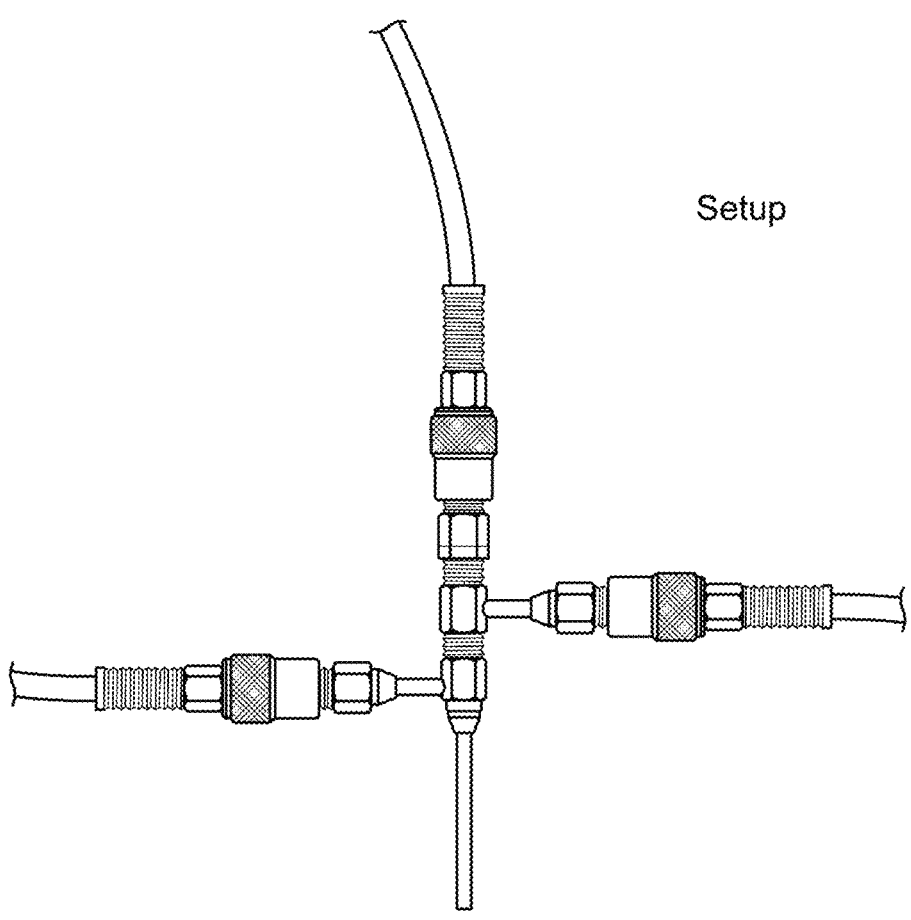
Figure 27C:
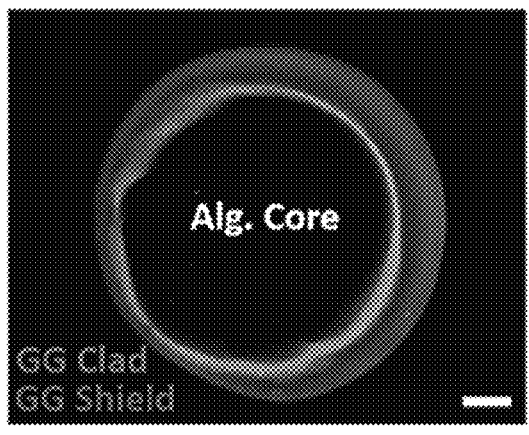
Figure 27D:
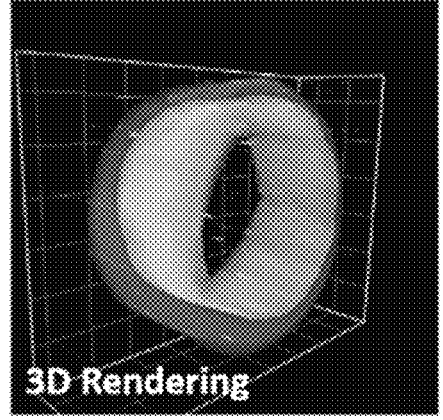
Figure 27E:
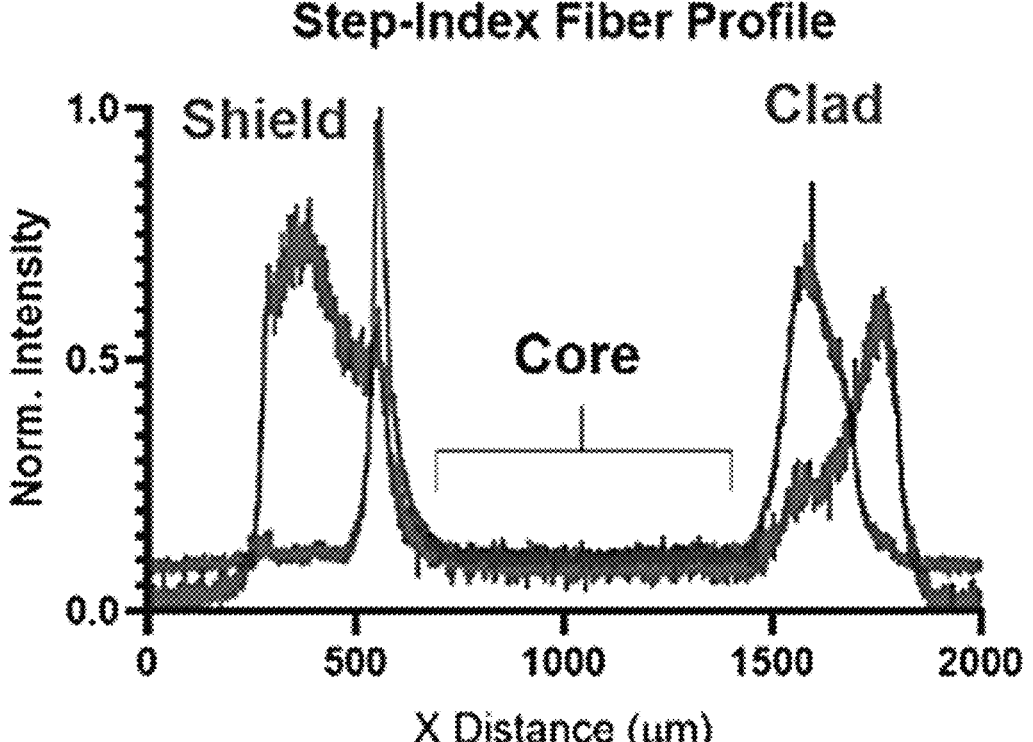
Figure 27F:
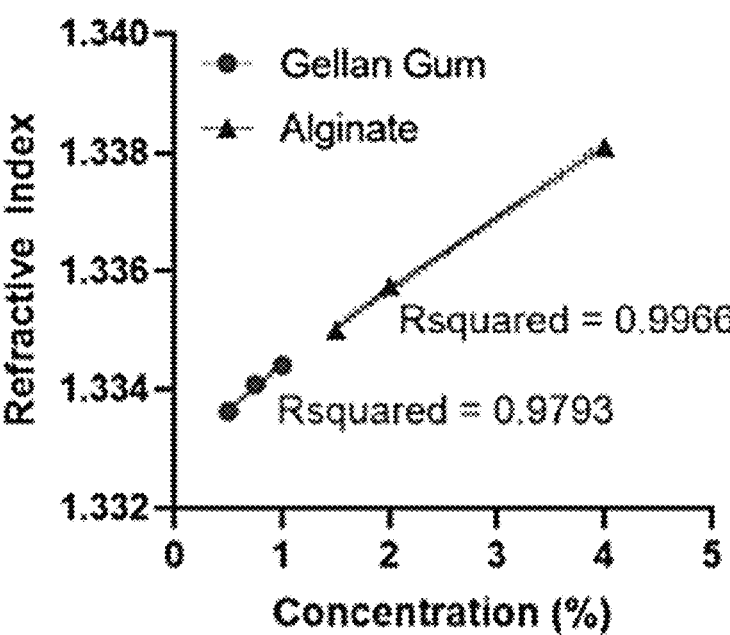
Figure 27G:
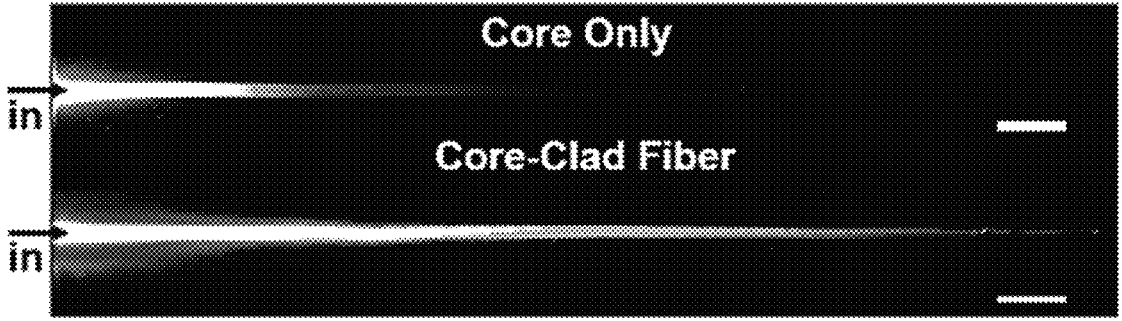
Figure 27H:
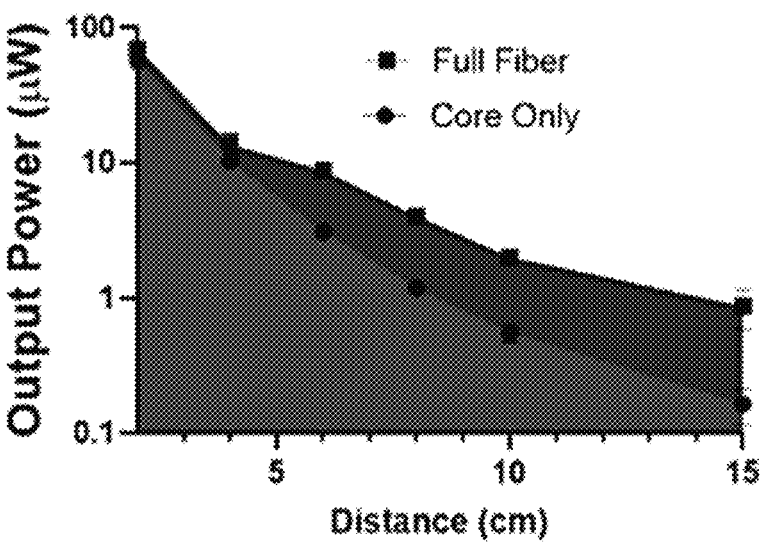
Figure 27I:
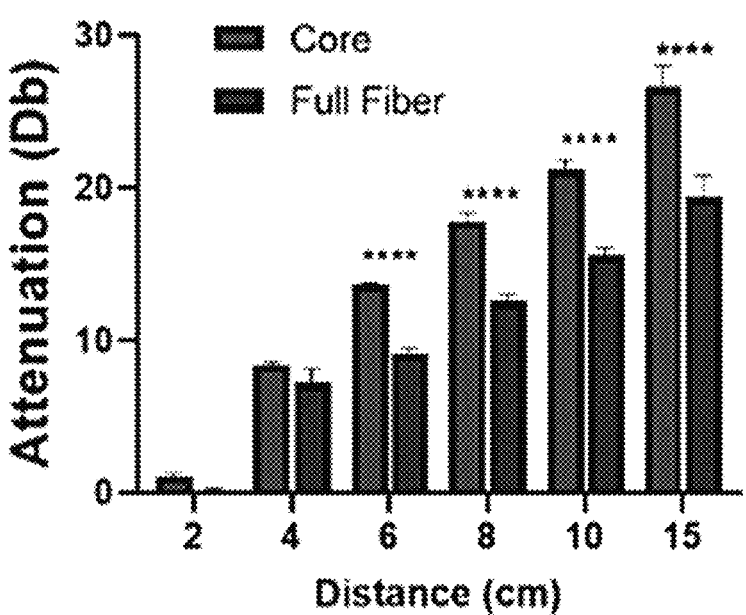
Figure 28A:
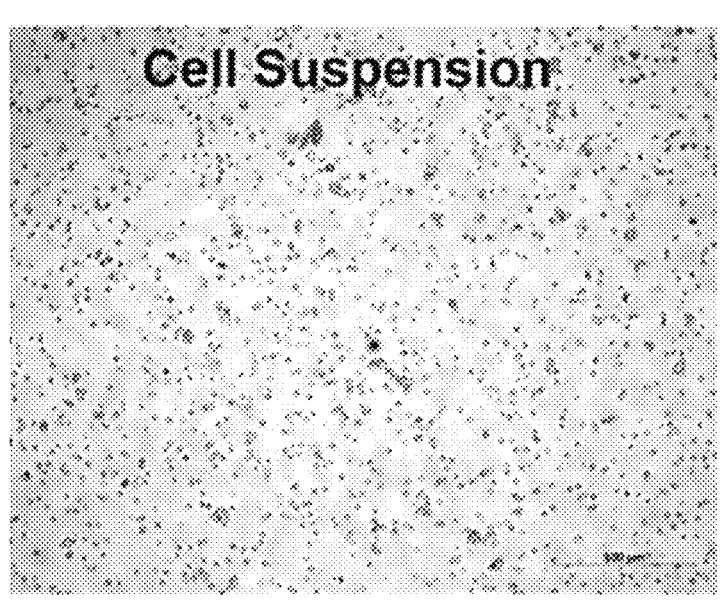
FIGS. 28A-28H: Living Cell Integration in the Hydrogel Optical Fibers.
Figure 28B:
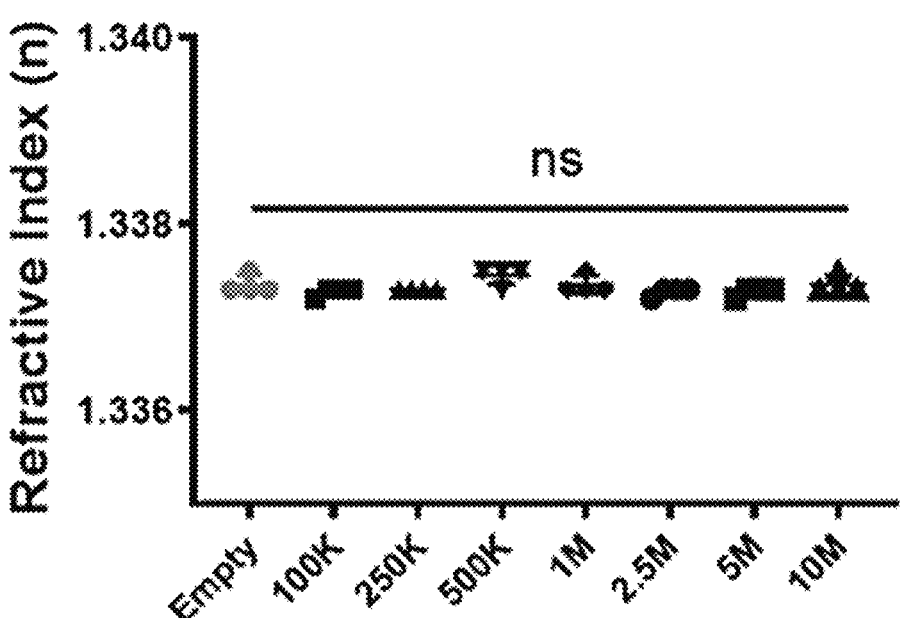
Figure 28C:
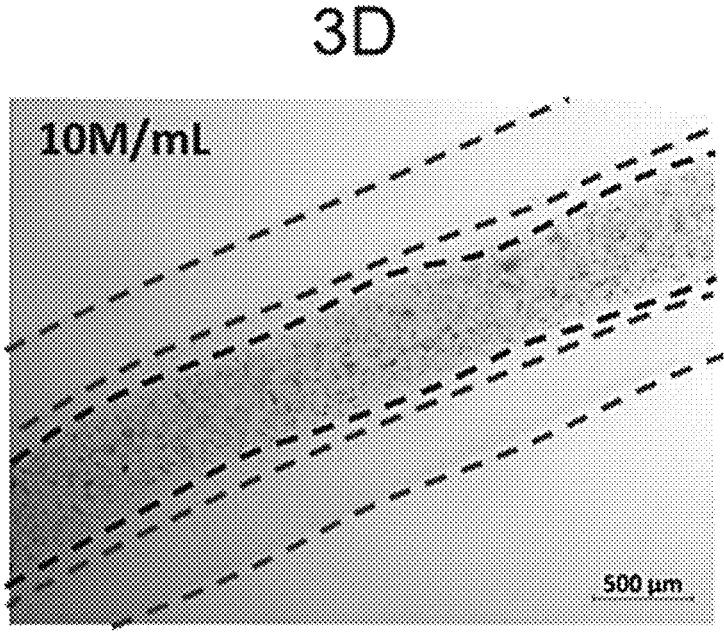
Figure 28D:
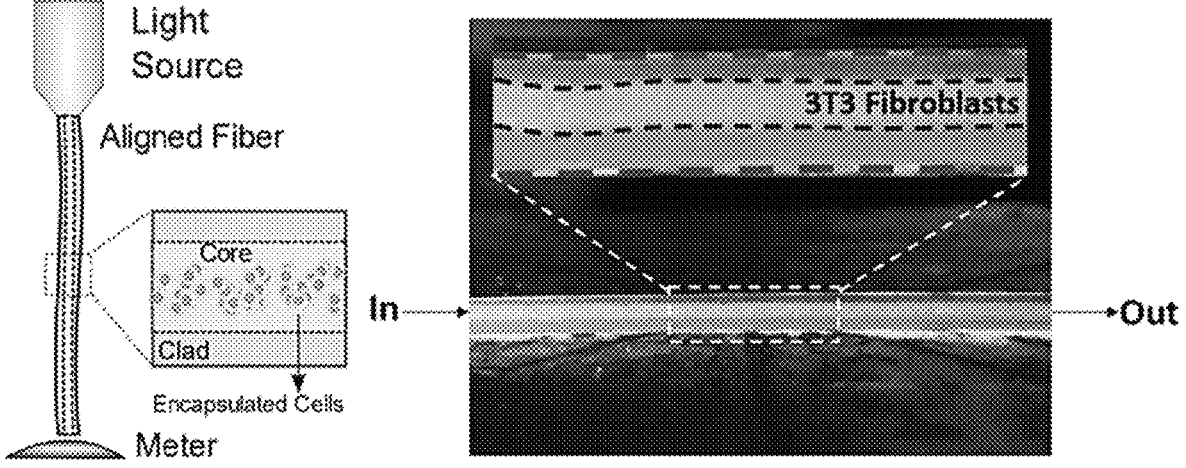
Figure 28E:
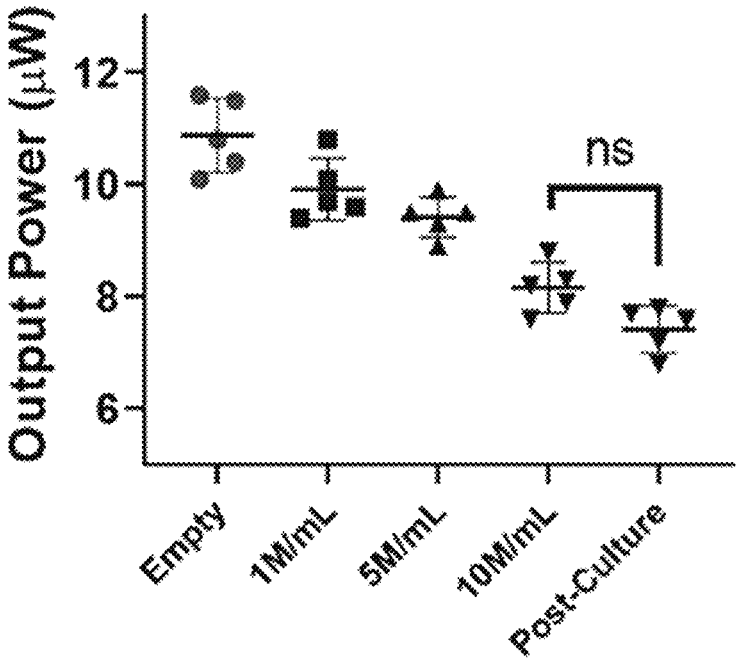
Figure 28F:
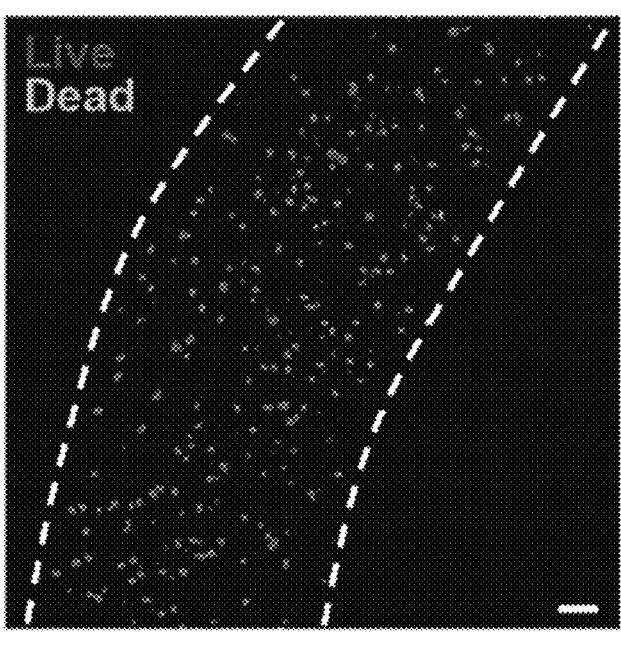
Figure 28G:
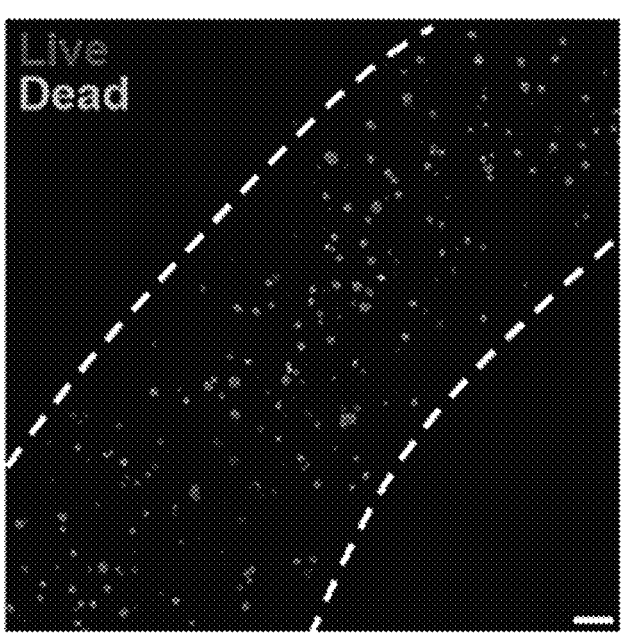
Figure 28H:
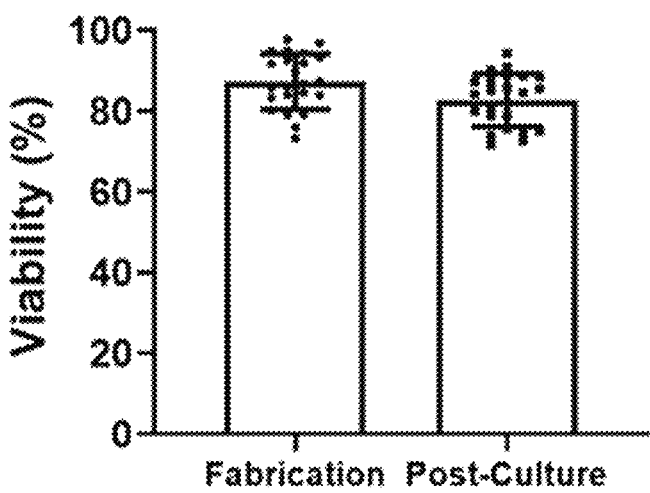
Figure 29A:
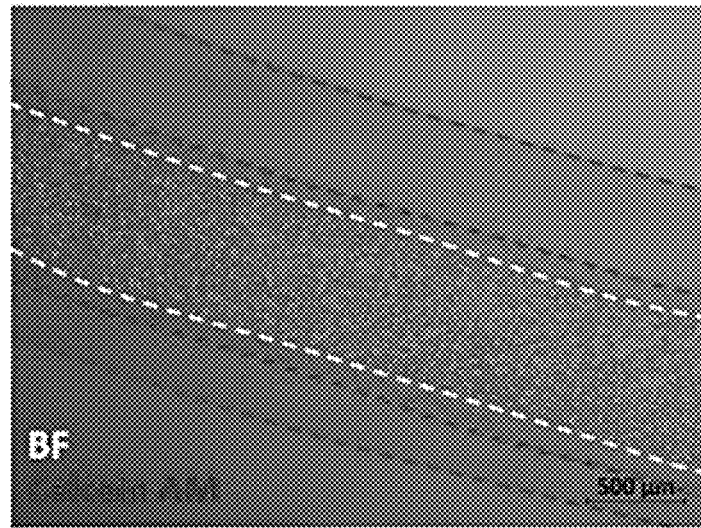
FIGS. 29A-29K: Fingerprinting Cellular Markers based on single-read optical output.
Figure 29B:
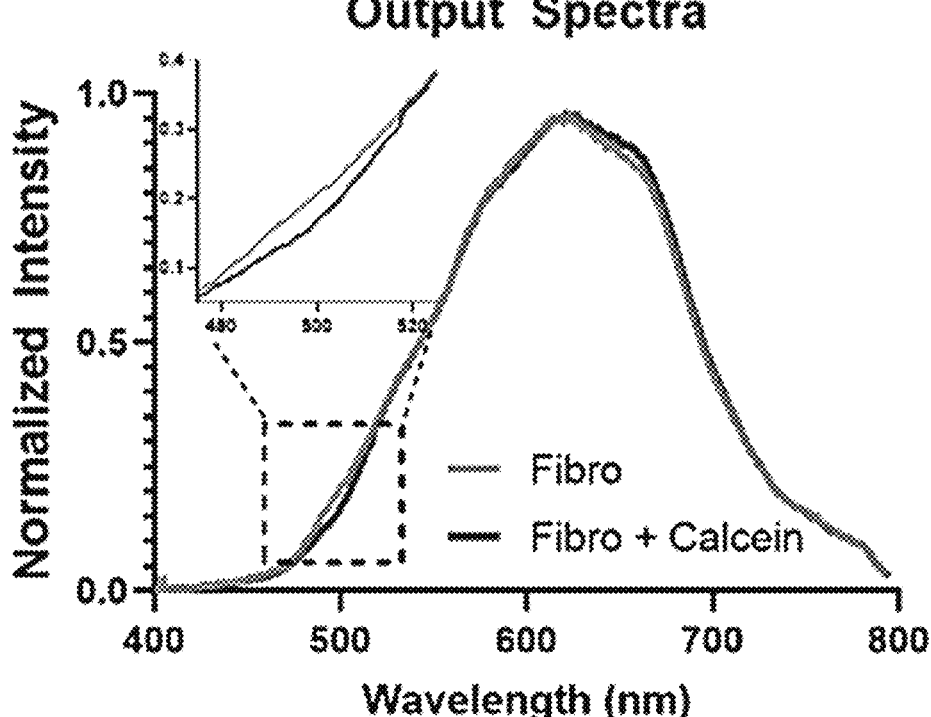
Figure 29C:
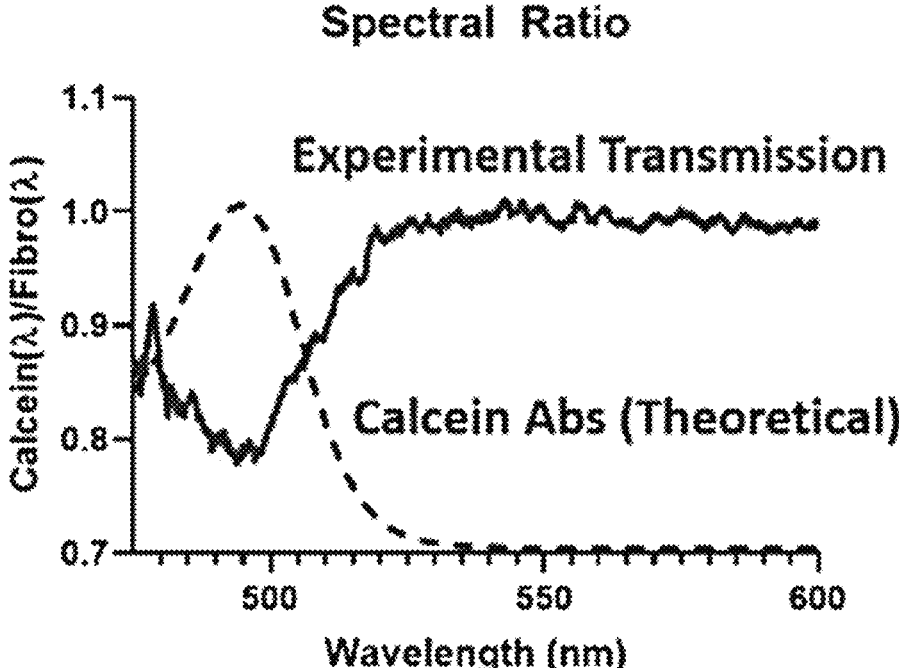
Figure 29D:
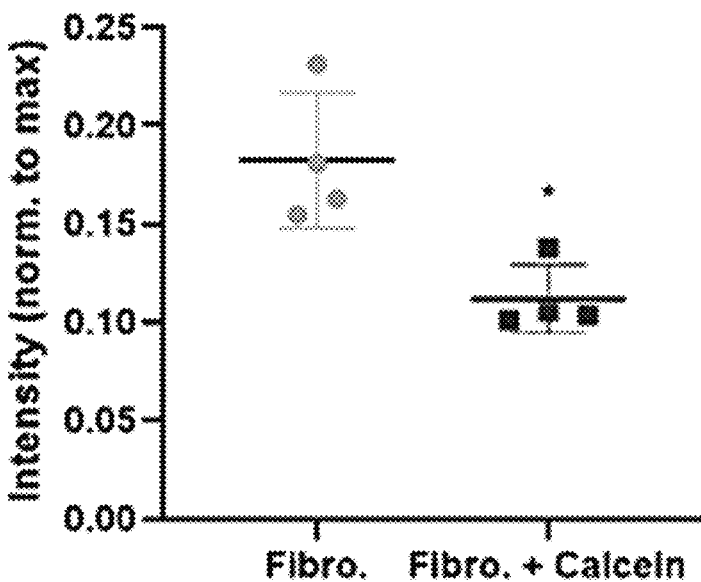
Figure 29E:
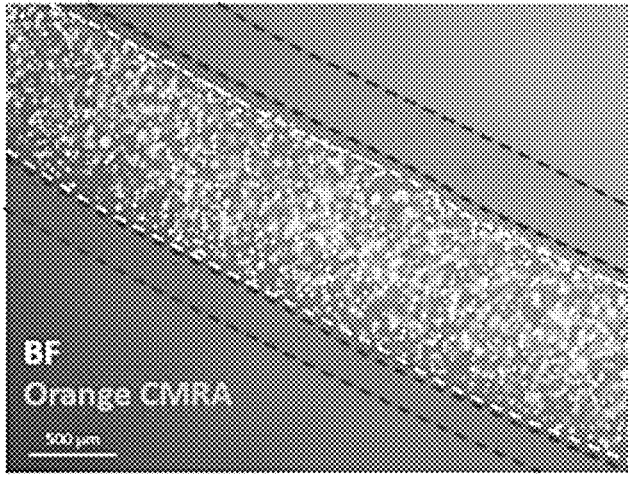
Figure 29F:
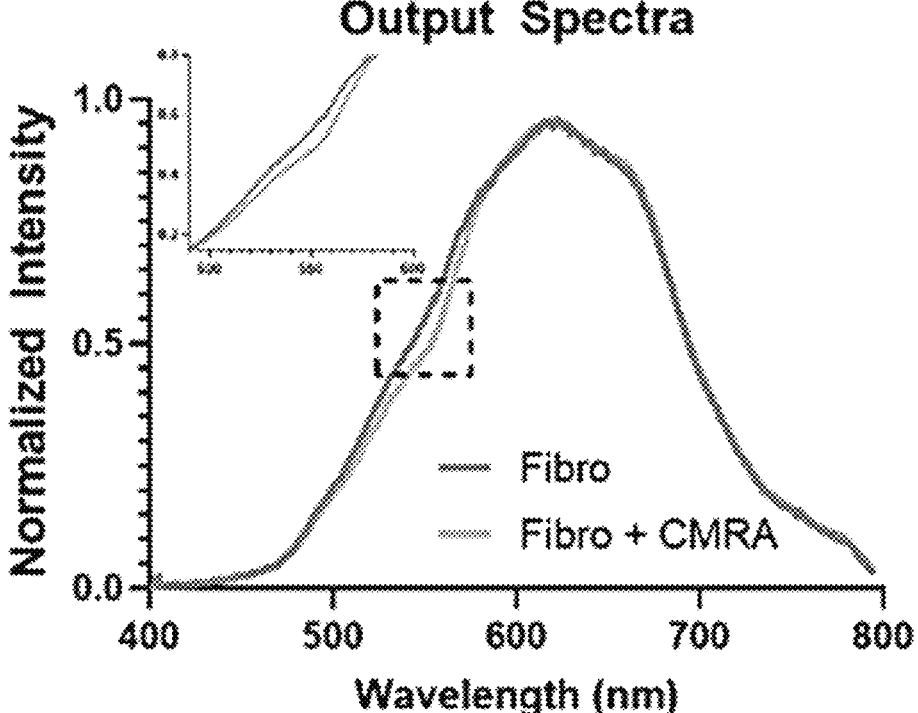
Figure 29G:
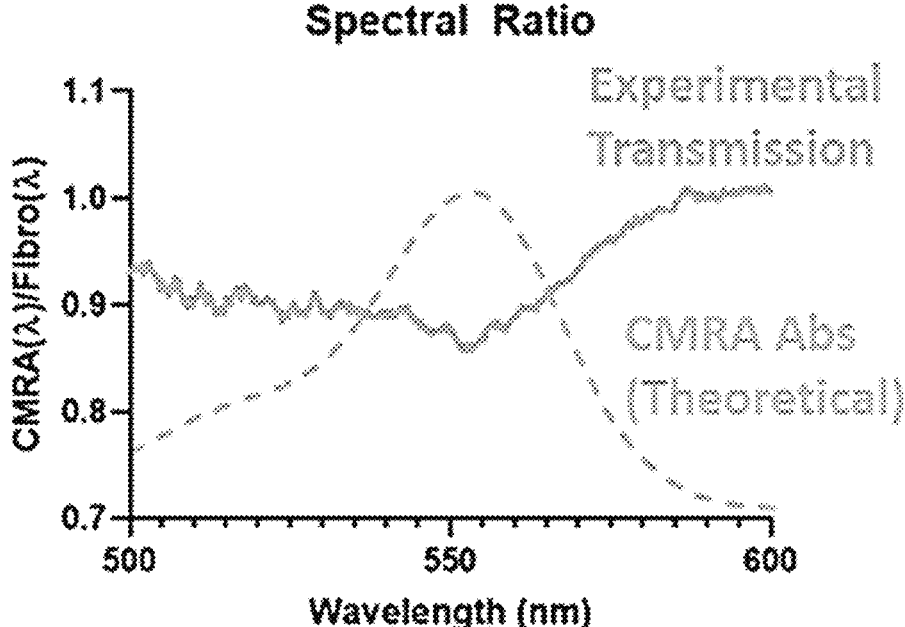
Figure 29H:
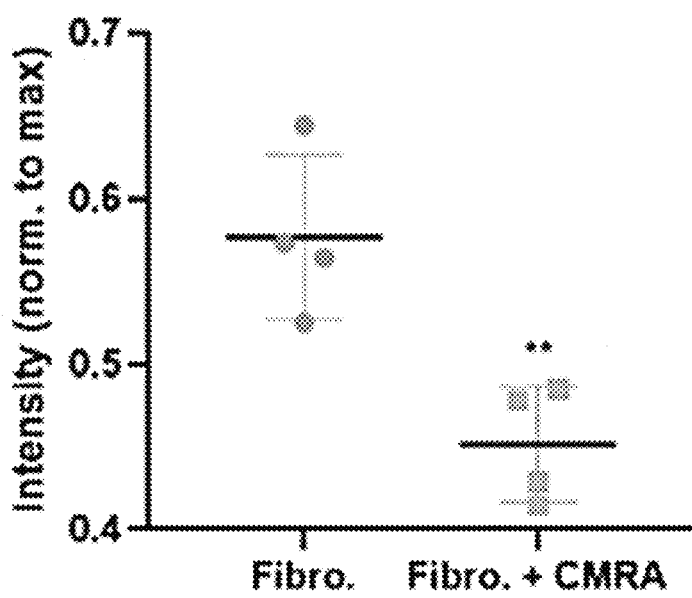
Figure 29I:
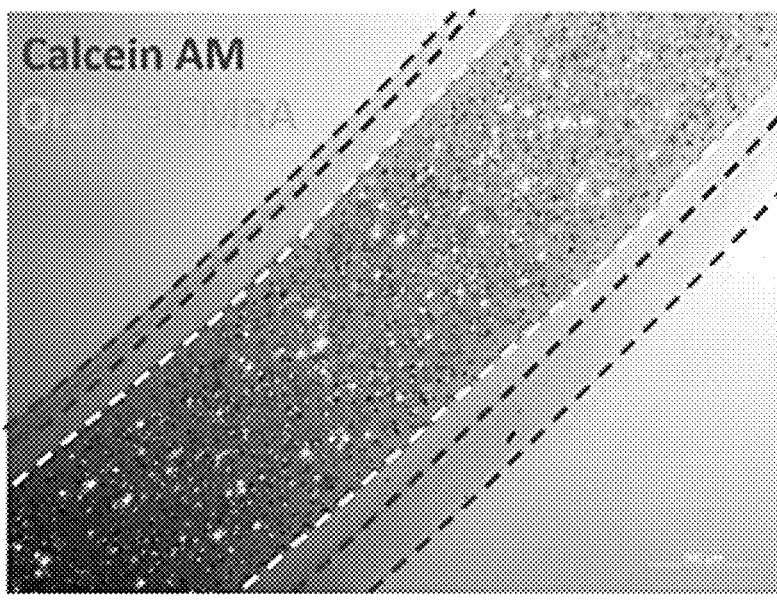
Figure 29J:
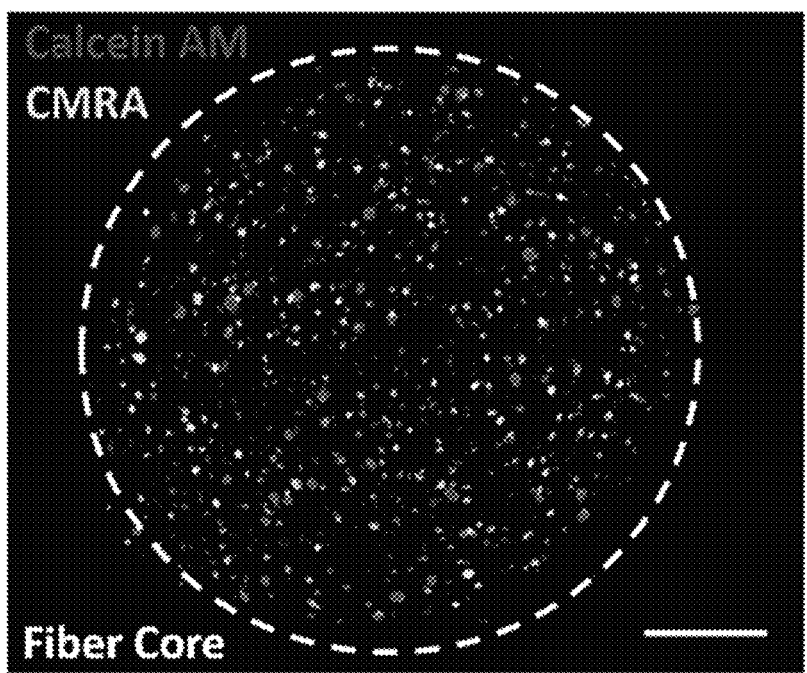
Figure 29K:
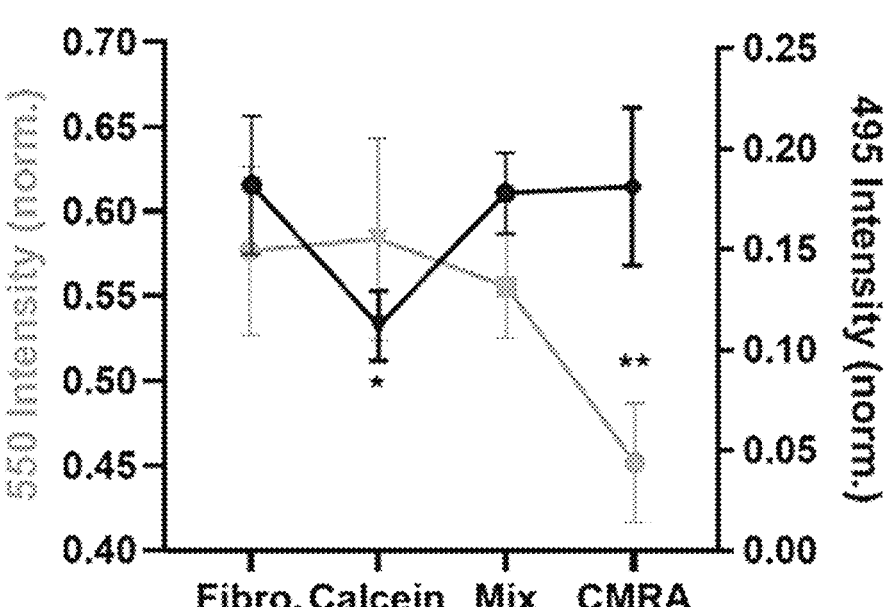
Figure 30B:
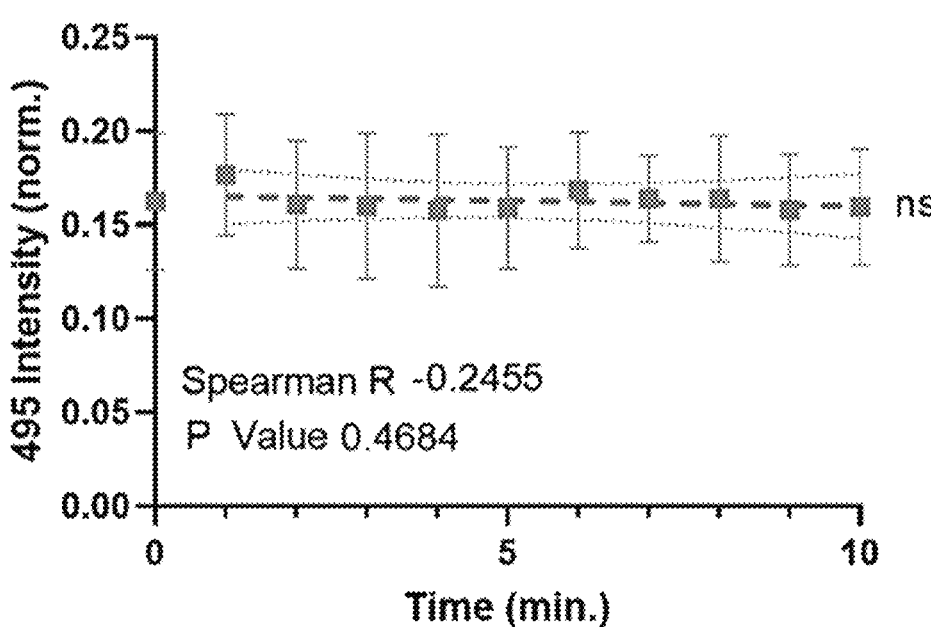
Figure 30C:
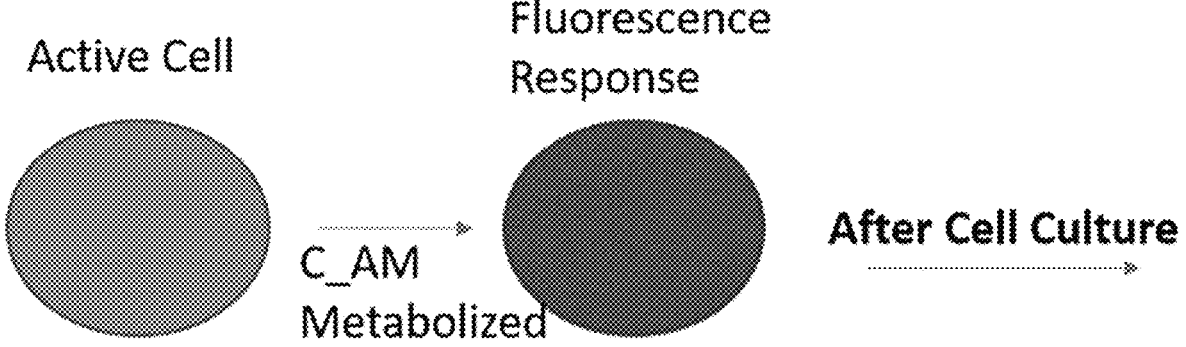
Figure 30D:
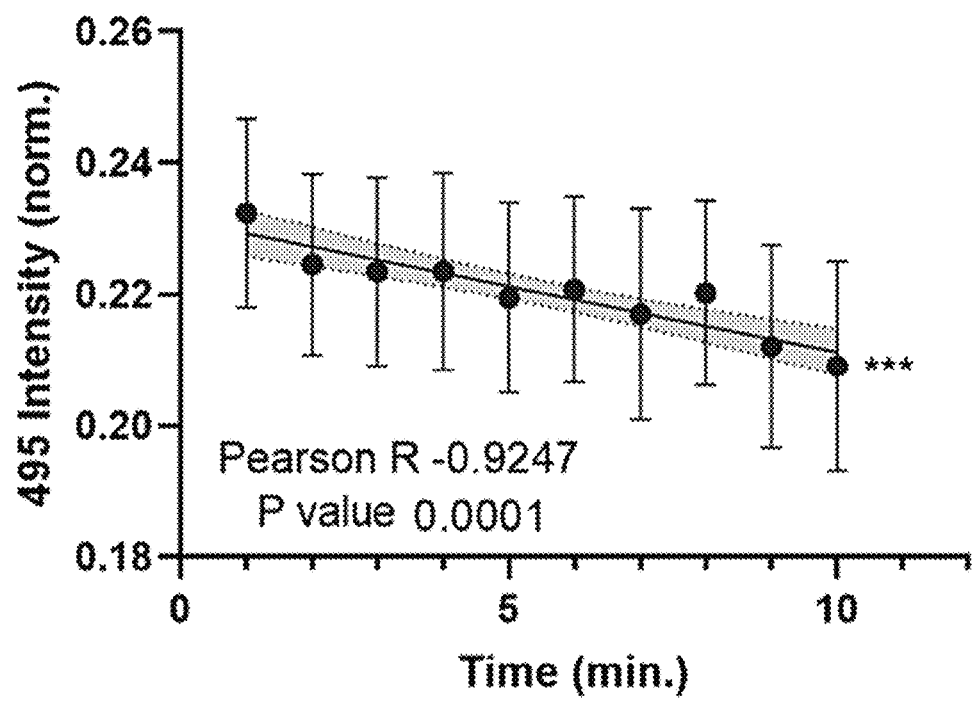
Figures 31A, 31B:
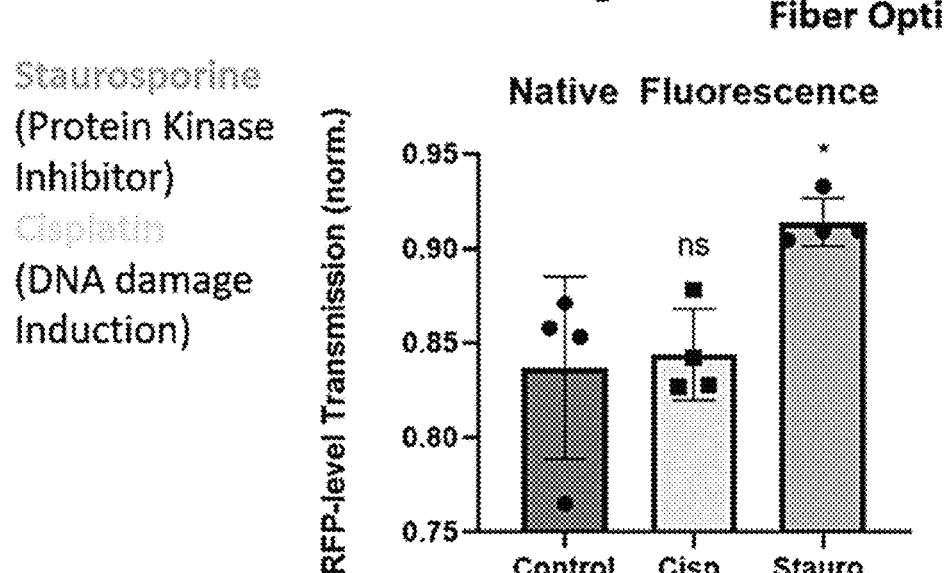
Figure 31C:
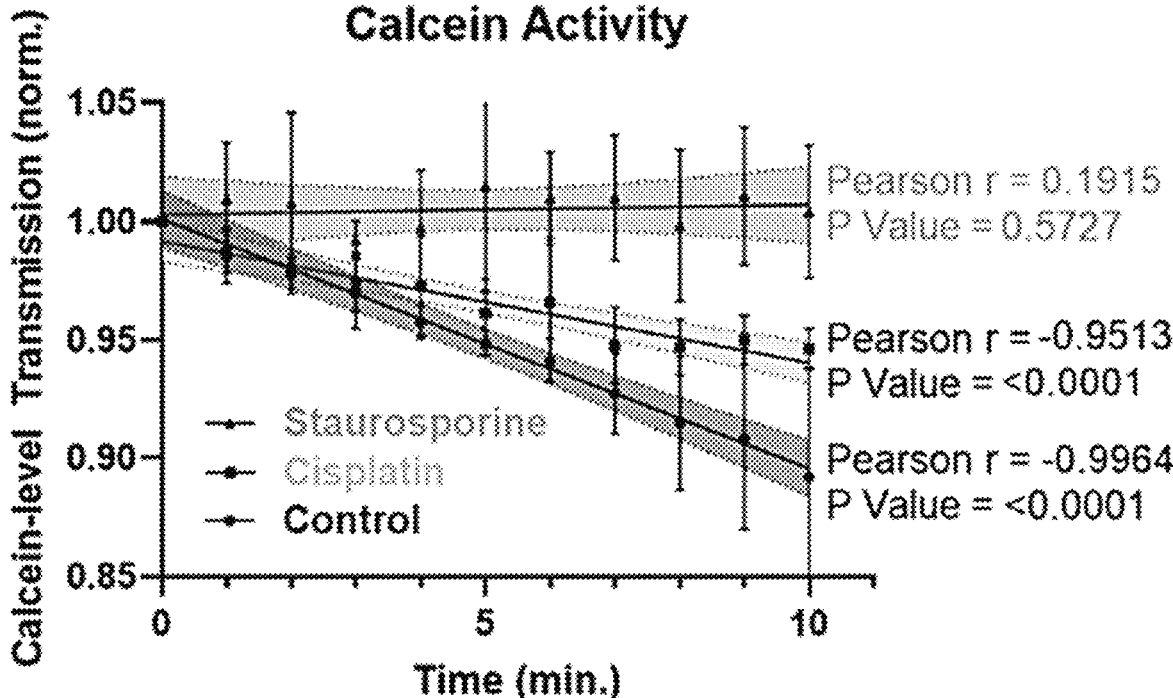
Figure 31D:
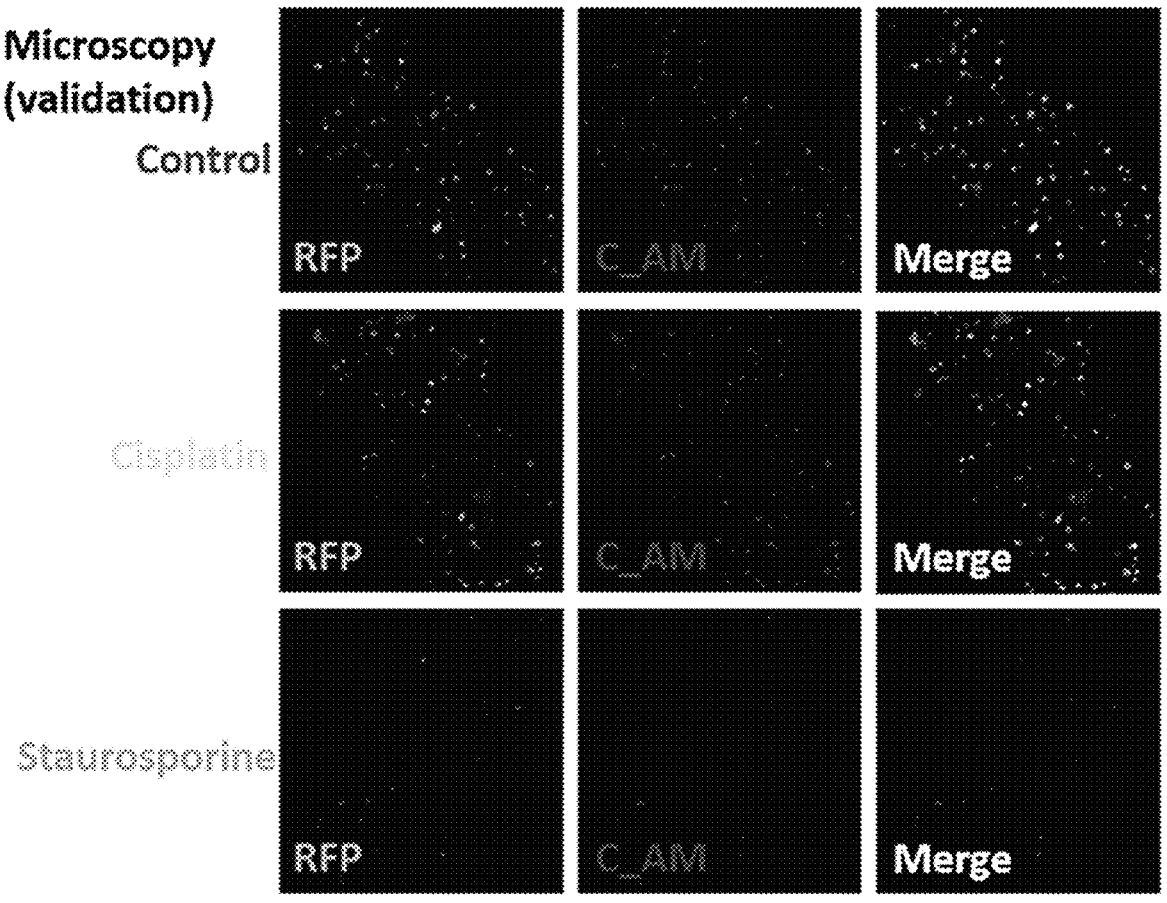
Figure 33:
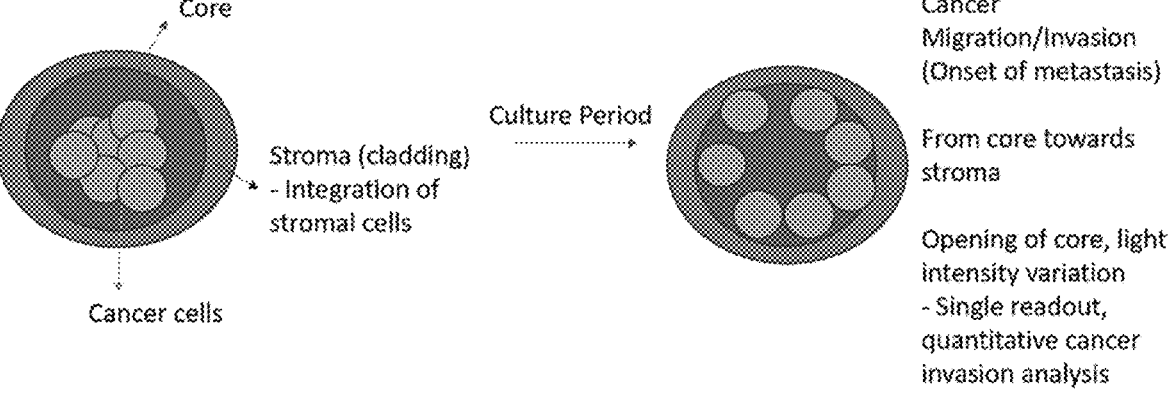
FIG. 33: Cancer invasion and migration optical quantification platform: Concept of using the living optical fibers to evaluate and quantify in a single readout approach the first steps behind metastatic disease: cancer cell invasion and migration. a | Schematic of fiber fabrication, where cancer cells can be randomly encapsulated in the biolabile core, shielded by cladding layers that can integrate also a stromal compartment (e.g. cancer associated fibroblasts). b | after a period of culture, the invasion and migration of cancer cells from random orientation towards the stromal compartment cause a change in the optical fiber core by opening the center to higher passage of light, leading to an increase in light intensity when cancer migration to the periphery happens. This intensity can be quickly quantified to translate the level of cancer cell migration. This system is to be combined with drugs and also cell-derived vesicles (exosomes) in order to study the effect of multiple conditions on metastatic cancer behavior, in a quantifiable manner based in a simple optical redout.

To take advantage of the common crosslinking and cyto-compatibility of all layer materials, we investigated the continuous printing of hydrogel optical fibers (FIG. 4A). Using a tri-coaxial 3D printing nozzle (FIGS. 4B, 21), we were able to continuously spin core-clad-shield optical fibers in a single step (FIG. 4C). Cells were encapsulated within the core hydrogel, remaining viable post-fabrication as well as after cell culture (FIG. 4D). These structures represent the first living optical fibers where cells interact directly with guided light as an active optical component (FIG. 4E). Optical output power decreased with cell density, tested up to 10 million cells/mL (FIGS. 4F, 4G). We then studied the capacity of light to transport wavelength-specific fluorophore information. Using two fluorescent markers (Orange Cell Tracker and Calcein AM), we were able to confirm their effect on the optical transmission, with dips coinciding with the marker's excitation curves (FIGS. 4H, 4I, 22). These optical fingerprints represent a direct quantification of fluorescent responses happening throughout the cell-laden core. Moreover, it is possible to observe the metabolic conversion of these molecules by intracellular enzymes in real time, by tracking the gradual decrease in specific wavelength transmission (FIG. 4J).

Figure 4M:
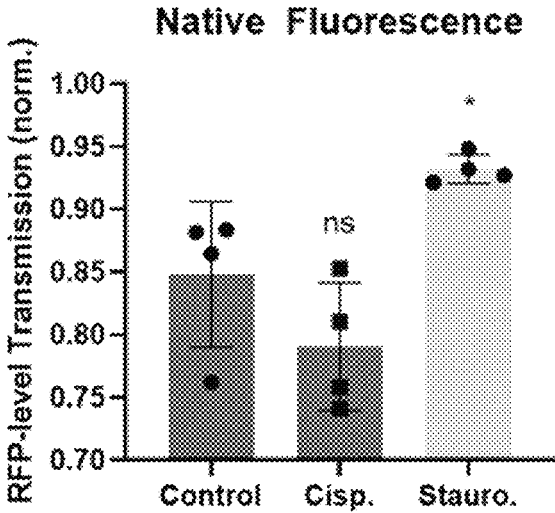
FIG. 4M) Immediate spectral fingerprinting of RFP-level transmission versus culture conditions. Statistical analysis through Brown-Forsythe Anova, *p<0.05, ns—not significant.
Figure 4N:
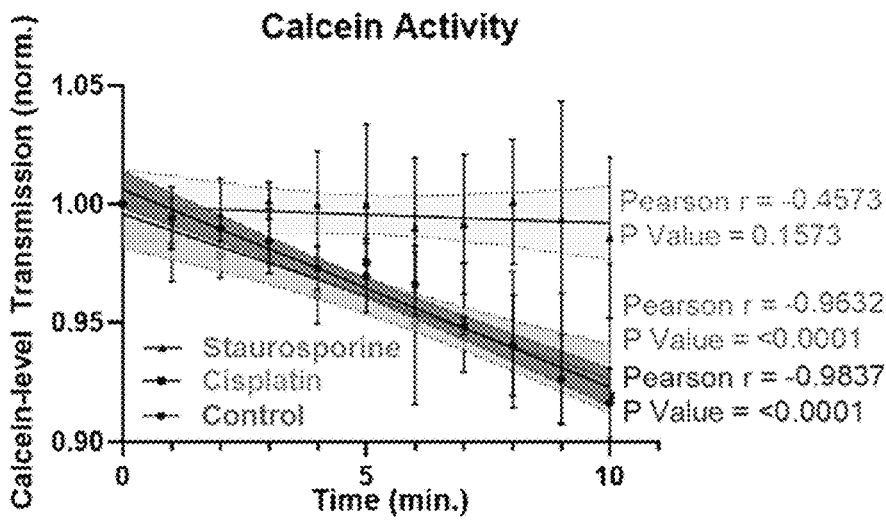

The optical spectrum fingerprinting was then used to detect, instantly and in a single readout, the expression of proteins of interest, here modeled by transfected RFP expression, combined with real-time tracking of metabolic calcein conversion (FIG. 4K). We performed a proof-of-concept study with distinct cancer cell lines and two model drugs (cisplatin and staurosporine) (FIG. 4I). Fiber-optics readouts showed staurosporine's significant reduction in RFP expression (increased RFP-level transmission), as well as a drastic inhibition in the capacity of DU145 cells to metabolize calcein. On the other hand, cisplatin had little impact on both responses (FIGS. 4M, 4N). Other cell lines reported slight variations in readouts, all of which were validated through microscopy (FIGS. 23-26). While staurosporine is a potent inducer of apoptosis via multiple pathways and protein kinase inhibition [37], cisplatin's effect is dependent on its interaction with DNA and as such more significant upon cell division [38]. Here, cells are encapsulated in a mostly inert matrix and analyzed after 48 h of culture, hence the limited effect of a low-concentration anti-proliferative drug versus a direct inducer of apoptosis. The fact that these responses can be analyzed and recapitulated with detail in the optical fibers shows their potential for fast, accessible, and widely adaptable testing.

Figure 5A:
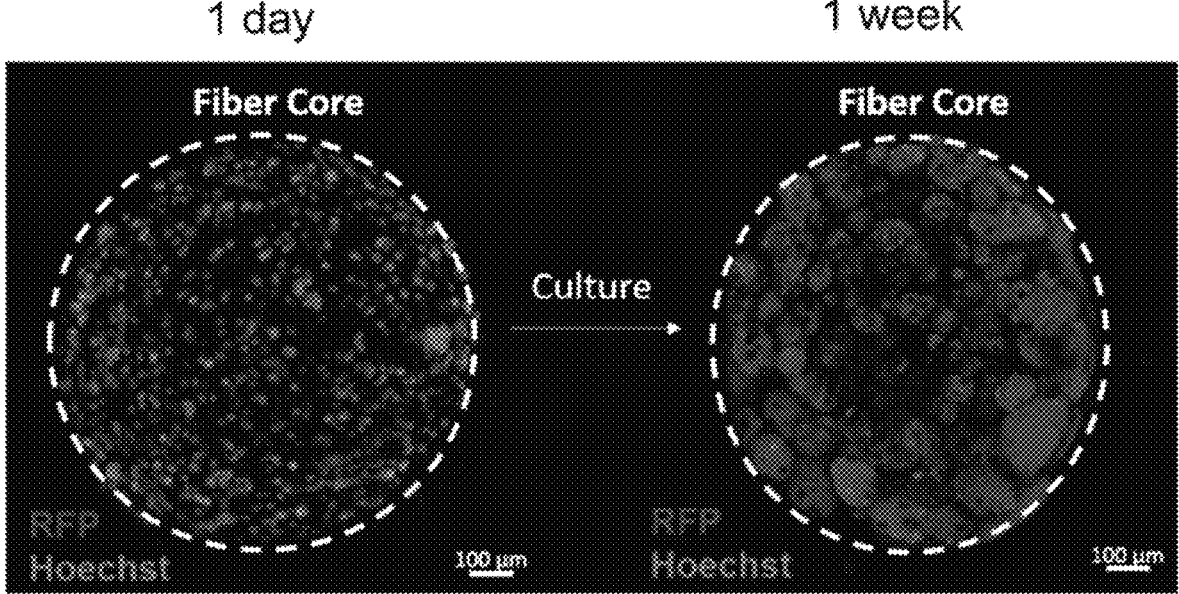
FIGS. 5A-5F: Living cancer optical fibers for the digitalization and quantification of 3D cancer growth and drug susceptibility assessment—FIG. 5A) Axial view of a biolabile optical fiber core after 1 day and 1 week of culture, encapsulating LnCaP-RFP-Trop2-OV prostate cancer cells.
Figure 5B:
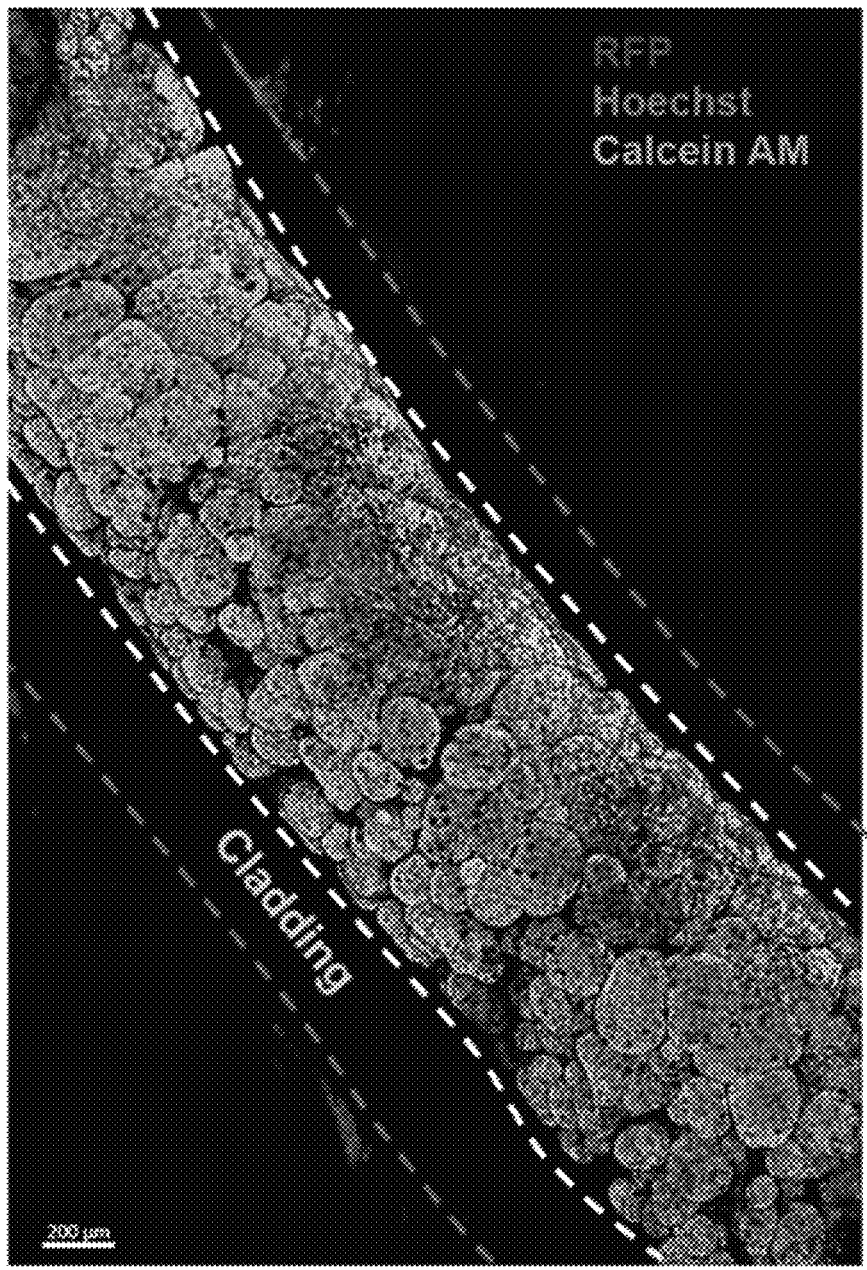
Figure 5C:
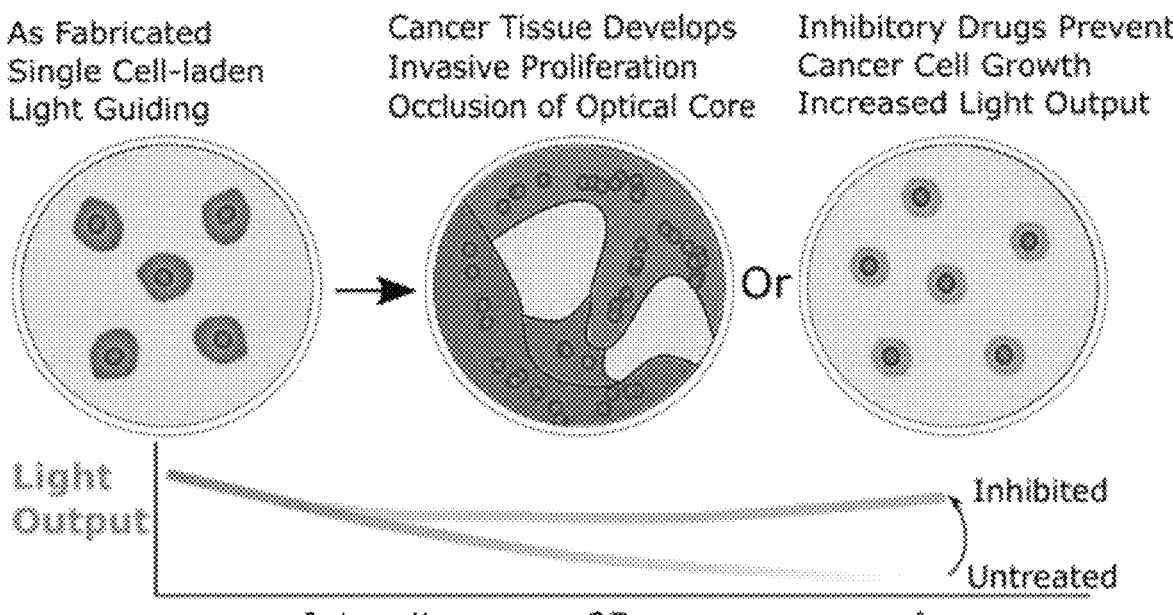
Figure 5D:
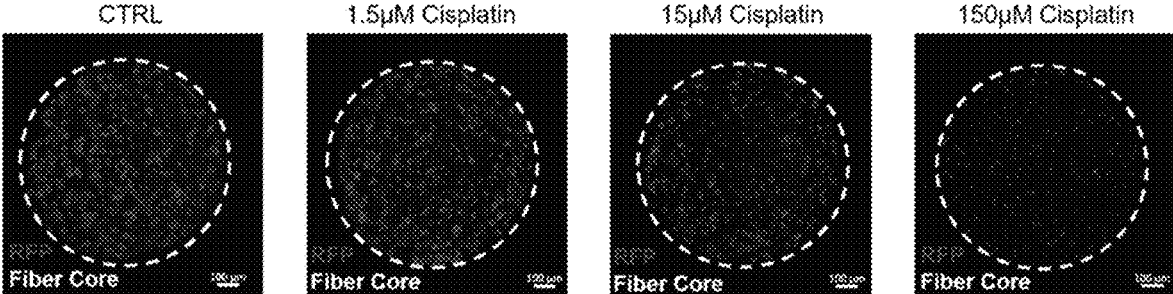
Figure 5E:
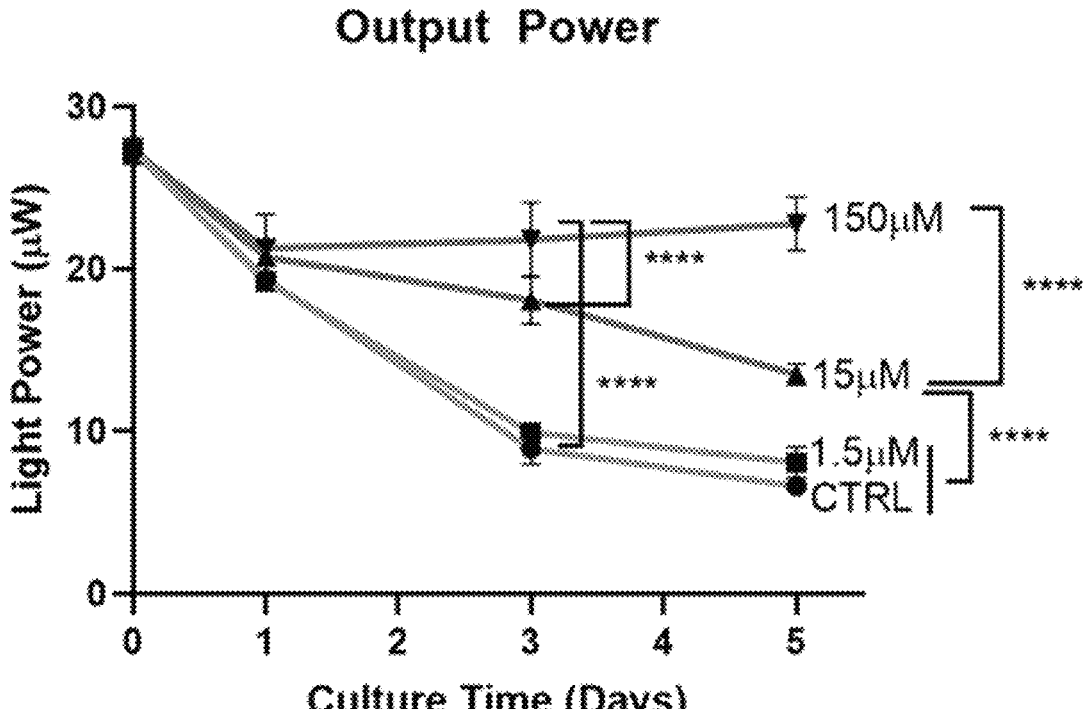
Figure 5F:
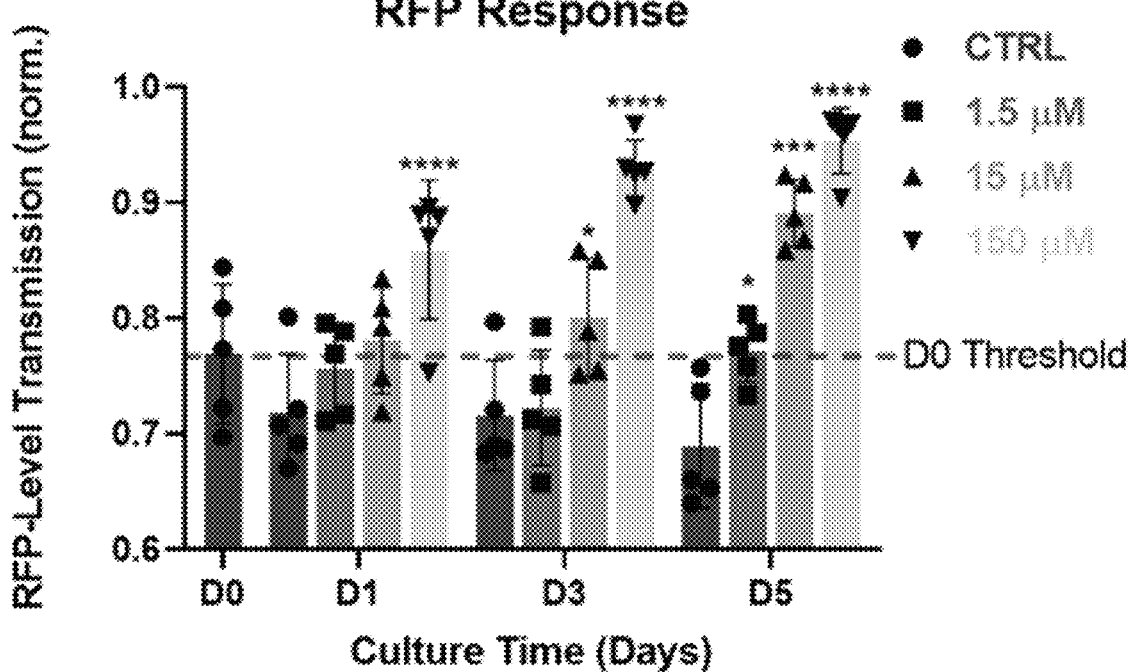
Figure 6A:
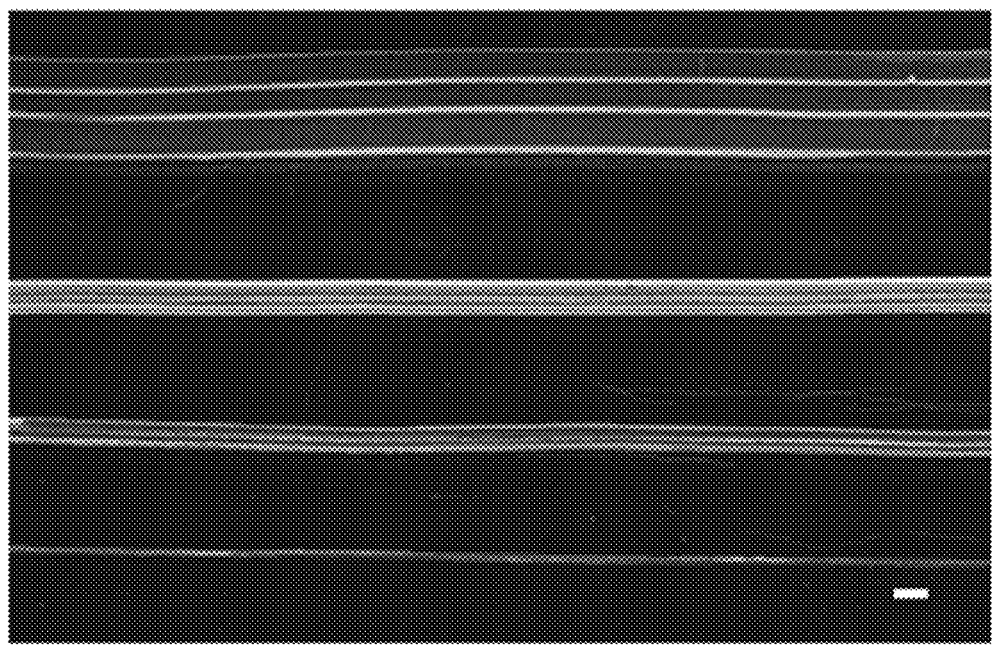
FIGS. 6A-6J: Tunable Core Size Diameter (FIG. 6A) and fiber flexibility at low dimensions (FIG. 6B). Fiber size as a function of flowing channel diameter (FIG. 6C). Output Fiber intensity of full cladded fibers at 10 cm with different core diameters (FIG. 6D), where the collected light at decreased dimensions leads to weaker output. Alginate refractive index as a function of concentration (wt %) (FIG. 6E). Gellan Gum refractive index as a function of concentration (wt %) (FIG. 6F). Comparison of the refractive indexes of Alginate 1 wt %, Gellan Gum 1 wt %, and a 1:1 blend of both solutions (FIG. 6G). Representation of the interaction of the 0.25% Gellan Gum (FIG. 6H) and 7% Alginate (FIG. 6I) solutions with light, where a change in light angle is evidence of increasing refractive index. Photographs of each type of hydrogel in a standard cylindrical shape can be observed in the upper left corners. Microscopic image of a transversal fiber cut (FIG. 6J), demonstrating the two hydrogels' layering structure (core stained with green micrometer-sized beads, clad with Nile red-fluorescent particles). Scale bar: 200 μm.
Figure 6B:
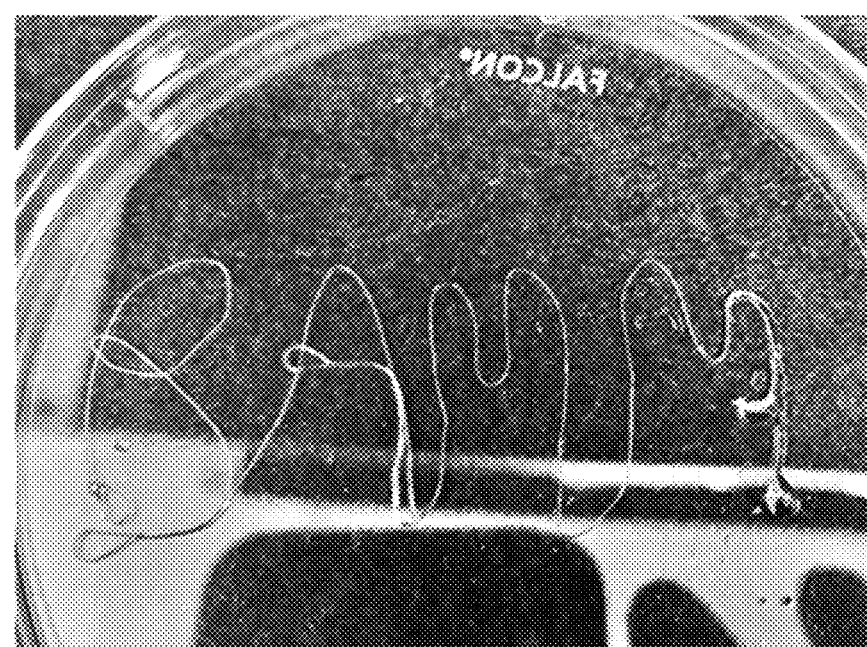
Figure 6C:
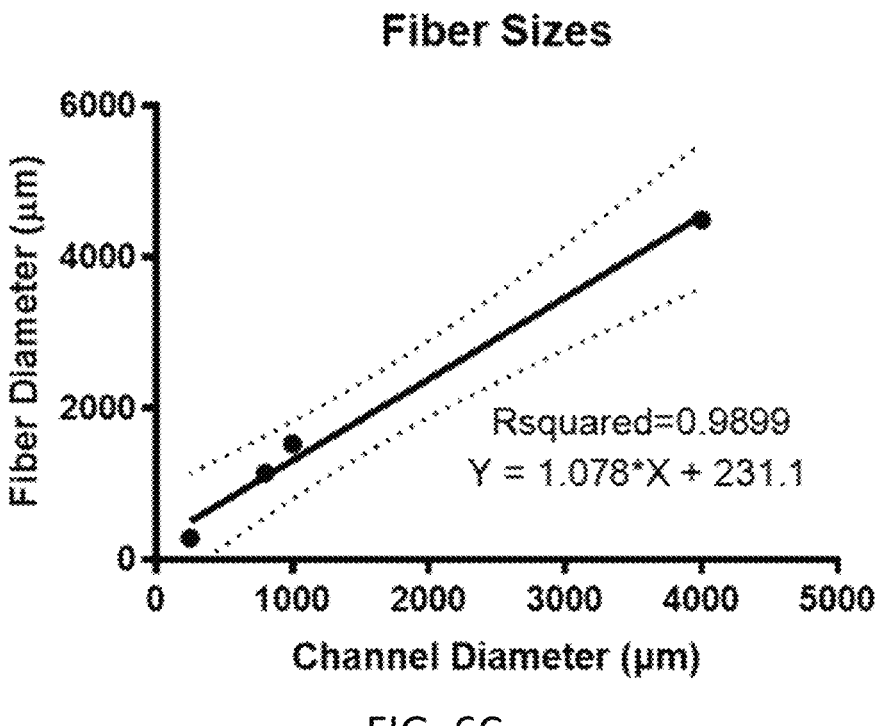
Figure 6D:
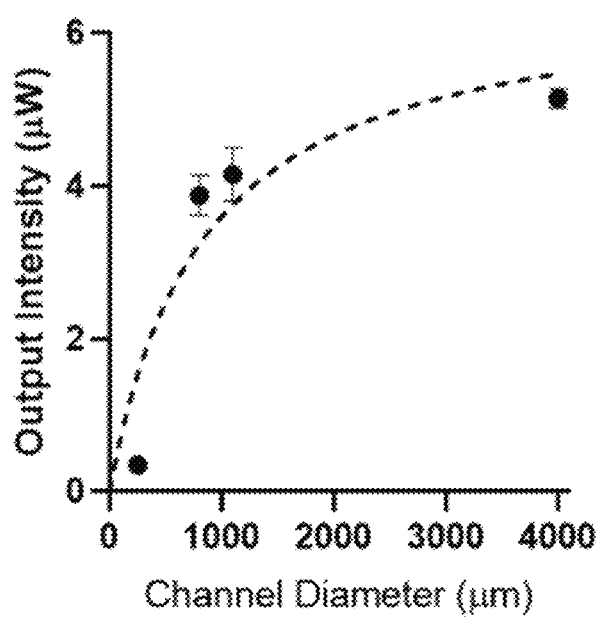
Figure 6E:
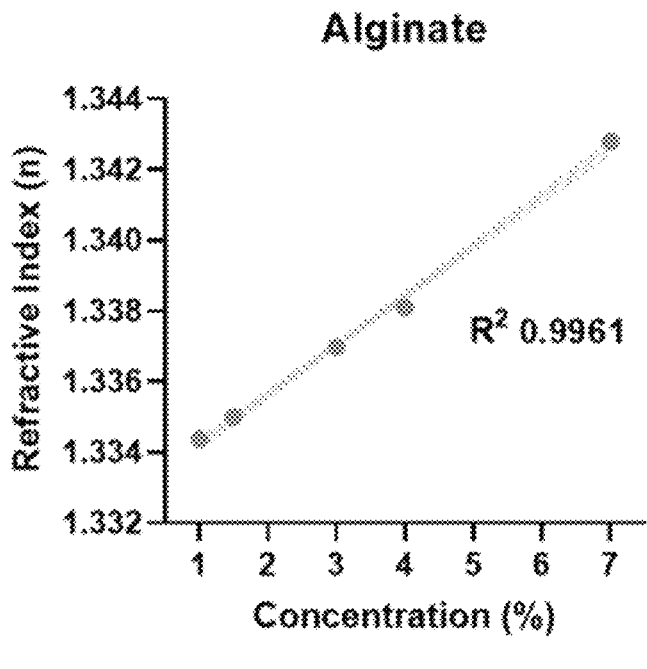
Figure 6F:
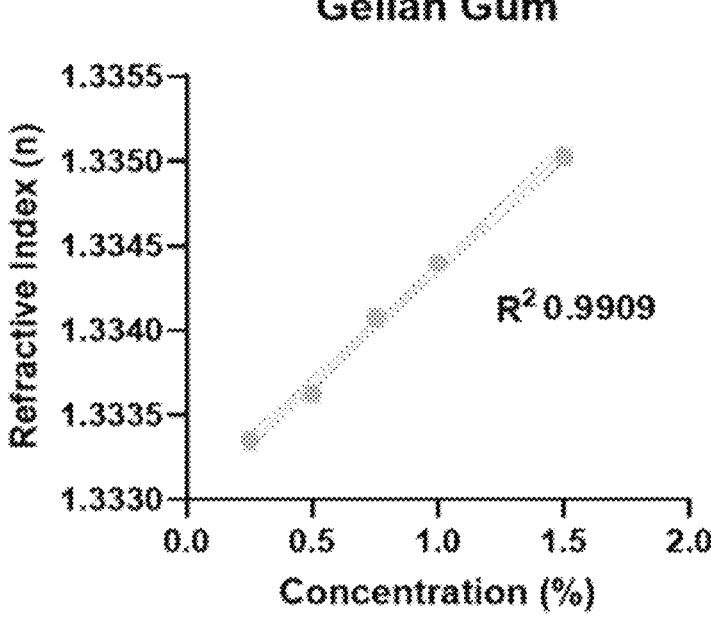
Figure 6G:
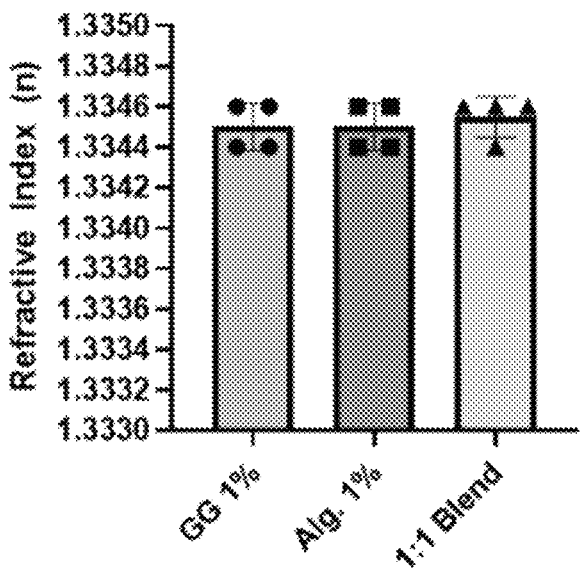
Figure 6H:
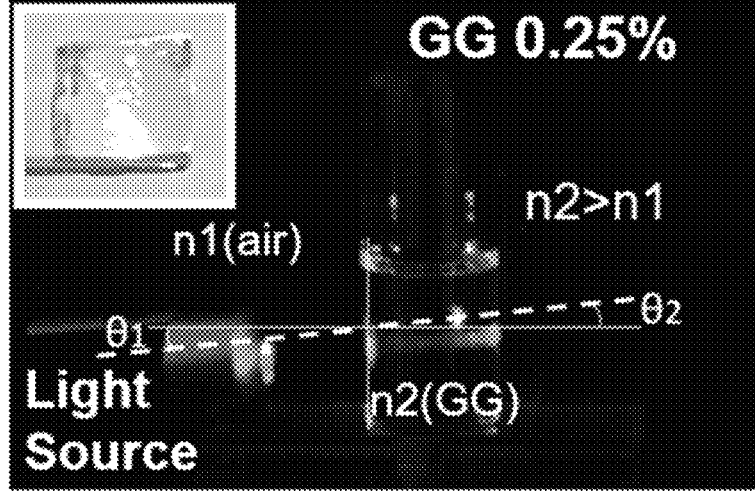
Figure 6I:
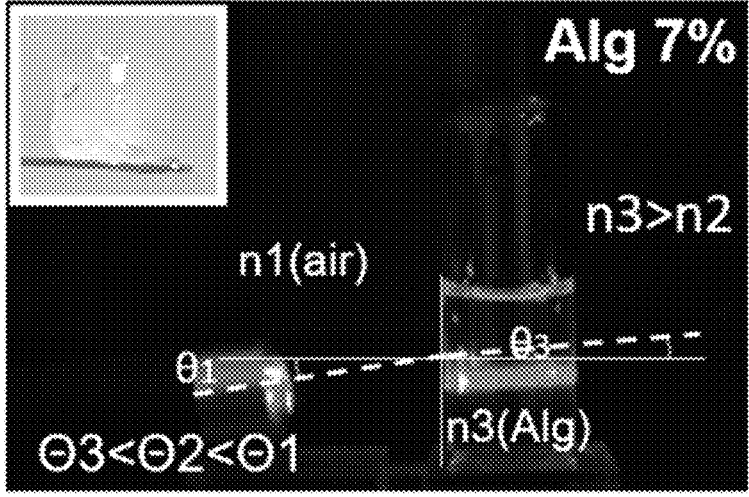
Figure 6J:
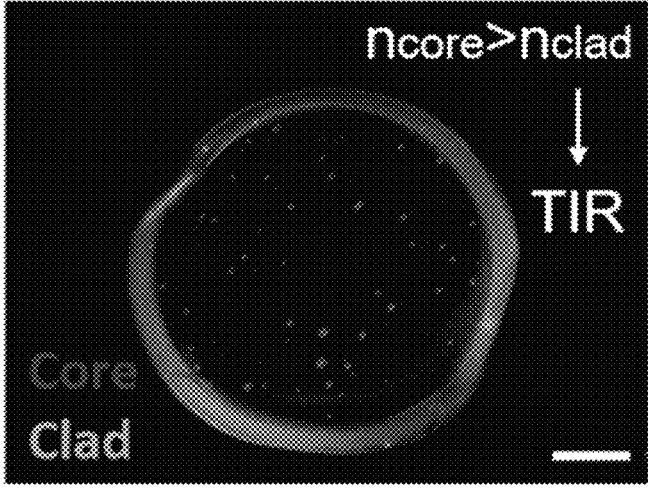

Quantitative Assessment of 3D Cancer Invasive Proliferation and Drug Susceptibility To elicit more prominent biological events in the hydrogel optical fibers, we blended a basement membrane extract with the core material encapsulating LnCAP-RFP-Trop2-OV cancer cells expressing RFP as model fluorescent protein. Upon 1 week culture, the single cell-laden structure gradually evolved to a fully occluded cancer core (FIG. 5A). Left unchecked, the cells invade their surrounding matrix and proliferate forming a mature fiberoid (fiber-shaped organoid) (FIG. 5B). We explored this response together with light guiding and optical readouts to create a platform able to directly convert 3D cancer growth into quantifiable data—the digitalization of a complex biological phenomenon by fast, non-destructive analysis (FIG. 5C). Since one-week maturation led to fully occluded fibers, we studied the evolution of the cancerous structure from fabrication to 5 days, in control conditions and with increasing concentration of cisplatin (FIG. 5D). We observed that control fibers presented gradually decreasing output light power, consequence of the cancer growth and core occlusion (FIG. 5E). The lowest concentration of cisplatin (1.5 µM) had no significant impact, but a magnitude higher (15 µM) already prevented considerable growth after 3 days, and 150 µM of the drug efficiently inhibited the invasive proliferation of the cancer cells. Simultaneously with this analysis, spectral fingerprinting of RFP-level responses offered additional insight on the impact of the drugs in the protein's expression. After 1 day of culture, a significant decrease in expression (increased RFP-level transmission) was observable in the highest cisplatin concentration (150 µM), whereas the intermediate 15 µM only had noticeable effect after day 3. The lowest concentration of 1.5 UM, which does not seem to prevent proliferation, presented some effect in the protein's expression by day 5 (FIG. 5F).

Overall, this platform enabled us to directly quantify 3D cancer invasive growth and its susceptibility to different drug concentrations, pinpointing inhibitory thresholds throughout culture time. The combination of multiple fingerprinting possibilities with variations in output power enables tracking multiple responses from cell proliferation to protein expression. Diverse proteins can be tagged with fluorophores and analyzed together via multiplexing. While several methods have been developed for assessing cancer cell invasion and proliferation, most of these rely in 2D cultures or overly time-consuming methods. Examples are scratch assays, Matrigel insert invasion, or other 3D cultures requiring extensive downstream processing [39]. Distinctly, living optical fibers technology allows for an almost instant and directly quantifiable analysis of true 3D cancer development by optical interactions. The method is non-invasive, and fibers can be analyzed and re-cultured if sterility is maintained. The simplicity and adaptability of this strategy may further be used to inform on distinct responses as specific matrix degradation, the effect of mechanical properties, other type of inhibitory molecules, or important cancer microenvironment components [40,41].

Discussion

The development of optical fibers has been predominately reliant on solid-state materials and static architectures. A tunable soft optical platform that can modulate light-guiding based on biocompatible materials provides a framework for a new class of optical devices, sensors, and actuators where material structure informs the optical output. We have demonstrated that ionic polysaccharides can produce flexible hydrogel fibers in continuous multi-layered architectures. Although hydrogel optical fibers have been previously reported [14-20], specific applications would benefit from more dynamic characteristics.

By a simple wet-spinning, ionic crosslinking protocol, we can provide innovative properties not reported before for optical hydrogel fibers, including (i) the first hydrogel optical fibers based solely on ionic-crosslinking, (ii) the splicing, repairing and fusion of fibers which enable (iv) the hierarchical multi-input/output optical hydrogel fiber photonic architectures, (v) high permeability that facilitates biotarget analyte detection and (vi) the continuous biofabrication of living optical fibers. These hydrogel photonic advances can be attributed to the unique manipulation of natural, cytocompatible polysaccharides and highly dynamic ionic crosslinking.

Due to the simplicity of our platform and easy adaptability to a broad range of applications, researchers may study these fibers as implantable structures on 3D constructs, organoids, or even in vivo tissue for multiplex detection or light delivery. Self-healing polymers may also be explored for even more dynamic structures for fiber repair without human intervention. Living optical fibers open exciting research avenues for quantifying complex 3D cellular events, where advances in protein fluorescent tagging can be combined with output power data for tracking the development of healthy and diseased tissues, drug research and functional threshold discovery, and, e.g., the optogenetic stimulation of engineered cells as molecular factories. Challenges in the adaptation of this platform to other types of biological models and responses can be expected due to varying characteristics of cell/material interactions depending on physical and biochemical hydrogel properties. This may require material changes or modification to address different biological events than those herein studied. Overall, ionic polysaccharide hydrogel fibers may lead to disruptive opportunities for flexible, soft, cost-effective, and straightforward photonic constructs that efficiently complement their solid-state counterparts with unprecedented application possibilities.

Methods

Ionic Optical Fiber Fabrication

Alginate and Gellan Gum (Gelzan) were purchased from Sigma-Aldrich. Alginate solutions were prepared by dissolving the powder in aqueous solution with stirring overnight. Gellan gum solutions were prepared by dissolving the powder in an aqueous solution at 90° C. for approximately 15-20 minutes until a clear solution was observable. The different formulations of alginate, gellan gum and blends were characterized optically using a portable refractometer (Milwaukee). To fabricate the optical fiber, a microfluidic wet-spinning setup was used. Briefly, the core polymer solutions were inserted into a syringe connected to a flow pump (Fusion 200, Chemyx) and directed through a microfluidic tube into a crosslinking solution (0.1M CaCl$_2$)). After fabricating the fiber core, the different cladding layers were added by dip-coating the core in different alginate or gellan gum solutions, followed by crosslinking in 0.1M CaCl$_2$). Step-index fibers were fabricated by coating the core with a hydrogel of lower concentration and refractive index while gradient index fibers were fabricated by adding up to 5 total layers of gradually increasing refractive index. The range of preliminary conditions tested can be seen in Supplementary Tables 1 and 2.

Optical Fiber Characterization

The characterization of light-guiding properties of the optical fibers was performed using a light-source and Powermeter setup. Briefly, fibers were aligned with a 100× objective connected to a broadband light source (OSL2 Fiber Illuminator, Thorlabs) as the light input, and a light power meter (Thorlabs) was aligned at the output extremity. To obtain the distance-power profile, fibers of 20 cm were placed within the system, and 2 cm were gradually cut from the fiber, with new power readings collected at each step. Attenuation was calculated as dB=log 10(PI/PO), with PI representing the power at each distance point and PO the maximum power at the smallest fiber dimension (1 cm). To test the ability of light-guiding through 3D biological meshes, core-clad fibers were inserted into a 5% porcine skin gelatin type A hydrogel (Sigma Aldrich). Fiber-bending tests were measured similarly to distance profiles. In brief, fibers were placed in a surface with angle degree grids, aligned with the different angles, and the light power was measured at the end. Cyclic tests were performed by bending fibers to 90° and back to 0°, with power measured at the output at each half-cycle. Representative Macroscopic pictures of the fibers were obtained by directly connecting them to an optical fiber end (Thorlabs) and imaged at high-contrast with a standard dual-camera.

Ionic Core Doping and Split Fusion

The optical fiber core doping procedure was done with minor modifications to the wet-spinning protocol. In brief, the Calcium Chloride 0.1M solution was replaced by Neodymium Chloride (Sigma Aldrich) 0.1M aqueous solution. The ionic precursor was then wet spun with a similar setup into the rare-earth metal solution. A blue dye (Procion MX, Turquoise) was added to the alginate solution to differentiate the doped core color for visualization only. To confirm the lasing capabilities of the doped fibers, the neodymium alginate core was cladded with 0.25% GG and shielded with 2 wt % alginate and aligned in the optical characterization setup. As input light, an 808 nm laser (Thorlabs) was used, and the Power Meter was set to measure light power at both 808 nm and 1080 nm. The 1080/808 nm ratio was then calculated to observe for a shift towards 1080 due to the doping and characteristic light amplification of neodymium.

Optical fiber core split-fusion was performed by a re-crosslinking protocol. Fibers with split ends were brought together, and the extremities were locally de-crosslinked by applying a drop of Sodium Citrate 55 mM (Sigma Aldrich) for 1 min. Afterwards, the extremities of the fibers were brought together, and re-crosslinked by adding 0.1M Calcium Chloride solution, and afterwards immersing the fiber in the crosslinking bath for complete re-crosslinking. Larger gaps between extremities were also fused by adding a microliter-sized alginate droplet of the same concentration as the fiber core to the junction, immediately before re-crosslinking. The same approach allowed for fabricating the multi-input/output optical architectures.

Multi-Output and Multi-Input System's Characterization

Multi-output systems were characterized in a manner like the linear optical fibers. Briefly, the light source was coupled at the input fiber side, and the power meter was then aligned with the different outputs to characterize the light power coming out of each of them. Fiber arms were moved to distinct positions and the different outputs were characterized similarly to plot the relationship between output power and optical fiber angles. For compression tests, the dual-output fibers were compressed by cylindrical weights with 5 mm diameter, which were gradually stacked to increase the total mass (m). Compression force (F) was then calculated using the F=m*g formula, with g being the gravitational acceleration (9.8 ms$^{-2}$).

Multi-input systems were characterized using two different light sources: a broadband light source (OSL2 Fiber Illuminator, Thorlabs), connected to a 100× objective as previously described for the first input and a narrowband Red Class II laser for the second input. In order to read the characteristics of guided light, the fiber output was aligned towards a collecting lens (Thorlabs) connected through a silica optical fiber to a Spectrometer (HR2000+, Ocean Optics). The different light sources were turned on and off alternatively and the output spectrum was collected in order to validate the ability to observe distinct light inputs in a single measurement.

Engineering Plasmonic-Core Optical Fibers for sensing

Plasmonic-Core optical fibers were obtained by encapsulating gold nanoparticles within the fiber core. Bare Gold nanoparticles (NanoComposiX) were dispersed in the alginate core solutions (an intermediate 4 wt % solution was used) at varying concentrations by vortexing thoroughly to ensure proper mixing. The fibers where then fabricated as previously described towards a core-clad architecture, and the guided light spectrum was obtained as described by aligning the fibers between a light source and lens collector, connected to the spectrometer. Increasing concentrations of gold nanoparticles were tested to observe their contribution to the light spectra. Fibers with AuNPs were also cut axially and freeze-dried for observation under scanning electron microscopy (SEM).

For transposing the platform towards the detection of target entities, protein-G coupled gold nanoparticles (100 nm) were purchased from Cytodiagnostics. These were used as a versatile platform for binding antibodies. In order to obtain anti-SARS-COV-2 Spike protein-conjugated gold particles, the anti-Spike (S1) mouse antibody (Sino Biologicals) was added to the protein-G gold solution at 1:10 dilution and left to bind for 1 hour at room temperature. After binding, the anti-spike gold nanoparticles were encapsulated within the optical fiber core to a final concentration of 20 μg/mL (optimized shift) and characterized as fabricated to observe the antibody-induced shift in light. Similar fibers were also incubated in parallel with SARS-COV-2 Spike protein (S1) (Ray Biotech) for 30 minutes at RT. The antigen was diluted 1:40 in PBS buffer solution (previously optimized detection range 1:40 to 1:4) where the fibers were immersed. After washing with calcium, fibers were aligned in the optical characterization setup to observe the shift in light caused by antigen binding. In all cases, a minimum of 4 individual fibers were tested.

Swab-Coupled Optical Fibers and SARS-COV-2 Detection

Sterile 15 cm swabs were purchased from Puritan and modified by cutting the top part of the shaft and creating an indentation for coupling the optical fibers. The swab-coupled fibers were then used to characterize their ability to bind and detect SARS-COV-2. Anti-Spike gold nanoparticle core fibers were fabricated as previously described and inserted within the swab indentations. The swab tip was separated from the shaft by cutting and the full shaft was split in smaller sections of around 3 cm. Several of these individual swab-fiber structures were then used as the model of swab-coupled sensing system. To recreate their interaction with bodily fluid and lavage, swab-coupled fibers were soaked with a PBSA solution containing gamma-inactivated SARS-COV-2 Viruses (Catalog #NR-52287, Isolate USA-WA1/2020, BEI Resources, 1:1000 Dilution), as well as similar incubation without the viral component and with Influenza H3N2 Virus at a similar dilution (Bioworld, Recombinant), for 1 hour at RT. Both fibers were then washed to remove unbound entities and aligned in the light-spectrometer system to derive an optical readout. For all cases, 4 individual swab-coupled fibers were tested.

To validate the presence of SARS-COV-2 in the hydrogel fibers, a similar protocol was followed up to the virus incubation and washing, point at which a reverse immuno-fluorescence protocol was pursued. The fibers were first blocked with 3% BSA (Sigma Aldrich) for 30 mins RT. These were then incubated with rabbit anti-nucleocapsid antibody (Sino Biologicals), 1:200 dilution, for 1 hour at RT. After washing thoroughly, the fibers were incubated with an Alexa 488 Anti-Rabbit antibody (Abcam) at 1:200 dilution for 1 hour at RT. The immunofluorescent setup and magnification rationales are further schematized in FIG. 13. Fibers were then washed thoroughly and taken for fluorescent microscope observation under different magnifications (Observer Z1, Zeiss).

RNA Extraction and LAMP-Based Detection

To further validate the presence of SARS-COV-2 viruses after incubation in the functionalized AuNP fibers, RNA was extracted using miRNeasy Kit (Qiagen). After incubation with virus and control solutions, fibers were thoroughly washed and placed on ice. These were incubated for 10 minutes in Sodium Citrate 55 mM (Sigma Aldrich) to chelate the calcium ions and facilitate the dissolution of the fibers. These were then processed according to the extraction kit manufacturers instruction. Extracted RNA was then analyzed using the COVID-19 Rapid Isothermal PCR Kit (RT-LAMP) (Raybiotech) according to the manufacturer's instruction. Briefly, extracted RNA and controls were placed in individual PCR tubes and mixed with the primer master mix. Tubes were then placed in a Thermocycler for 30 mins at 60° C. for the amplification reaction to take place, and then left at room temperature for stabilization of the reaction during 1 hour. At the end, the color changes were captured in a photograph, and the absorbance of the solutions was measured to obtain the 570/650 nm ratio, which is above 1 for SARS-COV-2 positive samples.

Dot-Blot Validation Tests

To confirm the capability and specificity of anti-spike antibodies to bind to the Spike antigen as well as SARS-COV-2 viruses, a standard dot blot approach was followed. Briefly, different dilutions of protein/antigen/virus solutions were blotted in a nitrocellulose membrane (BioRad), by pipetting 2 μL drops of each solution/replicate to different membrane locations (usually 3-4 mm diameter). After drying, membranes were blocked by soaking in 5% BSA (Sigma Aldrich) solution in TBS-T—0.05% Tween20 in TBS—(Sigma Aldrich) for 30 minutes, RT. Following blocking, membranes were incubated with primary antibody (Mouse Anti-Spike, 1:500 dilution) overnight at 4° C. Afterwards, membranes were washed three times with TBS-T and were then incubated with the secondary antibody (Goat Anti-Mouse, Alkaline Phosphatase Conjugate, Invitrogen, 1:1000 Dilution), for 1 hour at RT. Membranes were then washed three times with TBS-T, and posteriorly revealed with the AP-Conjugate Kit (Biorad). The revealing was stopped once the dots were visible and the membranes were then digitalized and converted to 8-bit. Using ImageJ blot tools, semi-quantitative analysis was performed to compare the different dot's values between dilutions and sample types.

Computational Modelling of Plasmonic Gold Transmission

A finite element method is used to model how gold nanoparticles affect transmission of the light through the fiber. The simulation space consists of a gold nanosphere with the diameter of 100 nm, a spherical dielectric shell with refractive index of n=1.33 which surrounds the nanosphere, and a PML layer. An incident plane wave shines the particle and scattered fields are calculated and employed to find the particle's extinction cross-section. Fiber transmission is calculated using the calculated extinction cross-section, the length of the fiber in experiments, and the concentration of gold nanoparticles in the fiber. Finally, the refractive index of the surrounding media increases in steps of $\Delta n=0.01$ and the transmission spectra is calculated for each step. These calculations showed that any increase in the refractive index around the nanospheres will redshift the resonance wavelength and decrease the transmission amplitude at long wavelengths.

Biofabrication of Living Optical Fibers

For continuously printing triple layered optical hydrogel fibers, a tri-coaxial 3D printing nozzle configuration (Ramé-Hart Instruments) was connected with syringes containing different core, clad layer hydrogel precursors. Detailed nozzle and channels dimensions can be found in FIG. 21. For initial tests with living cells, 3T3 fibroblasts were cultured with DMEM Complete Medium (Gibco) and upon confluence trypsinized and resuspended in the core Alginate (Sigma) 2 wt % solution. In order to ensure proper cell distribution, the suspension was thoroughly mixed without vigorous agitation that could induce air bubbles and compromise the fiber optical properties. A cladding layer of 0.5% gellan gum was used on the middle channel and a shielding layer of 1% gellan gum on the outer channel. All solutions were placed in 10 mL syringes (BD) and connected to individual syringe pumps at a flow of 0.4 ml/min, cross-linked in a 0.1M $CaCl_2$) bath as previously described. Viability tests were performed by Calcein AM/Ethidium Homodimer staining (Live/Dead) (Invitrogen) at 1:1000 dilution. Post-fabricated fibers and fibers cultured for 1 week were incubated in the live/dead solution for 30 minutes followed by imaging under confocal microscope (Zeiss). 3 images per replicate were taken at random, and Cell Profiler [42] software was then used to count the number of live and dead cells. Viability was then calculated as the percentage of live cells. Quantification of light output power as function of cell density was performed by fabricating fibers with varying 3T3 cell density in the core, and output characterization was done using an optical power meter (Thorlabs) as described in the optical fiber characterization section.

Fluorescent Fingerprinting Tests

To validate the possibility of light carrying information upon interaction with fluorescent molecules, 3T3 fibroblasts were stained with two model fluorescent markers of different wavelengths, namely Orange Cell Tracker CMRA and Calcein AM (Invitrogen) according to manufacturer's instructions. Briefly, 3T3 cells in suspension were incubated with each marker for 30 minutes under 37° C., washed with PBS, and introduced in the optical fiber core as described above. Fibers were then fabricated and aligned in the input-output setup as previously described the light source and spectrometer. Output spectra were collected and spectral ratios were obtained by dividing the spectra of fluorescent-tagged cell-laden fibers to those without fluorescent molecules, in order to confirm the presence of transmission dips in agreement with the marker's excitation curves. For performing calcein AM overtime metabolic tracking, 4 cm-long fibers with unstained cells were aligned in the optical readout setup, and 10 µL of a 1:100 Calcein AM solution in CaPBS was added dropwise along the optical fiber's length. The spectral output was then collected every minute for a total of 10 minutes after the beginning of the calcein AM metabolization. The 495 nm normalized transmission values were obtained by normalizing all spectral curves to their maximum and extracting the normalized intensity values as an average of the 493-495 nm window. These were then plotted overtime.

Cancer Cell Lines and Spectral Fingerprinting Experiments

LNCaP, 22Rv1, and DU145 cells were purchased from the American Type Culture Collection (ATCC; Manassas, VA). All cell lines were authenticated through Stanford Functional Genomics Facility. FUCRW plasmid was a kind gift from Dr. Owen Witte's laboratory at University of California Los Angeles. 22Rv1 and DU145 cells were infected with FUCRW virus expressing red fluorescent protein (RFP). RFP signal was confirmed 72 hours post infection. LNCaP-RFP-Trop2-OV cells expressing RFP and Trop2 oncogene were generated as previously described [43]. All cells were cultured in RPMI medium supplemented with 10% FBS, 4 mM L-glutamine, and 1% penicillin/streptomycin.

Spectral fingerprinting tests with the different cell lines were performed by integrating them within optical hydrogel fibers as described in the previous section. Briefly, cancer cells were resuspended in the core material at a density of 10 M/mL and cultured in different conditions, namely control medium, 1.5 µM Cisplatin (Biovision) or 1 µM Staurosporine (Biovision). After 48 h of culture, the living optical fibers were washed twice with PBS to remove media remains that could interfere with optical readouts (e.g., Phenol Red). Before measurement, fibers were placed in a 1 mM CaCl₂) solution to facilitate their manipulation and were then aligned in the optical characterization setup with spectrometer connection. RFP-level transmission readouts were immediately obtained from the first output collected, and calcein activity overtime was then tracked by the addition of calcein and spectral recording every minute for 10 minutes, as described in the previous section. Calcein-level transmissions were then plotted overtime, and Pearson correlation statistical analysis was performed in order to verify the presence of a positive correlation between time and decrease in calcein-level transmission. To validate fiber-optics data, fibers were also imaged in confocal microscope after incubation with calcein AM. Both RFP and calcein signals were analyzed in several pictures per replicate via Cell Profiler, in order to compare the relative post-incubation signal intensities to the relative decreases in fiber optics transmission at each specific wavelength instantly (RFP) and overtime (calcein).

Digitalization and Quantification of 3D Cancer Development

In order to evaluate the invasive proliferation of encapsulated cancer cells over time and quantify this response through optics upon exposure to different levels of the anti-proliferative drug cisplatin, the core material was modified by blending alginate with GelTrex (Growth-Factor Reduced Basement Membrane, Thermofisher) at a 50:50 ratio. Fibers with Cells were fabricated as described before with a 10 million/mL density and were cultured for 1 week to observe the cancer tissue development and the formation of fiberoid (fiber-shaped organoids) structures. To do so, fibers were incubated with Calcein AM 1:500 (Invitrogen) and Hoechst 33342 1:1000 (Thermo Scientific), washed with PBS and imaged under confocal microscope (Zeiss). As model cell line, we used the RFP-expressing LNCaP-RFP-Trop2-OV due to its aggressiveness and relevance in metastatic events. To then quantify the effect of cisplatin in the impedance of 3D tumor growth, fibers were cultured over a 5-days period under control conditions and increasing concentrations of cisplatin (1.5, 15 and 150 µM). After each time point, fibers were washed twice with CaPBS, briefly dipped in 1 mM CaCl₂) and aligned in the optical characterization setup. Two types of immediate readouts were acquired: output power via powermeter reading and spectral response through spectrometer connection. Output power was directly used as an indicator of light attenuation induced by tumor growth and spectral data was processed to extract RFP-level transmission values, as plotted in the maintext. In parallel, fibers were also axially sectioned and imaged in confocal microscope for observing the distribution of cancer cells and aggregates within the fiber structure overtime and validate the fiber optics readouts.

Statistical Analysis

Globally, samples and replicates were firstly tested for the probability of normal distribution via Shappiro-Wilk normality test. In the case of a positive normality test, differences between conditions were then analyzed via parametric ANOVA or T-test. In the case of a negative normality test, difference between conditions were analyzed via non-parametric Kruskal-Wallis or Mann-Whitney tests. The detailed statistical tests are reported in the different data figures and captions. In all cases, differences between conditions were considered statistically significant when $p < 0.05$.

Supplementary Equations for deriving the effect and relationship between gold resonance transmission and absorption.

For the Blank Fiber:

$$I_B(\lambda) = I_{bulb}(\lambda) \times H_{Fiber}(\lambda) \tag{1}$$

For the AuNP Embedded Fiber:

$$I_{AuNP}(\lambda) = I_{bulb}(\lambda) \times H_{Fiber}(\lambda) \times T_{AuNP}(\lambda) \tag{2}$$

$$T_{AuNP} = 1 - A_{AuNP}(\lambda) \tag{3}$$

$$\Rightarrow I_B(\lambda) - I_{AuNP}(\lambda) = I_{bulb}(\lambda) \times H_{Fiber}(\lambda) \times A_{AuNP}(\lambda) \tag{4}$$

$$A_{AuNP}(\lambda) = \frac{I_{AuNP}(\lambda) - I_B(\lambda)}{I_B(\lambda)} \tag{5}$$

$I_B(\lambda)$: Transmission Spectra of the Blank Fiber
$I_{AuNP}(\lambda)$: Transmission Spectra of the Gold Embedded Fiber
$T_{AuNP}(\lambda)$: Transmission Spectra of Gold Nanoparticles
$A_{AuNP}(\lambda)$: Absorption Spectra of Gold Nanoparticles

REFERENCES

1. Lin, C. In memory of Charles Kao. *Nat. Photonics* 12, 715-717 (2018).
2. DeCusatis, C. *Handbook of Fiber Optic Data Communication* (2008). doi: 10.1016/B978-O-12-374216-2.X5001-7
3. Palais, J. C. Optical communication: Long distance fiber optic communications. in *Broadcasting and Optical Communication Technology* (2017). doi: 10.1201/9781420003116
4. Yablon, A. D. *Optical Fiber Fusion Splicing. Optical Fiber Fusion Splicing* (Springer, 2005). doi:10.1007/b137759
5. Šulc, J. & Jelínková, H. *Solid-state lasers for medical applications. Lasers for Medical Applications: Diagnostics, Therapy and Surgery* (Woodhead Publishing Limited, 2013). doi: 10.1533/9780857097545.2.127
6. Taffoni, F., Formica, D., Saccomandi, P., Di Pino, G. & Schena, E. Optical fiber-based MR-compatible sensors for medical applications: An overview. *Sensors (Switzerland)* 13, 14105-14120 (2013).
7. Fermann, M. E. & Hartl, I. Ultrafast fibre lasers. *Nat. Photonics* 7, 868-874 (2013).
8. Xu, C. & Wise, F. W. Recent advances in fibre lasers for nonlinear microscopy. *Nat. Photonics* 7, 875-882 (2013).
9. Gallego, D. & Lamela, H. High-sensitivity ultrasound interferometric single-mode polymer optical fiber sensors for biomedical applications. *Opt. Lett.* 34, 1807 (2009).
10. Nizamoglu, S., Gather, M. C. & Yun, S. H. All-biomaterial laser using vitamin and biopolymers. *Adv. Mater.* 25, 5943-5947 (2013).
11. Haufová, P., Knejzlík, Z., Hanuš, J., Zadražil, A. & Štěpánek, F. Reversible buckling and diffusion properties of silica-coated hydrogel particles. *J. Colloid Interface Sci.* 357, 109-115 (2011).
12. Guimarães, C. F., Ahmed, R., Marques, A. P., Reis, R. L. & Demirci, U. Engineering Hydrogel-Based Biomedical Photonics: Design, Fabrication and Applications. *Adv. Mater.* (2021). doi:10.1002/adma.202006582.
13. Guimarães, C. F., Gasperini, L., Marques, A. P. & Reis, R. L. The stiffness of living tissues and its implications for tissue engineering. *Nat. Rev. Mater.* 5, 351-370 (2020).
14. Feng, J. et al. Printed Degradable Optical Waveguides for Guiding Light into Tissue. *Adv. Funct. Mater.* 2004327, 1-14 (2020).
15. Elsherif, M., Hassan, M. U., Yetisen, A. K. & Butt, H. Hydrogel optical fibers for continuous glucose monitoring. *Biosens. Bioelectron.* 137, 25-32 (2019).
16. Zhou, M., Guo, J. & Yang, C. Ratiometric fluorescence sensor for Fe3+ ions detection based on quantum dot-doped hydrogel optical fiber. *Sensors Actuators, B Chem.* 264, 52-58 (2018).
17. Yetisen, A. K. et al. Glucose-Sensitive Hydrogel Optical Fibers Functionalized with Phenylboronic Acid. *Adv. Mater.* 29, (2017).
18. Choi, M., Humar, M., Kim, S. & Yun, S. H. Step-Index Optical Fiber Made of Biocompatible Hydrogels. *Adv. Mater.* 27, 4081-4086 (2015).
19. Choi, M. et al. Light-guiding hydrogels for cell-based sensing and optogenetic synthesis in vivo. *Nat. Photonics* 7, 987-994 (2013).
20. Guo, J. et al. Highly Stretchable, Strain Sensing Hydrogel Optical Fibers. *Adv. Mater.* 28, 10244-10249 (2016).
21. Onoe, H. et al. Metre-long cell-laden microfibres exhibit tissue morphologies and functions. *Nat. Mater.* 12, 584-590 (2013).

22. Guimarães, C. F. et al. High-throughput Fabrication of Cell-Laden 3D Biomaterial Gradients. *Mater. Horizons* (2020) doi:10.1039/C7MH00043J.
23. Lee, K. Y. & Mooney, D. J. Alginate: Properties and biomedical applications. *Prog. Polym. Sci.* 37, 106-126 (2012).
24. Oliveira, J. T. et al. Gellan gum: A new biomaterial for cartilage tissue engineering applications. *J. Biomed. Mater. Res.—Part A* 93, 852-863 (2010).
25. Tran, N. M. et al. An appropriate selection of a 3d alginate culture model for hepatic Huh-7 cell line encapsulation intended for viral studies. *Tissue Eng.—Part A* 19, 103-113 (2013).
26. Madrigal, J. L., Shams, S., Stilhano, R. S. & Silva, E. A. Characterizing the encapsulation and release of lentivectors and adeno-associated vectors from degradable alginate hydrogels. *Biomater. Sci.* 7, 645-656 (2019).
27. Lee, H. P., Gu, L., Mooney, D. J., Levenston, M. E. & Chaudhuri, O. Mechanical confinement regulates cartilage matrix formation by chondrocytes. *Nat. Mater.* 16, 1243-1251 (2017).
28. Shin, H., Olsen, B. D. & Khademhosseini, A. The mechanical properties and cytotoxicity of cell-laden double-network hydrogels based on photocrosslinkable gelatin and gellan gum biomacromolecules. *Biomaterials* 33, 3143-3152 (2012).
29. Poole, S. B. P., Payne, D. N. & Fermann, M. E. Fabrication Of Low-Loss Optical Fibres Containing Rare-Earth Ions. *Electron. Lett.* 21, 737-738 (1985).
30. Bao, Y. et al. The redshift of surface plasmon resonance of colloidal gold nanoparticles induced by pressure with diamond anvil cell. *J. Appl. Phys.* 115, (2014).
31. Tokarev, I., Tokareva, I. & Minko, S. Gold-nanoparticle-enhanced plasmonic effects in a responsive polymer gel. *Adv. Mater.* 20, 2730-2734 (2008).
32. Björck, L. & Kronvall, G. Purification and some properties of streptococcal protein G, a novel IgG-binding reagent. *J. Immunol.* 133, 969-74 (1984).
33. Ahmed, R. et al. Tunable Fano-Resonant Metasurfaces on a Disposable Plastic-Template for Multimodal and Multiplex Biosensing. *Adv. Mater.* 1907160, 1-11 (2020).
34. Chi, X. et al. A neutralizing human antibody binds to the N-terminal domain of the Spike protein of SARS-COV-2. *Science* (80-.). 369, 650-655 (2020).
35. Zhu, N. et al. A novel coronavirus from patients with pneumonia in China, 2019. *N. Engl. J. Med.* 382, 727-733 (2020).
36. Gasperini, L., Mano, J. F. & Reis, R. L. Natural polymers for the microencapsulation of cells. *J. R. Soc. Interface* 11, 20140817-20140817 (2014).
37. Belmokhtar, C. A., Hillion, J. & Ségal-Bendirdjian, E. Staurosporine induces apoptosis through both caspase-dependent and caspase-independent mechanisms. *Oncogene* 20, 3354-3362 (2001).
38. Alderden, R. A., Hall, M. D. & Hambley, T. W. The discovery and development of cisplatin. *J. Chem. Educ.* 83, 728-734 (2006).
39. Moutasim, K. A., Nystrom, M. L. & Thomas, G. J. Cell Migration and Invasion Assays. in *Cancer Cell Culture: Methods and Protocols* (ed. Cree, I. A.) 333-343 (Humana Press, 2011). doi: 10.1007/978-1-61779-080-5_27
40. Carvalho, P. D. et al. KRAS oncogenic signaling extends beyond cancer cells to orchestrate the microenvironment. *Cancer Res.* 78, 7-14 (2018).
41. Hanahan, D. & Weinberg, R. A. Hallmarks of cancer: The next generation. *Cell* 144, 646-674 (2011).

42. Carpenter, A. E. et al. CellProfiler: Image analysis software for identifying and quantifying cell phenotypes. *Genome Biol.* 7, (2006).

43. Hsu, E. C. et al. Trop2 is a driver of metastatic prostate cancer with neuroendocrine phenotype via PARP1. *Proc. Natl. Acad. Sci. U.S.A* 117, 2032-2042 (2020).

TABLE 1

Preliminary core-clad and core-clad-shield tests with varying polymer concentrations and visually detectable light guiding distances.

| Core | Clad | Shield | Visible Light Output (cm) |
|---|---|---|---|
| GG 1% | NA | NA | 4 |
| Alg 2% | NA | NA | 4.5 |
| Alg 2% | GG 1% | NA | 7 |
| GG 1% | Alg 2% | NA | 6 |
| GG 1.5% | Alg 1% | NA | 10 |
| GG 1.5% | Alg 1.5% | Alg 1% | 9 |
| Alg 2% | Alg 1% | NA | 10 |
| Alg 2% | Alg 1.5% | Alg 1% | 9 |
| Alg 2% | GG 0.5% | NA | 12 |
| Alg 4% | GG 0.25% | Alg 2% | 14 |
| Alg 7% | GG 0.25% | Alg 2% | 19 |

TABLE 2

Preliminary gradient-index tests with varying polymer concentrations and visually detectable light guiding distances.

| Core | Clad1 | Clad2 | Clad3 | Visible Light Output (cm) |
|---|---|---|---|---|
| Alg 2% | Alg 1.5% | Alg 1% | NA | 11 cm |
| Alg 3% | Alg 2% | Alg 1% | NA | 10 cm |
| Alg 3% | Alg 2% | Alg 1.5% | NA | 11 cm |
| Alg 4% | Alg 2% | Alg 1.5% | Alg 1% | 12 cm |
| Alg 3% | Alg 2% | Alg 1.5% | Alg 1% | 16 cm |

Example 2

Endotracheal Tubes. Anti-bacterial Fibers with Nanorough Coating

Hydrogel optical fibers can be coupled with endotracheal tubes in order to guide light and monitor physiologically relevant responses within an organism. Their biocompatible nature and non-adhesive surface prevents them from attaching to the tissue, with the addition of a nanorough coating to the outer layers in order to imbue fibers with antibacterial action. This prevents bacterial adhesion and promote bacterial death, therefore avoiding the formation of bacterial biofilms.

Example 3

Wound Healing Tracking and Drug Release

Wound healing is a complex process in which several cellular entities come into play in a complex microenvironment constantly going through renewal where multiple forces are also relevant for wound contraction and closure. We have shown that our fibers are able to inform on changes in force and shape and can therefore be used to monitor wound healing throughout time. Additionally, the hydrogels that make up the optical fibers can also be used as a delivery vehicle for pro-regenerative drugs and anti-scarring molecules acting two-in-one approach where wound healing can be monitored and simultaneously promoted through controlled drug release.

Example 4

Optogenetic Cell Activation

We show that cells can be encapsulated and exposed to light, using the same optical components to derive meaningful cell responses. Additionally, bioengineered cells are able to express designer proteins upon light stimulation. These cells can be integrated in the optical fiber and specific types of light can be coupled to the fibers at desired timepoints in order to trigger the release of certain molecules, using cells as living factories for a wide range of molecules that can then be released from the cells into living environments, e.g., targeting tumor cells by optogenetic promotion of tumor-penetrating, pro-apoptotic factors.

Example 5

Deep Brain Stimulation

By developing soft optical fibers which are fully made by natural-derived, biocompatible materials, these can be directly implanted in the brain tissue in order to stimulate specific regions of the brain. Advances in electro-conductive hydrogels can be integrated in the fibers by modifying some of the layers with conductive molecules or particles that can act to guide electrical impulses together with optical signals to selected brain regions. The fibers can be engineered to degrade after a certain period of time in order to avoid additional neurosurgery, or alternatively remain in place and resist degradation for long-term applications such as Parkinson's disease therapy.

Example 6

Hollow Fibers

To obtain hollow, perfusable architectures, two types of protocols can be employed. The first is based on the fabrication of hydrogel core and shell with posterior core hydrogel liquification and hollow fiber formation. The second takes advantage of viscous solutions which can flow in similar continuous, coaxial regimens, where the core material does not crosslink upon wet spinning but remains liquid and can easily be removed or diffuse from the core, being replaced by cell culture medium or other perfusing solutions. Hollow fibers can then be perfused with solutions containing cells for inner surface coating as well as different materials which can add a higher range of refractive index, ranging from totally hollow (air), aqueous solutions, or other hydrogel materials namely synthetic hydrogels such as PEG or acrylamide for higher refractive index and longer light guiding applications.

Figure 34:
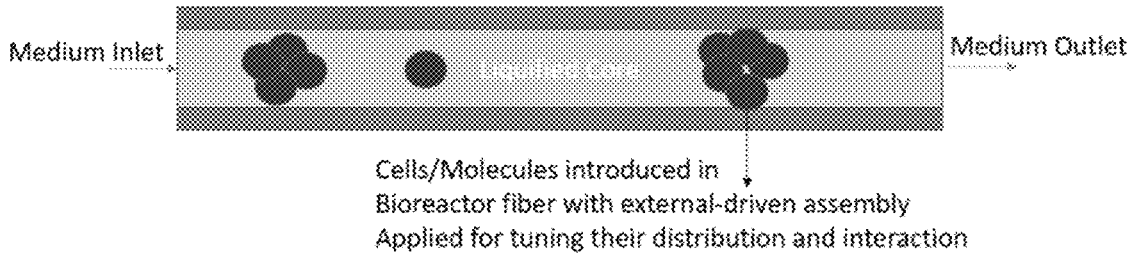
FIG. 34: Hollow fibers useable as a bioreactor that can be perfused with different types of cells of molecules within a liquid core environment, for long-term maturation of cellular aggregates within a fiber-confined liquid environment. External driven actuation such as magnetic or acoustic forces can be employed to arrange cells within the liquid core for the biofabrication of different biological architectures.

These hollow fibers are also useable as a bioreactor that can be perfused with different types of cells of molecules within a liquid core environment, for long-term maturation of cellular aggregates within a fiber-confined liquid environment. External driven actuation such as magnetic or acoustic forces can be employed to arrange cells within the liquid core for the biofabrication of different biological architectures, as depicted in FIG. 34.

Example 7

Introduction of Air Bubbles for Air-Light Interaction and Sonoluminescence

By replacing the inner hydrogel material by an air flow, the introduction of air droplets within the optical fiber core is possible. This enables distinct applications. The first is the use of lower air refractive index as a localized inducer of light refraction, acting as light intensity valves where the distribution of droplets along the fiber can be controlled to reduce the intensity of traveling light, designed as a function of distance.

Additionally, air can be stimulated through high intensity acoustic bursts, causing the air bubbles to collapse and emit light (sonoluminescence), that can then be guided through the optical fiber, converting an acoustic input into an optical output. As such, these fibers can have multiple type of input stimuli such as acoustic, electric, magnetic, or mechanic, all of which can then translate into differences in optical output that can be collected and analyzed.

Figure 35:
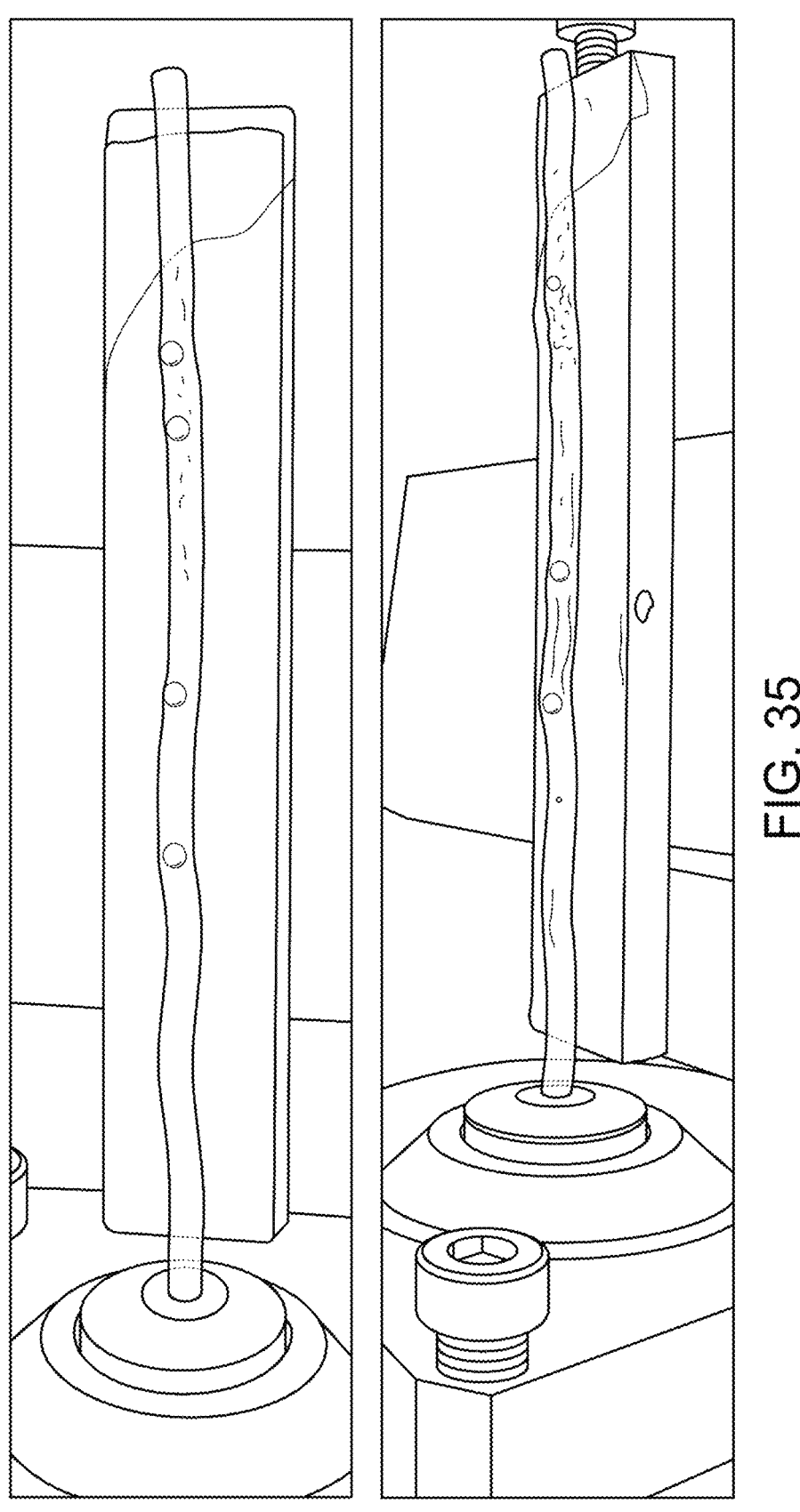
FIG. 35: Air droplets in the optical fiber core directly interact with light causing localized refraction and increasing overall attenuation.

As depicted in FIG. 35, fibers present air bubbles trapped in the hydrogel core that scatter light due to the abrupt decrease in refractive index at the hydrogel-air interface.

Example 8

Altering Core Material Geometry

Figure 36:
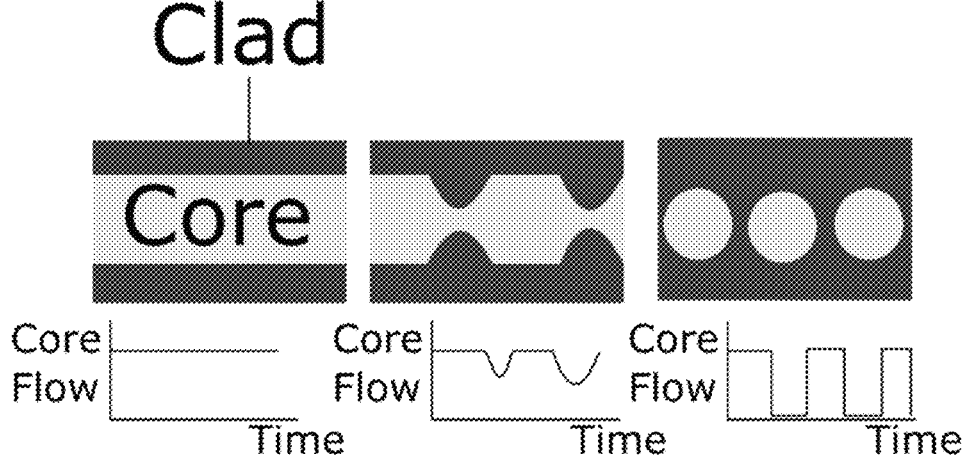
FIG. 36: Flow Control overtime can be applied in order to alter core geometry.

By changing the flow of the core hydrogel precursor over time, it is also possible to change the shape of the optical fiber core and provide different geometries to the overall structure and imbue it with additional optical characteristics by non-continuous core medium. As depicted in FIG. 36, by reducing and increasing the core flow overtime, it is possible to move from a continuous diameter core to regions of lower diameter or even individualized hydrogel geometries (as droplets). This can be achieved by using a quick actuating valve which can turn the core flow on and off over time with different periodicity yielding material droplets of different dimensions and distribution.

Example 9

Fiber/Droplet Configurations

The total fiber geometry can also be modified by interrupting all material's flow, preventing a continuous fiber to form, and allowing for the creation of e.g., individualized hydrogel droplets. This can be achieved by allowing droplets to form outside the crosslinking bath and allowing them to fall by the force of gravity or, alternatively, using air shear to push droplets out of the nozzle's tip, which can also be controlled to tune droplet dimensions.

Figure 37:
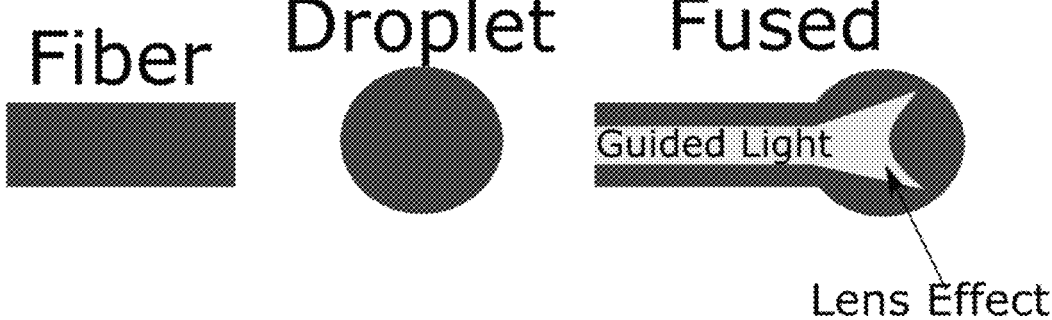
FIG. 37: Fibers can be discontinued by gravity or air shear forming independent droplets. These droplets can also be combined with the fibers (e.g., via the fusion method previously explained) for light guiding until the droplet which can act as a lens.
Figure 38A:
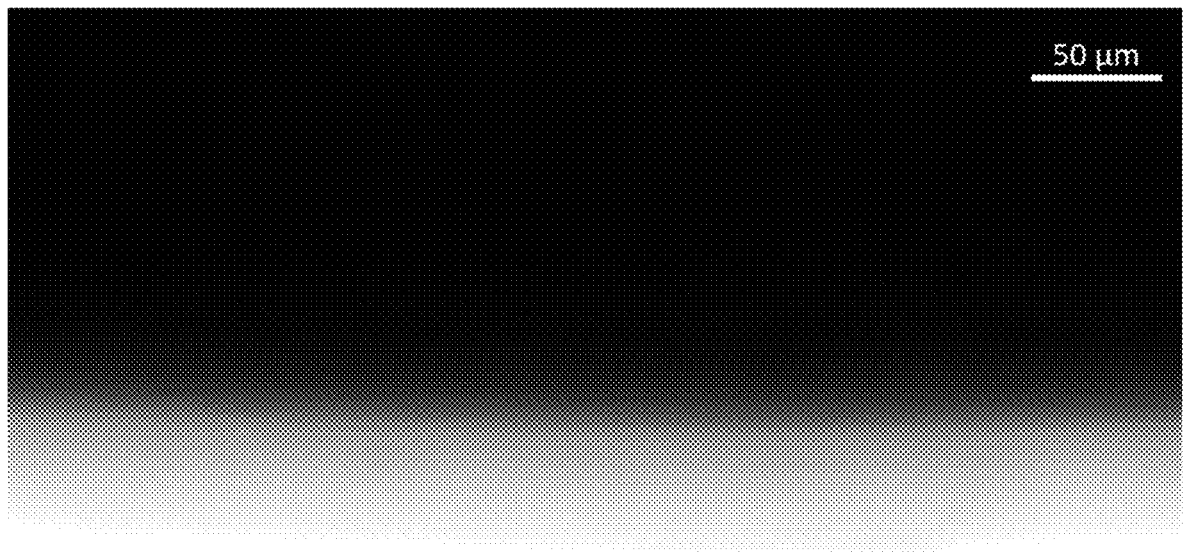
FIGS. 38A-38C: Validation of the lowest concentration threshold capable of forming a uniform hydrogel cladding layer. Images of a fiber with an alginate core (FIG. 38A) and 0.1% Gellan Gum cladding (FIG. 38B) are shown.
Figure 38B:
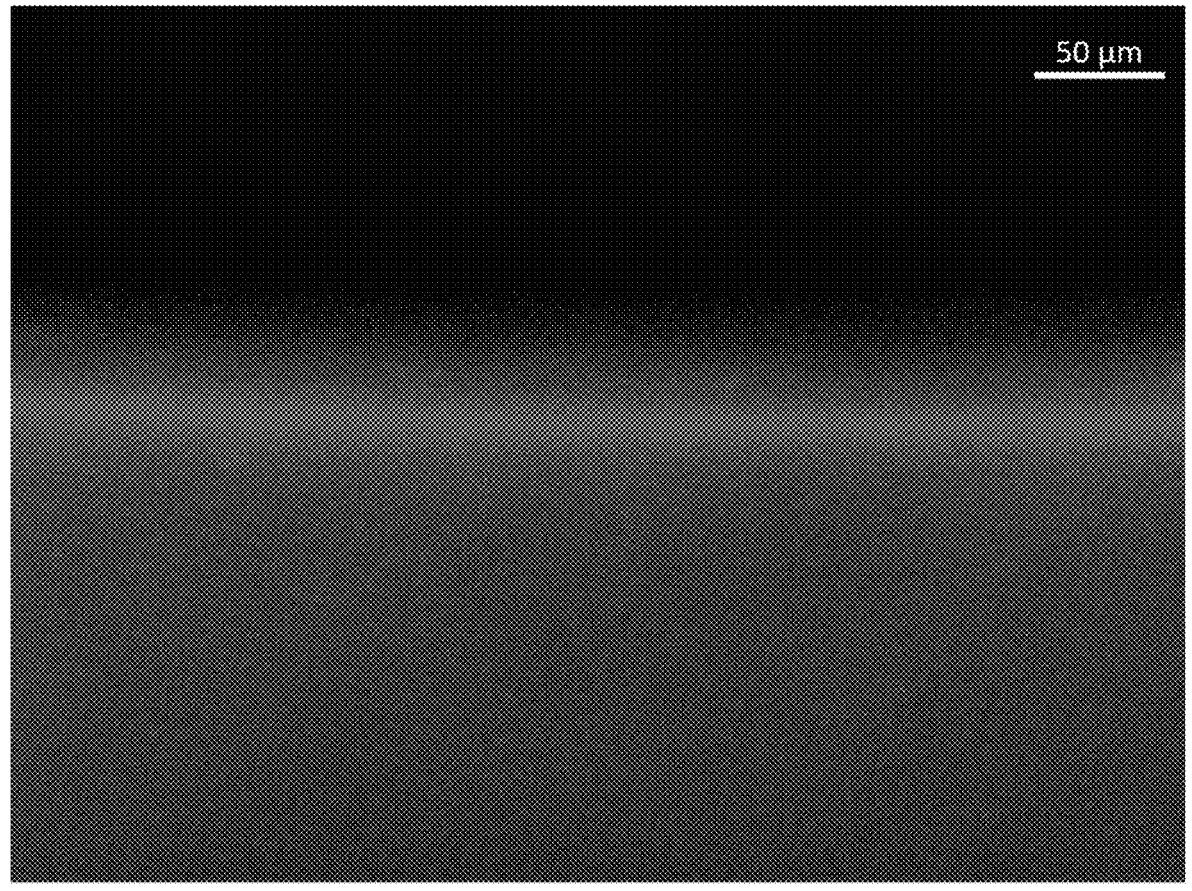
Figure 38C:
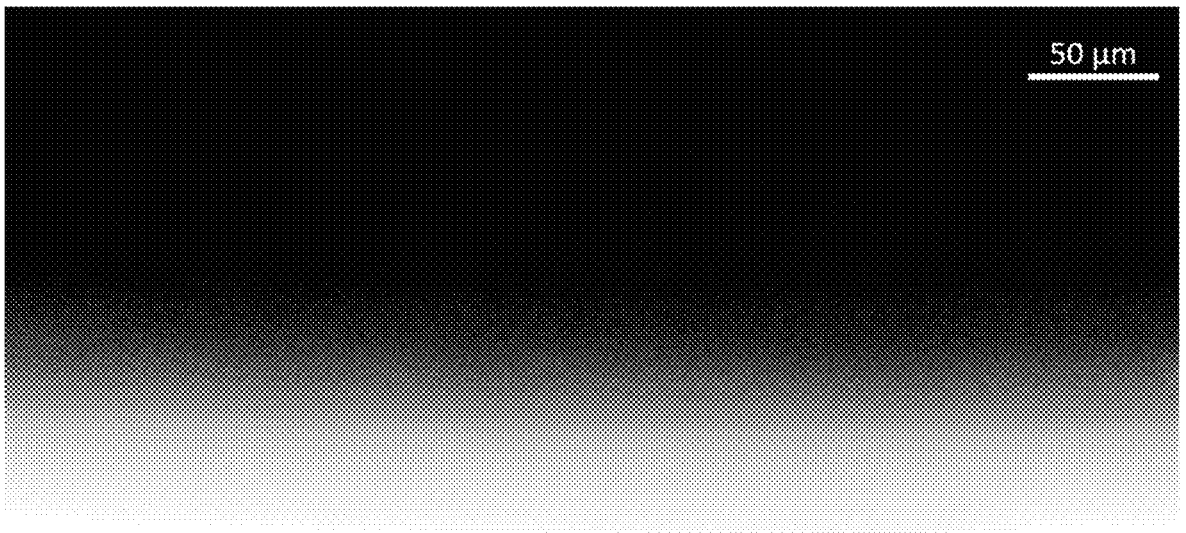

These droplets can still integrate the multiple materials of the optical fibers, act as an optical lens upon interaction with light, and even be fused to the fiber using the previously outlined fiber fusion methodology, as depicted in FIG. 37.

What is claimed is:

1. An optical fiber comprising:
   a) one or more hydrogel cladding layers comprising polysaccharides crosslinked ionically by metal cations; and
   b) a core, wherein the core is an ionically crosslinked hydrogel core, a liquid core, a hollow core, or a gaseous core, wherein the core is encapsulated by the one or more hydrogel cladding layers, wherein the hydrogel cladding layers have a lower refractive index than the core of the optical fiber.

2. The optical fiber of claim 1, wherein the hydrogel cladding layers comprise gellan gum or alginate.

3. The method of claim 2, wherein the hydrogel cladding layers comprise about 0.1 weight % to 1.0 weight % gellan gum or about 1.0 weight % to 2.0 weight % alginate.

4. A method of activating a photoactivatable prodrug, the method comprising:

administering the photoactivatable prodrug to a subject;
exposing the photoactivatable prodrug to excitation light guided by the optical fiber of claim 1, wherein activity of the prodrug is increased in response to exposure to the excitation light.

5. A method of performing photodynamic therapy (PDT), the method comprising:

administering a photosensitizing chemical substance to a subject; and
exposing the photosensitizing chemical substance to excitation light guided by the optical fiber of claim 1, wherein radicals or reactive oxygen species are generated by the photosensitizing chemical substance in response to exposure to the excitation light.

6. The optical fiber of claim 1, wherein the metal cations comprise alkaline earth metal cations.

7. A method of monitoring expression of a fluorescently labeled protein in a cell, the method comprising:

introducing the cell into the core of the optical fiber of claim 1, wherein the fluorescently labeled protein is expressed in the cell;
exposing the cell to excitation light guided by the optical fiber; and
monitoring fluorescent light or a decrease in excitation-range light transmission intensity output from the optical fiber.

8. A method of guiding light to a target using the optical fiber of claim 1, the method comprising:

introducing the target into the core of the optical fiber of claim 1; and
aligning a light source with an end of the optical fiber, wherein light from the light source passes through the optical fiber to the target.

9. The optical fiber of claim 1, wherein the hydrogel core comprises alginate or gellan gum.

10. The method of claim 9, wherein the hydrogel core comprises about 2 weight % to about 7 weight % alginate or about 1.0 weight % to about 1.5 weight % gellan gum.

11. A method of monitoring proliferation of a cell, the method comprising:

culturing the cell within the core of the optical fiber of claim 1;
aligning a light source with an end of the optical fiber; and
monitoring output light power from the optical fiber, wherein the output light power decreases with increasing cell density resulting from proliferation of the cell.

12. The optical fiber of claim 1, wherein the core has a continuous diameter, a varying diameter, or is discontinuous along the length of the optical fiber.

13. The optical fiber of claim 1, wherein the hydrogel core comprises a mixture of at least two ionically crosslinked polysaccharides or at least one ionically crosslinked polysaccharide and a non-polysaccharide hydrogel polymer.

14. The optical fiber of claim 1, further comprising an endotracheal tube or a medical swab coupled to the optical fiber.

15. The optical fiber of claim 1, wherein the hydrogel cladding layers and the hydrogel core have a step-index or gradient-index architecture, or wherein the optical fiber has a gradient of refractive index values along the length of the optical fiber.

16. The optical fiber of claim 1, wherein the hydrogel cladding layers have alternating refractive index values.

17. The optical fiber of claim 1, wherein the hydrogel core comprises polysaccharides crosslinked ionically by metal cations.

18. The optical fiber of claim 17, wherein the hydrogel core is doped with rare earth metal cations.

19. A method of guiding light to a target using the optical fiber of claim 1, the method comprising:

placing the optical fiber of claim 1 such that a first end of the optical fiber is attached to or near the target; and aligning a light source with a second end of the optical fiber, wherein light from the light source passes through the optical fiber to the target.

20. The method of claim 19, further comprising introducing a bubble into the core of the optical fiber.

21. The method of claim 19, further comprising applying an acoustic stimulus, an electric stimulus, a magnetic stimulus, or a mechanical stimulus to the optical fiber, wherein optical output from the optical fiber is modulated.

22. A photonic device comprising the optical fiber of claim 1 and a light source coupled to the optical fiber.

23. The photonic device of claim 22, further comprising optics to focus light from the light source into the core of the optical fiber.

24. The photonic device of claim 22, further comprising a photodetector.

25. The method of claim 22, wherein the light source is a laser diode, a light-emitting diode (LED), a superluminescent diode, a microfocus X-ray source, or a lamp.

26. The optical fiber of claim 1, wherein the optical fiber has a multi-input architecture or a multi-output architecture or both a multi-input architecture and a multi-output architecture.

27. The optical fiber of claim 1, further comprising a shielding layer.

28. The optical fiber of claim 27, wherein the shielding layer comprises alginate or gellan gum.

29. The method of claim 28, wherein the shielding layer comprises 1 weight % to 2 weight % alginate or 0.5 weight % to 1.5 weight % gellan gum.

30. The optical fiber of claim 1, further comprising a plasmonic nanoparticle or a quantum dot, wherein the plasmonic nanoparticle or the quantum dot is encapsulated within the core, wherein the plasmonic nanoparticle comprises a noble metal, a metal-oxide, a transition metal nitride, or a plasmonic metal-metal oxide nanocomposite.

31. A method of detecting a target of interest, the method comprising measuring the plasmonic response of the plasmonic nanoparticle or the spectral response or change in photoluminescent lifetime of the quantum dot encapsulated within the core of the optical fiber of claim 30 upon binding of the target of interest to the capture agent.

32. The optical fiber of claim 30, further comprising a capture agent that selectively binds to a target of interest, wherein said capture agent is attached to the outer surface of the plasmonic nanoparticle or the quantum dot, wherein the capture agent comprises an antibody, an antibody mimetic, an aptamer, a peptoid, or a ligand, and wherein the target of interest is an antigen, an antibody, a protein, a nucleic acid, a metabolite, a toxin, a drug, a pollutant, a cell, a virus, a bacterium, a parasite, a tissue, an organoid, or an organism.

33. The optical fiber of claim 32, wherein the capture agent comprises an antibody that selectively binds to a spike protein of severe acute respiratory syndrome coronavirus 2 (SARS-COV-2).

* * * * *